US009504762B2

(12) United States Patent
Colosi et al.

(10) Patent No.: US 9,504,762 B2
(45) Date of Patent: Nov. 29, 2016

(54) ADENO-ASSOCIATED VIRUS FACTOR VIII VECTORS

(71) Applicant: BIOMARIN PHARMACEUTICAL INC., Novato, CA (US)

(72) Inventors: Peter Cameron Colosi, San Anselmo, CA (US); Amit Nathwani, London (GB); Jenny Mcintosh, London (GB); Edward Tuddenham, London (GB)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

(21) Appl. No.: 14/482,648

(22) Filed: Sep. 10, 2014

(65) Prior Publication Data

US 2015/0071883 A1 Mar. 12, 2015

Related U.S. Application Data

(60) Provisional application No. 61/877,042, filed on Sep. 12, 2013.

(51) Int. Cl.

| | |
|---|---|
| ***A01N 63/00*** | (2006.01) |
| ***A01N 65/00*** | (2009.01) |
| ***A61K 48/00*** | (2006.01) |
| ***C12N 7/00*** | (2006.01) |
| ***C07K 14/755*** | (2006.01) |
| ***C12N 15/86*** | (2006.01) |

(52) U.S. Cl.

CPC ....... *A61K 48/0066* (2013.01); *A61K 48/0058* (2013.01); *C07K 14/755* (2013.01); *C12N 7/00* (2013.01); *C12N 15/86* (2013.01); *C12N 2750/14142* (2013.01); *C12N 2750/14143* (2013.01); *C12N 2800/22* (2013.01); *C12N 2830/008* (2013.01)

(58) Field of Classification Search

USPC ..................... 424/93.1, 93.2; 435/320.1, 325
See application file for complete search history.

(56) References Cited

U.S. PATENT DOCUMENTS 6,200,560 B1 3/2001 Couto et al.
6,221,349 B1 4/2001 Couto et al.
6,383,794 B1 * 5/2002 Mountz .................. C12N 15/86 435/235.1
7,351,577 B2 4/2008 Couto et al.
8,030,065 B2 10/2011 Gray
2007/0042462 A1 2/2007 Hildinger
2008/0131403 A1 * 6/2008 Wang ................. C12N 15/1137 424/93.6
2013/0024960 A1 1/2013 Nathwani et al.

FOREIGN PATENT DOCUMENTS

WO WO-2011/005968 A1 1/2011

OTHER PUBLICATIONS

Edelstein (Journal Gene Med., 2004, vol. 6, p. 597-602).*
Wu (Mol. Therapy, 2008, vol. 16, No. 2, p. 280-289).*
Lu (Human Gene Therapy, Jun. 2008, vol. 19, No. 6, p. 648-654).*
McIntosh (Blood Apr., 2013, vol. 121, No. 17, p. 3335-3344).*
Ishiwata (J. Gene Med., 2009, vol. 11, p. 1020-1029).*
Rogers (Front Biosci., 2015, vol. 20, p. 556-603).*
De Simone et al., Cis- and trans-acting elements responsible for the cell-specific expression of the human alpha 1-antitrypsin gene, EMBO J., 6(9):2759-66 (1987).
Ghosh et al., Expanding adeno-associated viral vector capacity: a tale of two vectors, Biotechnol. Genet. Eng. Rev., 24:165-77 (2007).
Hirsch et al., Little vector, big gene transduction: fragmented genome reassembly of adeno-associated virus, Mol. Ther., 18(1):6-8 (2010).
International Search Report and Written Opinion, International Application No. PCT/US2014/054960, mailed Dec. 22, 2014.
McIntosh et al., Therapeutic levels of FVIII following a single peripheral vein administration of rAAV vector encoding a novel human factor VIII variant, Blood, 121(17):3335-44 (2013).
Nathwani et al., Adenovirus-associated virus vector-mediated gene transfer in hemophilia B, N. Engl. J. Med., 365(25):2357-65 (2011).
Sarkar et al., A single adeno-associated virus (AAV)-murine factor VIII vector partially corrects the hemophilia A phenotype, J. Thromb. Haemost., 1(2):220-6 (2003).
Ward et al., Codon optimization of human factor VIII cDNAs leads to high-level expression, Blood, 117(3):798-807 (2011).
Wu et al., Optimization of self-complementary AAV vectors for liver-directed expression results in sustained correction of hemophilia B at low vector dose, Mol. Ther., 16(2):280-9 (2008).
Yan et al., Inverted terminal repeat sequences are important for intermolecular recombination and circularization of adeno-associated virus genomes, J. Virol., 79(1):364-79 (2005).

* cited by examiner

*Primary Examiner* — Michael Wilson
(74) *Attorney, Agent, or Firm* — Marshall, Gerstein & Borun LLP

(57) ABSTRACT

The invention provides improved adeno-associated virus (AAV) Factor VIII (FVIII) vectors, including AAV FVIII vectors that produce a functional Factor VIII polypeptide and AAV FVIII vectors with high expression activity.

9 Claims, 21 Drawing Sheets

Schematic of UCL SQ

Schematic of Proto 6

Schematic of Proto 7

ADENO-ASSOCIATED VIRUS FACTOR VIII VECTORS

This application claims priority to the U.S. Provisional Patent Application Ser. No. 61/877,042, filed Sep. 12, 2013, which is incorporated by reference herein its entirety.

FIELD OF INVENTION

The invention relates to adeno-associated virus (AAV) Factor VIII (FVIII) vectors, including AAV FVIII vectors with high expression activity and AAV FVIII vectors that express full-length or truncated functional FVIII. The invention also relates to methods of making the herein described AAV FVIII vectors and associated therapeutic uses of thereof.

BACKGROUND

Adeno-associated virus (AAV) is a small, replication-defective, non-enveloped animal virus that infects humans and some other primate species. Several features of AAV make this virus an attractive vehicle for delivery of therapeutic proteins by gene therapy, including, for example, that AAV is not known to cause human disease and induces a mild immune response, and that AAV vectors can infect both dividing and quiescent cells without integrating into the host cell genome. Gene therapy vectors using AAV have been successfully used in some clinical trials, for example, for the delivery of human Factor IX (FIX) to the liver for the treatment of Hemophilia B (Nathwani et al., New Engl. J. Med. 365:2357-2365, 2011).

AAV gene therapy vectors do have some drawbacks, however. In particular, the cloning capacity of AAV vectors is limited as a consequence of the DNA packaging capacity of the virus. The single-stranded DNA genome of wild-type AAV is about 4.7 kilobases (kb). In practice, AAV genomes of up to about 5.0 kb appear to be completely packaged, i.e., be full-length, into AAV virus particles. With the requirement that the nucleic acid genome in AAV vectors must have two AAV inverted terminal repeats (ITRs) of about 145 bases, the DNA packaging capacity of an AAV vector is such that a maximum of about 4.4 kb of protein-coding sequence can be encapsidated.

Due to this size constraint, large therapeutic genes, i.e., those greater than about 4.4 kb in length, are generally not suitable for use in AAV vectors. One such therapeutic gene is the Factor VIII (FVIII) gene, which has an mRNA of about 7.0 kb that encodes a polypeptide of 2332 amino acids comprising, from N- to C-terminus, a 19 amino acid signal peptide, and three large domains (i.e., the heavy chain or A domain, the central or B domain, and the light chain or C domain). One strategy that had been employed to overcome the AAV vector size limitation for FVIII was to use two AAV vectors, one encoding the heavy chain or A domain, and the other encoding the light chain or C domain (see, e.g., Coutu et al., U.S. Pat. Nos. 6,221,349, 6,200,560 and 7,351,577). Another strategy to circumvent this size constraint was to generate AAV vectors encoding FVIII in which the central portion or B domain of the protein has been deleted and replaced with a 14 amino acid linker, known as the SQ sequence (Ward et al., Blood, 117:798-807, 2011, and McIntosh et al., Blood 121:3335-3344, 2013).

While AAV vectors have been reported in the literature having AAV genomes of >5.0 kb, in many of these cases the 5' or 3' ends of the encoded genes appear to be truncated (see Hirsch et al., Molec. Ther. 18-6-8, 2010, and Ghosh et al., Biotech. Genet. Engin. Rev. 24:165-178, 2007). It has been shown, however, that overlapping homologous recombination occurs in AAV infected cells between nucleic acids having 5' end truncations and 3' end truncations so that a "complete" nucleic acid encoding the large protein is generated, thereby reconstructing a functional, full-length gene.

There is a need for novel AAV vectors encoding a functional Factor VIII protein useful in gene therapy approaches for the treatment of hemophilia A. As such, the present invention relates to AAV vectors that encode functionally active FVIII such that either the AAV virions encapsidate the entire nucleic acid encoding the therapeutic protein, i.e., completely packaged AAV FVIII vectors, thereby avoiding the above-mentioned problems of oversized genomes, or at least produce a functionally active Factor VIII protein, which may or may not be truncated. Moreover, to avoid capsid directed immune response, AAV vectors should have the highest possible transduction/expression activity of the target protein per capsid particle. This invention also relates to the production of completely AAV FVIII vectors with high expression activity. Finally, the present invention relates to methods for producing the herein described AAV Factor VIII vectors and associated methods for using the same.

SUMMARY OF INVENTION

The present invention provides AAV vectors encoding functionally active FVIII (referred to herein as "AAV FVIII vectors"). The genomes encoding functionally active FVIII are preferably at most 7.0 kb in length, more preferably at most 6.5 kb in length, yet more preferably at most 6.0 kb in length, yet more preferably at most 5.5 kb in length, yet more preferably at most 5.0 kb in length, with enhanced promoter function.

As used herein, a "functionally active FVIII" is a FVIII protein that has the functionality of a wild-type FVIII protein in vitro, when expressed in cultured cells, or in vivo, when expressed in cells or body tissues. This includes, for example, allowing for blood coagulation to occur and decreasing the time that it takes for blood to clot in a subject suffering from Hemophilia A. Wild-type FVIII participates in blood coagulation via the coagulation cascade, acting as a co-factor for activated FIX (FIXa) which, in the presence of calcium ions and phospholipids forms a complex that converts Factor X (FX) into activated FX (FXa). Accordingly, a functionally active FVIII can form a complex with FIXa, which can convert FX to FXa.

As used herein, an "AAV vector" refers to nucleic acids, either single-stranded or double-stranded, having an AAV 5' inverted terminal repeat (ITR) sequence and an AAV 3' ITR flanking a protein-coding sequence operably linked to transcription regulatory elements, i.e., one or more promoters and/or enhancers, and a polyadenylation sequence, and, optionally, one or more introns inserted between exons of the protein-coding sequence. A single-stranded AAV vector refers to nucleic acids that are present in the genome of an AAV virus particle, and can be either the sense strand or the anti-sense strand of the nucleic acid sequences disclosed herein. The size of such single-stranded nucleic acids is provided in bases. A double-stranded AAV vector refers to nucleic acids that are present in the DNA of plasmids, e.g., pUC19, or genome of a double-stranded virus, e.g., baculovirus, used to express or transfer the AAV vector nucleic acids. The size of such double-stranded nucleic acids in provided in base pairs (bp).

The term "inverted terminal repeat (ITR)" as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from, and integration of a nucleotide sequence interposed between two flanking ITRs into a host cell genome. Sequences of certain AAV-associated ITRs are disclosed by Yan et al., J. Virol. 79(1):364-379 (2005) which is herein incorporated by reference in its entirety.

A "transcription regulatory element" refers to nucleotide sequences of a gene involved in regulation of genetic transcription including a promoter, plus response elements, activator and enhancer sequences for binding of transcription factors to aid RNA polymerase binding and promote expression, and operator or silencer sequences to which repressor proteins bind to block RNA polymerase attachment and prevent expression. The term "liver specific transcription regulatory element" refers to a regulatory element that modulates gene expression specifically in the liver tissue. Examples of liver specific regulatory elements include, but are not limited to, the mouse thyretin promoter (mTTR), the endogenous human factor VIII promoter (F8), human alpha-1-antitrypsin promoter (hAAT) and active fragments thereof, human albumin minimal promoter, and mouse albumin promoter. Enhancers derived from liver specific transcription factor binding sites are also contemplated, such as EBP, DBP, HNF1, HNF3, HNF4, HNF6, with Enh1.

In one embodiment, the AAV vector of the invention comprises a nucleic acid encoding functionally active FVIII having the B domain replaced by the 14 amino acid SQ sequence, i.e., encoding FVIII SQ. The SQ sequence is disclosed in Ward et al., Blood, 117:798-807, 2011, and McIntosh et al., Blood 121:3335-3344, 2013. The FVIII coding region sequence is a codon-optimized sequence (see Nathwani et al., US Pat. App. Pub. No. 2013/0024960A1, published Jan. 24, 2013, which is incorporated herein by reference in its entirety, and McIntosh et al., Blood 121: 3335-3344, 2013). This sequence is referred herein as the "UCL SQ FVIII."

In a first aspect, the AAV vector of the invention comprises Proto 1, which is depicted schematically in FIG. 2A, and comprises the nucleic acid sequence set forth in SEQ ID NO: 1.

In a second aspect, the AAV vector of the invention comprises Proto 1S, which is depicted schematically in FIG. 2B, and comprises the nucleic acid sequence set forth in SEQ ID NO: 2.

In a third aspect, the AAV vector of the invention comprises Proto 2S, which is depicted schematically in FIG. 2C, and comprises the nucleic acid sequence set forth in SEQ ID NO: 3.

In a fourth aspect, the AAV vector of the invention comprises Proto 3S, which is depicted schematically in FIG. 2D, and comprises the nucleic acid sequence set forth in SEQ ID NO: 4.

In another embodiment, the AAV vector of the invention comprises a nucleic acid encoding FVIII lacking the entire B domain, including the SQ sequence, and the a3 domain, which is located just N-terminal to the light chain or C domain. The FVIII coding region sequence is a codon-optimized sequence (see Nathwani et al., US Pat. App. Pub. No. 2013/0024960A1, published Jan. 24, 2013, which is incorporated herein by reference in its entirety, and McIntosh et al., Blood 121:3335-3344, 2013).

In a first aspect, the AAV vector of the invention comprises Proto 4, which is depicted schematically in FIG. 3A, and comprises the nucleic acid sequence set forth in SEQ ID NO: 5.

In a second aspect, the AAV vector of the invention comprises Proto 5, which is depicted schematically in FIG. 3B, and comprises the nucleic acid sequence set forth in SEQ ID NO: 6.

In a third aspect, the AAV vector of the invention comprises Proto 6, which is depicted schematically in FIG. 3C, and comprises the nucleic acid sequence set forth in SEQ ID NO: 7.

In a fourth aspect, the AAV vector of the invention comprises Proto 7, which is depicted schematically in FIG. 3D, and comprises the nucleic acid sequence set forth in SEQ ID NO: 8.

In another embodiment, the AAV vector of the invention comprises a nucleic acid comprising an AAV2 5' inverted terminal repeat (ITR), a liver-specific transcription regulatory region, a codon-optimized functionally active FVIII coding region, optionally one or more introns, a polyadenylation sequence, and an AAV2 3' ITR. In a preferred embodiment, the liver-specific transcription regulatory region comprises a shortened ApoE enhancer sequence, a 186 base human alpha anti-trypsin (hAAT) proximal promoter, including 42 bases of the 5' untranslated region (UTR), and one or more enhancers selected from the group consisting of (i) a 34 base human ApoE/C1 enhancer, (ii) a 32 base human AAT promoter distal X region and (iii) 80 additional bases of distal element of the human AAT proximal promoter; and a codon-optimized functionally active FVIII coding regions encodes the FVIII SQ variant. In another preferred embodiment, the liver specific transcription regulatory region comprises a al microglobulin enhancer sequence and the 186 base human alpha anti-trypsin (AAT) proximal promoter.

In a first aspect, the AAV vector of the invention comprises Construct 100ATG comprising the nucleic acid sequence forth in SEQ ID NO: 9.

In a second aspect, the AAV vector of the invention comprises Construct 100ATG bGH poly A comprising the nucleic acid sequence set forth in SEQ ID NO: 10.

In a third aspect, the AAV vector of the invention comprises Construct 100ATG short bGH polyA sequence set forth in SEQ ID NO: 11.

In a fourth aspect, the AAV vector of the invention comprises Construct 103ATG comprising the nucleic acid sequence forth in SEQ ID NO: 12.

In a fifth aspect, the AAV vector of the invention comprises Construct 103ATG short bGH poly A comprising the nucleic acid sequence set forth in SEQ ID NO: 13.

In a sixth aspect, the AAV vector of the invention comprises Construct 105ATG bGH poly A comprising the nucleic acid sequence set forth in SEQ ID NO: 14.

In a seventh aspect, the AAV vector of the invention comprises Construct DC172ATG FVIII comprising the nucleic acid sequence set forth in SEQ ID NO: 15.

In an eighth aspect, the AAV vector of the invention comprises Construct DC172ATG FVIII hAAT comprising the nucleic acid sequence set forth in SEQ ID NO: 16.

In a ninth aspect, the AAV vector of the invention comprises Construct DC172 2×HCR ATG FVIII comprising the nucleic acid sequence set forth in SEQ ID NO: 17.

In a tenth aspect, the AAV vector of the invention comprises Construct DC172 2×HCR ATG FVIII hAAT comprising the nucleic acid sequence set forth in SEQ ID NO: 18.

In an eleventh aspect, the AAV vector of the invention comprises Construct 2× SerpinA hAAT ATG FVIII comprising the nucleic acid sequence set forth in SEQ ID NO: 19.

In a twelfth aspect, the AAV vector of the invention comprises Construct 2× SerpinA hAAT ATG FVIII 2× μ-globulin enhancer comprising the nucleic acid sequence set forth in SEQ ID NO: 20.

In a thirteenth aspect, the AAV vector of the invention Construct 100ATG short polyA 2× μ-globulin enhancer comprising the nucleic acid sequence set forth in SEQ ID NO: 21.

In a fourteenth aspect, the AAV vector of the invention comprises Construct Factor VIII-BMN001 comprising the nucleic acid sequence set forth in SEQ ID NO: 22.

In a fifteenth aspect, the AAV vector of the invention comprises Construct Factor VIII-BMN002 sequence set forth in SEQ ID NO: 23.

In a sixteenth aspect, the AAV vector of the invention comprises Construct 99 comprising the nucleic acid sequence set forth in SEQ ID NO: 24.

In a seventeenth aspect, the AAV vector of the invention comprises Construct 100 comprising the nucleic acid sequence set forth in SEQ ID NO: 25.

In an eighteenth aspect, the AAV vector of the invention comprises Construct 100 reverse orientation comprising the nucleic acid sequence set forth in SEQ ID NO: 26.

In a nineteenth aspect, the AAV vector of the invention Construct 100AT comprising the nucleic acid sequence set forth in SEQ ID NO: 27.

In a twentieth aspect, the AAV vector of the invention Construct 100AT 2×MG comprising the nucleic acid sequence set forth in SEQ ID NO: 28.

In a twenty-first aspect, the AAV vector of the invention comprises Construct 100AT 2×MG bGH polyA comprising the nucleic acid sequence set forth in SEQ ID NO: 29.

In a twenty-second aspect, the AAV vector of the invention comprises Construct 100AT 2×MG (reverse) bGH polyA comprising the nucleic acid sequence set forth in SEQ ID NO: 30.

In a twenty-third aspect, the AAV vector of the invention comprises Construct 100 bGH polyA comprising the nucleic acid sequence set forth in SEQ ID NO: 31.

In a twenty-fourth aspect, the AAV vector of the invention comprises Construct 100-400 comprising the nucleic acid sequence set forth in SEQ ID NO: 32.

In a twenty-fifth aspect, the AAV vector of the invention comprises Construct 101 comprising the nucleic acid sequence set forth in SEQ ID NO: 33.

In a twenty-sixth aspect, the AAV vector of the invention comprises Construct 102 sequence comprising the nucleic acid sequence set forth in SEQ ID NO: 34.

In a twenty-seventh aspect, the AAV vector of the invention comprises Construct 103 comprising the nucleic acid sequence set forth in SEQ ID NO: 35.

In a twenty-ninth aspect, the AAV vector of the invention comprises Construct 103 reverse orientation comprising the nucleic acid sequence set forth in SEQ ID NO: 36.

In a thirtieth aspect, the AAV vector of the invention comprises Construct 103AT comprising the nucleic acid sequence set forth in SEQ ID NO: 37.

In a thirty-first aspect, the AAV vector of the invention comprises Construct 103AT 2×MG comprising the nucleic acid sequence set forth in SEQ ID NO: 38.

In a thirty-second aspect, the AAV vector of the invention comprises Construct 103AT 2×MG bGH polyA comprising the nucleic acid sequence set forth in SEQ ID NO: 39.

In a thirty-third aspect, the AAV vector of the invention comprises the Construct 103 bGH polyA comprising the nucleic acid sequence set forth in SEQ ID NO: 40.

In a thirty-fourth aspect, the AAV vector of the invention comprises Construct 104 comprising the nucleic acid comprising the nucleic acid sequence set forth in SEQ ID NO: 41.

In a thirty-fifth aspect, the AAV vector of the invention comprises Construct 105 comprising the nucleic acid sequence set forth in SEQ ID NO: 42.

In a thirty-sixth aspect, the AAV vector of the invention comprises Construct 106 comprising the nucleic acid sequence set forth in SEQ ID NO: 43.

In a thirty-seventh aspect, the AAV vector of the invention comprises Construct 106AT comprising the nucleic acid sequence set forth in SEQ ID NO: 44.

In a thirty-eighth aspect, the AAV vector of the invention comprises Construct 2× SerpinA hAAT comprising the nucleic acid sequence set forth in SEQ ID NO: 45.

In yet other embodiments, the present invention is directed to vector constructs encoding a functional Factor VIII polypeptide, wherein said constructs comprise one or more of the individual elements of the above described constructs and combinations thereof, in one or more different orientation(s). The present invention is also directed to the above described constructs in an opposite orientation.

The AAV vectors of the invention in single strand is less than about 7.0 kb in length, or is less than 6.5 kb in length, or is less than 6.4 kb in length, or is less than 6.3 kb in length, or is less than 6.2 kb in length, or is less than 6.0 kb in length, or is less than 5.8 kb in length, or is less than 5.6 kb in length, or is less than 5.5 kb in length, or is less than 5.4 kb in length, or is less than 5.4 kb in length, or is less than 5.2 kb in length or is less than 5.0 kb in length. The AAV vectors of the invention in single strand ranges from about 5.0 kb to about 6.5 kb in length, or ranges from about 4.8 kb to about 5.2 k in length, or 4.8 kb to 5.3 kb in length, or ranges from about 4.9 kb to about 5.5 kb in length, or about 4.8 kb to about 6.0 kb in length, or about 5.0 kb to 6.2 kb in length or about 5.1 kb to about 6.3 kb in length, or about 5.2 kb to about 6.4 kb in length, or about 5.5 kb to about 6.5 kb in length.

In another embodiment, the invention provides for methods of producing a recombinant adeno-associated virus (AAV) particle comprising any of the AAV vectors of the invention. The methods comprise the steps of culturing a cell that has been transfected with any of the AAV vectors of the invention and recovering recombinant AAV from the supernatant of the transfected cell.

The cells of the invention are any cell type are susceptible to baculovirus infection, including insect cells such as High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38. Preferred mammalian cells used can be HEK293, HeLa, CHO, NS0, SP2/0, PER.C6, Vero, RD, BHK, HT 1080, A549, Cos-7, ARPE-19 and MRC-5 cells, and including mammalian cells such as HEK293, HeLa, CHO, NS0, SP2/0, PER.C6, Vero, RD, BHK, HT 1080, A549, Cos-7, ARPE-19 and MRC-5 cells.

The invention also provides for a viral particle comprising any of the AAV vectors of the invention or any viral particle produced by the forgoing methods of the invention.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

The invention also provides for cells comprising any of the AAV vectors of the invention, and viral particles produced by these cells of the invention.

In another embodiment, the invention provides for methods of treating a patient suffering from hemophilia A comprising administering to the patient an effective amount of any of the AAV vectors of the invention, or a viral particle of the invention or a viral particles produced by a method of the invention.

In a further embodiment, the invention provides for a use of any of the AAV vectors of the invention for preparation of a medicament for the treatment of hemophilia A. In one aspect, the medicament comprises an amount of AAV vector that expresses human FVIII in an amount effective to treat hemophilia A.

In another embodiment, the invention provides for a composition comprising any of the AAV vectors of the invention for the treatment of hemophilia A. In one aspect, the composition comprises an amount of AAV vector that expresses human FVIII in an amount effective to treat hemophilia A.

In another embodiment, the AAV vectors of the invention are used to produce AAV viral particles that are useful to treat a patient suffering from Hemophilia A.

DESCRIPTION OF DRAWINGS

FIG. 2A provides a schematic of the Proto 1 vector. Starting from the UCL SQ vector (see FIG. 1), the extraneous wild-type AAV2 viral sequences were deleted, and sequences corresponding to restriction sites between the human AAT 5' UTR and the human FVIII coding region, and between the human FVIII termination codon and the synthetic polyadenylation sequence, were removed. FIG. 2B provides a schematic of the Proto 1S vector. Starting from the Proto 1 vector, 10 bases at the 3' end of the AAV2 5'ITR and 10 bases at the 5' end of the 3' ITR were deleted. FIG. 2C provides a schematic of the Proto 2S vector. Starting from the Proto 1S vector, the human ApoE/C1 enhancer and human AAT promoter distal X region were moved into a 100 base synthetic intron that was inserted between exons 1 and 2 of the human FVIII sequence. As indicated by the arrows, the orientation of the human ApoE/C1 enhancer and human AAT promoter distal X region are reversed compared to their orientation in Proto 1S. FIG. 2D provides a schematic of the Proto 3S vector. Starting from Proto 2S, the human AAT promoter distal X region is replaced by a second copy of the human ApoE/C1 enhancer in the reverse orientation.

FIG. 3A provides a schematic of the Proto 4 vector. Starting from the Proto 1 vector, the SQ sequence and a3 domain were deleted. FIG. 3B provides a schematic of the Proto 5 vector. Starting from the Proto 4 vector, a 129 base FVIII intron was inserted between exons 1 and 2 of the human Factor VIII sequence. FIG. 3C provides a schematic of the Proto 6 vector. Starting from the Proto 5 vector, a second copy of the human ApoE/C1 enhancer was inserted in the forward orientation into the FVIII intron. FIG. 3R provides a schematic of the Proto 7 vector. Starting from the Proto 5 vector, a second copy of the human ApoE/C1 enhancer was inserted in the reverse orientation into the FVIII intron.

FIG. 4A provides a schematic of Construct 100ATG. FIG. 4B provides a schematic of Construct 100ATG bGH polyA. FIG. 4C provides a schematic of Construct 100ATG short bGH poly A. FIG. 4D provides a schematic of Construct 103ATG. FIG. 4E provides a schematic of Construct 103ATG short bGH poly A. FIG. 4F provides a schematic of Construct 105ATG bGH polyA. FIG. 4G provides a schematic of Construct DC172ATG FVIII. FIG. 4H provides a schematic of Construct DC172ATG FVIII hAAT. FIG. 4I provides a schematic of Construct DC172 2×HCR ATG FVIII. FIG. 4J provides a schematic of Construct DC 172 2×HCR ATG FVIII hAAT. FIG. 4K provides a schematic Construct 2× SerpinA hAAT ATG FVIII. FIG. 4AA provides a schematic of Construct 103. FIG. 4BB provides a schematic of Construct 103 reverse orientation. FIG. 4CC provides a schematic of Construct 103AT. FIG. 4DD provides a schematic of Construct 103AT 2×MG. FIG. 4EE provides a schematic of Construct 103AT 2×MG bGH poly A. FIG. 4FF provides a schematic of 103 sbGH poly A. FIG. 4GG provides a schematic of Construct 104. FIG. 4HH provides a schematic of Construct 105. FIG. 4II provides a schematic of Construct 106. FIG. 4JJ provides a schematic of Construct 106AT. FIG. 4KK provides a schematic of Construct 2× SerpinA hAAT.

DETAILED DESCRIPTION

Oversized AAV vectors are randomly truncated at the 5' ends and lack a 5' AAV ITR. Because AAV is a single-stranded DNA virus, and packages either the sense or antisense strand, the sense strand in oversized AAV vectors lacks the 5' AAV ITR and possibly portions of the 5' end of the target protein-coding gene, and the antisense strand in oversized AAV vectors lacks the 3' ITR and possibly portions of the 3' end of the target protein-coding gene. A functional transgene is produced in oversized AAV vector infected cells by annealing of the sense and antisense truncated genomes within the target cell.

The invention provides for AAV vectors encoding functionally active FVIII, i.e., completely packaged AAV FVIII vectors or AAV FVIII vectors with high expression activity. The AAV FVIII vectors of the invention have improved expression/particle, as well as improved AAV virus production yield and simplified purification. Introducing one or more introns into the FVIII protein-coding region enhances expression. Reconfiguring the number and positioning of enhancers also enhances expression.

UCL SQ Vector

Figure 1:
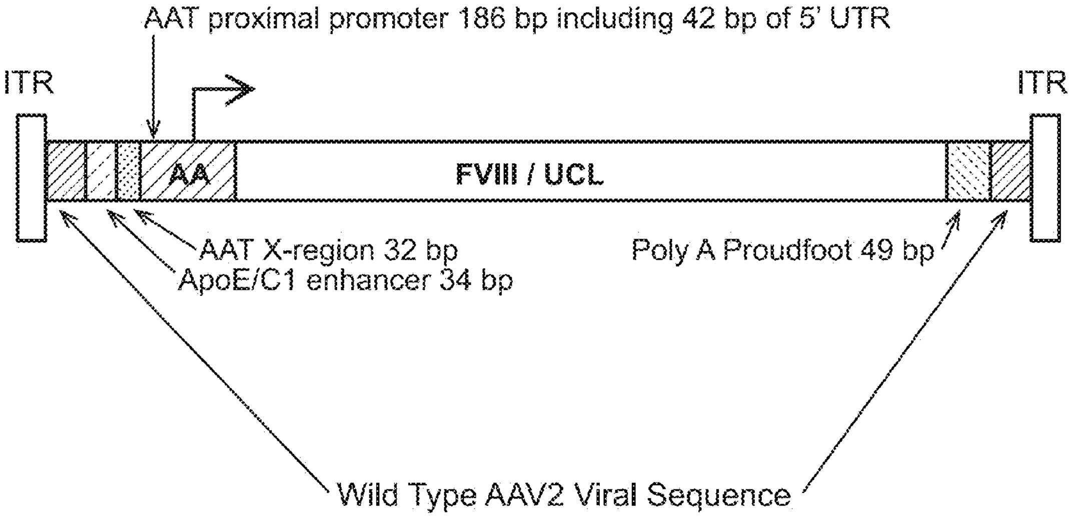
FIG. 1 provides a schematic of the UCL SQ vector. From left to right, the UCL SQ vector comprises the AAV2 5' ITR, wild-type AAV2 viral sequence, the 34 base human ApoE/C1 enhancer, the 32 base human AAT promoter distal X region, the 186 base human AAT promoter, including 42 bases of 5' UTR sequence, the codon-optimized human FVIII SQ sequence (see Nathwani et al., US Pat. App. Pub. No. 2013/0024960A1, published Jan. 24, 2013, which is incorporated herein by reference in its entirety, and McIntosh et al., Blood 121:3335-3344, 2013), the 49 bases synthetic polyadenylation sequence, wild-type AAV2 viral sequence, and the AAV2 3'ITR. The UCL SQ vector is 5081 bases in length.

The UCL SQ vector, which is described in detail in Nathwani et al., US Pat. App. Pub. No. 2013/0024960A1, published Jan. 24, 2013, which is incorporated herein by reference in its entirety, and McIntosh et al., Blood 121: 3335-3344, 2013, is an oversized, i.e., greater than 5.0 kb, AAV vector. As shown in FIG. 1, the UCL SQ vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3'ITR. The UCL SQ vector is 5081 bases in length.

As shown in Nathwani et al., US Pat. App. Pub. No. 2013/0024960A1, published Jan. 24, 2013, and McIntosh et al., Blood 121:3335-3344, 2013, the UCL SQ vector expresses functionally active FVIII in vitro and in vivo.

Proto 1, Proto 1S, Proto 2S and Proto 3S Vectors

To avoid the problem of over-sized AAV vectors and/or to increase the expression of the AAV vectors, the invention provides completely packaged, smaller, i.e., less than 5.0 kb, AAV vectors encoding the FVIII SQ variant. The 4970 bp nucleotide sequence of Proto 1 is set forth in SEQ ID NO: 1.

To generate the AAV vector Proto 1, sequences that appear to be unnecessary for production of functionally active FVIII were deleted as compared to the UCL SQ vector. As shown in Example 1, 110 bases of extraneous DNA were removed, including 53 bases of AAV2 viral sequence 3' to the AAV2 5'ITR, 46 bases of AAV2 viral sequence 5' to the AAV2 3'ITR, and 11 bases adjacent to the codon-optimized FVIII SQ coding region. The resultant Proto 1 vector is 4970 bases in length. When designed, it was unknown whether the Proto 1 vector would be capable of expressing functional FVIII polypeptide, either in vitro or in vivo.

To generate the AAV vector Proto 1S, 10 bases at the 3' end of the AAV2 5'ITR, and 10 bases at the 5' end of the AAV32 3'ITR, were removed from the Proto 1 vector. The resultant Proto 1S vector is 4950 bases in length. The nucleotide sequence of sequence of Proto 1S is set forth in SEQ ID NO: 2.

To generate the AAV vector Proto 2S, a synthetic 100 base intron was inserted between exons 1 and 2 of the codon-optimized FVIII SQ sequence in the Proto 1S vector. The 34 bases ApoE/C1 enhancer and 32 base human AAT promoter distal X region was removed from upstream of the human AAT promoter and inserted into the synthetic intron in the reverse orientation (as compared to the orientation when these elements are located upstream of the human AAT promoter). The resultant Proto 2S vector is 4983 bases in length. The nucleotide sequence of sequence of Proto 2S is set forth in SEQ ID NO: 3.

To generate the AAV vector Proto 3S, the human AAT promoter distal X region was removed from the Proto 2S vector, and replaced with a second copy of the 34 bases ApoE/C1 enhancer in the reverse orientation. The resultant Proto 3S vector is 4984 bases in length. The nucleotide sequence of sequence of Proto 3S is set forth in SEQ ID NO: 4.

Proto 4, Proto S, Proto 6 and Proto 7 Vectors

To reduce the size of AAV vectors and/or increase the expression of the AAV vectors, the invention also provides completely packaged, smaller, i.e., less than 5.0 kb, AAV vectors encoding B domain and a3 domain deleted FVIII.

To generate the AAV vector Proto 4, the 14 amino acid SQ sequence and the a3 domain located adjacent to the C domain was removed from the Proto 1 vector. The total amount of FVIII sequence deleted is 55 amino acids or 165 bases. The resultant Proto 4 vector is 4805 bases in length. The nucleotide sequence of sequence of Proto 4 is set forth in SEQ ID NO: 5.

To generate the AAV vector Proto 5, a 129 base truncated FVIII intron was inserted between exons 1 and 2 of the codon-optimized FVIII sequence in the Proto 4 vector. The resultant Proto 5 vector is 4934 bases in length. The nucleotide sequence of sequence of Proto 5 is set forth in SEQ ID NO: 6.

To generate the AAV Proto 6 vector, 34 bases of the FVIII intron were replaced with a second copy of the 34 base human ApoE/C1 enhancer in the forward orientation in the Proto 5 vector. The resultant Proto 6 vector is 4934 bases in length. The nucleotide sequence of sequence of Proto 6 is set forth in SEQ ID NO: 7.

To generate the AAV Proto 7 vector, 34 bases of the FVIII intron were replaced with a second copy of the 34 base human ApoE/C1 enhancer in the reverse orientation in the Proto 5 vector. The resultant Proto 7 vector is 4934 bases in length. The nucleotide sequence of sequence of Proto 7 is set forth in SEQ ID NO: 8.

Additional AAV FVIII Vectors with Improved Promoter/Enhancer Sequences

Oversized AAV vectors with strong promoters were generated to increase expression of B domain and a3 domain deleted FVIII, and these constructs were generated with modified enhancer and/or promoter sequences. In some embodiments, the AAV FVIII vectors express a truncated functional FVIII. These constructs comprised one or more promoter and enhancer sequences such as ApoE HCR or fragments thereof, the μ-globulin enhancer or fragments thereof, the human alpha 1 antitrypsin promoter (hAAT) or fragments thereof, Serpin A enhancer or fragments thereof, the LP1 promoter enhancer or fragments thereof or macroglobulin enhancer or fragment thereof. These constructs comprise a polyadenylation sequence such as the bGH poly A sequence or the synthetic rabbit β-globin poly A sequence. In some embodiment, the constructs comprise an intron or fragments of an intron such as a hAAT intron or a human β-globin intron.

Construct 100ATG is 5511 bases in length. This construct is set forth in SEQ ID NO: 9 in which bases 1-145 are the 5'AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5352 are a synthetic rabbit β-globin poly A and bases 5367-5511 are the 3' AAV2 ITR.

Construct 100ATG bGH poly A is 5688 bases in length. This construct is set forth in SEQ ID NO: 10 in which bases 1-145 are the 5' AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5529 are a bGH poly A and bases 5544-5688 are the 3' AAV2 ITR.

Construct 100ATG short bGH poly A is 5613 bases in length. This construct is set forth in SEQ ID NO: 11 in which bases 1-145 are the 5' AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5454 are a short bGH poly A and bases 5469-5613 are the 3' AAV2 ITR.

Construct 103ATG is 5362 bases in length. This construct is set forth in SEQ ID NO: 12 in which bases 1-145 are the 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are a codon optimized SQ FVIII, bases 5156-5203 are a synthetic rabbit β-globin poly A and bases 5218-5362 are the 3' AAV2 ITR.

Construct 103ATG short bGH poly A is 5464 bases in length. This construct is set forth in SEQ ID NO: 13 in which bases 1-145 are the 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are a codon optimized SQ FVIII, bases 5156-5305 are a bGH short poly A and bases 5320-5464 are the 3' AAV2 ITR.

Construct 105ATG bGH polyA is 6354 bases in length. This construct is set forth in SEQ ID NO: 14 in which bases 1-145 are the 5' AAV2 ITR, bases 173-512 are two copies (2×) of a 170 bp microglobulin enhancer, bases 519-736 are a hAAT promoter, bases 737-920 are a modified human β-globin $2^{nd}$ intron, bases 933-5306 are a codon optimized SQ FVIII, bases 5315-5539 are a bGH poly A, bases 5546-6195 are two copies (2×) of a 325 bp ApoE HCR and bases 6210-6354 are the 3' AAV2 ITR.

Construct DC172ATG FVIII is 6308 bases in length. This construct is set forth in SEQ ID NO: 15 in which bases 1-145 are the 5' AAV2 ITR, bases 160-449 are two copies (2×) of a 145 bp macroglobulin enhancer, bases 450-1347 are an 898 bp hAAT promoter, bases 1348-1531 are a modified human β-globin $2^{nd}$ intron, bases 1544-5917 are a codon optimized SQ FVIII, bases 5926-6149 are a bGH poly A and bases 6164-6308 are the 3' AAV2 ITR.

Construct DC172ATG FVIII hAAT is 5635 bases in length, This construct is set forth as SEQ ID NO: 16 in which bases 1-145 are the 5' AAV2 ITR, bases 160-449 are two copies (2×) of a 145 bp macroglobulin enhancer, bases 457-674 are a hAAT promoter, bases 675-858 are a modified human β-globin $2^{nd}$ intron, bases 871-5244 are a codon optimized SQ FVIII, bases 5253-5476 are a bGH poly A and bases 5490-5635 are the 3' AAV2 ITR.

Construct DC172 2×HCR ATG FVIII is 6962 bases in length. This construct is set forth in SEQ ID NO: 17 in which bases 1-145 are the 5' AAV2 ITR, bases 160-807 are two copies (2×) of a 321 bp ApoE HCR, bases 814-1103 are two copies (2×) of a 145 bp macroglobulin enhancer, bases 1104-2001 are a 898 bp hAAT promoter, bases 2002-2185 are a modified human β-globin $2^{nd}$ intron, bases 2198-6571 are a codon optimized SQ FVIII, bases 6580-6803 are a bGH poly A and bases 6818-6962 are the 3' AAV2 ITR.

Construct DC172 2×HCR ATG FVIII hAAT is 6289 bases in length. This construct is set forth in SEQ ID NO: 18 in which bases 1-145 are the 5' AAV2 ITR, bases 160-807 are two copies (2×) of a 321 bp ApoE HCR, bases 814-1103 are two copies (2×) of a 145 bp macroglobulin enhancer, bases 1111-1328 are a hAAT promoter, bases 1329-1512 are a modified human β-globin $2^{nd}$ intron, bases 1525-5898 are a codon optimized SQ FVIII, bases 5907-6130 are a bGH poly A and bases 6245-6289 are the 3' AAV2 ITR.

Construct 2× SerpinA hAAT ATG FVIII is 5430 bases in length. This construct is set forth in SEQ ID NO: 19 in which bases 1-145 are the 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are a codon optimized SQ FVIII, bases 5122-5271 are a short bGH poly A, and bases 5286-5430 are the 3' AAV2 ITR.

Construct 2× SerpinA hAAT ATG FVIII 2× μ-globulin enhancer is 5779 bases in length. This construct is set forth in SEQ ID NO: 20 in which bases 1-145 are the 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are a codon optimized SQ FVIII, bases 5122-5271 are a short bGH poly A, bases 5279-5618 are two copies (2×) of a 170 bp μ-globulin enhancer and bases 5635-5779 are the 3' AAV2 ITR.

Construct 100ATG short bGH poly A 2× μ-globulin enhancer is 5962 bases in length. This construct is set forth in SEQ ID NO: 21 in which bases 1-145 are the 5' AAV2 ITR, bases 160-502 are an ApoE HCR, bases 509-726 are a hAAT promoter, bases 727-910 are a modified human β-globin $2^{nd}$ intron, bases 923-5296 are a codon optimized SQ FVIII, bases 5305-5454 are a short bGH poly A, bases 5462-5801 are two copies (2×) of a 170 bp microglobulin enhancer and bases 5818-5962 are the 3' AAV2 ITR.

Construct Factor VIII-BMN001 is 5919 bases in length. This construct is set forth in SEQ ID NO: 22 in which bases 1-145 are the 5' AAV2 ITR, bases 160-480 are an ApoE HCR, bases 487-884 are a 398 bp hAAT promoter, bases 885-1145 are a truncated hAAT intron, bases 1155-5528 are a codon optimized SQ FVIII, bases 5537-5760 are a bGH poly A and bases 5775-5919 are the 3' AAV2 ITR.

Construct FVIII-BMN002 is 5306 bases in length. This construct is set forth in SEQ ID NO: 23 in which bases 1-145 are the 5' AAV2 ITR, bases 175-705 are an LP1 promoter/enhancer, bases 718-5091 are a codon optimized SQ FVIII, bases 5100-5147 are a synthetic rabbit β-globin poly A and bases 5162-5306 are the 3' AAV2 ITR.

Construct 99 is 5461 bases in length. This construct is set forth in SEQ ID NO: 24 in which bases 1-145 are the 5' AAV2 ITR, bases 169-627 are an ApoE HCR/MAR, bases 634-866 are a hAAT promoter, bases 873-5246 are a codon optimized SQ FVIII, bases 5255-5302 are a synthetic rabbit β-globin poly A and bases 5317-5461 are the 3' AAV2 ITR.

Construct 100 is 5327 bases in length. This construct is set forth in SEQ ID NO: 25 in which bases 1-145 are the 5' AAV2 ITR, bases 169-493 are an ApoE HCR, bases 509-726 are a hAAT promoter, bases 739-5112 are a codon optimized SQ FVIII, bases 5121-5168 are a synthetic rabbit β-globin poly A and bases 5183-5327 are the 3' AAV2 ITR.

Construct 100 reverse orientation is 5309 bases in length. This construct is set forth in SEQ ID NO: 26 in which bases 1-145 are the 5' AAV2 ITR, bases 160-484 are an ApoE HCR in reverse orientation, bases 491-708 are a hAAT promoter, bases 721-5094 are a codon optimized SQ FVIII, bases 5103-5150 are a synthetic rabbit β-globin poly A and bases 5165-5309 are the 3' AAV2 ITR.

Construct 100AT is 5532 bases in length. This construct is set forth in SEQ ID NO: 27 in which bases 1-145 are the 5' AAV2 ITR, bases 169-493 are an ApoE HCR, bases 509-726 are a hAAT promoter, bases 727-931 are a hAAT intron, bases 944-5317 are a codon optimized SQ FVIII, bases 5326-5373 are a synthetic rabbit β-globin poly A and bases 5388-5532 are the 3' AAV2 ITR.

Construct 100AT 2×MG is 5877 bases in length. This construct is set forth in SEQ ID NO: 28 in which bases 1-145 are the 5' AAV2 ITR, bases 169-493 are an ApoE HCR, bases 508-847 are two copies (2×) of a 170 bp μ-globulin enhancer, bases 854-1071 are a hAAT promoter, bases 1072-1276 are a hAAT intron, bases 1289-5662 are a codon optimized SQ FVIII, bases 5671-5718 are a synthetic rabbit β-globin poly A and bases 5733-5877 are the 3' AAV2 ITR.

Construct 100AT 2×MG bGH poly A is 6054 bases in length. This construct is set forth in SEQ ID NO: 29 in which bases 1-145 are the 5' AAV2 ITR, bases 169-493 are an ApoE HCR, bases 508-847 are two copies (2×) of a 170 bp μ-globulin enhancer, bases 854-1071 are a hAAT promoter, bases 1072-1276 are a hAAT intron, bases 1289-5662 are a codon optimized SQ FVIII, bases 5671-5895 are a bGH poly A and bases 5910-6054 are the 3' AAV2 ITR.

Construct 100AT 2×MG (reverse) bGH poly A is 6054 bases in length. This construct is set forth in SEQ ID NO: 30 in which bases 1-145 are the 5' AAV2 ITR, bases 169-493 are an ApoE HCR, bases 508-847 are two copies (2×) of a 170 bp μ-globulin enhancer in reverse orientation, bases 854-1071 are a hAAT promoter, bases 1072-1276 are a hAAT intron, bases 1289-5662 are a codon optimized SQ FVIII, bases 5671-5895 are a bGH poly A and bases 5910-6054 are the 3' AAV2 ITR.

Construct 100 bGH poly A is 5504 bases in length. This construct is set forth in SEQ ID NO: 31 in which bases 1-145 are the 5' AAV2 ITR, bases 169-493 are an ApoE HCR, bases 509-726 are a hAAT promoter, bases 739-5112 are a codon optimized SQ FVIII, base pairs 5121-5345 are a bGH poly A and bases 5360-5504 are the 3' AAV2 ITR.

Construct 100-400 is 5507 bases in length. This construct is set forth in SEQ ID NO: 32 in which bases 1-145 are the 5' AAV2 ITR, bases 169-493 are an ApoE HCR, bases 512-906 are a 398 bp hAAT promoter, bases 919-5292 are a codon optimized SQ FVIII, bases 5301-5348 are a synthetic rabbit β-globin poly A and bases 5363-5507 are the 3' AAV2 ITR.

Construct 101 is 5311 base in length. This construct is set forth in SEQ ID NO: 33 in which bases 1-145 are the 5' AAV2 ITR, bases 170-477 are two copies (2×) of a 154 bp ApoE HCR, bases 493-710 are a hAAT promoter, bases 723-5096 are a codon optimized SQ FVIII, bases 5105-5152 are a synthetic rabbit β-globin poly A and bases 5167-5311 are the 3' AAV2 ITR.

Construct 102 is 5156 bases in length. This construct is set forth in SEQ ID NO: 34 in which bases 1-145 are the 5' AAV2 ITR, bases 169-322 are a 154 bp ApoE HCR, bases 338-555 are a hAAT promoter, bases 568-4941 are a codon optimized SQ FVIII, bases 4950-4997 are a synthetic rabbit β-globin poly A and bases 5012-5156 are the 3' AAV2 ITR.

Construct 103 is 5178 bases in length. This construct is set forth in SEQ ID NO: 35 in which bases 1-145 are the 5' AAV2 ITR, bases 169-344 are four copies (4×) of a 44 bp ApoE HCR, bases 360-577 are a hAAT promoter, bases 590-4963 are a codon optimized SQ FVIII, bases 4972-5019 are a synthetic rabbit β-globin poly A and bases 5034-5178 are the 3' AAV2 ITR.

Construct 103 reverse orientation is 5160 bases in length. This construct is set forth in SEQ ID NO: 36 in which bases 1-145 are the 5' AAV2 ITR, bases 160-335 are four copies (4×) of a 44 bp ApoE HCR in reverse orientation, bases 342-559 are a hAAT promoter, bases 572-4945 are a codon optimized SQ FVIII, bases 4954-5001 are a synthetic rabbit β-globin poly A and bases 5016-5160 are the 3' AAV2 ITR.

Construct 103AT is 5383 bases in length. This construct is set forth in SEQ ID NO: 37 in which bases 1-145 are the 5' AAV2 ITR, bases 169-344 are four copies (4×) of a 44 bp ApoE HCR, bases 360-577 are a hAAT promoter, bases 578-782 are a hAAT intron, bases 795-4374 are a codon optimized SQ FVIII, bases 5177-5224 are a synthetic rabbit β-globin poly A and bases 5239-5383 are the 3' AAV2 ITR.

Construct 103AT 2×MG is 5728 bases in length. This construct is set forth in SEQ ID NO: 38 in which bases 1-145 are the 5' AAV2 ITR, bases 169-344 are four copies (4×) of a 44 bp ApoE HCR, bases 359-698 are two copies (2×) of a 170 bp μ-globulin enhancer, bases 705-922 are a hAAT promoter, bases 923-1127 are a hAAT intron, bases 1140-5513 are a codon optimized SQ FVIII, bases 5522-5569 are a synthetic rabbit β-globin poly A and bases 5584-5728 are the 3' AAV2 ITR.

Construct 103AT 2×MG bGH poly A is 5905 bases in length. This construct is set forth in SEQ ID NO: 39 in which bases 1-145 are the 5' AAV2 ITR, bases 169-344 are four copies (4×) of a 44 bp ApoE HCR, bases 359-698 are two copies (2×) of a 170 bp μ-globulin enhancer, bases 705-922 are a hAAT promoter, bases 923-1127 are a hAAT intron, bases 1140-5513 are a codon optimized SQ FVIII, bases 5522-5746 are a synthetic rabbit β-globin poly A and bases 5761-5905 are the 5' AAV2 ITR.

Construct 103 bGH poly A is 5355 bases in length. This construct is set forth in SEQ ID NO: 40 in which bases 1-145 are the 5' AAV2 ITR, bases 169-344 are four copies (4×) of a 44 bp ApoE HCR, bases 360-577 are a hAAT promoter, bases 590-4963 are a codon optimized SQ FVIII, bases 4972-5196 are a synthetic rabbit β-globin poly A and bases 5211-5355 are the 3' AAV2 ITR.

Construct 104 is 5618 bases in length. This construct is set forth in SEQ ID NO: 41 in which bases 1-145 are the 5' AAV2 ITR, bases 169-784 are four copies (4×) of a 154 bp ApoE HCR, bases 800-1017 are a hAAT promoter, bases 1030-5403 are a codon optimized SQ FVIII, bases 5412-5459 are a synthetic rabbit β-globin poly A and bases 5474-5618 are the 3' AAV2 ITR.

Construct 105 is 5993 bases in length. This construct is set forth in SEQ ID NO: 42 in which bases 1-145 are the 5' AAV2 ITR, bases 173-512 are two copies (2×) of a 170 bp μ-globulin enhancer, bases 519-736 are a hAAT promoter, bases 749-5122 are a codon optimized SQ FVIII, bases 5131-5178 are a synthetic rabbit β-globin poly A, bases 5185-5834 are two copies (2×) of an ApoE HCR and bases 5849-5993 are the 3' AAV2 ITR.

Construct 106 is 5337 bases in length. This construct is set forth in SEQ ID NO: 43 in which bases 1-145 are the 5' AAV2 ITR, bases 173-512 are two copies (2×) of a 170 bp μ-globulin enhancer, bases 519-736 are a hAAT promoter, bases 749-5122 are a codon optimized SQ FVIII, bases 5131-5178 are a synthetic rabbit β-globin poly A and bases 5193-5337 are the 3' AAV2 ITR.

Construct 106AT is 5542 bases in length. This construct is set forth in SEQ ID NO: 44 in which bases 1-145 are the 5' AAV2 ITR, bases 173-512 are two copies (2×) of a 170 bp μ-globulin enhancer, bases 519-736 are a hAAT promoter, bases 737-941 are a hAAT intron, bases 954-5327 are a codon optimized SQ FVIII, bases 5336-5383 are a synthetic rabbit β-globin poly A and bases 5398-5542 are the 3' AAV2 ITR.

Construct 2× SerpinA hAAT is 5126 base. This construct is set forth in SEQ ID NO: 45 in which bases 1-145 are the 5' AAV2 ITR, bases 160-301 are an ApoE HCR, bases 308-525 are a hAAT promoter, bases 538-4911 are a codon optimized SQ FVIII, bases 4920-4967 are a synthetic rabbit β-globin poly A and bases 4982-5126 are the 3' AAV2 ITR.

AAV Vectors

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized, as shown below in Table 1. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV 6. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap gene in accordance with the present invention encodes a Cap protein which is capable of packaging AAV vectors in the presence of rep and adeno helper function and is capable of binding target cellular receptors. In some embodiments, the AAV cap gene encodes a capsid protein having an amino acid sequence derived from a particular AAV serotype, for example the serotypes shown in Table 1.

TABLE 1

AAV serotypes

| AAV Serotype | Genbank Accession No. |
|---|---|
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

The AAV sequences employed for the production of AAV can be derived from the genome of any AAV serotype. Generally, the AAV serotypes have genomic sequences of significant homology at the amino acid and the nucleic acid levels, provide a similar set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chlorini et al., J. Vir. 71: 6823-33 (1997); Srivastava et al., J. Vir. 45:555-64 (1983); Chlorini et al., J. Vir. 73:1309-1319 (1999); Rutledge et al., J. Vir. 72:309-319 (1998); and Wu et al., J. Vir. 74: 8635-47 (2000).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter.

In some embodiments, a nucleic acid sequence encoding an AAV capsid protein is operably linked to expression control sequences for expression in a specific cell type, such as Sf9 or HEK cells. Techniques known to one skilled in the art for expressing foreign genes in insect host cells or mammalian host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W.H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of a nucleotide sequence encoding an AAV capsid protein is e.g. the polyhedron promoter. However, other promoters that are active in insect cells are known in the art, e.g. the p10, p35 or IE-1 promoters and further promoters described in the above references are also contemplated.

Use of insect cells for expression of heterologous proteins is well documented, as are methods of introducing nucleic acids, such as vectors, e.g., insect-cell compatible vectors, into such cells and methods of maintaining such cells in culture. See, for example, METHODS IN MOLECULAR BIOLOGY, ed. Richard, Humana Press, NJ (1995); O'Reilly et al., BACULOVIRUS EXPRESSION VECTORS, A LABORATORY MANUAL, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kirnbauer et al., Vir. 219:37-44 (1996); Zhao et al., Vir. 272:382-93 (2000); and Samulski et al., U.S. Pat. No. 6,204,059. In some embodiments, the nucleic acid construct encoding AAV in insect cells is an insect cell-compatible vector. An "insect cell-compatible vector" or "vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In some embodiments, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm) NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

Methods for Producing Recombinant AAVs

The present disclosure provides materials and methods for producing recombinant AAVs in insect or mammalian cells. In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vector disclosed in the present application can be used in the method as the viral construct to produce the recombinant AAV.

In some embodiments, the helper functions are provided by one or more helper plasmids or helper viruses comprising adenoviral or baculoviral helper genes. Non-limiting examples of the adenoviral or baculoviral helper genes include, but are not limited to, E1A, E1B, E2A, E4 and VA, which can provide helper functions to AAV packaging.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088 (the disclosure of which is incorporated herein by reference), helper vectors pHELP (Applied Viromics). A skilled artisan will appreciate that any helper virus or helper plasmid of AAV that can provide adequate helper function to AAV can be used herein.

In some embodiments, the AAV cap genes are present in a plasmid. The plasmid can further comprise an AAV rep gene. The cap genes and/or rep gene from any AAV serotype (including, but not limited to, AAV1, AAV2, AAV4, AAV5, AAV6, AAV7, AAV8, AAV9, AAV10, AAV11, AAV12, AAV13 and any variants thereof) can be used herein to produce the recombinant AAV. In some embodiments, the AAV cap genes encode a capsid from serotype 1, serotype 2, serotype 4, serotype 5, serotype 6, serotype 7, serotype 8, serotype 9, serotype 10, serotype 11, serotype 12, serotype 13 or a variant thereof.

In some embodiments, the insect or mammalian cell can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Recombinant AAV can also be produced using any conventional methods known in the art suitable for producing infectious recombinant AAV. In some instances, a recombinant AAV can be produced by using an insect or mammalian cell that stably expresses some of the necessary components for AAV particle production. For example, a plasmid (or multiple plasmids) comprising AAV rep and cap genes, and a selectable marker, such as a neomycin resistance gene, can be integrated into the genome of the cell. The insect or mammalian cell can then be co-infected with a helper virus (e.g., adenovirus or baculovirus providing the helper functions) and the viral vector comprising the 5' and 3' AAV ITR (and the nucleotide sequence encoding the heterologous protein, if desired). The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

Cell Types Used in AAV Production

The viral particles comprising the AAV vectors of the invention may be redocued using any invertebrate cell type which allows for production of AAV or biologic products and which can be maintained in culture. For example, the insect cell line used can be from *Spodoptera frugiperda*, such as SF9, SF21, SF900+, *drosophila* cell lines, mosquito cell lines, e.g., *Aedes albopictus* derived cell lines, domestic silkworm cell lines, e.g. Bombyxmori cell lines, *Trichoplusia ni* cell lines such as High Five cells or *Lepidoptera* cell lines such as *Ascalapha odorata* cell lines. Preferred insect cells are cells from the insect species which are susceptible to baculovirus infection, including High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (BmNPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

In another aspect of the invention, the methods of the invention are also carried out with any mammalian cell type which allows for replication of AAV or production of biologic products, and which can be maintained in culture. Preferred mammalian cells used can be HEK293, HeLa, CHO, NS0, SP2/0, PER.C6, Vero, RD, BHK, HT 1080, A549, Cos-7, ARPE-19 and MRC-5 cells.

Testing of AAV FVIII Vectors

Assays to test the completely packaged AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice. These assays are described in greater detail in the Examples.

The completely packaged AAV FVIII vectors of the invention display at least the same expression and/or activity as the UCL SQ vector, and preferably 1.5-fold, 2-fold, 3-fold, 4-fold, or 5-fold or more expression and/or activity as compared to the UCL SQ vector.

The completely packaged AAV FVIII vectors of the invention have high vector yield with little or no fragmentary genome contaminants, and preferably 1.5-fold, 2-fold, 3-fold, 4-fold, or 5-fold greater vector yield as compared to the UCL SQ vector.

Other aspects and advantages of the present invention will be understood upon consideration of the following illustrative examples.

EXAMPLES

Example 1

Generation of Proto 1, Proto 15, Proto 2S and Proto 3S Vectors

The UCL SQ vector, which is described in detail in Nathwani et al., US Pat. App. Pub. No. 2013/0024960A1, published Jan. 24, 2013, which is incorporated herein by reference in its entirety, and McIntosh et al., Blood 121: 3335-3344, 2013, is an oversized, i.e., greater than 5.0 kb, AAV vector. As shown in FIG. 1, the UCL SQ vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3'ITR. The UCL SQ vector is 5081 bases in length.

Figure 2A:
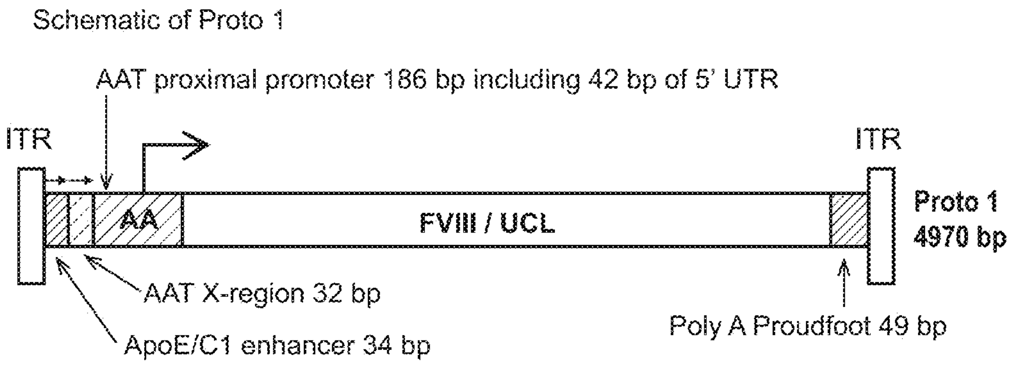
FIGS. 2A-2D provide schematics and sequences of the Proto 1, Proto 1S, Proto 2S and Proto 3S vectors.

To obtain a vector that is smaller than the UCL SQ vector, DNA sequences believed by the inventors herein to be unnecessary for FVIII expression and/or activity, or for AAV virion production, were removed from the UCL SQ vector sequence. Extraneous DNA sequence was removed, including 53 bases of AAV2 viral sequence 3' to the AAV2 5'ITR, 46 bases of AAV2 viral sequence 5' to the AAV2 3'ITR, and 11 bases adjacent to the codon-optimized FVIII SQ coding region. The resultant Proto 1 vector, which is 4970 bases in length, is shown in schematic form in FIG. 2A, and the sequence is set forth in SEQ ID NO: 1. Proto 1 produced infectious virus and encodes a functional Factor VIII polypeptide.

Figure 2B:
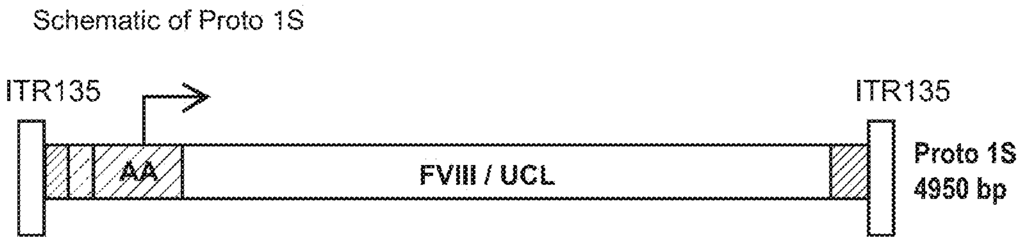

Sequences adjacent to the hairpin loop in the AAV2 ITR may also be dispensable in recombinant AAV vectors (see Srivastava et al., U.S. Pat. No. 6,521,225; Wang et al., J. Virol. 70:1668-1677, 1996; and Wang et al., J. Virol. 71:3077-3082, 1997). To further reduce the size of the Proto 1 vector, 10 bases of AAV2 sequence was removed directly 3' to the hairpin loop in the AAV2 5'ITR and 10 bases of AAV2 sequence was removed directly 5' to the hairpin loop in the AAV2 3'ITR. The resultant Proto 1S vector, which is 4950 bases in length, is shown in schematic form in FIG. 2B, and the sequence is set forth in SEQ ID NO: 2.

In an effort to increase the expression of the FVIII SQ variant in the Proto 15 vector, a 100 base synthetic intron was inserted between exons 1 and 2 in the codon-optimized FVIII sequence. It is known that insertion of an intron can result in increased level of mRNA expression in otherwise intron-less genes, such as, for example, the interferon genes.

Enhancers are defined as working in a distance- and orientation-independent manner. The 34 base ApoE/C1 enhancer works in a distance- and orientation-independent manner with respect to FVIII expression, as exemplified by its presumptive enhancer activity in Gray et al., U.S. Pat. No. 8,030,065 (FIX expression) and in Nathwani et al., US Pat. App. Pub. No. 2013/0024960 (FVIII expression), both of which are incorporated herein by reference in their entirety. The 32 base human AAT promoter distal X region, described in Di Simone et al., EMBO J. 6:2759-2766, 1987, is located within a regulatory domain that enhances expression of a heterologous promoter.

Figure 2C:
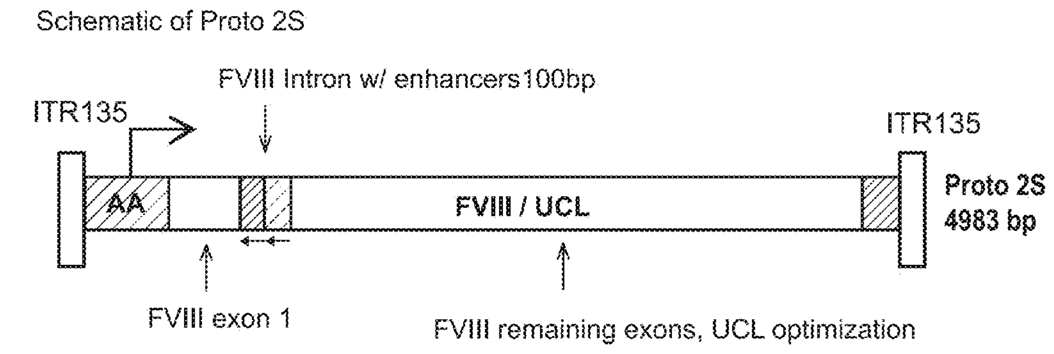

In another attempt to further increase the expression of the FVIII SQ variant in the Proto 15 vector, the synthetic intron sequence incorporated the 34 base human ApoE/C1 enhancer and 32 base human AAT promoter distal X region, which was moved from its location upstream of the human AAT promoter. These two regulatory elements were inserted in the reverse orientation with respect to their orientation in Proto 1S. The resultant Proto 2S vector, which is 4983 bases in length, is shown in schematic form in FIG. 2C, and the sequence set forth in SEQ ID NO: 3.

Figure 2D:
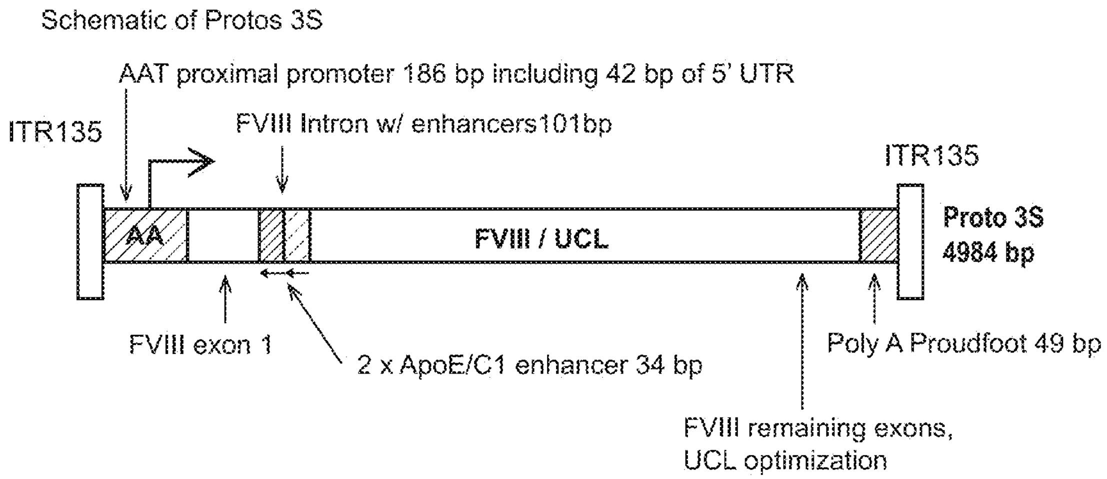

As the human AAT promoter distal X region had not previously been shown to function downstream from the transcriptional start site in an intron, this regulatory element in the Proto 2S vector was replaced with a second copy of the 34 base human ApoE/C1 enhancer in the same orientation as the first copy of the enhancer in the intron. The resultant Proto 3S vector, which is 4985 bases in length, is shown in schematic form in FIG. 2D, and the sequence is set forth in SEQ ID NO: 4.

The Proto 1, Proto 15, Proto 2S and Proto 3S vector nucleic acids were cloned into the pUC19 bacterial expression plasmid, thereby generating double-stranded forms of the AAV FVIII vectors.

Example 2

Generation of Proto 4, Proto 5, Proto 6 and Proto 7 Vectors

To further reduce the size of the Proto 1 vector and/or increase the expression of FVIII as compared to the Proto 1 vector, the a3 domain, which is located adjacent to the light chain or C domain, was deleted. The a3 domain is involved in binding to von Willenbrand Factor, but may be dispensable for functionally active FVIII in vivo.

Figure 3A:
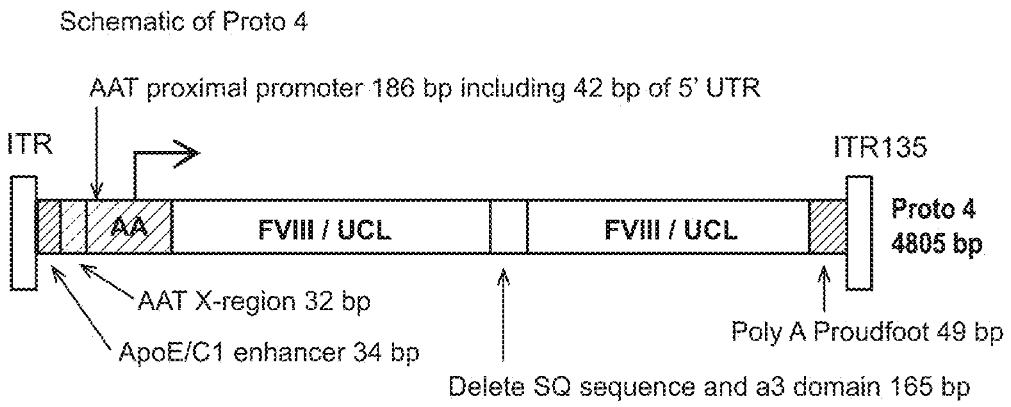
FIGS. 3A-3D provide schematics of the Proto 4, Proto 5, Proto 6 and Proto 7 vectors.

Starting from the Proto 1 vector, the 14 amino acid SQ sequence and 41 amino acids a3 domain (corresponding to amino acids 1649-1689 of wild-type FVIII) were deleted. The resultant Proto 4 vector, which is 4805 bases in length, is shown in schematic form in FIG. 3A, and the sequence is set forth in SEQ ID NO: 5.

Figure 3B:
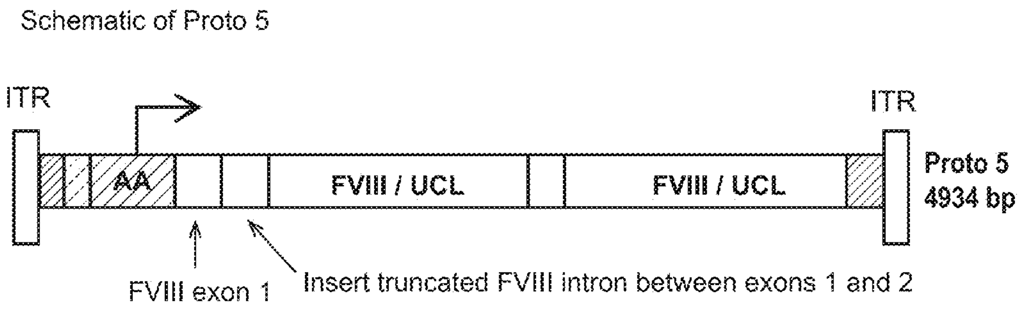

In an attempt to increase the expression of the B domain and a3 domain deleted FVIII, a 129 base, truncated FVIII intron was inserted between exons 1 and 2 in the codon-optimized FVIII sequence in the Proto 4 vector. The resultant Proto 5 vector, which is 4934 bases in length, is shown in schematic form in FIG. 3B, and the sequence is set forth in SEQ ID NO: 6.

Figure 3C:
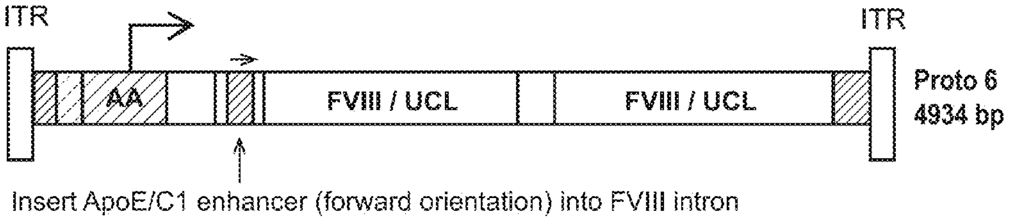

In an attempt to further increase the expression of the B domain and a3 domain deleted FVIII, a second copy of the 34 base human ApoE/C1 enhancer was inserted in either the forward or reverse orientation in the Proto 5 vector. The resultant Proto 6 vector, which is 4934 bases in length and has the intronic ApoE/C1 enhancer in the forward orientation, is shown in schematic form in FIG. 3C, and the sequence is set forth in SEQ ID NO: 7.

Figure 3D:
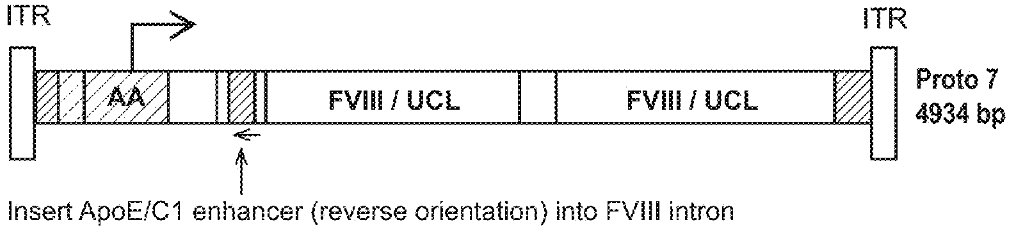
Figure 4A:
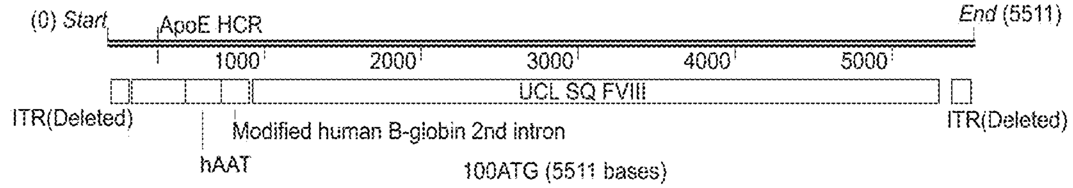
FIGS. 4A-4KK provide schematics of the AAV FVIII vectors with improved promoter/enhancer sequences.
Figure 4B:
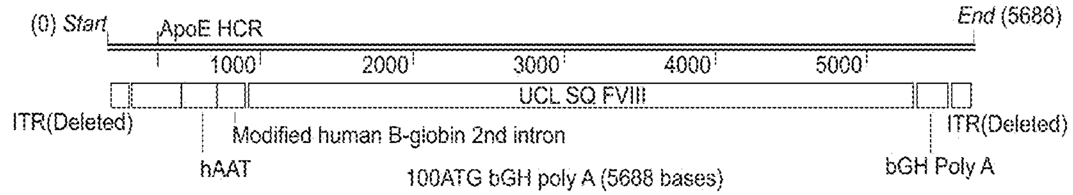
Figure 4C:
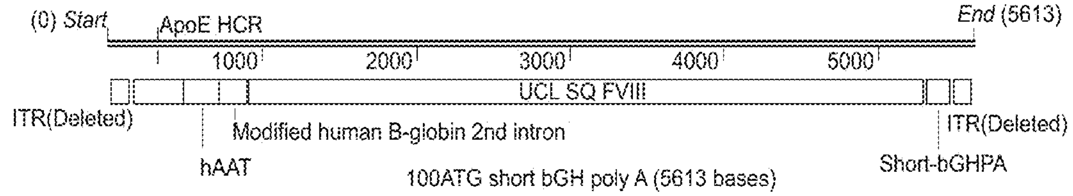
Figure 4D:
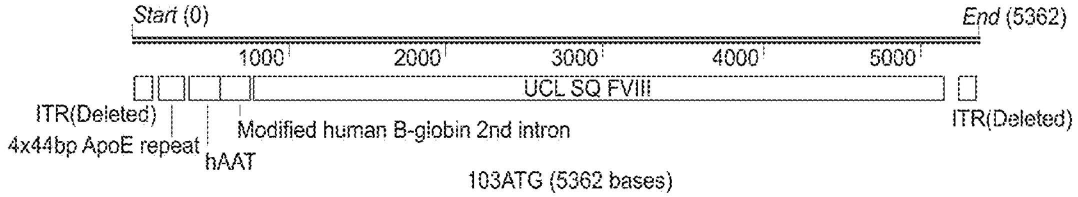
Figure 4E:
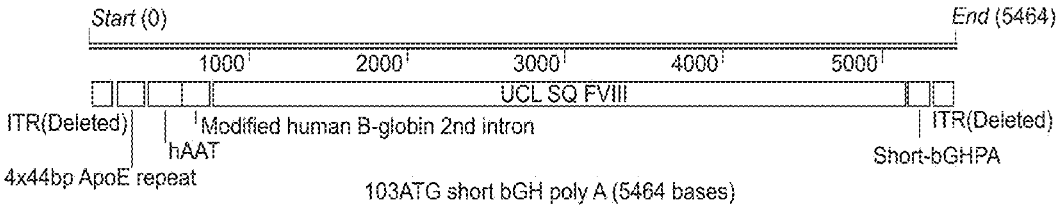
Figure 4F:
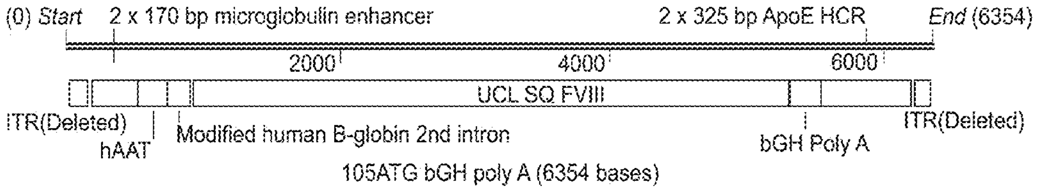
Figure 4G:
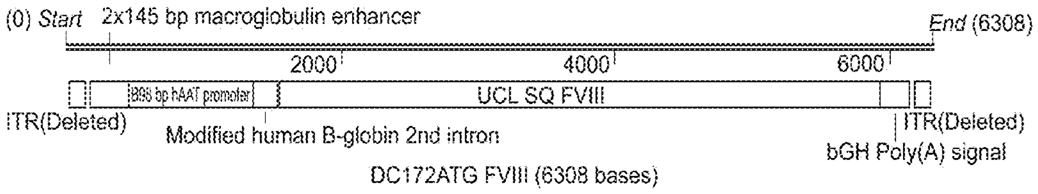
Figure 4H:
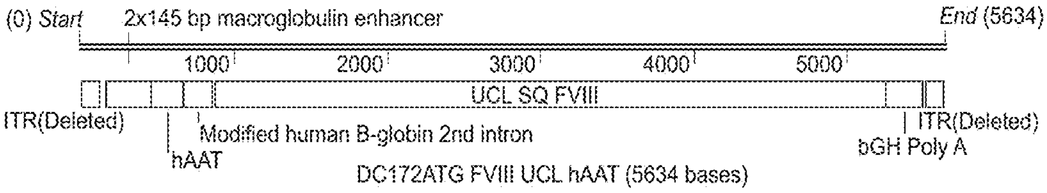
Figure 4I:
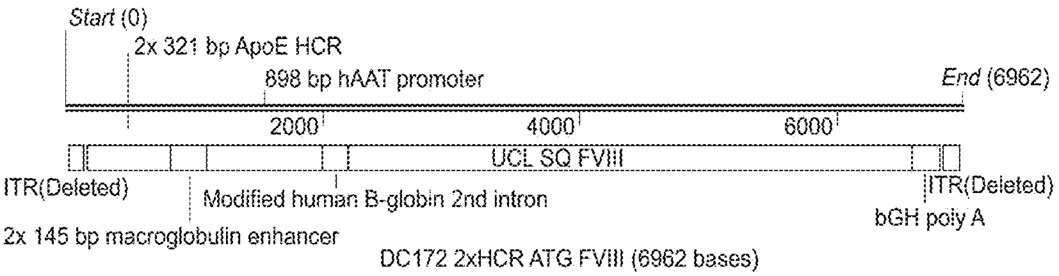
Figure 4J:
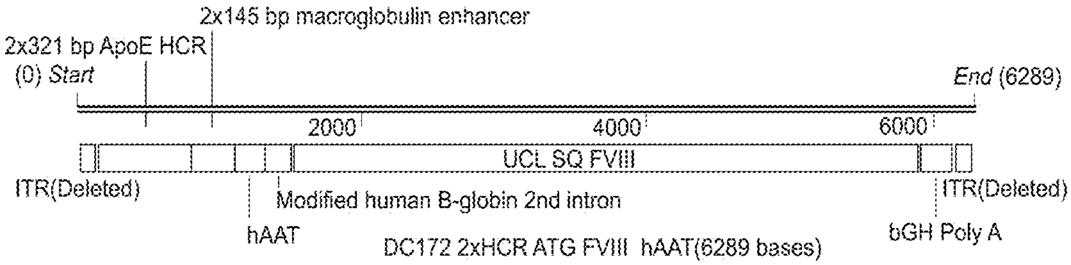
Figure 4K:
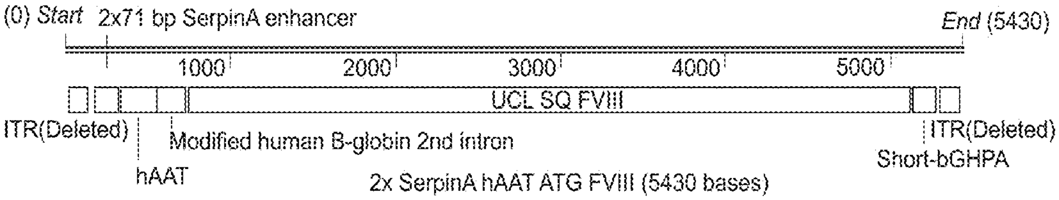
Figure 4L:
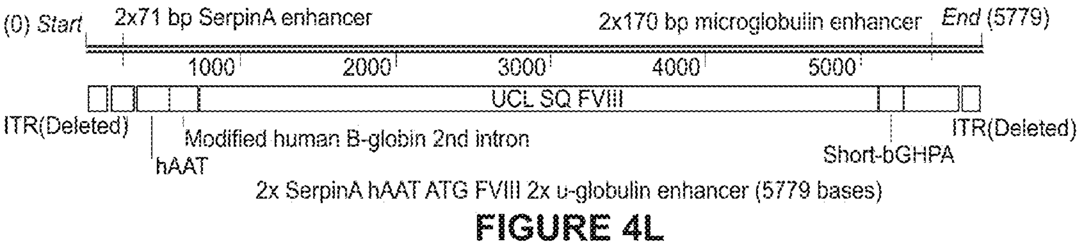
FIG. 4L provides a schematic of Construct 2× SerpinA hAAT ATG FVIII 2× μ-globulin enhancer.
Figure 4M:
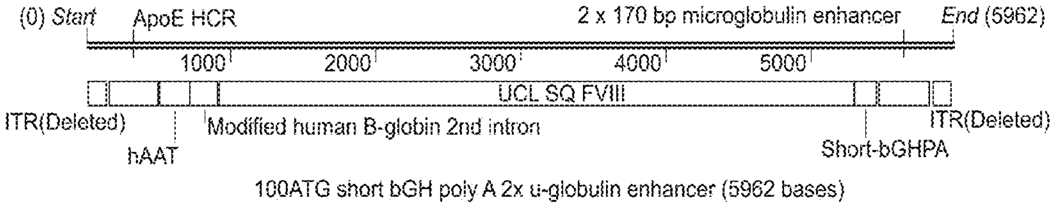
FIG. 4M provides a schematic Construct 100ATG short bGH poly A 2× μ-globulin enhancer.
Figure 4N:
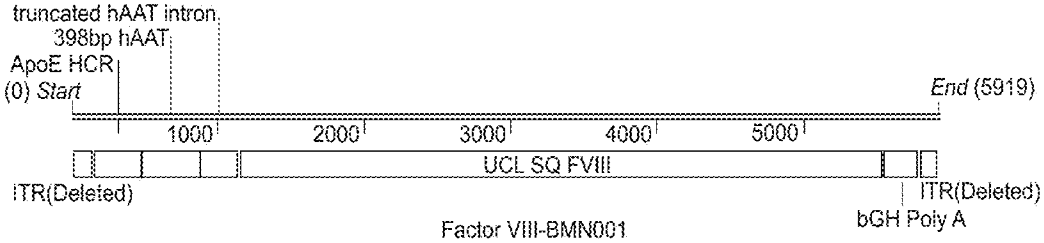
FIG. 4N provides a schematic of Construct Factor VIII-BMN001.
Figure 4O:
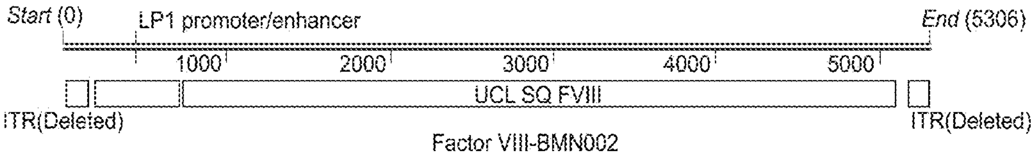
FIG. 4O provides a schematic of Construct FVIII-BMN002.
Figure 4P:
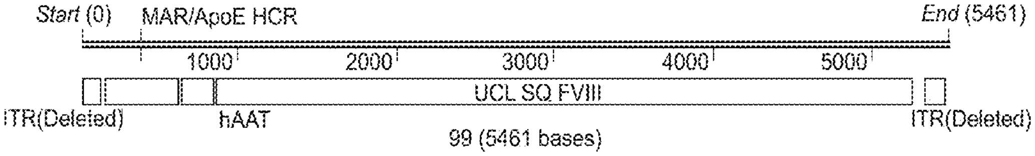
FIG. 4P provides a schematic of Construct 99.
Figure 4Q:
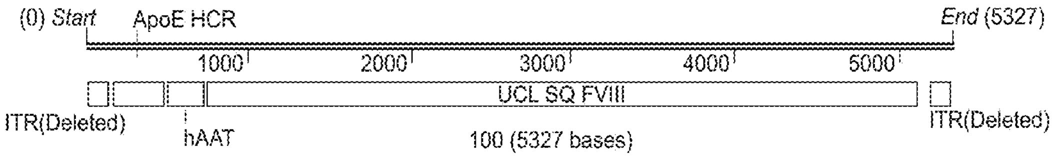
FIG. 4Q provides a schematic of Construct 100.
Figure 4R:
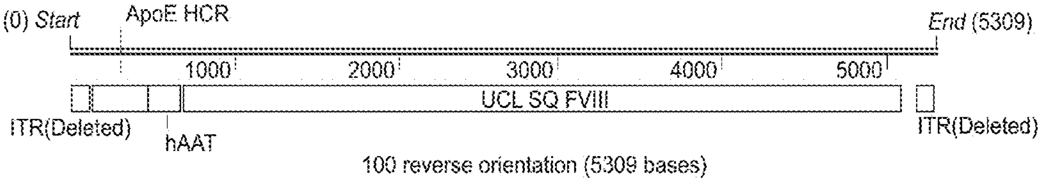
FIG. 4R provides a schematic of Construct 100 reverse orientation.
Figure 4S:
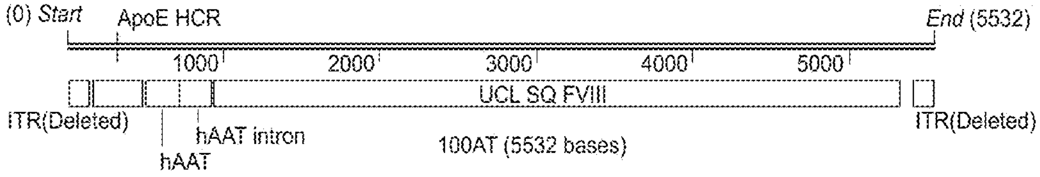
FIG. 4S provides a schematic of Construct 100AT.
Figure 4T:
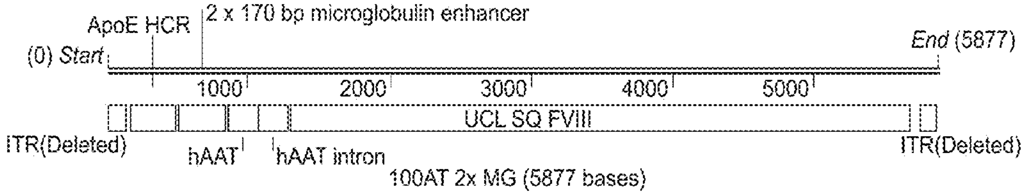
FIG. 4T provides a schematic of Construct 100AT 2×MG.
Figure 4U:
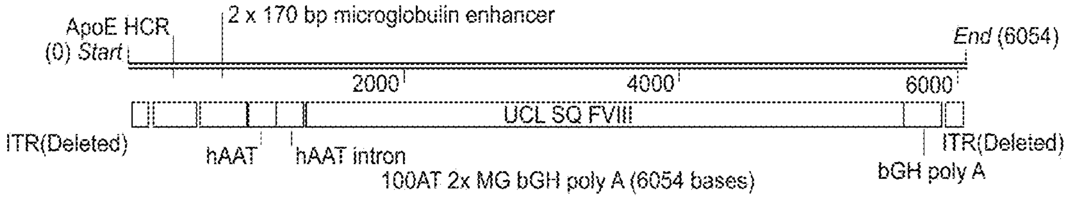
FIG. 4U provides a schematic of Construct 100AT 2×MG bGH polyA.
Figure 4V:
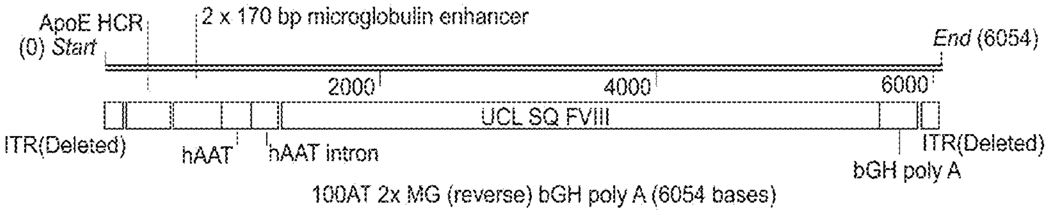
FIG. 4V provides a schematic of Construct 100AT 2×MG (reverse) bGH poly A.
Figure 4W:
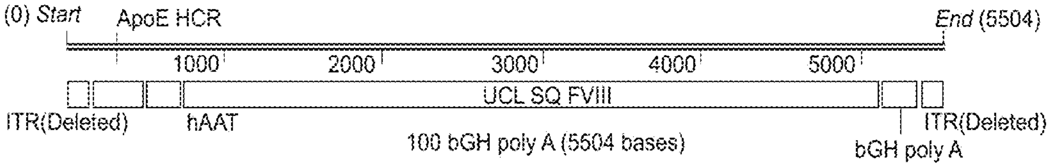
FIG. 4W provides a schematic of Construct 100 bGH poly A.
Figure 4X:
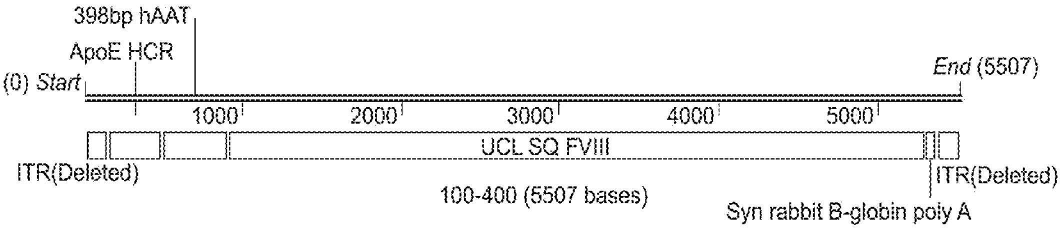
FIG. 4X provides a schematic of Construct 100-400.
Figure 4Y:
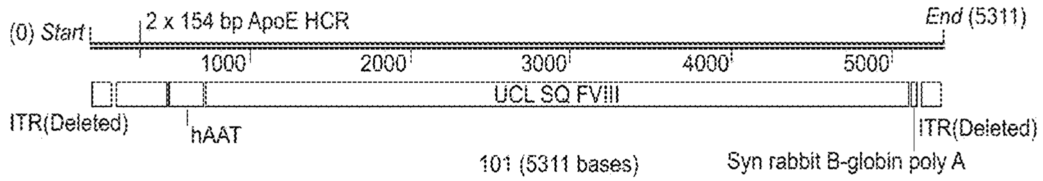
FIG. 4Y provides a schematic of Construct 101.
Figure 4Z:
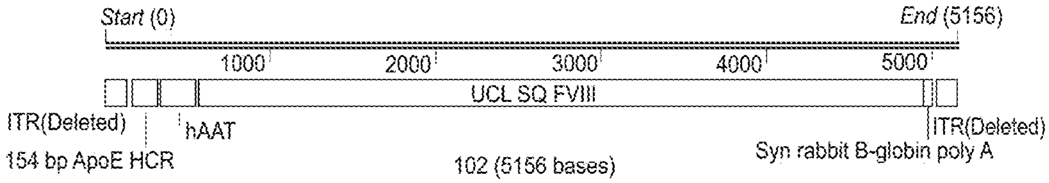
FIG. 4Z provides a schematic of Construct 102.
Figure 4A:
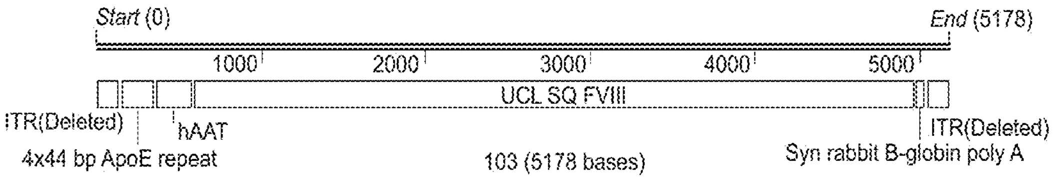
Figure 4B:
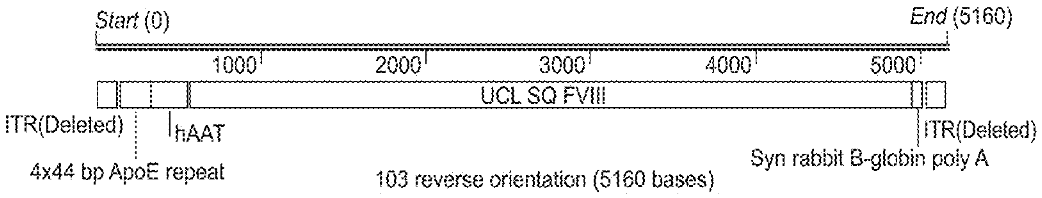
Figure 4C:
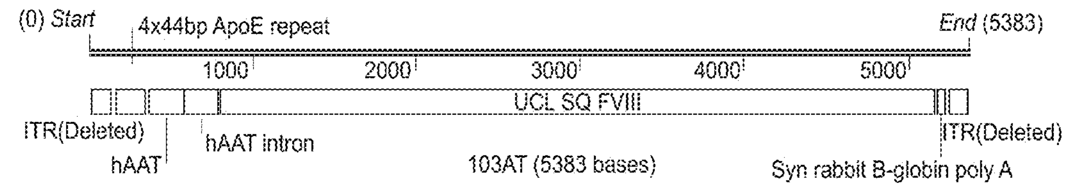
Figure 4D:
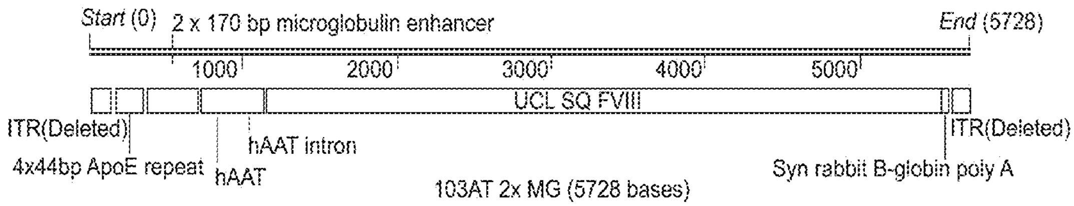
Figure 4E:
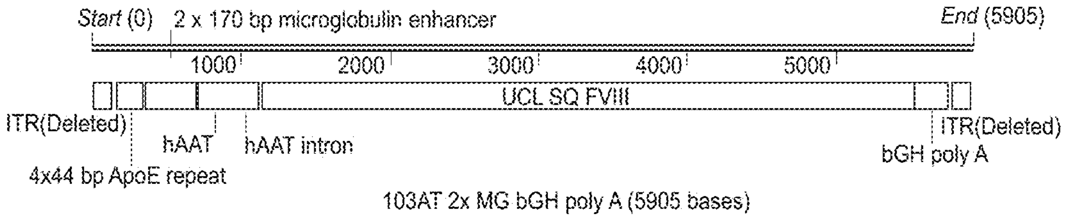
Figure 4F:
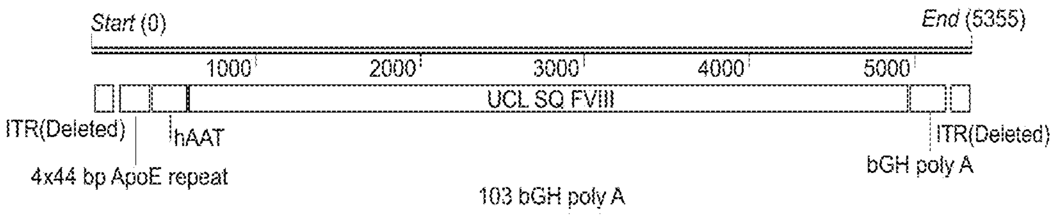
Figure 4G:
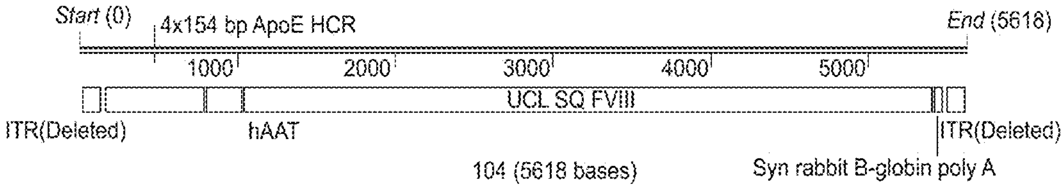
Figure 4H:
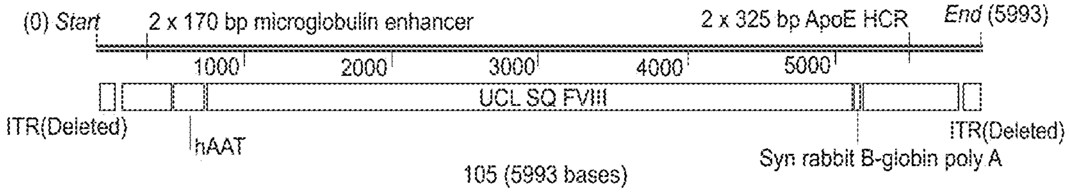
Figure 4I:
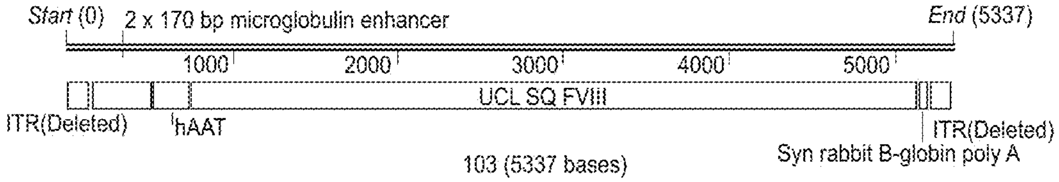
Figure 4J:
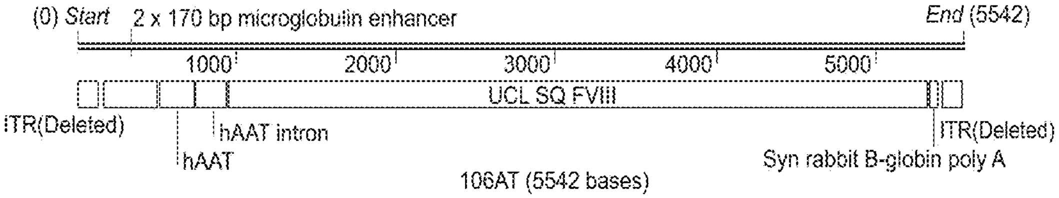
Figure 4K:
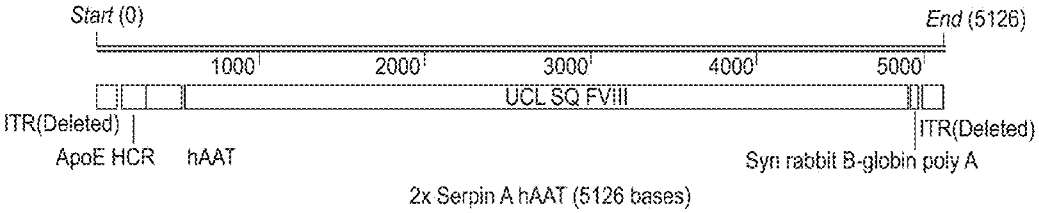

The resultant Proto 7 vector, which is 4934 bases in length and has the intronic ApoE/C1 enhancer in the reverse orientation, is shown in schematic form in FIG. 3D, and the sequence is set forth in SEQ ID NO: 8.

The Proto 4, Proto 5, Proto 6 and Proto 7 vector nucleic acids were cloned into the pUC19 bacterial expression plasmid, thereby generating double-stranded forms of the AAV FVIII vectors.

Example 3

Assays to Test the Expression and Activity of AAV FVIII Vectors

Assays to test the AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice.

Transient Transfection Assays.

A preliminary in vitro assay is performed to compare the FVIII expression and activity from the AAV FVIII vectors of the present invention with that from the UCL SQ vector. Double-stranded forms of the AAV FVIII vectors of the present invention are transiently transfected into the human liver cell line, HepG2. After transfection, for example, 24 or 48 hours later, FVIII antigen and activity in the culture supernatants is measured.

Using this assay, the FVIII activity in HepG2 cells transiently transfected with the Proto 1, Proto 1S and Proto 2S vectors was similar to the FVIII activity obtained using the UCL SQ vector, demonstrating that the Proto 1, Proto 1S and Proto 2S vectors were capable of expressing functional Factor VIII protein.

Production of AAV Virions in 293 cells and Baculovirus-Infected Insect Cells.

To demonstrate that the AAV FVIII vectors of the present invention indeed package the nucleic acids encoding FVIII, the double-stranded forms of the AAV FVIII vectors generated as described in Examples 1 and 2 are introduced into cells capable of producing AAV virions. In a first AAV virus production system, plasmids comprising the AAV FVIII vector nucleic acids in double-stranded form are co-transfected into 293 cells together with a plasmid that expresses the AAV Cap and Rep proteins and a plasmid that expresses Adenovirus helper functions needed to for AAV virion production. In a second AAV virus production system, baculovirus constructs are generated expressing the AAV FVIII vector nucleic acids and the AAV Cap and Rep proteins, and then are co-infected into insect Sf9 cells. The resultant AAV virions produced in the transiently transfected 293 cells or baculovirus-infected Sf9 cells are purified and analyzed by standard methods known in the art.

Evaluation by Alkaline Gel and Replication Assay

An alkaline gel electrophoresis assay is used to determine the size of the packaged nucleic acid. A replication center assay is used to determine which AAV FVIII vectors are packaged in an intact form by both packaging methods.

A primer extension assay is used to quantify the amount of AAV FVIII vectors nucleic acids that have complete ends, i.e., terminate at the 5' end of the hairpin loop in the AAV2 5'ITR (sense strand) or 3'ITR (anti-sense strand).

Alternatively, a PCR assay is used to determine whether the AAV FVIII vectors nucleic acids have complete ends, i.e., terminate at the 5' end of the hairpin loop in the AAV2 5'ITR (sense strand) or 3'ITR (anti-sense strand).

Evaluation in Rag2 Mice

The AAV virions produced in transiently transfected 293 cells or baculovirus-infected Sf9 cells packaged vectors are tested for FVIII expression and activity in Rag2 mice at 2e11, 2e12, and 2e13 viral genomes (vg)/kg, given intravenously. Rag2 mice are used in this assay because FVIII expression and/or activity is/are not complicated by the presence of a host immune response to the AAV virus or human FVIII protein.

FVIII antigen is determined using an ELISA-based assay. FVIII activity is determined using a FXa activation assay and/or a coagulation assay. Using the FVIII antigen and activity assays, the FVIII specific activity is determined.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

Example 4

Generation of Constructs with Improved Promoter/Enhancer Sequences

To generate additional AAV vectors with strong promoters that increase expression of functional FVIII, constructs were generated with modified enhancer and/or promoter sequences. In some embodiments, the constructs comprised shortened versions of the ApoE or the μ-globulin enhancers. These constructs were generated using standard DNA cloning techniques and the sequences thereof are shown in SEQ IS NOS: 9-45.

Example 5

Generation of AAV Viral Particles

Generation of Recombinant Bacmid

DH10 Bac competent cells were thawed on ice. Recombinant shuttle plasmid (e.g., pFB-GFP) was added and gently mixed with the competent cells and incubated on ice for 30 minutes. The competent cells were then subjected to heat at a temperature of approximately 42° C. for 30 seconds and then chilled on ice for 2 minutes. The competent cells were shocked with heat for 30 seconds at 42° C. and chilled on ice for 2 min. SOC was added to the cells and allowed to incubate at 37° C. with agitation for 4 hours to allow recombination to take place. During the incubation period, X-gal was spread onto two LB-plates (additionally containing various antibiotics (e.g., kanamycin, gentamycin and tetracycline) for transformation, is followed by IPTG.

An amount of the incubation mixture was obtained, diluted and then spread onto the two LB-plates and incubated at 37° C. for approximately 30-48 hours. Several white colonies were selected from each plate and cultured overnight in LB medium containing the same combination of antibiotics provided in the LB-plates. Next, Bacmid DNA and a glycerol stock was prepared and stored at −80° C.

Purification of Recombinant Bacmid DNA

An amount of the Bacmid glycerol stock is removed and inoculated in LB medium containing the same combination of antibiotic provided in the LB-plates described in Example 1. Cultures are allowed to grow overnight at 37° C. with shaking. Next, an amount of the culture is spun in a microfuge at full speed for approximately 30 seconds.

The pellets were resuspended in a resuspension buffer using a pipette followed by a lysis buffer, and the tube was inverted several times to mix the buffer and then incubated at room temperature for approximately 5 minutes. An exemplary resuspension buffer comprises 50 mM Tris-CL, pH 8.0, 10 mM EDTA and 100 ug/mL RNase A. An exemplary lysis buffer comprises 200 mM NaOH and 1% SDS. An amount of precipitate buffer (e.g., a buffer comprising 3.0 M potassium acetate, pH 5.5) was slowly added and the tube was inverted several times to mix the buffer and then incubated on ice for approximately 10 minutes. The tube was centrifuged for approximately 10 minutes at full speed and the supernatant is poured into a tube containing isopropanol. The tube was inverted several times to mix the solution.

Next, the solution was centrifuged at full speed for approximately 15 minutes at room temperature and the supernatant was removed immediately after centrifuge with pipette.

An amount of 70% ethanol was added to rinse the pellet and spun again at full speed for 1 minute. The ethanol was then removed and the solution is spun again to remove trace of the ethanol. An amount of TE/EB Buffer was added to each tube and the pellet is carefully dissolved by pipette. The solution was stored at −20° C. if not used immediately.

Production of P0 Stock of Recombinant Baculovirus

Sf9 cells were seeded at approximately $1\times10^6$ cells/well in a 6-well plate (or $6\times10^6$ cells in a 10-cm plate or $1.7\times10^7$ cells in a 15-cm dish) and the cells were allowed to attach for at least 1 hour before transfection.

Transfection solutions A and B are prepared as follows: Solution A: an amount of the Bacmid was diluted into an amount of serum free media without antibiotics in a 15-mL tube. Solution B: an amount of CellFectin was diluted into an amount of serum free media without antibiotics in a 15-mL tube. Solution B was added to Solution A and gently mixed by pipette approximately 3 times by pipette, and incubated at room temperature for 30~45 minutes. Next, medium from the plate was aspirated and an amount of serum free media without antibiotics was added to wash the cells. An amount of SF900II without antibiotics was added to each tube containing lipid-DNA mixtures.

The medium from the cells was aspirated, the transfection solution was added to the cells and the cells were incubated for approximately 5 hours at 28° C. The transfection solution was removed and an amount of and serum free media+antibiotics is added, and incubated for approximately 4 days at 28° C. Media that contains the recombinant baculovirus was collected and spun for approximately 5 minutes at 1000 rpm to remove cell debris. The baculovirus was stored at 4° C. under dark.

Amplification of Baculovirus (P1)

Sf9 cells were grown to approximately $4\times10^6$ cells/mL and diluted to approximately $2\times10^6$ cells/mL with fresh medium in shaking flasks. An amount of the Sf9 cells were infected with an amount of the P0 stock baculovirus. The multiplicity of infection (MOI) is approximately 0.1.

The Sf9 cells were incubated for approximately 3 days and the baculovirus was harvested. The cells were spun at 2,000 rpm for 5 minutes to pellet the cells and the supernatant was collected and stored at 4° C. under dark. The titer of the baculovirus was determined according to Clontech's Rapid Titer Kit protocol.

Production of AAV Using P1 Recombinant Baculoviruses

Sf9 cells were grown to about $1\times10^7$ cells/mL and diluted to about $5\times10^6$ cells/mL. An amount of the diluted Sf9 cells were infected with Bac-vector (5 Moi) and Bac-helper (15 Moi) for 3 days. Cell viability was assessed on the third day (approximately 50%~70% dead cells are observed).

Cell pellets were harvested by centrifugation at 3000 rpm for 10 minutes. Media was removed and the cells lysed (or the cell pellets were stored at −20° C. if not used immediately).

Lysis and Banding Protocol

An amount of Sf9 lysis buffer plus Benzonase is added to each cell pellet and vortexed thoroughly to resuspend the cells. The resuspended Sf9 cells were incubated on ice for approximately 10 min. to cool lysate. The lysate was sonicated for approximately 20 seconds to lyse the cells thoroughly and then incubated at 37° C. for approximately 30 minutes.

An amount of 5M NaCl was added and the mixture is vortexed and then incubated for another 30 minutes at 37° C. An amount of NaCl was added to bring the salt concentration to about 500 mM, vortexed and centrifuged at 8,000 rpm for 20 minutes at 15° C. to produce a cleared lysate.

The cleared lysate proceeds to ultracentrifugation steps. A CsCl-gradient was prepared by adding the cleared lysate first, then an amount of 1.32 g/cc and an amount of 1.55 g/cc CsCl solutions through a syringe with long needle. The interface between the CsCl solutions was marked. PBS was added up to the top of the centrifuge tubes and the tubes are carefully balanced and sealed.

The tubes were centrifuged at 55,000 rpm for approximately 20 hours at 15° C. A hole was puncture on the top of each tube and the AAV band located slightly above the interface mark of the two CsCl solutions is marked.

A second CsCl centrifugation is conducted by transferring the AAV solution to centrifuge tube for 70.1 Ti rotor and an amount of CsCl solution to near top of the tube was added. The tubes were balanced and sealed. The tubes are centrifuged at 65,000 rpm for approximately 20 hours and the AAV band (lower band, the higher band is empty capsids) was collected.

Example 5

Evaluation of the Constructs in Rag2 Mice

AAV genomes which comprise a codon optimized SQ FVIII-encoding gene sequence were generated using baculovirus and 293 cells using the UCL SQ, Proto 1, Proto S1, Proto S2 and Proto S3 constructs. The packaging limits are 4800 bp for baculovirus and 4950 for 293 cells.

Figure 5:
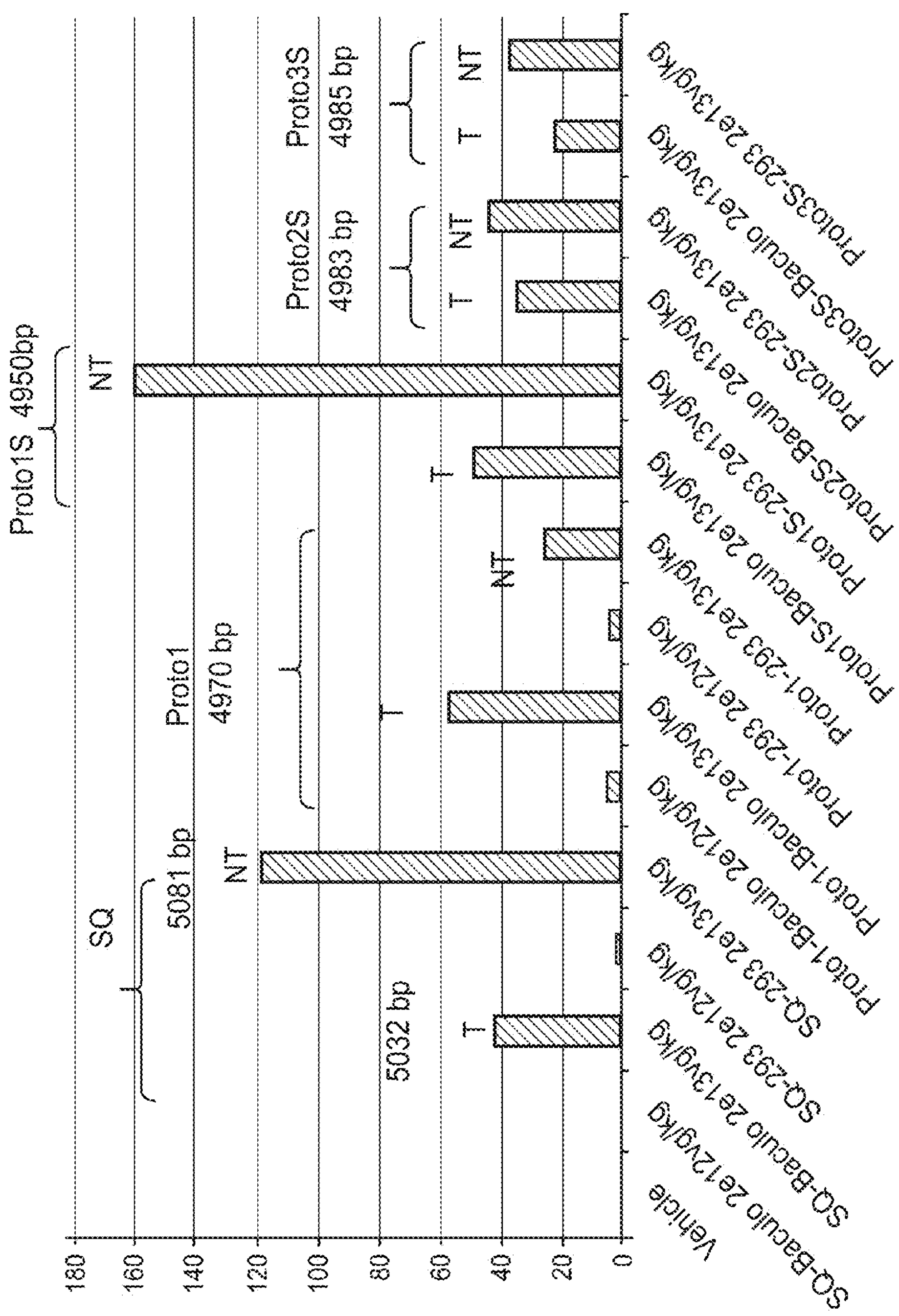
FIG. 5 provides the results of the evaluation of the Proto Constructs in Rag2 mice, and demonstrates Proto 1 transduces FVIII similarly to wild type.
Figure 6:
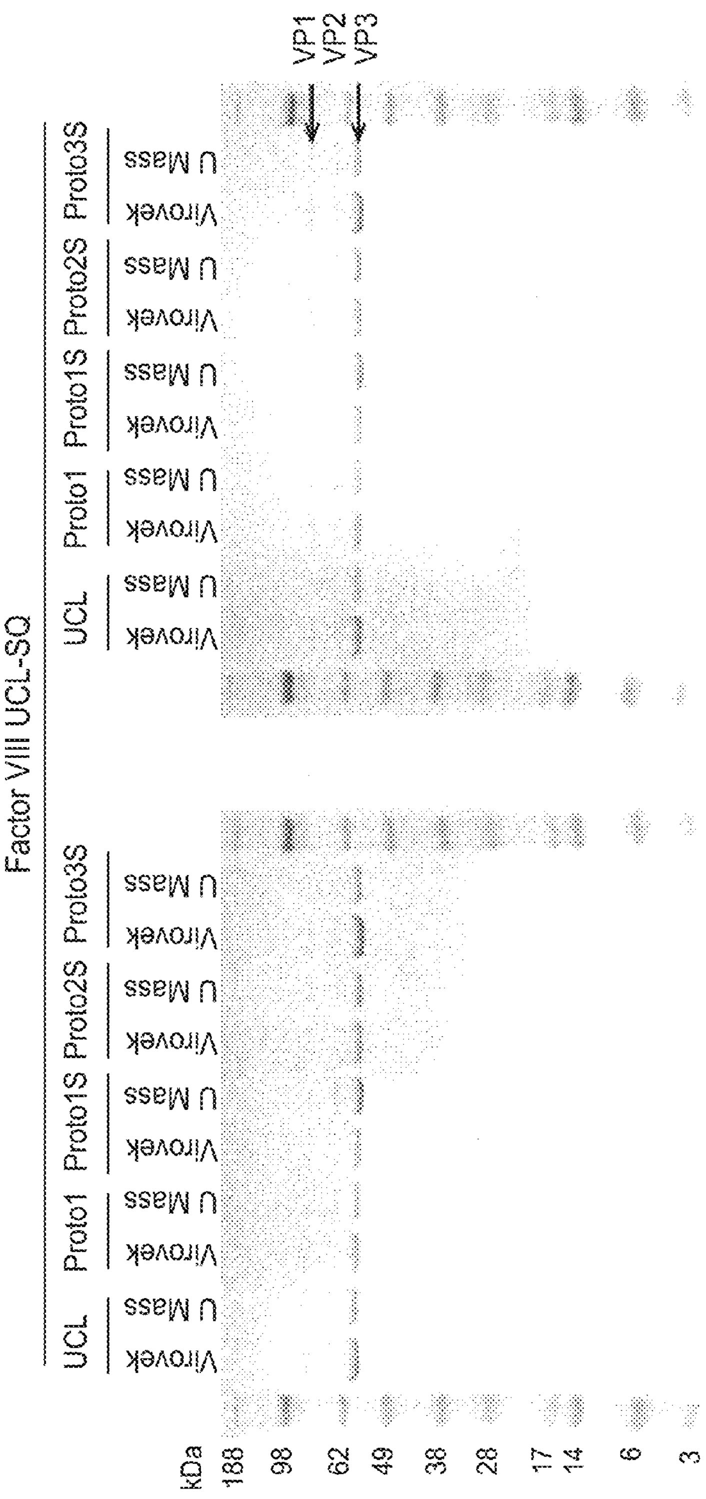
FIGS. 6 and 7 demonstrate that Proto 1, Proto 1S, Proto 2S and Proto 3S express the VP1, VP2 and VP3 protein (FIG. 5) and the VP1, VP2 and VP3 DNA (FIG. 6).
Figure 7:
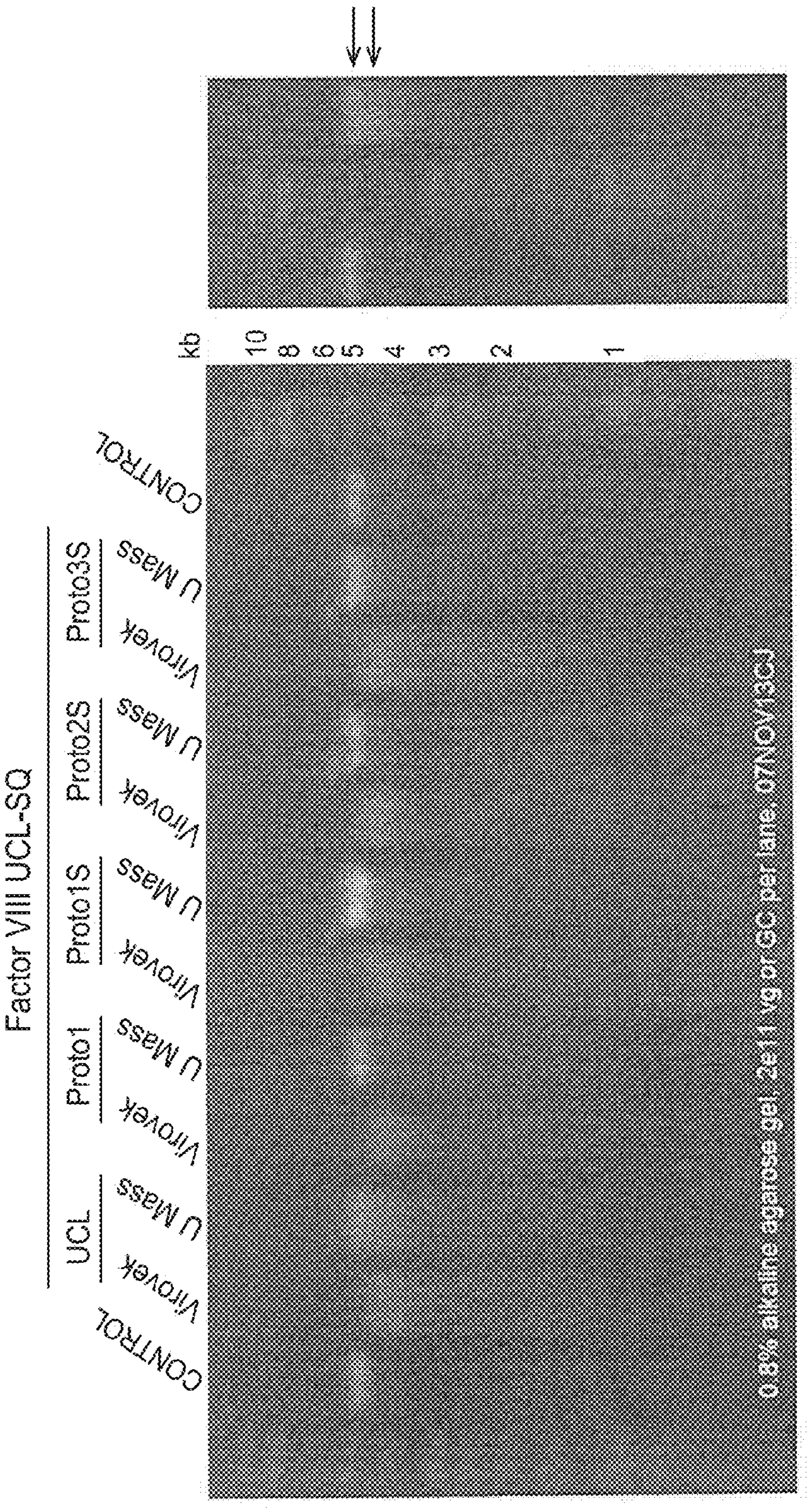

As shown in FIG. 5, Proto 1 with truncated or non-truncated genomes transduce FVIII similar to the UCL SQ construct. The AAV5.2 produced from baculovirus and 293T cell lysates as measured on a on 4-12% Bis-Tris Gel. Each samples expressed VP1, VP2 and VP3 protein, as shown in the FIG. 6. The genomic DNA from the AAV samples was run on 0.8% alkaline agarose gels, as shown in FIG. 7.

Transduction of Proto 1 was similar to the UCL SQ construct when these AAV were made by the baculovirus system. The inclusion of the intron containing Proto2S and 3S did not transduce better than Proto 1. The UCL SQ vector containing the AAV flanking sequences made in 293 cells were more potent than the UCL SQ lacking the AAV sequence made in baculovirus. As a result, additional enhancers were added to Proto 1, e.g. Construct 101, 102, 102 and 104, in an attempt to increase potency.

Example 6

Expression and Activity of AAV FVIII Vectors with Improved Promoters/Enhancer Sequences The expression and activity of AAV vectors comprising Constructs 99 to Construct 106 were tested using the hydrodynamic injection protocol. Hydrodynamic delivery is a rapid method to screen liver promoters in vivo. AAV plasmid DNA was generated using the method described in Example 5 and then diluted in TransIT-QR Hydrodynamic Delivery Solution. The plasmid DNA was injected into the tail vein of 5-6 week old C57Bl/6 mice (18-25 g) at a volume determined by (mouse weight (g)/10)=0.1 ml delivery solution). The injection time was less than 5 seconds. Plasma from each mouse was collected 48 hours after injection and the amount of FVIII antigen expressed was measured using an ELISA assay.

Increasing doses of Proto 1 plasmid (2.5, 5, 12.5 and 50 μg) were injected into the tail vein of mice. The amount of FVIII in the plasma of the injected mouse was measured using an ELISA test and recombinant FVIII (Xyntha SQ equivalents) was used as a standard for comparison.

Figure 8:
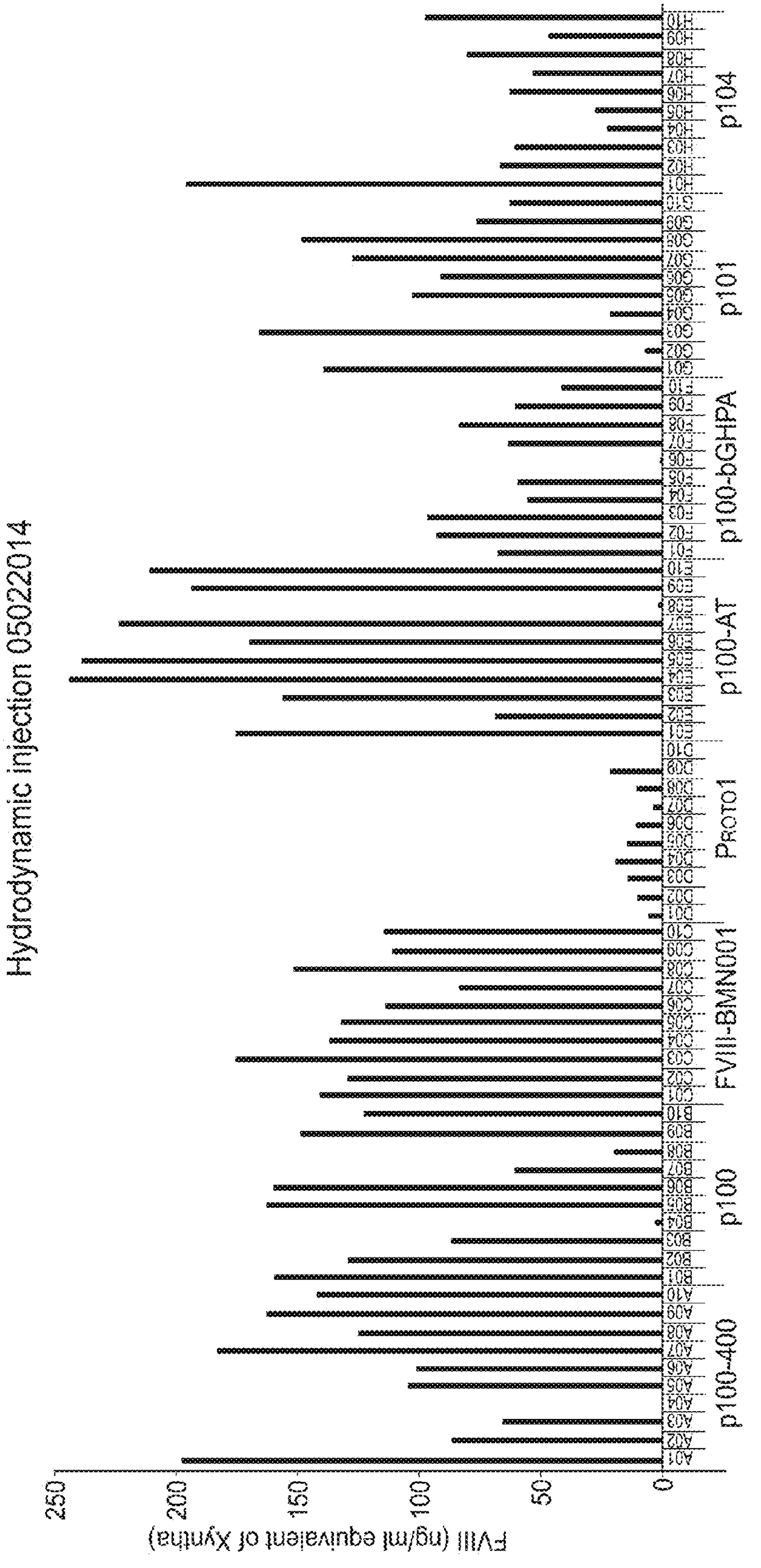
FIGS. 8-10 demonstrate that improved promoter constructs have increased expression of FVIII.

To investigate expression the improved promoter/enhancer elements of construct p100-400, Construct 100 (p100), Construct FVIII-BMN001 (pFVIII-BMN001), Protol, Construct 100AT (p100-AT), Construct 100 bGH poly A (p100-bGHPA), Construct 101 (p101) and Construct 104 (p104). As shown in FIG. 8, all constructs produced functional FVIII at varying levels of efficiency.

Figure 9:
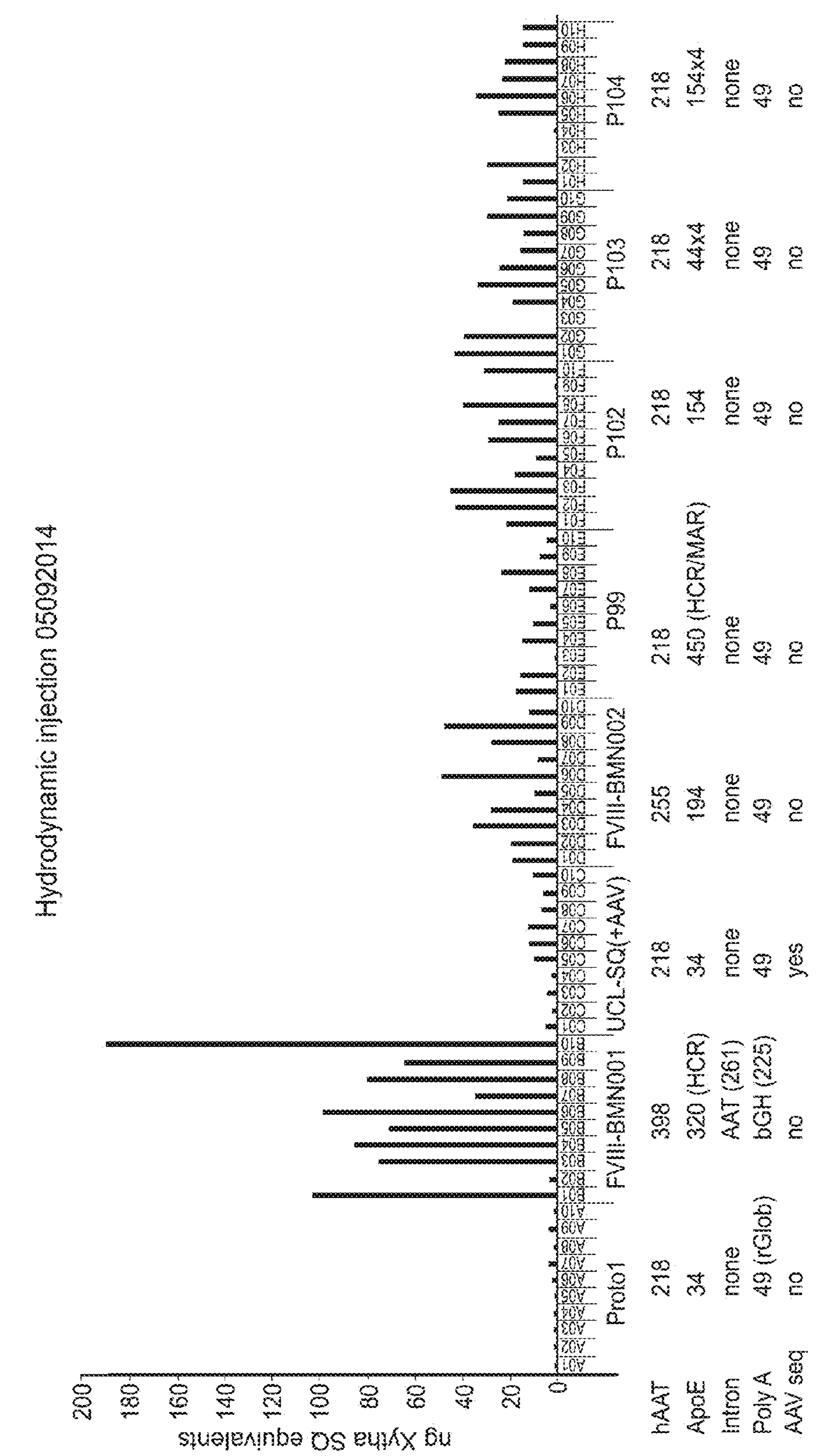
Figure 10:
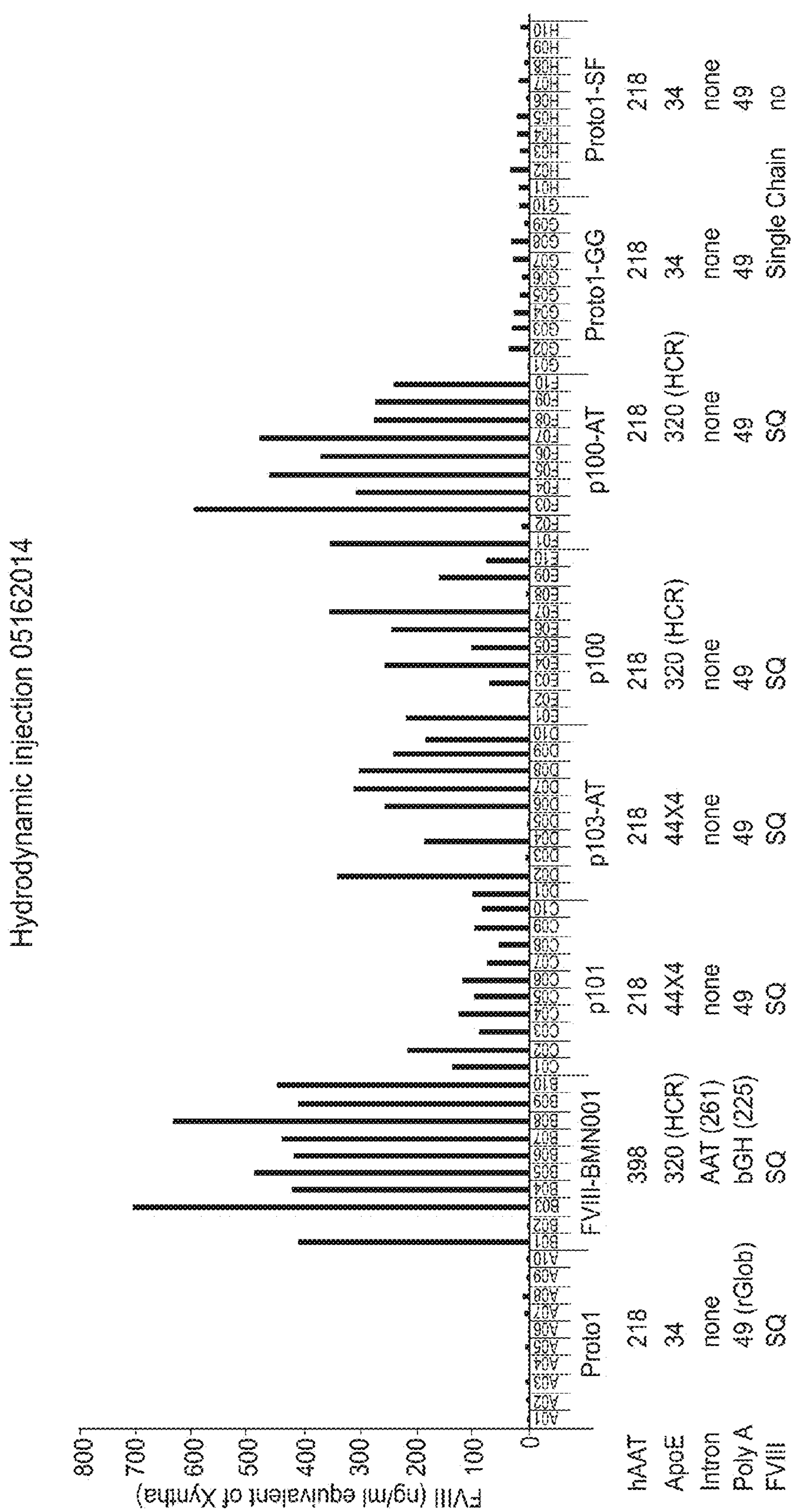

FIGS. 9 and 10 provide data for injection of 1 μg of plasmid of various constructs. As shown in FIG. 8, injection of Construct FVIII-BMN001, Construct FVIII-BMN002, Construct 102 (p102), Construct 103 (p103) and Construct 104 (p104) resulted in expression of at least 20 ng of FVIII in 5 out of 10 mice. As shown in FIG. 9, injection of Construct FVIII-BMN001, Construct 103 (p103), Construct 103-AT (p103-AT; 398 bp hAAT promoter), Construct 100 (p100), Construct 100AT (p100-AT; 398 bp hAAT promoter) resulted in expression of at least 100 ng/ml of FVIII in 5 out of 10 mice.

What is claimed:

1. An adeno-associated virus (AAV) vector, comprising an AAV2 5' inverted terminal repeat (ITR), a liver specific transcriptional regulatory region, a functionally active FVIII coding region, a polyadenylation sequence, an AAV2 3' ITR, and optionally one or more introns, wherein the functionally active FVIII coding region comprises nucleotides 923-5296 of SEQ ID NO: 9.

2. A method of producing a recombinant adeno-associated virus (AAV) particle comprising A) culturing a cell that has been transfected with an AAV vector of claim 1; and B) recovering recombinant AAV particle from the supernatant of the transfected cell.

3. A viral particle comprising an AAV vector of claim 1.

4. A method of treating a patient suffering from hemophilia A comprising intravenously administering to the patient an effective amount of an AAV vector of claim 1.

5. A composition comprising an AAV vector of claim 1 for the treatment of hemophilia A.

6. An isolated nucleic acid encoding a functionally active FVIII protein, said isolated nucleic acid comprising nucleotides 923-5296 of SEQ ID NO:9.

7. An adeno-associated virus (AAV) vector comprising the nucleotide sequence of SEQ ID NO: 1.

8. A viral particle comprising an AAV vector of claim 7.

9. A method of treating a patient suffering from hemophilia A comprising intravenously administering to the patient an effective amount of an AAV vector of claim 7.

* * * * *

SEQUENCE LISTING

<160> NUMBER OF SEQ ID NOS: 45

<210> SEQ ID NO 1
<211> LENGTH: 4970
<212> TYPE: DNA
<213> ORGANISM: Adeno-Associated Virus
<400> SEQUENCE: 1
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgtttg ctgcttgcaa tgtttgccca ttttagggtg 180
gacacaggac gctgtggttt ctgagccagg gggcgactca gatcccagcc agtggactta 240
gcccctgttt gctcctccga taactggggt gaccttggtt aatattcacc agcagcctcc 300
cccgttgccc ctctggatcc actgcttaaa tacggacgag gacagggccc tgtctcctca 360
gcttcaggca ccaccactga cctgggacag tgaatcgcca ccatgcagat tgagctgagc 420
acctgcttct tcctgtgcct gctgaggttc tgcttctctg ccaccaggag atactacctg 480
ggggctgtgg agctgagctg ggactacatg cagtctgacc tgggggagct gcctgtggat 540
gccaggttcc cccccagagt gcccaagagc ttccccttca acacctctgt ggtgtacaag 600
aagaccctgt ttgtggagtt cactgaccac ctgttcaaca ttgccaagcc caggcccccc 660
tggatgggcc tgctgggccc caccatccag gctgaggtgt atgacactgt ggtgatcacc 720
ctgaagaaca tggccagcca ccctgtgagc ctgcatgctg tgggggtgag ctactggaag 780
gcctctgagg gggctgagta tgatgaccag accagccaga gggagaagga ggatgacaag 840
gtgttccctg gggcagcca cacctatgtg tggcaggtgc tgaaggagaa tggccccatg 900
gcctctgacc ccctgtgcct gacctacagc tacctgagcc atgtggacct ggtgaaggac 960
ctgaactctg gcctgattgg ggccctgctg gtgtgcaggg agggcagcct ggccaaggag 1020
aagacccaga ccctgcacaa gttcatcctg ctgtttgctg tgtttgatga gggcaagagc 1080
tggcactctg aaaccaagaa cagcctgatg caggacaggg atgctgcctc tgccagggcc 1140
tggcccaaga tgcacactgt gaatggctat gtgaacagga gcctgcctgg cctgattggc 1200
tgccacagga agtctgtgta ctggcatgtg attggcatgg gcaccacccc tgaggtgcac 1260
agcatcttcc tggagggcca caccttcctg gtcaggaacc acaggcaggc cagcctggag 1320
atcagcccca tcaccttcct gactgcccag accctgctga tggacctggg ccagttcctg 1380
ctgttctgcc acatcagcag ccaccagcat gatggcatgg aggcctatgt gaaggtggac 1440
agctgccctg aggagcccca gctgaggatg aagaacaatg aggaggctga ggactatgat 1500
gatgacctga ctgactctga gatggatgtg gtgaggtttg atgatgacaa cagccccagc 1560
ttcatccaga tcaggtctgt ggccaagaag caccccaaga cctgggtgca ctacattgct 1620
gctgaggagg aggactggga ctatgccccc ctggtgctgg cccctgatga caggagctac 1680
aagagccagt acctgaacaa tggcccccag aggattggca ggaagtacaa gaaggtcagg 1740
ttcatggcct acactgatga aaccttcaag accagggagg ccatccagca tgagtctggc 1800
atcctgggcc ccctgctgta tggggaggtg ggggacaccc tgctgatcat cttcaagaac 1860
caggccagca ggccctacaa catctacccc catggcatca ctgatgtgag gcccctgtac 1920
agcaggaggc tgcccaaggg ggtgaagcac ctgaaggact tccccatcct gcctggggag 1980
atcttcaagt acaagtggac tgtgactgtg gaggatggcc ccaccaagtc tgaccccagg 2040
tgcctgacca gatactacag cagctttgtg aacatggaga gggacctggc ctctggcctg 2100

-continued

```
attggccccc tgctgatctg ctacaaggag tctgtggacc agaggggcaa ccagatcatg   2160
tctgacaaga ggaatgtgat cctgttctct gtgtttgatg agaacaggag ctggtacctg   2220
actgagaaca tccagaggtt cctgcccaac cctgctgggg tgcagctgga ggaccctgag   2280
ttccaggcca gcaacatcat gcacagcatc aatggctatg tgtttgacag cctgcagctg   2340
tctgtgtgcc tgcatgaggt ggcctactgg tacatcctga gcattggggc ccagactgac   2400
ttcctgtctg tgttcttctc tggctacacc ttcaagcaca agatggtgta tgaggacacc   2460
ctgaccctgt tccccttctc tggggagact gtgttcatga gcatggagaa ccctggcctg   2520
tggattctgg gctgccacaa ctctgacttc aggaacaggg gcatgactgc cctgctgaaa   2580
gtctccagct gtgacaagaa cactggggac tactatgagg acagctatga ggacatctct   2640
gcctacctgc tgagcaagaa caatgccatt gagcccagga gcttcagcca gaacccccca   2700
gtgctgaaga ggcaccagag ggagatcacc aggaccaccc tgcagtctga ccaggaggag   2760
attgactatg atgacaccat ctctgtggag atgaagaagg aggactttga catctacgac   2820
gaggacgaga accagagccc caggagcttc cagaagaaga ccaggcacta cttcattgct   2880
gctgtggaga ggctgtggga ctatggcatg agcagcagcc cccatgtgct gaggaacagg   2940
gcccagtctg gctctgtgcc ccagttcaag aaggtggtgt tccaggagtt cactgatggc   3000
agcttcaccc agcccctgta cagaggggag ctgaatgagc acctgggcct gctgggcccc   3060
tacatcaggg ctgaggtgga ggacaacatc atggtgacct tcaggaacca ggccagcagg   3120
ccctacagct tctacagcag cctgatcagc tatgaggagg accagaggca gggggctgag   3180
cccaggaaga actttgtgaa gcccaatgaa accaagacct acttctggaa ggtgcagcac   3240
cacatggccc ccaccaagga tgagtttgac tgcaaggcct gggcctactt ctctgatgtg   3300
gacctggaga aggatgtgca ctctggcctg attggccccc tgctggtgtg ccacaccaac   3360
accctgaacc ctgcccatgg caggcaggtg actgtgcagg agtttgccct gttcttcacc   3420
atctttgatg aaaccaagag ctggtacttc actgagaaca tggagaggaa ctgcagggcc   3480
ccctgcaaca tccagatgga ggaccccacc ttcaaggaga actacaggtt ccatgccatc   3540
aatggctaca tcatggacac cctgcctggc ctggtgatgg cccaggacca gaggatcagg   3600
tggtacctgc tgagcatggg cagcaatgag aacatccaca gcatccactt ctctggccat   3660
gtgttcactg tgaggaagaa ggaggagtac aagatggccc tgtacaacct gtaccctggg   3720
gtgtttgaga ctgtggagat gctgcccagc aaggctggca tctggagggt ggagtgcctg   3780
attggggagc acctgcatgc tggcatgagc accctgttcc tggtgtacag caacaagtgc   3840
cagacccccc tgggcatggc ctctggccac atcagggact tccagatcac tgcctctggc   3900
cagtatggcc agtgggcccc caagctggcc aggctgcact actctggcag catcaatgcc   3960
tggagcacca aggagccctt cagctggatc aaggtggacc tgctggcccc catgatcatc   4020
catggcatca agacccaggg ggccaggcag aagttcagca gcctgtacat cagccagttc   4080
atcatcatgt acagcctgga tggcaagaag tggcagacct acaggggcaa cagcactggc   4140
accctgatgg tgttctttgg caatgtggac agctctggca tcaagcacaa catcttcaac   4200
ccccccatca ttgccagata catcaggctg caccccaccc actacagcat caggagcacc   4260
ctgaggatgg agctgatggg ctgtgacctg aacagctgca gcatgcccct gggcatggag   4320
agcaaggcca tctctgatgc ccagatcact gccagcagct acttcaccaa catgtttgcc   4380
acctggagcc ccagcaaggc caggctgcac ctgcagggca ggagcaatgc ctggaggccc   4440
```

-continued

```
caggtcaaca accccaagga gtggctgcag gtggacttcc agaagaccat gaaggtgact   4500

ggggtgacca cccagggggt gaagagcctg ctgaccagca tgtatgtgaa ggagttcctg   4560

atcagcagca gccaggatgg ccaccagtgg accctgttct tccagaatgg caaggtgaag   4620

gtgttccagg gcaaccagga cagcttcacc cctgtggtga acagcctgga cccccccctg   4680

ctgaccagat acctgaggat tcacccccag agctgggtgc accagattgc cctgaggatg   4740

gaggtgctgg gctgtgaggc ccaggacctg tactgaaata aaagatcttt attttcatta   4800

gatctgtgtg ttggtttttt gtgtgaggaa cccctagtga tggagttggc cactccctct   4860

ctgcgcgctc gctcgctcac tgaggccggg cgaccaaagg tcgcccgacg cccgggcttt   4920

gcccgggcgg cctcagtgag cgagcgagcg cgcagagagg gagtggccaa              4970


<210> SEQ ID NO 2
<211> LENGTH: 4950
<212> TYPE: DNA
<213> ORGANISM: Adeno-Associated Virus

<400> SEQUENCE: 2

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactgtttg ctgcttgcaa tgtttgccca ttttagggtg gacacaggac    180

gctgtggttt ctgagccagg gggcgactca gatcccagcc agtggactta gcccctgttt    240

gctcctccga taactggggt gaccttggtt aatattcacc agcagcctcc cccgttgccc    300

ctctggatcc actgcttaaa tacggacgag gacagggccc tgtctcctca gcttcaggca    360

ccaccactga cctgggacag tgaatcgcca ccatgcagat tgagctgagc acctgcttct    420

tcctgtgcct gctgaggttc tgcttctctg ccaccaggag atactacctg gggggctgtgg    480

agctgagctg ggactacatg cagtctgacc tgggggagct gcctgtggat gccaggttcc    540

cccccagagt gcccaagagc ttccccttca acacctctgt ggtgtacaag aagaccctgt    600

ttgtggagtt cactgaccac ctgttcaaca ttgccaagcc caggcccccc tggatgggcc    660

tgctgggccc caccatccag gctgaggtgt atgacactgt ggtgatcacc ctgaagaaca    720

tggccagcca ccctgtgagc ctgcatgctg tgggggtgag ctactggaag gcctctgagg    780

gggctgagta tgatgaccag accagccaga gggagaagga ggatgacaag gtgttccctg    840

ggggcagcca cacctatgtg tggcaggtgc tgaaggagaa tggccccatg gcctctgacc    900

ccctgtgcct gacctacagc tacctgagcc atgtggacct ggtgaaggac ctgaactctg    960

gcctgattgg ggccctgctg gtgtgcaggg agggcagcct ggccaaggag aagacccaga   1020

ccctgcacaa gttcatcctg ctgtttgctg tgtttgatga gggcaagagc tggcactctg   1080

aaaccaagaa cagcctgatg caggacaggg atgctgcctc tgccagggcc tggcccaaga   1140

tgcacactgt gaatggctat gtgaacagga gcctgcctgg cctgattggc tgccacagga   1200

agtctgtgta ctggcatgtg attggcatgg gcaccacccc tgaggtgcac agcatcttcc   1260

tggagggcca caccttcctg gtcaggaacc acaggcaggc cagcctggag atcagcccca   1320

tcaccttcct gactgcccag accctgctga tggacctggg ccagttcctg ctgttctgcc   1380

acatcagcag ccaccagcat gatggcatgg aggcctatgt gaaggtggac agctgccctg   1440

aggagcccca gctgaggatg aagaacaatg aggaggctga ggactatgat gatgacctga   1500

ctgactctga gatggatgtg gtgaggtttg atgatgacaa cagccccagc ttcatccaga   1560

tcaggtctgt ggccaagaag caccccaaga cctgggtgca ctacattgct gctgaggagg   1620
```

-continued

```
aggactggga ctatgccccc ctggtgctgg cccctgatga caggagctac aagagccagt   1680
acctgaacaa tggcccccag aggattggca ggaagtacaa gaaggtcagg ttcatggcct   1740
acactgatga aaccttcaag accagggagg ccatccagca tgagtctggc atcctgggcc   1800
ccctgctgta tggggaggtg gggacaccc tgctgatcat cttcaagaac caggccagca   1860
ggccctacaa catctacccc catggcatca ctgatgtgag gcccctgtac agcaggaggc   1920
tgcccaaggg ggtgaagcac ctgaaggact tccccatcct gcctggggag atcttcaagt   1980
acaagtggac tgtgactgtg gaggatggcc ccaccaagtc tgaccccagg tgcctgacca   2040
gatactacag cagctttgtg aacatggaga gggacctggc ctctggcctg attggccccc   2100
tgctgatctg ctacaaggag tctgtggacc agaggggcaa ccagatcatg tctgacaaga   2160
ggaatgtgat cctgttctct gtgtttgatg agaacaggag ctggtacctg actgagaaca   2220
tccagaggtt cctgcccaac cctgctgggg tgcagctgga ggaccctgag ttccaggcca   2280
gcaacatcat gcacagcatc aatggctatg tgtttgacag cctgcagctg tctgtgtgcc   2340
tgcatgaggt ggcctactgg tacatcctga gcattggggc ccagactgac ttcctgtctg   2400
tgttcttctc tggctacacc ttcaagcaca agatggtgta tgaggacacc ctgaccctgt   2460
tccccttctc tggggagact gtgttcatga gcatggagaa ccctggcctg tggattctgg   2520
gctgccacaa ctctgacttc aggaacaggg gcatgactgc cctgctgaaa gtctccagct   2580
gtgacaagaa cactggggac tactatgagg acagctatga ggacatctct gcctacctgc   2640
tgagcaagaa caatgccatt gagcccagga gcttcagcca gaaccccccca gtgctgaaga   2700
ggcaccagag ggagatcacc aggaccaccc tgcagtctga ccaggaggag attgactatg   2760
atgacaccat ctctgtggag atgaagaagg aggactttga catctacgac gaggacgaga   2820
accagagccc caggagcttc cagaagaaga ccaggcacta cttcattgct gctgtggaga   2880
ggctgtggga ctatggcatg agcagcagcc cccatgtgct gaggaacagg gcccagtctg   2940
gctctgtgcc ccagttcaag aaggtggtgt tccaggagtt cactgatggc agcttcaccc   3000
agcccctgta cagaggggag ctgaatgagc acctgggcct gctgggcccc tacatcaggg   3060
ctgaggtgga ggacaacatc atggtgacct tcaggaacca ggccagcagg ccctacagct   3120
tctacagcag cctgatcagc tatgaggagg accagaggca gggggctgag cccaggaaga   3180
actttgtgaa gcccaatgaa accaagacct acttctggaa ggtgcagcac cacatggccc   3240
ccaccaagga tgagtttgac tgcaaggcct gggcctactt ctctgatgtg gacctggaga   3300
aggatgtgca ctctggcctg attggccccc tgctggtgtg ccacaccaac accctgaacc   3360
ctgcccatgg caggcaggtg actgtgcagg agtttgccct gttcttcacc atctttgatg   3420
aaaccaagag ctggtacttc actgagaaca tggagaggaa ctgcagggcc ccctgcaaca   3480
tccagatgga ggaccccacc ttcaaggaga actacaggtt ccatgccatc aatggctaca   3540
tcatggacac cctgcctggc ctggtgatgg cccaggacca gaggatcagg tggtacctgc   3600
tgagcatggg cagcaatgag aacatccaca gcatccactt ctctggccat gtgttcactg   3660
tgaggaagaa ggaggagtac aagatggccc tgtacaacct gtaccctggg gtgtttgaga   3720
ctgtggagat gctgcccagc aaggctggca tctggagggt ggagtgcctg attggggagc   3780
acctgcatgc tggcatgagc accctgttcc tggtgtacag caacaagtgc cagacccccc   3840
tgggcatggc ctctggccac atcagggact tccagatcac tgcctctggc cagtatggcc   3900
agtgggcccc caagctggcc aggctgcact actctggcag catcaatgcc tggagcacca   3960
```

-continued

```
aggagccctt cagctggatc aaggtggacc tgctggcccc catgatcatc catggcatca   4020
agacccaggg ggccaggcag aagttcagca gcctgtacat cagccagttc atcatcatgt   4080
acagcctgga tggcaagaag tggcagacct acaggggcaa cagcactggc accctgatgg   4140
tgttctttgg caatgtggac agctctggca tcaagcacaa catcttcaac ccccccatca   4200
ttgccagata catcaggctg caccccaccc actacagcat caggagcacc ctgaggatgg   4260
agctgatggg ctgtgacctg aacagctgca gcatgcccct gggcatggag agcaaggcca   4320
tctctgatgc ccagatcact gccagcagct acttcaccaa catgtttgcc acctggagcc   4380
ccagcaaggc caggctgcac ctgcagggca ggagcaatgc ctggaggccc caggtcaaca   4440
accccaagga gtggctgcag gtggacttcc agaagaccat gaaggtgact ggggtgacca   4500
cccagggggt gaagagcctg ctgaccagca tgtatgtgaa ggagttcctg atcagcagca   4560
gccaggatgg ccaccagtgg accctgttct tccagaatgg caaggtgaag gtgttccagg   4620
gcaaccagga cagcttcacc cctgtggtga acagcctgga ccccccccctg ctgaccagat   4680
acctgaggat tcacccccag agctgggtgc accagattgc cctgaggatg gaggtgctgg   4740
gctgtgaggc ccaggacctg tactgaaata aaagatcttt attttcatta gatctgtgtg   4800
ttggtttttt gtgtgagtga tggagttggc cactccctct ctgcgcgctc gctcgctcac   4860
tgaggccggg cgaccaaagg tcgcccgacg cccgggcttt gcccgggcgg cctcagtgag   4920
cgagcgagcg cgcagagagg gagtggccaa                                    4950
```

<210> SEQ ID NO 3
<211> LENGTH: 4983
<212> TYPE: DNA
<213> ORGANISM: Adeno-Associated Virus

<400> SEQUENCE: 3

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactgggcg actcagatcc cagccagtgg acttagcccc tgtttgctcc    180
tccgataact ggggtgacct tggttaatat tcaccagcag cctcccccgt tgcccctctg    240
gatccactgc ttaaatacgg acgaggacag ggccctgtct cctcagcttc aggcaccacc    300
actgacctgg gacagtgaat cgccaccatg cagattgagc tgagcacctg cttcttcctg    360
tgcctgctga gattctgctt tagtgccacc agaagatact acctgggtgc agtggaactg    420
tcatgggact atatgcaaag tgatctcggt gagctgcctg tggacgcaag gtaaatgccc    480
taaaatgggc aaacattgca agcagcaaac aacctggctc agaaaccaca gcgtcctgtg    540
tccattctaa tttttccttt cttcacgcag atttcctcct agagtgccaa aatcttttcc    600
attcaacacc tcagtcgtgt acaaaaagac tctgtttgta gaattcacgg atcacctttt    660
caacatcgct aagcccaggc ccccctggat gggcctgctg ggccccacca tccaggctga    720
ggtgtatgac actgtggtga tcaccctgaa gaacatggcc agccaccctg tgagcctgca    780
tgctgtgggg gtgagctact ggaaggcctc tgagggggct gagtatgatg accagaccag    840
ccagagggag aaggaggatg acaaggtgtt ccctgggggc agccacacct atgtgtggca    900
ggtgctgaag gagaatggcc ccatggcctc tgaccccctg tgcctgacct acagctacct    960
gagccatgtg gacctggtga aggacctgaa ctctggcctg attggggccc tgctggtgtg   1020
cagggagggc agcctggcca aggagaagac ccagaccctg cacaagttca tcctgctgtt   1080
tgctgtgttt gatgagggca agagctggca ctctgaaacc aagaacagcc tgatgcagga   1140
```

-continued

```
cagggatgct gcctctgcca gggcctggcc caagatgcac actgtgaatg gctatgtgaa   1200
caggagcctg cctggcctga ttggctgcca caggaagtct gtgtactggc atgtgattgg   1260
catgggcacc acccctgagg tgcacagcat cttcctggag ggccacacct tcctggtcag   1320
gaaccacagg caggccagcc tggagatcag ccccatcacc ttcctgactg cccagaccct   1380
gctgatggac ctgggccagt tcctgctgtt ctgccacatc agcagccacc agcatgatgg   1440
catggaggcc tatgtgaagg tggacagctg ccctgaggag ccccagctga ggatgaagaa   1500
caatgaggag gctgaggact atgatgatga cctgactgac tctgagatgg atgtggtgag   1560
gtttgatgat gacaacagcc ccagcttcat ccagatcagg tctgtggcca agaagcaccc   1620
caagacctgg gtgcactaca ttgctgctga ggaggaggac tgggactatg ccccccctggt   1680
gctggcccct gatgacagga gctacaagag ccagtacctg aacaatggcc cccagaggat   1740
tggcaggaag tacaagaagg tcaggttcat ggcctacact gatgaaacct tcaagaccag   1800
ggaggccatc cagcatgagt ctggcatcct gggccccctg ctgtatgggg aggtggggga   1860
caccctgctg atcatcttca agaaccaggc cagcaggccc tacaacatct acccccatgg   1920
catcactgat gtgaggcccc tgtacagcag gaggctgccc aagggggtga agcacctgaa   1980
ggacttcccc atcctgcctg gggagatctt caagtacaag tggactgtga ctgtggagga   2040
tggccccacc aagtctgacc ccaggtgcct gaccagatac tacagcagct ttgtgaacat   2100
ggagagggac ctggcctctg gcctgattgg cccccctgctg atctgctaca aggagtctgt   2160
ggaccagagg ggcaaccaga tcatgtctga caagaggaat gtgatcctgt tctctgtgtt   2220
tgatgagaac aggagctggt acctgactga gaacatccag aggttcctgc ccaaccctgc   2280
tggggtgcag ctggaggacc ctgagttcca ggccagcaac atcatgcaca gcatcaatgg   2340
ctatgtgttt gacagcctgc agctgtctgt gtgcctgcat gaggtggcct actggtacat   2400
cctgagcatt ggggcccaga ctgacttcct gtctgtgttc ttctctggct acaccttcaa   2460
gcacaagatg gtgtatgagg acaccctgac cctgttcccc ttctctgggg agactgtgtt   2520
catgagcatg gagaaccctg gcctgtggat tctgggctgc cacaactctg acttcaggaa   2580
caggggcatg actgccctgc tgaaagtctc cagctgtgac aagaacactg gggactacta   2640
tgaggacagc tatgaggaca tctctgccta cctgctgagc aagaacaatg ccattgagcc   2700
caggagcttc agccagaacc ccccagtgct gaagaggcac cagagggaga tcaccaggac   2760
caccctgcag tctgaccagg aggagattga ctatgatgac accatctctg tggagatgaa   2820
gaaggaggac tttgacatct acgacgagga cgagaaccag agccccagga gcttccagaa   2880
gaagaccagg cactacttca ttgctgctgt ggagaggctg tgggactatg gcatgagcag   2940
cagcccccat gtgctgagga acagggccca gtctggctct gtgccccagt tcaagaaggt   3000
ggtgttccag gagttcactg atggcagctt cacccagccc ctgtacagag gggagctgaa   3060
tgagcacctg ggcctgctgg gcccctacat cagggctgag gtggaggaca acatcatggt   3120
gaccttcagg aaccaggcca gcaggcccta cagcttctac agcagcctga tcagctatga   3180
ggaggaccag aggcaggggg ctgagcccag gaagaacttt gtgaagccca atgaaaccaa   3240
gacctacttc tggaaggtgc agcaccacat ggcccccacc aaggatgagt ttgactgcaa   3300
ggcctgggcc tacttctctg atgtggacct ggagaaggat gtgcactctg gcctgattgg   3360
cccccctgctg gtgtgccaca ccaacaccct gaaccctgcc catggcaggc aggtgactgt   3420
gcaggagttt gccctgttct tcaccatctt tgatgaaacc aagagctggt acttcactga   3480
```

-continued gaacatggag aggaactgca gggccccctg caacatccag atggaggacc ccaccttcaa 3540
ggagaactac aggttccatg ccatcaatgg ctacatcatg gacaccctgc ctggcctggt 3600
gatggcccag gaccagagga tcaggtggta cctgctgagc atgggcagca atgagaacat 3660
ccacagcatc cacttctctg gccatgtgtt cactgtgagg aagaaggagg agtacaagat 3720
ggccctgtac aacctgtacc ctggggtgtt tgagactgtg gagatgctgc ccagcaaggc 3780
tggcatctgg agggtggagt gcctgattgg ggagcacctg catgctggca tgagcaccct 3840
gttcctggtg tacagcaaca agtgccagac cccccctgggc atggcctctg gccacatcag 3900
ggacttccag atcactgcct ctggccagta tggccagtgg gcccccaagc tggccaggct 3960
gcactactct ggcagcatca atgcctggag caccaaggag cccttcagct ggatcaaggt 4020
ggacctgctg gcccccatga tcatccatgg catcaagacc cagggggcca ggcagaagtt 4080
cagcagcctg tacatcagcc agttcatcat catgtacagc ctggatggca agaagtggca 4140
gacctacagg ggcaacagca ctggcaccct gatggtgttc tttggcaatg tggacagctc 4200
tggcatcaag cacaacatct tcaacccccc catcattgcc agatacatca ggctgcaccc 4260
cacccactac agcatcagga gcaccctgag gatggagctg atgggctgtg acctgaacag 4320
ctgcagcatg cccctgggca tggagagcaa ggccatctct gatgcccaga tcactgccag 4380
cagctacttc accaacatgt ttgccacctg gagccccagc aaggccaggc tgcacctgca 4440
gggcaggagc aatgcctgga ggccccaggt caacaacccc aaggagtggc tgcaggtgga 4500
cttccagaag accatgaagg tgactggggt gaccacccag gggtgaaga gcctgctgac 4560
cagcatgtat gtgaaggagt tcctgatcag cagcagccag gatggccacc agtggaccct 4620
gttcttccag aatggcaagg tgaaggtgtt ccagggcaac caggacagct tcacccctgt 4680
ggtgaacagc ctggaccccc ccctgctgac cagatacctg aggattcacc cccagagctg 4740
ggtgcaccag attgccctga ggatggaggt gctgggctgt gaggcccagg acctgtacta 4800
ataaaagatc tttattttca ttagatctgt gtgttggttt tttgtgtgag tgatggagtt 4860
ggccactccc tctctgcgcg ctcgctcgct cactgaggcc gggcgaccaa aggtcgcccg 4920
acgcccgggc tttgcccggg cggcctcagt gagcgagcga gcgcgcagag agggagtggc 4980
caa 4983

<210> SEQ ID NO 4
<211> LENGTH: 4984
<212> TYPE: DNA
<213> ORGANISM: Adeno-Associated Virus

<400> SEQUENCE: 4
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactgggcg actcagatcc cagccagtgg acttagcccc tgtttgctcc 180
tccgataact ggggtgacct tggttaatat tcaccagcag cctcccccgt tgcccctctg 240
gatccactgc ttaaatacgg acgaggacag ggccctgtct cctcagcttc aggcaccacc 300
actgacctgg gacagtgaat cgccaccatg cagattgagc tgagcacctg cttcttcctg 360
tgcctgctga gattctgctt tagtgccacc agaagatact acctgggtgc agtggaactg 420
tcatgggact atatgcaaag tgatctcggt gagctgcctg tggacgcaag gtaaatgccc 480
taaaatgggc aaacattgca agcagcaaac accctaaaat gggcaaacat tgcaagcagc 540
aaacattcta atttttcctt tcttcacgca gatttcctcc tagagtgcca aaatcttttc 600

-continued

```
cattcaacac ctcagtcgtg tacaaaaaga ctctgtttgt agaattcacg gatcaccttt    660
tcaacatcgc taagcccagg ccccctgga tgggcctgct gggccccacc atccaggctg    720
aggtgtatga cactgtggtg atcaccctga agaacatggc cagccaccct gtgagcctgc    780
atgctgtggg ggtgagctac tggaaggcct ctgagggggc tgagtatgat gaccagacca    840
gccagaggga gaaggaggat gacaaggtgt tccctggggg cagccacacc tatgtgtggc    900
aggtgctgaa ggagaatggc cccatggcct ctgacccccct gtgcctgacc tacagctacc    960
tgagccatgt ggacctggtg aaggacctga actctggcct gattggggcc ctgctggtgt   1020
gcagggaggg cagcctggcc aaggagaaga cccagaccct gcacaagttc atcctgctgt   1080
ttgctgtgtt tgatgagggc aagagctggc actctgaaac caagaacagc ctgatgcagg   1140
acagggatgc tgcctctgcc agggcctggc ccaagatgca cactgtgaat ggctatgtga   1200
acaggagcct gcctggcctg attggctgcc acaggaagtc tgtgtactgg catgtgattg   1260
gcatgggcac cacccctgag gtgcacagca tcttcctgga gggccacacc ttcctggtca   1320
ggaaccacag gcaggccagc ctggagatca gccccatcac cttcctgact gcccagaccc   1380
tgctgatgga cctgggccag ttcctgctgt tctgccacat cagcagccac cagcatgatg   1440
gcatggaggc ctatgtgaag gtggacagct gccctgagga gccccagctg aggatgaaga   1500
acaatgagga ggctgaggac tatgatgatg acctgactga ctctgagatg gatgtggtga   1560
ggtttgatga tgacaacagc cccagcttca tccagatcag gtctgtggcc aagaagcacc   1620
ccaagacctg ggtgcactac attgctgctg aggaggagga ctgggactat gcccccctgg   1680
tgctggcccc tgatgacagg agctacaaga gccagtacct gaacaatggc ccccagagga   1740
ttggcaggaa gtacaagaag gtcaggttca tggcctacac tgatgaaacc ttcaagacca   1800
gggaggccat ccagcatgag tctggcatcc tgggcccccct gctgtatggg gaggtggggg   1860
acaccctgct gatcatcttc aagaaccagg ccagcaggcc ctacaacatc taccccccatg   1920
gcatcactga tgtgaggccc ctgtacagca ggaggctgcc caagggggtg aagcacctga   1980
aggacttccc catcctgcct ggggagatct tcaagtacaa gtggactgtg actgtggagg   2040
atggccccac caagtctgac cccaggtgcc tgaccagata ctacagcagc tttgtgaaca   2100
tggagaggga cctggcctct ggcctgattg gccccctgct gatctgctac aaggagtctg   2160
tggaccagag gggcaaccag atcatgtctg acaagaggaa tgtgatcctg ttctctgtgt   2220
ttgatgagaa caggagctgg tacctgactg agaacatcca gaggttcctg cccaaccctg   2280
ctggggtgca gctggaggac cctgagttcc aggccagcaa catcatgcac agcatcaatg   2340
gctatgtgtt tgacagcctg cagctgtctg tgtgcctgca tgaggtggcc tactggtaca   2400
tcctgagcat tggggcccag actgacttcc tgtctgtgtt cttctctggc tacaccttca   2460
agcacaagat ggtgtatgag gacaccctga ccctgttccc cttctctggg gagactgtgt   2520
tcatgagcat ggagaaccct ggcctgtgga ttctgggctg ccacaactct gacttcagga   2580
acaggggcat gactgccctg ctgaaagtct ccagctgtga caagaacact ggggactact   2640
atgaggacag ctatgaggac atctctgcct acctgctgag caagaacaat gccattgagc   2700
ccaggagctt cagccagaac ccccccagtgc tgaagaggca ccagagggag atcaccagga   2760
ccaccctgca gtctgaccag gaggagattg actatgatga caccatctct gtggagatga   2820
agaaggagga ctttgacatc tacgacgagg acgagaacca gagccccagg agcttccaga   2880
agaagaccag gcactacttc attgctgctg tggagaggct gtgggactat ggcatgagca   2940
```

-continued

```
gcagccccca tgtgctgagg aacagggccc agtctggctc tgtgccccag ttcaagaagg   3000
tggtgttcca ggagttcact gatggcagct tcacccagcc cctgtacaga ggggagctga   3060
atgagcacct gggcctgctg ggcccctaca tcagggctga ggtggaggac aacatcatgg   3120
tgaccttcag gaaccaggcc agcaggccct acagcttcta cagcagcctg atcagctatg   3180
aggaggacca gaggcagggg gctgagccca ggaagaactt tgtgaagccc aatgaaacca   3240
agacctactt ctggaaggtg cagcaccaca tggcccccac caaggatgag tttgactgca   3300
aggcctgggc ctacttctct gatgtggacc tggagaagga tgtgcactct ggcctgattg   3360
gcccccctgct ggtgtgccac accaacaccc tgaaccctgc ccatggcagg caggtgactg   3420
tgcaggagtt tgccctgttc ttcaccatct ttgatgaaac caagagctgg tacttcactg   3480
agaacatgga gaggaactgc agggcccccct gcaacatcca gatggaggac cccaccttca   3540
aggagaacta caggttccat gccatcaatg gctacatcat ggacaccctg cctggcctgg   3600
tgatggccca ggaccagagg atcaggtggt acctgctgag catgggcagc aatgagaaca   3660
tccacagcat ccacttctct ggccatgtgt tcactgtgag gaagaaggag gagtacaaga   3720
tggccctgta caacctgtac cctggggtgt ttgagactgt ggagatgctg cccagcaagg   3780
ctggcatctg gagggtggag tgcctgattg gggagcacct gcatgctggc atgagcaccc   3840
tgttcctggt gtacagcaac aagtgccaga cccccctggg catggcctct ggccacatca   3900
gggacttcca gatcactgcc tctggccagt atggccagtg ggcccccaag ctggccaggc   3960
tgcactactc tggcagcatc aatgcctgga gcaccaagga gcccttcagc tggatcaagg   4020
tggacctgct ggcccccatg atcatccatg gcatcaagac ccaggggggcc aggcagaagt   4080
tcagcagcct gtacatcagc cagttcatca tcatgtacag cctggatggc aagaagtggc   4140
agacctacag gggcaacagc actggcaccc tgatggtgtt ctttggcaat gtggacagct   4200
ctggcatcaa gcacaacatc ttcaaccccc ccatcattgc cagatacatc aggctgcacc   4260
ccacccacta cagcatcagg agcaccctga ggatggagct gatgggctgt gacctgaaca   4320
gctgcagcat gcccctgggc atggagagca aggccatctc tgatgcccag atcactgcca   4380
gcagctactt caccaacatg tttgccacct ggagccccag caaggccagg ctgcacctgc   4440
agggcaggag caatgcctgg aggccccagg tcaacaaccc caaggagtgg ctgcaggtgg   4500
acttccagaa gaccatgaag gtgactgggg tgaccaccca gggggtgaag agcctgctga   4560
ccagcatgta tgtgaaggag ttcctgatca gcagcagcca ggatggccac cagtggaccc   4620
tgttcttcca gaatggcaag gtgaaggtgt tccagggcaa ccaggacagc ttcacccctg   4680
tggtgaacag cctggacccc cccctgctga ccagatacct gaggattcac ccccagagct   4740
gggtgcacca gattgccctg aggatggagg tgctgggctg tgaggcccag gacctgtact   4800
aataaaagat ctttattttc attagatctg tgtgttggtt ttttgtgtga gtgatggagt   4860
tggccactcc ctctctgcgc gctcgctcgc tcactgaggc cgggcgacca aaggtcgccc   4920
gacgcccggg ctttgcccgg gcggcctcag tgagcgagcg agcgcgcaga gagggagtgg   4980
ccaa                                                                4984
```

<210> SEQ ID NO 5
<211> LENGTH: 4805
<212> TYPE: DNA
<213> ORGANISM: Adeno-Associated Virus

<400> SEQUENCE: 5

```
ttggccactc cctctctgcg cgctcgctcg ctcactgagg ccgcccgggc aaagcccggg     60
```

-continued

```
cgtcgggcga cctttggtcg cccggcctca gtgagcgagc gagcgcgcag agagggagtg    120
gccaactcca tcactagggg ttcctgtttg ctgcttgcaa tgtttgccca ttttagggtg    180
gacacaggac gctgtggttt ctgagccagg gggcgactca gatcccagcc agtggactta    240
gcccctgttt gctcctccga taactggggt gaccttggtt aatattcacc agcagcctcc    300
cccgttgccc ctctggatcc actgcttaaa tacggacgag gacagggccc tgtctcctca    360
gcttcaggca ccaccactga cctgggacag tgaatcgcca ccatgcagat tgagctgagc    420
acctgcttct tcctgtgcct gctgaggttc tgcttctctg ccaccaggag atactacctg    480
ggggctgtgg agctgagctg ggactacatg cagtctgacc tgggggagct gcctgtggat    540
gccaggttcc cccccagagt gcccaagagc ttccccttca acacctctgt ggtgtacaag    600
aagaccctgt ttgtggagtt cactgaccac ctgttcaaca ttgccaagcc caggcccccc    660
tggatgggcc tgctgggccc caccatccag gctgaggtgt atgacactgt ggtgatcacc    720
ctgaagaaca tggccagcca ccctgtgagc ctgcatgctg tgggggtgag ctactggaag    780
gcctctgagg gggctgagta tgatgaccag accagccaga gggagaagga ggatgacaag    840
gtgttccctg gggcagcca cacctatgtg tggcaggtgc tgaaggagaa tggccccatg    900
gcctctgacc ccctgtgcct gacctacagc tacctgagcc atgtggacct ggtgaaggac    960
ctgaactctg gcctgattgg ggccctgctg gtgtgcaggg agggcagcct ggccaaggag   1020
aagacccaga ccctgcacaa gttcatcctg ctgtttgctg tgtttgatga gggcaagagc   1080
tggcactctg aaaccaagaa cagcctgatg caggacaggg atgctgcctc tgccagggcc   1140
tggcccaaga tgcacactgt gaatggctat gtgaacagga gcctgcctgg cctgattggc   1200
tgccacagga agtctgtgta ctggcatgtg attggcatgg gcaccacccc tgaggtgcac   1260
agcatcttcc tggagggcca caccttcctg gtcaggaacc acaggcaggc cagcctggag   1320
atcagcccca tcaccttcct gactgcccag accctgctga tggacctggg ccagttcctg   1380
ctgttctgcc acatcagcag ccaccagcat gatggcatgg aggcctatgt gaaggtggac   1440
agctgccctg aggagcccca gctgaggatg aagaacaatg aggaggctga ggactatgat   1500
gatgacctga ctgactctga gatggatgtg gtgaggtttg atgatgacaa cagccccagc   1560
ttcatccaga tcaggtctgt ggccaagaag caccccaaga cctgggtgca ctacattgct   1620
gctgaggagg aggactggga ctatgccccc ctggtgctgg cccctgatga caggagctac   1680
aagagccagt acctgaacaa tggcccccag aggattggca ggaagtacaa gaaggtcagg   1740
ttcatggcct acactgatga aaccttcaag accagggagg ccatccagca tgagtctggc   1800
atcctgggcc ccctgctgta tggggaggtg ggggacaccc tgctgatcat cttcaagaac   1860
caggccagca ggccctacaa catctacccc catggcatca ctgatgtgag gcccctgtac   1920
agcaggaggc tgcccaaggg ggtgaagcac ctgaaggact tccccatcct gcctggggag   1980
atcttcaagt acaagtggac tgtgactgtg gaggatggcc ccaccaagtc tgaccccagg   2040
tgcctgacca gatactacag cagctttgtg aacatggaga gggacctggc ctctggcctg   2100
attggccccc tgctgatctg ctacaaggag tctgtggacc agaggggcaa ccagatcatg   2160
tctgacaaga ggaatgtgat cctgttctct gtgtttgatg agaacaggag ctggtacctg   2220
actgagaaca tccagaggtt cctgcccaac cctgctgggg tgcagctgga ggaccctgag   2280
ttccaggcca gcaacatcat gcacagcatc aatggctatg tgtttgacag cctgcagctg   2340
tctgtgtgcc tgcatgaggt ggcctactgg tacatcctga gcattggggc ccagactgac   2400
```

-continued

```
ttcctgtctg tgttcttctc tggctacacc ttcaagcaca agatggtgta tgaggacacc   2460

ctgaccctgt tccccttctc tggggagact gtgttcatga gcatggagaa ccctggcctg   2520

tggattctgg gctgccacaa ctctgacttc aggaacaggg gcatgactgc cctgctgaaa   2580

gtctccagct gtgacaagaa cactggggac tactatgagg acagctatga ggacatctct   2640

gcctacctgc tgagcaagaa caatgccatt gagcccagga gcttccagaa gaagaccagg   2700

cactacttca ttgctgctgt ggagaggctg tgggactatg gcatgagcag cagcccccat   2760

gtgctgagga acagggccca gtctggctct gtgccccagt tcaagaaggt ggtgttccag   2820

gagttcactg atggcagctt cacccagccc ctgtacagag gggagctgaa tgagcacctg   2880

ggcctgctgg gcccctacat cagggctgag gtggaggaca acatcatggt gaccttcagg   2940

aaccaggcca gcaggcccta cagcttctac agcagcctga tcagctatga ggaggaccag   3000

aggcaggggg ctgagcccag gaagaacttt gtgaagccca atgaaaccaa gacctacttc   3060

tggaaggtgc agcaccacat ggcccccacc aaggatgagt ttgactgcaa ggcctgggcc   3120

tacttctctg atgtggacct ggagaaggat gtgcactctg gcctgattgg cccccctgctg  3180

gtgtgccaca ccaacaccct gaaccctgcc catggcaggc aggtgactgt gcaggagttt   3240

gccctgttct tcaccatctt tgatgaaacc aagagctggt acttcactga gaacatggag   3300

aggaactgca gggccccctg caacatccag atggaggacc ccaccttcaa ggagaactac   3360

aggttccatg ccatcaatgg ctacatcatg gacaccctgc ctggcctggt gatggcccag   3420

gaccagagga tcaggtggta cctgctgagc atgggcagca atgagaacat ccacagcatc   3480

cacttctctg gccatgtgtt cactgtgagg aagaaggagg agtacaagat ggccctgtac   3540

aacctgtacc ctggggtgtt tgagactgtg gagatgctgc ccagcaaggc tggcatctgg   3600

agggtggagt gcctgattgg ggagcacctg catgctggca tgagcaccct gttcctggtg   3660

tacagcaaca agtgccagac ccccctgggc atggcctctg gccacatcag ggacttccag   3720

atcactgcct ctggccagta tggccagtgg gcccccaagc tggccaggct gcactactct   3780

ggcagcatca atgcctggag caccaaggag cccttcagct ggatcaaggt ggacctgctg   3840

gcccccatga tcatccatgg catcaagacc caggggggcca ggcagaagtt cagcagcctg   3900

tacatcagcc agttcatcat catgtacagc ctggatggca agaagtggca gacctacagg   3960

ggcaacagca ctggcaccct gatggtgttc tttggcaatg tggacagctc tggcatcaag   4020

cacaacatct tcaacccccc catcattgcc agatacatca ggctgcaccc cacccactac   4080

agcatcagga gcaccctgag gatggagctg atgggctgtg acctgaacag ctgcagcatg   4140

cccctgggca tggagagcaa ggccatctct gatgcccaga tcactgccag cagctacttc   4200

accaacatgt ttgccacctg gagccccagc aaggccaggc tgcacctgca gggcaggagc   4260

aatgcctgga ggccccaggt caacaacccc aaggagtggc tgcaggtgga cttccagaag   4320

accatgaagg tgactggggt gaccacccag ggggtgaaga gcctgctgac cagcatgtat   4380

gtgaaggagt tcctgatcag cagcagccag gatggccacc agtggaccct gttcttccag   4440

aatggcaagg tgaaggtgtt ccagggcaac caggacagct tcacccctgt ggtgaacagc   4500

ctggaccccc ccctgctgac cagatacctg aggattcacc cccagagctg ggtgcaccag   4560

attgccctga ggatggaggt gctgggctgt gaggcccagg acctgtactg aaataaaaga   4620

tctttatttt cattagatct gtgtgttggt tttttgtgtg aggaacccct agtgatggag   4680

ttggccactc cctctctgcg cgctcgctcg ctcactgagg ccgggcgacc aaaggtcgcc   4740

cgacgcccgg gctttgcccg ggcggcctca gtgagcgagc gagcgcgcag agagggagtg   4800
```

-continued gccaa 4805

<210> SEQ ID NO 6
<211> LENGTH: 4934
<212> TYPE: DNA
<213> ORGANISM: Adeno-Associated Virus

<400> SEQUENCE: 6
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgtttg ctgcttgcaa tgtttgccca ttttagggtg 180
gacacaggac gctgtggttt ctgagccagg gggcgactca gatcccagcc agtggactta 240
gcccctgttt gctcctccga taactggggt gaccttggtt aatattcacc agcagcctcc 300
cccgttgccc ctctggatcc actgcttaaa tacggacgag gacagggccc tgtctcctca 360
gcttcaggca ccaccactga cctgggacag tgaatcgcca ccatgcagat tgagctgagc 420
acctgcttct tcctgtgcct gctgagattc tgctttagtg ccaccagaag atactacctg 480
ggtgcagtgg aactgtcatg ggactatatg caaagtgatc tcggtgagct gcctgtggac 540
gcaaggtaaa ggcatgtcct gtagggtctg atcggggcca ggattgtggg gatgtaagtc 600
tgcttggagg aaggtgcaga catcgggtta ggatggttgt gatgctattc tgactttttc 660
ctttcttcac gcagatttcc tcctagagtg ccaaaatctt ttccattcaa cacctcagtc 720
gtgtacaaaa agactctgtt tgtagaattc acggatcacc ttttcaacat cgctaagccc 780
aggcccccct ggatgggcct gctgggcccc accatccagg ctgaggtgta tgacactgtg 840
gtgatcaccc tgaagaacat ggccagccac cctgtgagcc tgcatgctgt gggggtgagc 900
tactggaagg cctctgaggg ggctgagtat gatgaccaga ccagccagag ggagaaggag 960
gatgacaagg tgttccctgg gggcagccac acctatgtgt ggcaggtgct gaaggagaat 1020
ggccccatgg cctctgaccc cctgtgcctg acctacagct acctgagcca tgtggacctg 1080
gtgaaggacc tgaactctgg cctgattggg gccctgctgg tgtgcaggga gggcagcctg 1140
gccaaggaga agacccagac cctgcacaag ttcatcctgc tgtttgctgt gtttgatgag 1200
ggcaagagct ggcactctga aaccaagaac agcctgatgc aggacaggga tgctgcctct 1260
gccagggcct ggcccaagat gcacactgtg aatggctatg tgaacaggag cctgcctggc 1320
ctgattggct gccacaggaa gtctgtgtac tggcatgtga ttggcatggg caccacccct 1380
gaggtgcaca gcatcttcct ggagggccac accttcctgg tcaggaacca caggcaggcc 1440
agcctggaga tcagccccat caccttcctg actgcccaga ccctgctgat ggacctgggc 1500
cagttcctgc tgttctgcca catcagcagc caccagcatg atggcatgga ggcctatgtg 1560
aaggtggaca gctgccctga ggagccccag ctgaggatga agaacaatga ggaggctgag 1620
gactatgatg atgacctgac tgactctgag atggatgtgg tgaggtttga tgatgacaac 1680
agccccagct tcatccagat caggtctgtg gccaagaagc accccaagac ctgggtgcac 1740
tacattgctg ctgaggagga ggactgggac tatgcccccc tggtgctggc ccctgatgac 1800
aggagctaca agagccagta cctgaacaat ggcccccaga ggattggcag gaagtacaag 1860
aaggtcaggt tcatggccta cactgatgaa accttcaaga ccagggaggc catccagcat 1920
gagtctggca tcctgggccc cctgctgtat ggggaggtgg gggacaccct gctgatcatc 1980
ttcaagaacc aggccagcag gccctacaac atctaccccc atggcatcac tgatgtgagg 2040

-continued

```
ccccctgtaca gcaggaggct gcccaagggg gtgaagcacc tgaaggactt ccccatcctg   2100
```

cctggggaga tcttcaagta caagtggact gtgactgtgg aggatggccc caccaagtct   2160
gaccccaggt gcctgaccag atactacagc agctttgtga acatggagag ggacctggcc   2220
tctggcctga ttggccccct gctgatctgc tacaaggagt ctgtggacca gaggggcaac   2280
cagatcatgt ctgacaagag gaatgtgatc ctgttctctg tgtttgatga gaacaggagc   2340
tggtacctga ctgagaacat ccagaggttc ctgcccaacc ctgctggggt gcagctggag   2400
gaccctgagt tccaggccag caacatcatg cacagcatca atggctatgt gtttgacagc   2460
ctgcagctgt ctgtgtgcct gcatgaggtg gcctactggt acatcctgag cattggggcc   2520
cagactgact tcctgtctgt gttcttctct ggctacacct tcaagcacaa gatggtgtat   2580
gaggacaccc tgaccctgtt ccccttctct ggggagactg tgttcatgag catggagaac   2640
cctggcctgt ggattctggg ctgccacaac tctgacttca ggaacagggg catgactgcc   2700
ctgctgaaag tctccagctg tgacaagaac actggggact actatgagga cagctatgag   2760
gacatctctg cctacctgct gagcaagaac aatgccattg agcccaggag cttccagaag   2820
aagaccaggc actacttcat tgctgctgtg gagaggctgt gggactatgg catgagcagc   2880
agcccccatg tgctgaggaa cagggcccag tctggctctg tgccccagtt caagaaggtg   2940
gtgttccagg agttcactga tggcagcttc acccagcccc tgtacagagg ggagctgaat   3000
gagcacctgg gcctgctggg cccctacatc agggctgagg tggaggacaa catcatggtg   3060
accttcagga accaggccag caggccctac agcttctaca gcagcctgat cagctatgag   3120
gaggaccaga ggcagggggc tgagcccagg aagaactttg tgaagcccaa tgaaaccaag   3180
acctacttct ggaaggtgca gcaccacatg gcccccacca aggatgagtt tgactgcaag   3240
gcctgggcct acttctctga tgtggacctg gagaaggatg tgcactctgg cctgattggc   3300
cccctgctgg tgtgccacac caacaccctg aaccctgccc atggcaggca ggtgactgtg   3360
caggagtttg ccctgttctt caccatcttt gatgaaacca agagctggta cttcactgag   3420
aacatggaga ggaactgcag ggcccccctgc aacatccaga tggaggaccc caccttcaag   3480
gagaactaca ggttccatgc catcaatggc tacatcatgg acaccctgcc tggcctggtg   3540
atggcccagg accagaggat caggtggtac ctgctgagca tgggcagcaa tgagaacatc   3600
cacagcatcc acttctctgg ccatgtgttc actgtgagga agaaggagga gtacaagatg   3660
gccctgtaca acctgtaccc tggggtgttt gagactgtgg agatgctgcc cagcaaggct   3720
ggcatctgga gggtggagtg cctgattggg gagcacctgc atgctggcat gagcaccctg   3780
ttcctggtgt acagcaacaa gtgccagacc cccctgggca tggcctctgg ccacatcagg   3840
gacttccaga tcactgcctc tggccagtat ggccagtggg cccccaagct ggccaggctg   3900
cactactctg gcagcatcaa tgcctggagc accaaggagc ccttcagctg gatcaaggtg   3960
gacctgctgg cccccatgat catccatggc atcaagaccc aggggggccag gcagaagttc   4020 agcagcctgt acatcagcca gttcatcatc atgtacagcc tggatggcaa gaagtggcag   4080
acctacaggg gcaacagcac tggcaccctg atggtgttct ttggcaatgt ggacagctct   4140
ggcatcaagc acaacatctt caaccccccc atcattgcca gatacatcag gctgcacccc   4200
acccactaca gcatcaggag caccctgagg atggagctga tgggctgtga cctgaacagc   4260
tgcagcatgc cctgggcat ggagagcaag gccatctctg atgcccagat cactgccagc   4320
agctacttca ccaacatgtt tgccacctgg agccccagca aggccaggct gcacctgcag   4380
ggcaggagca atgcctggag gccccaggtc aacaacccca aggagtggct gcaggtggac   4440
ttccagaaga ccatgaaggt gactggggtg accacccagg gggtgaagag cctgctgacc 4500
agcatgtatg tgaaggagtt cctgatcagc agcagccagg atggccacca gtggaccctg 4560
ttcttccaga atggcaaggt gaaggtgttc cagggcaacc aggacagctt cacccctgtg 4620
gtgaacagcc tggacccccc cctgctgacc agatacctga ggattcaccc ccagagctgg 4680
gtgcaccaga ttgccctgag gatggaggtg ctgggctgtg aggcccagga cctgtactga 4740
aataaaagat ctttattttc attagatctg tgtgttggtt ttttgtgtga ggaaccccta 4800
gtgatggagt tggccactcc ctctctgcgc gctcgctcgc tcactgaggc cgggcgacca 4860
aaggtcgccc gacgcccggg ctttgcccgg gcggcctcag tgagcgagcg agcgcgcaga 4920
gagggagtgg ccaa 4934

<210> SEQ ID NO 7
<211> LENGTH: 4934
<212> TYPE: DNA
<213> ORGANISM: Adeno-Associated Virus

<400> SEQUENCE: 7
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgtttg ctgcttgcaa tgtttgccca ttttagggtg 180
gacacaggac gctgtggttt ctgagccagg gggcgactca gatcccagcc agtggactta 240
gcccctgttt gctcctccga taactggggt gaccttggtt aatattcacc agcagcctcc 300
cccgttgccc ctctggatcc actgcttaaa tacggacgag gacagggccc tgtctcctca 360
gcttcaggca ccaccactga cctgggacag tgaatcgcca ccatgcagat tgagctgagc 420
acctgcttct tcctgtgcct gctgagattc tgctttagtg ccaccagaag atactacctg 480
ggtgcagtgg aactgtcatg ggactatatg caaagtgatc tcggtgagct gcctgtggac 540
gcaaggtaaa ggctgtttgc tgcttgcaat gtttgcccat tttagggggg gatgtaagtc 600
tgcttggagg aaggtgcaga catcgggtta ggatggttgt gatgctattc tgactttttc 660
ctttcttcac gcagatttcc tcctagagtg ccaaaatctt ttccattcaa cacctcagtc 720
gtgtacaaaa agactctgtt tgtagaattc acggatcacc ttttcaacat cgctaagccc 780
aggcccccct ggatgggcct gctgggcccc accatccagg ctgaggtgta tgacactgtg 840
gtgatcaccc tgaagaacat ggccagccac cctgtgagcc tgcatgctgt gggggtgagc 900
tactggaagg cctctgaggg ggctgagtat gatgaccaga ccagccagag ggagaaggag 960
gatgacaagg tgttccctgg gggcagccac acctatgtgt ggcaggtgct gaaggagaat 1020
ggccccatgg cctctgaccc cctgtgcctg acctacagct acctgagcca tgtggacctg 1080
gtgaaggacc tgaactctgg cctgattggg gccctgctgg tgtgcaggga gggcagcctg 1140
gccaaggaga agacccagac cctgcacaag ttcatcctgc tgtttgctgt gtttgatgag 1200
ggcaagagct ggcactctga aaccaagaac agcctgatgc aggacaggga tgctgcctct 1260
gccagggcct ggcccaagat gcacactgtg aatggctatg tgaacaggag cctgcctggc 1320
ctgattggct gccacaggaa gtctgtgtac tggcatgtga ttggcatggg caccacccct 1380
gaggtgcaca gcatcttcct ggagggccac accttcctgg tcaggaacca caggcaggcc 1440
agcctggaga tcagccccat caccttcctg actgcccaga ccctgctgat ggacctgggc 1500
cagttcctgc tgttctgcca catcagcagc caccagcatg atggcatgga ggcctatgtg 1560

-continued aaggtggaca gctgccctga ggagccccag ctgaggatga agaacaatga ggaggctgag 1620
gactatgatg atgacctgac tgactctgag atggatgtgg tgaggtttga tgatgacaac 1680
agccccagct tcatccagat caggtctgtg gccaagaagc accccaagac ctgggtgcac 1740
tacattgctg ctgaggagga ggactgggac tatgcccccc tggtgctggc ccctgatgac 1800
aggagctaca agagccagta cctgaacaat ggcccccaga ggattggcag gaagtacaag 1860
aaggtcaggt tcatggccta cactgatgaa accttcaaga ccagggaggc catccagcat 1920
gagtctggca tcctgggccc cctgctgtat ggggaggtgg gggacaccct gctgatcatc 1980
ttcaagaacc aggccagcag gccctacaac atctaccccc atggcatcac tgatgtgagg 2040
cccctgtaca gcaggaggct gcccaagggg gtgaagcacc tgaaggactt ccccatcctg 2100
cctggggaga tcttcaagta caagtggact gtgactgtgg aggatggccc caccaagtct 2160
gaccccaggt gcctgaccag atactacagc agctttgtga acatggagag ggacctggcc 2220
tctggcctga ttggcccccct gctgatctgc tacaaggagt ctgtggacca gaggggcaac 2280
cagatcatgt ctgacaagag gaatgtgatc ctgttctctg tgtttgatga gaacaggagc 2340
tggtacctga ctgagaacat ccagaggttc ctgcccaacc ctgctggggt gcagctggag 2400
gaccctgagt tccaggccag caacatcatg cacagcatca atggctatgt gtttgacagc 2460
ctgcagctgt ctgtgtgcct gcatgaggtg gcctactggt acatcctgag cattggggcc 2520
cagactgact tcctgtctgt gttcttctct ggctacacct tcaagcacaa gatggtgtat 2580
gaggacaccc tgaccctgtt ccccttctct ggggagactg tgttcatgag catggagaac 2640
cctggcctgt ggattctggg ctgccacaac tctgacttca ggaacagggg catgactgcc 2700
ctgctgaaag tctccagctg tgacaagaac actggggact actatgagga cagctatgag 2760
gacatctctg cctacctgct gagcaagaac aatgccattg agcccaggag cttccagaag 2820
aagaccaggc actacttcat tgctgctgtg gagaggctgt gggactatgg catgagcagc 2880
agcccccatg tgctgaggaa cagggcccag tctggctctg tgccccagtt caagaaggtg 2940
gtgttccagg agttcactga tggcagcttc acccagcccc tgtacagagg ggagctgaat 3000
gagcacctgg gcctgctggg cccctacatc agggctgagg tggaggacaa catcatggtg 3060
accttcagga accaggccag caggccctac agcttctaca gcagcctgat cagctatgag 3120
gaggaccaga ggcagggggc tgagcccagg aagaactttg tgaagcccaa tgaaaccaag 3180
acctacttct ggaaggtgca gcaccacatg gcccccacca aggatgagtt tgactgcaag 3240
gcctgggcct acttctctga tgtggacctg gagaaggatg tgcactctgg cctgattggc 3300
cccctgctgg tgtgccacac caacaccctg aaccctgccc atggcaggca ggtgactgtg 3360
caggagtttg ccctgttctt caccatcttt gatgaaacca agagctggta cttcactgag 3420
aacatggaga ggaactgcag ggcccccctgc aacatccaga tggaggaccc caccttcaag 3480
gagaactaca ggttccatgc catcaatggc tacatcatgg acaccctgcc tggcctggtg 3540
atggcccagg accagaggat caggtggtac ctgctgagca tgggcagcaa tgagaacatc 3600
cacagcatcc acttctctgg ccatgtgttc actgtgagga agaaggagga gtacaagatg 3660
gccctgtaca acctgtaccc tggggtgttt gagactgtgg agatgctgcc cagcaaggct 3720
ggcatctgga gggtggagtg cctgattggg gagcacctgc atgctggcat gagcaccctg 3780
ttcctggtgt acagcaacaa gtgccagacc cccctgggca tggcctctgg ccacatcagg 3840
gacttccaga tcactgcctc tggccagtat ggccagtggg cccccaagct ggccaggctg 3900
cactactctg gcagcatcaa tgcctggagc accaaggagc ccttcagctg gatcaaggtg 3960

-continued

```
gacctgctgg cccccatgat catccatggc atcaagaccc agggggccag gcagaagttc   4020
agcagcctgt acatcagcca gttcatcatc atgtacagcc tggatggcaa gaagtggcag   4080
acctacaggg gcaacagcac tggcaccctg atggtgttct ttggcaatgt ggacagctct   4140
ggcatcaagc acaacatctt caaccccccc atcattgcca gatacatcag gctgcacccc   4200
acccactaca gcatcaggag caccctgagg atggagctga tgggctgtga cctgaacagc   4260
tgcagcatgc ccctgggcat ggagagcaag gccatctctg atgcccagat cactgccagc   4320
agctacttca ccaacatgtt tgccacctgg agccccagca aggccaggct gcacctgcag   4380
ggcaggagca atgcctggag gccccaggtc aacaacccca aggagtggct gcaggtggac   4440
ttccagaaga ccatgaaggt gactggggtg accacccagg gggtgaagag cctgctgacc   4500
agcatgtatg tgaaggagtt cctgatcagc agcagccagg atggccacca gtggaccctg   4560
ttcttccaga atggcaaggt gaaggtgttc cagggcaacc aggacagctt caccccctgtg   4620
gtgaacagcc tggaccccccc cctgctgacc agatacctga ggattcaccc ccagagctgg   4680
gtgcaccaga ttgccctgag gatggaggtg ctgggctgtg aggcccagga cctgtactga   4740
aataaaagat ctttattttc attagatctg tgtgttggtt ttttgtgtga ggaaccccta   4800
gtgatggagt tggccactcc ctctctgcgc gctcgctcgc tcactgaggc cgggcgacca   4860
aaggtcgccc gacgcccggg ctttgcccgg gcggcctcag tgagcgagcg agcgcgcaga   4920
gagggagtgg ccaa                                                     4934
```

<210> SEQ ID NO 8
<211> LENGTH: 4934
<212> TYPE: DNA
<213> ORGANISM: Adeno-Associated Virus

<400> SEQUENCE: 8

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgtttg ctgcttgcaa tgtttgccca ttttagggtg    180
gacacaggac gctgtggttt ctgagccagg gggcgactca gatcccagcc agtggactta    240
gcccctgttt gctcctccga taactggggt gaccttggtt aatattcacc agcagcctcc    300
cccgttgccc ctctggatcc actgcttaaa tacggacgag gacagggccc tgtctcctca    360
gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa ggcatgtcct gtagggtctg atcggggcca ggattgtggg gatgtaagtc    600
tgcttggagg aagccctaaa atgggcaaac attgcaagca gcaaacattc tgactttttc    660
ctttcttcac gcagatttcc tcctagagtg ccaaaatctt ttccattcaa cacctcagtc    720
gtgtacaaaa agactctgtt tgtagaattc acggatcacc ttttcaacat cgctaagccc    780
aggccccccct ggatgggcct gctgggcccc accatccagg ctgaggtgta tgacactgtg    840
gtgatcaccc tgaagaacat ggccagccac cctgtgagcc tgcatgctgt gggggtgagc    900
tactggaagg cctctgaggg ggctgagtat gatgaccaga ccagccagag ggagaaggag    960
gatgacaagg tgttccctgg gggcagccac acctatgtgt ggcaggtgct gaaggagaat   1020
ggccccatgg cctctgaccc cctgtgcctg acctacagct acctgagcca tgtggacctg   1080
```

-continued

```
gtgaaggacc tgaactctgg cctgattggg gccctgctgg tgtgcaggga gggcagcctg   1140
gccaaggaga agacccagac cctgcacaag ttcatcctgc tgtttgctgt gtttgatgag   1200
ggcaagagct ggcactctga aaccaagaac agcctgatgc aggacaggga tgctgcctct   1260
gccagggcct ggcccaagat gcacactgtg aatggctatg tgaacaggag cctgcctggc   1320
ctgattggct gccacaggaa gtctgtgtac tggcatgtga ttggcatggg caccacccct   1380
gaggtgcaca gcatcttcct ggagggccac accttcctgg tcaggaacca caggcaggcc   1440
agcctggaga tcagccccat caccttcctg actgcccaga ccctgctgat ggacctgggc   1500
cagttcctgc tgttctgcca catcagcagc caccagcatg atggcatgga ggcctatgtg   1560
aaggtggaca gctgccctga ggagccccag ctgaggatga agaacaatga ggaggctgag   1620
gactatgatg atgacctgac tgactctgag atggatgtgg tgaggtttga tgatgacaac   1680
agccccagct tcatccagat caggtctgtg gccaagaagc accccaagac ctgggtgcac   1740
tacattgctg ctgaggagga ggactgggac tatgccccc tggtgctggc cctgatgac   1800
aggagctaca agagccagta cctgaacaat ggcccccaga ggattggcag gaagtacaag   1860
aaggtcaggt tcatggccta cactgatgaa accttcaaga ccagggaggc catccagcat   1920
gagtctggca tcctgggccc cctgctgtat ggggaggtgg gggacaccct gctgatcatc   1980
ttcaagaacc aggccagcag gccctacaac atctaccccc atggcatcac tgatgtgagg   2040
cccctgtaca gcaggaggct gcccaagggg gtgaagcacc tgaaggactt ccccatcctg   2100
cctggggaga tcttcaagta caagtggact gtgactgtgg aggatggccc caccaagtct   2160
gaccccaggt gcctgaccag atactacagc agctttgtga acatggagag ggacctggcc   2220
tctggcctga ttggccccct gctgatctgc tacaaggagt ctgtggacca gaggggcaac   2280
cagatcatgt ctgacaagag gaatgtgatc ctgttctctg tgtttgatga gaacaggagc   2340
tggtacctga ctgagaacat ccagaggttc ctgcccaacc ctgctggggt gcagctggag   2400
gaccctgagt tccaggccag caacatcatg cacagcatca atggctatgt gtttgacagc   2460
ctgcagctgt ctgtgtgcct gcatgaggtg gcctactggt acatcctgag cattggggcc   2520
cagactgact tcctgtctgt gttcttctct ggctacacct tcaagcacaa gatggtgtat   2580
gaggacaccc tgaccctgtt ccccttctct ggggagactg tgttcatgag catggagaac   2640
cctggcctgt ggattctggg ctgccacaac tctgacttca ggaacagggg catgactgcc   2700
ctgctgaaag tctccagctg tgacaagaac actggggact actatgagga cagctatgag   2760
gacatctctg cctacctgct gagcaagaac aatgccattg agcccaggag cttccagaag   2820
aagaccaggc actacttcat tgctgctgtg gagaggctgt gggactatgg catgagcagc   2880
agcccccatg tgctgaggaa cagggcccag tctggctctg tgccccagtt caagaaggtg   2940
gtgttccagg agttcactga tggcagcttc acccagcccc tgtacagagg ggagctgaat   3000
gagcacctgg gcctgctggg cccctacatc agggctgagg tggaggacaa catcatggtg   3060
accttcagga accaggccag caggccctac agcttctaca gcagcctgat cagctatgag   3120
gaggaccaga ggcagggggc tgagcccagg aagaactttg tgaagcccaa tgaaaccaag   3180
acctacttct ggaaggtgca gcaccacatg gcccccacca aggatgagtt tgactgcaag   3240
gcctgggcct acttctctga tgtggacctg gagaaggatg tgcactctgg cctgattggc   3300
cccctgctgg tgtgccacac caacaccctg aaccctgccc atggcaggca ggtgactgtg   3360
caggagtttg ccctgttctt caccatcttt gatgaaacca agagctggta cttcactgag   3420
aacatggaga ggaactgcag ggcccctgc aacatccaga tggaggaccc caccttcaag   3480
```

-continued gagaactaca ggttccatgc catcaatggc tacatcatgg acaccctgcc tggcctggtg 3540
atggcccagg accagaggat caggtggtac ctgctgagca tgggcagcaa tgagaacatc 3600
cacagcatcc acttctctgg ccatgtgttc actgtgagga agaaggagga gtacaagatg 3660
gccctgtaca acctgtaccc tggggtgttt gagactgtgg agatgctgcc cagcaaggct 3720
ggcatctgga gggtggagtg cctgattggg gagcacctgc atgctggcat gagcaccctg 3780
ttcctggtgt acagcaacaa gtgccagacc cccctgggca tggcctctgg ccacatcagg 3840
gacttccaga tcactgcctc tggccagtat ggccagtggg cccccaagct ggccaggctg 3900
cactactctg gcagcatcaa tgcctggagc accaaggagc ccttcagctg gatcaaggtg 3960
gacctgctgg cccccatgat catccatggc atcaagaccc aggggggccag gcagaagttc 4020 agcagcctgt acatcagcca gttcatcatc atgtacagcc tggatggcaa gaagtggcag 4080
acctacaggg gcaacagcac tggcaccctg atggtgttct ttggcaatgt ggacagctct 4140
ggcatcaagc acaacatctt caaccccccc atcattgcca gatacatcag gctgcacccc 4200
acccactaca gcatcaggag caccctgagg atggagctga tgggctgtga cctgaacagc 4260
tgcagcatgc ccctgggcat ggagagcaag gccatctctg atgcccagat cactgccagc 4320
agctacttca ccaacatgtt tgccacctgg agccccagca aggccaggct gcacctgcag 4380
ggcaggagca atgcctggag gccccaggtc aacaacccca aggagtggct gcaggtggac 4440
ttccagaaga ccatgaaggt gactggggtg accacccagg gggtgaagag cctgctgacc 4500
agcatgtatg tgaaggagtt cctgatcagc agcagccagg atggccacca gtggaccctg 4560
ttcttccaga atggcaaggt gaaggtgttc cagggcaacc aggacagctt cacccctgtg 4620
gtgaacagcc tggacccccc cctgctgacc agatacctga ggattcaccc ccagagctgg 4680
gtgcaccaga ttgccctgag gatggaggtg ctgggctgtg aggcccagga cctgtactga 4740
aataaaagat ctttattttc attagatctg tgtgttggtt ttttgtgtga ggaaccccta 4800
gtgatggagt tggccactcc ctctctgcgc gctcgctcgc tcactgaggc cgggcgacca 4860
aaggtcgccc gacgcccggg ctttgcccgg gcggcctcag tgagcgagcg agcgcgcaga 4920
gagggagtgg ccaa 4934

<210> SEQ ID NO 9
<211> LENGTH: 5511
<212> TYPE: DNA
<213> ORGANISM: Adeno-Associated Virus 2

<400> SEQUENCE: 9
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgaccc ctctcacact 180
acctaaacca cgccaggaca acctctgctc ctctccaccg aaattccaag ggtcgagtg 240 gatgttggag gtggcatggg cccagagagg tctctgacct ctgccccagc tccaaggtca 300
gcaggcaggg agggctgtgt gtttgctgtt tgctgcttgc aatgtttgcc cattttaggg 360
acatgagtag gctgaagttt gttcagtgtg gacttcagag gcagcacaca aacagctgct 420
ggaggatggg aactgagggg ttggaagggg gcagggtgag cccagaaact cctgtgtgcc 480
tctgagcctg cagacgcgaa acgtcgactg gacacaggac gctgtggttt ctgagccagg 540
gggcgactca gatcccagcc agtggactta gcccctgttt gctcctccga taactggggt 600

-continued gaccttggtt aatattcacc agcagcctcc cccgttgccc ctctggatcc actgcttaaa 660
tacggacgag gacagggccc tgtctcctca gcttcaggca ccaccactga cctgggacag 720
tgaatcgtaa gtactagcag ctacaatcca gctaccattc tgcttttatt ttatggttgg 780
gataaggctg gattattctg agtccaagct aggccctttt gctaatcatg ttcatacctc 840
ttatcttcct cccacagctc ctgggcaacg tgctggtctg tgtgctggcc catcactttg 900
gcaaagaatt gcgatcgcca ccatgcagat tgagctgagc acctgcttct tcctgtgcct 960
gctgaggttc tgcttctctg ccaccaggag atactacctg ggggctgtgg agctgagctg 1020
ggactacatg cagtctgacc tgggggagct gcctgtggat gccaggttcc cccccagagt 1080
gcccaagagc ttccccttca acacctctgt ggtgtacaag aagaccctgt ttgtggagtt 1140
cactgaccac ctgttcaaca ttgccaagcc caggcccccc tggatgggcc tgctgggccc 1200
caccatccag gctgaggtgt atgacactgt ggtgatcacc ctgaagaaca tggccagcca 1260
ccctgtgagc ctgcatgctg tgggggtgag ctactggaag gcctctgagg gggctgagta 1320
tgatgaccag accagccaga gggagaagga ggatgacaag gtgttccctg gggcagcca 1380 cacctatgtg tggcaggtgc tgaaggagaa tggccccatg gcctctgacc ccctgtgcct 1440
gacctacagc tacctgagcc atgtggacct ggtgaaggac ctgaactctg gcctgattgg 1500
ggccctgctg gtgtgcaggg agggcagcct ggccaaggag aagacccaga ccctgcacaa 1560
gttcatcctg ctgtttgctg tgtttgatga gggcaagagc tggcactctg aaaccaagaa 1620
cagcctgatg caggacaggg atgctgcctc tgccagggcc tggcccaaga tgcacactgt 1680
gaatggctat gtgaacagga gcctgcctgg cctgattggc tgccacagga agtctgtgta 1740
ctggcatgtg attggcatgg gcaccacccc tgaggtgcac agcatcttcc tggagggcca 1800
caccttcctg gtcaggaacc acaggcaggc cagcctggag atcagcccca tcaccttcct 1860
gactgcccag accctgctga tggacctggg ccagttcctg ctgttctgcc acatcagcag 1920
ccaccagcat gatggcatgg aggcctatgt gaaggtggac agctgccctg aggagcccca 1980
gctgaggatg aagaacaatg aggaggctga ggactatgat gatgacctga ctgactctga 2040
gatggatgtg gtgaggtttg atgatgacaa cagccccagc ttcatccaga tcaggtctgt 2100
ggccaagaag caccccaaga cctgggtgca ctacattgct gctgaggagg aggactggga 2160
ctatgccccc ctggtgctgg cccctgatga caggagctac aagagccagt acctgaacaa 2220
tggcccccag aggattggca ggaagtacaa gaaggtcagg ttcatggcct acactgatga 2280
aaccttcaag accagggagg ccatccagca tgagtctggc atcctgggcc ccctgctgta 2340
tggggaggtg gggacaccc tgctgatcat cttcaagaac caggccagca ggccctacaa 2400
catctacccc catggcatca ctgatgtgag gcccctgtac agcaggaggc tgcccaaggg 2460
ggtgaagcac ctgaaggact tccccatcct gcctggggag atcttcaagt acaagtggac 2520
tgtgactgtg gaggatggcc ccaccaagtc tgaccccagg tgcctgacca gatactacag 2580
cagctttgtg aacatggaga gggacctggc ctctggcctg attggccccc tgctgatctg 2640
ctacaaggag tctgtggacc agaggggcaa ccagatcatg tctgacaaga ggaatgtgat 2700
cctgttctct gtgtttgatg agaacaggag ctggtacctg actgagaaca tccagaggtt 2760
cctgcccaac cctgctgggg tgcagctgga ggaccctgag ttccaggcca gcaacatcat 2820
gcacagcatc aatggctatg tgtttgacag cctgcagctg tctgtgtgcc tgcatgaggt 2880
ggcctactgg tacatcctga gcattggggc ccagactgac ttcctgtctg tgttcttctc 2940
tggctacacc ttcaagcaca agatggtgta tgaggacacc ctgaccctgt tccccttctc 3000

-continued

```
tggggagact gtgttcatga gcatggagaa ccctggcctg tggattctgg gctgccacaa   3060

ctctgacttc aggaacaggg gcatgactgc cctgctgaaa gtctccagct gtgacaagaa   3120

cactggggac tactatgagg acagctatga ggacatctct gcctacctgc tgagcaagaa   3180

caatgccatt gagcccagga gcttcagcca gaaccccca gtgctgaaga ggcaccagag   3240

ggagatcacc aggaccaccc tgcagtctga ccaggaggag attgactatg atgacaccat   3300

ctctgtggag atgaagaagg aggactttga catctacgac gaggacgaga accagagccc   3360

caggagcttc cagaagaaga ccaggcacta cttcattgct gctgtggaga ggctgtggga   3420

ctatggcatg agcagcagcc cccatgtgct gaggaacagg gcccagtctg gctctgtgcc   3480

ccagttcaag aaggtggtgt tccaggagtt cactgatggc agcttcaccc agcccctgta   3540

cagaggggag ctgaatgagc acctgggcct gctgggcccc tacatcaggg ctgaggtgga   3600

ggacaacatc atggtgacct tcaggaacca ggccagcagg ccctacagct tctacagcag   3660

cctgatcagc tatgaggagg accagaggca gggggctgag cccaggaaga actttgtgaa   3720

gcccaatgaa accaagacct acttctggaa ggtgcagcac cacatggccc ccaccaagga   3780

tgagtttgac tgcaaggcct gggcctactt ctctgatgtg gacctggaga aggatgtgca   3840

ctctggcctg attggccccc tgctggtgtg ccacaccaac accctgaacc ctgcccatgg   3900

caggcaggtg actgtgcagg agtttgccct gttcttcacc atctttgatg aaaccaagag   3960

ctggtacttc actgagaaca tggagaggaa ctgcagggcc ccctgcaaca tccagatgga   4020

ggaccccacc ttcaaggaga actacaggtt ccatgccatc aatggctaca tcatggacac   4080

cctgcctggc ctggtgatgg cccaggacca gaggatcagg tggtacctgc tgagcatggg   4140

cagcaatgag aacatccaca gcatccactt ctctggccat gtgttcactg tgaggaagaa   4200

ggaggagtac aagatggccc tgtacaacct gtaccctggg gtgtttgaga ctgtggagat   4260

gctgcccagc aaggctggca tctggagggt ggagtgcctg attggggagc acctgcatgc   4320

tggcatgagc accctgttcc tggtgtacag caacaagtgc cagacccccc tgggcatggc   4380

ctctggccac atcagggact tccagatcac tgcctctggc cagtatggcc agtgggcccc   4440

caagctggcc aggctgcact actctggcag catcaatgcc tggagcacca aggagccctt   4500

cagctggatc aaggtggacc tgctggcccc catgatcatc catggcatca agacccaggg   4560

ggccaggcag aagttcagca gcctgtacat cagccagttc atcatcatgt acagcctgga   4620

tggcaagaag tggcagacct acaggggcaa cagcactggc accctgatgg tgttctttgg   4680

caatgtggac agctctggca tcaagcacaa catcttcaac ccccccatca ttgccagata   4740

catcaggctg caccccaccc actacagcat caggagcacc ctgaggatgg agctgatggg   4800

ctgtgacctg aacagctgca gcatgcccct gggcatggag agcaaggcca tctctgatgc   4860

ccagatcact gccagcagct acttcaccaa catgtttgcc acctggagcc ccagcaaggc   4920

caggctgcac ctgcagggca ggagcaatgc ctggaggccc caggtcaaca accccaagga   4980

gtggctgcag gtggacttcc agaagaccat gaaggtgact ggggtgacca cccagggggt   5040

gaagagcctg ctgaccagca tgtatgtgaa ggagttcctg atcagcagca gccaggatgg   5100

ccaccagtgg accctgttct tccagaatgg caaggtgaag gtgttccagg gcaaccagga   5160

cagcttcacc cctgtggtga acagcctgga ccccccccctg ctgaccagat acctgaggat   5220

tcacccccag agctgggtgc accagattgc cctgaggatg gaggtgctgg gctgtgaggc   5280

ccaggacctg tactgacctc gaggaataaa ggaaatttat tttcattgca atagtgtgtt   5340
```

```
ggttttttgt gtcacgtggc ggccgcagga acccctagtg atggagttgg ccactccctc   5400

tctgcgcgct cgctcgctca ctgaggccgg gcgaccaaag gtcgcccgac gcccgggctt   5460

tgcccgggcg gcctcagtga gcgagcgagc gcgcagagag ggagtggcca a            5511
```

<210> SEQ ID NO 10
<211> LENGTH: 5688
<212> TYPE: DNA
<213> ORGANISM: Adeno-Associated Virus 2

<400> SEQUENCE: 10

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgaccc ctctcacact    180

acctaaacca cgccaggaca acctctgctc ctctccaccg aaattccaag ggtcgagtg    240

gatgttggag gtggcatggg cccagagagg tctctgacct ctgccccagc tccaaggtca    300

gcaggcaggg agggctgtgt gtttgctgtt tgctgcttgc aatgtttgcc cattttaggg    360

acatgagtag gctgaagttt gttcagtgtg gacttcagag gcagcacaca aacagctgct    420

ggaggatggg aactgagggg ttggaagggg gcagggtgag cccagaaact cctgtgtgcc    480

tctgagcctg cagacgcgaa acgtcgactg gacacaggac gctgtggttt ctgagccagg    540

gggcgactca gatcccagcc agtggactta gcccctgttt gctcctccga taactggggt    600

gaccttggtt aatattcacc agcagcctcc cccgttgccc ctctggatcc actgcttaaa    660

tacggacgag gacagggccc tgtctcctca gcttcaggca ccaccactga cctgggacag    720

tgaatcgtaa gtactagcag ctacaatcca gctaccattc tgcttttatt ttatggttgg    780

gataaggctg gattattctg agtccaagct aggccctttt gctaatcatg ttcatacctc    840

ttatcttcct cccacagctc ctgggcaacg tgctggtctg tgtgctggcc catcactttg    900

gcaaagaatt gcgatcgcca ccatgcagat tgagctgagc acctgcttct tcctgtgcct    960

gctgaggttc tgcttctctg ccaccaggag atactacctg gggctgtgg agctgagctg   1020

ggactacatg cagtctgacc tgggggagct gcctgtggat gccaggttcc cccccagagt   1080

gcccaagagc ttccccttca acacctctgt ggtgtacaag aagaccctgt ttgtggagtt   1140

cactgaccac ctgttcaaca ttgccaagcc caggcccccc tggatgggcc tgctgggccc   1200

caccatccag gctgaggtgt atgacactgt ggtgatcacc ctgaagaaca tggccagcca   1260

ccctgtgagc ctgcatgctg tgggggtgag ctactggaag gcctctgagg gggctgagta   1320

tgatgaccag accagccaga gggagaagga ggatgacaag gtgttccctg gggcagcca   1380

cacctatgtg tggcaggtgc tgaaggagaa tggccccatg gcctctgacc ccctgtgcct   1440

gacctacagc tacctgagcc atgtggacct ggtgaaggac ctgaactctg gcctgattgg   1500

ggccctgctg gtgtgcaggg agggcagcct ggccaaggag aagacccaga ccctgcacaa   1560

gttcatcctg ctgtttgctg tgtttgatga gggcaagagc tggcactctg aaaccaagaa   1620

cagcctgatg caggacaggg atgctgcctc tgccagggcc tggcccaaga tgcacactgt   1680

gaatggctat gtgaacagga gcctgcctgg cctgattggc tgccacagga agtctgtgta   1740

ctggcatgtg attggcatgg gcaccacccc tgaggtgcac agcatcttcc tggagggcca   1800

caccttcctg gtcaggaacc acaggcaggc cagcctggag atcagcccca tcaccttcct   1860

gactgcccag accctgctga tggacctggg ccagttcctg ctgttctgcc acatcagcag   1920

ccaccagcat gatggcatgg aggcctatgt gaaggtggac agctgccctg aggagcccca   1980
```

-continued

```
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg gggacaccc  tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgaccccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
tggctacacc ttcaagcaca agatggtgta tgaggacacc ctgaccctgt tccccttctc   3000
tggggagact gtgttcatga gcatggagaa ccctggcctg tggattctgg gctgccacaa   3060
ctctgacttc aggaacaggg gcatgactgc cctgctgaaa gtctccagct gtgacaagaa   3120
cactggggac tactatgagg acagctatga ggacatctct gcctacctgc tgagcaagaa   3180
caatgccatt gagcccagga gcttcagcca gaacccccca gtgctgaaga ggcaccagag   3240
ggagatcacc aggaccaccc tgcagtctga ccaggaggag attgactatg atgacaccat   3300
ctctgtggag atgaagaagg aggactttga catctacgac gaggacgaga accagagccc   3360
caggagcttc cagaagaaga ccaggcacta cttcattgct gctgtggaga ggctgtggga   3420
ctatggcatg agcagcagcc cccatgtgct gaggaacagg gcccagtctg gctctgtgcc   3480
ccagttcaag aaggtggtgt tccaggagtt cactgatggc agcttcaccc agcccctgta   3540
cagaggggag ctgaatgagc acctgggcct gctgggcccc tacatcaggg ctgaggtgga   3600
ggacaacatc atggtgacct tcaggaacca ggccagcagg ccctacagct tctacagcag   3660
cctgatcagc tatgaggagg accagaggca gggggctgag cccaggaaga actttgtgaa   3720
gcccaatgaa accaagacct acttctggaa ggtgcagcac cacatggccc ccaccaagga   3780
tgagtttgac tgcaaggcct gggcctactt ctctgatgtg gacctggaga aggatgtgca   3840
ctctggcctg attggccccc tgctggtgtg ccacaccaac accctgaacc ctgcccatgg   3900
caggcaggtg actgtgcagg agtttgccct gttcttcacc atctttgatg aaaccaagag   3960
ctggtacttc actgagaaca tggagaggaa ctgcagggcc ccctgcaaca tccagatgga   4020
ggaccccacc ttcaaggaga actacaggtt ccatgccatc aatggctaca tcatggacac   4080
cctgcctggc ctggtgatgg cccaggacca gaggatcagg tggtacctgc tgagcatggg   4140
cagcaatgag aacatccaca gcatccactt ctctggccat gtgttcactg tgaggaagaa   4200
ggaggagtac aagatggccc tgtacaacct gtaccctggg gtgtttgaga ctgtggagat   4260
gctgcccagc aaggctggca tctggagggt ggagtgcctg attggggagc acctgcatgc   4320
```

-continued

```
tggcatgagc accctgttcc tggtgtacag caacaagtgc cagacccccc tgggcatggc   4380

ctctggccac atcagggact tccagatcac tgcctctggc cagtatggcc agtgggcccc   4440

caagctggcc aggctgcact actctggcag catcaatgcc tggagcacca aggagccctt   4500

cagctggatc aaggtggacc tgctggcccc catgatcatc catggcatca agacccaggg   4560

ggccaggcag aagttcagca gcctgtacat cagccagttc atcatcatgt acagcctgga   4620

tggcaagaag tggcagacct acaggggcaa cagcactggc accctgatgg tgttctttgg   4680

caatgtggac agctctggca tcaagcacaa catcttcaac ccccccatca ttgccagata   4740

catcaggctg caccccaccc actacagcat caggagcacc ctgaggatgg agctgatggg   4800

ctgtgacctg aacagctgca gcatgcccct gggcatggag agcaaggcca tctctgatgc   4860

ccagatcact gccagcagct acttcaccaa catgtttgcc acctggagcc ccagcaaggc   4920

caggctgcac ctgcagggca ggagcaatgc ctggaggccc caggtcaaca accccaagga   4980

gtggctgcag gtggacttcc agaagaccat gaaggtgact ggggtgacca cccagggggt   5040

gaagagcctg ctgaccagca tgtatgtgaa ggagttcctg atcagcagca gccaggatgg   5100

ccaccagtgg accctgttct tccagaatgg caaggtgaag gtgttccagg gcaaccagga   5160

cagcttcacc cctgtggtga acagcctgga cccccccctg ctgaccagat acctgaggat   5220

tcacccccag agctgggtgc accagattgc cctgaggatg gaggtgctgg gctgtgaggc   5280

ccaggacctg tactgacctc gaggtgtgcc ttctagttgc cagccatctg ttgtttgccc   5340

ctcccccgtg ccttccttga ccctggaagg tgccactccc actgtccttt cctaataaaa   5400

tgaggaaatt gcatcgcatt gtctgagtag gtgtcattct attctggggg gtggggtggg   5460

gcaggacagc aagggggagg attgggaaga caatagcagg catgctgggg atgcggtggg   5520

ctctatgggc acgtggcggc cgcaggaacc cctagtgatg gagttggcca ctccctctct   5580

gcgcgctcgc tcgctcactg aggccgggcg accaaaggtc gcccgacgcc cgggctttgc   5640

ccgggcggcc tcagtgagcg agcgagcgcg cagagaggga gtggccaa                5688
```

<210> SEQ ID NO 11
<211> LENGTH: 5613
<212> TYPE: DNA
<213> ORGANISM: Adeno-Associated Virus 2

<400> SEQUENCE: 11

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgaccc ctctcacact    180

acctaaacca cgccaggaca acctctgctc ctctccaccg aaattccaag ggtcgagtg     240

gatgttggag gtggcatggg cccagagagg tctctgacct ctgccccagc tccaaggtca    300

gcaggcaggg agggctgtgt gtttgctgtt tgctgcttgc aatgtttgcc cattttaggg    360

acatgagtag gctgaagttt gttcagtgtg gacttcagag gcagcacaca aacagctgct    420

ggaggatggg aactgagggg ttggaagggg gcagggtgag cccagaaact cctgtgtgcc    480

tctgagcctg cagacgcgaa acgtcgactg gacacaggac gctgtggttt ctgagccagg    540

gggcgactca gatcccagcc agtggactta gcccctgttt gctcctccga taactggggt    600

gaccttggtt aatattcacc agcagcctcc cccgttgccc ctctggatcc actgcttaaa    660

tacggacgag gacagggccc tgtctcctca gcttcaggca ccaccactga cctgggacag    720

tgaatcgtaa gtactagcag ctacaatcca gctaccattc tgcttttatt ttatggttgg    780
```

-continued

```
gataaggctg gattattctg agtccaagct aggccctttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg gggctgtgg agctgagctg   1020
ggactacatg cagtctgacc tgggggagct gcctgtggat gccaggttcc cccccagagt   1080
gcccaagagc ttccccttca acacctctgt ggtgtacaag aagaccctgt ttgtggagtt   1140
cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tgggggtgag ctactggaag gcctctgagg gggctgagta   1320
tgatgaccag accagccaga gggagaagga ggatgacaag gtgttccctg gggcagcca   1380
cacctatgtg tggcaggtgc tgaaggagaa tggccccatg gcctctgacc ccctgtgcct   1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgaccccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
tggctacacc ttcaagcaca agatggtgta tgaggacacc ctgaccctgt tccccttctc   3000
tggggagact gtgttcatga gcatggagaa ccctggcctg tggattctgg gctgccacaa   3060
ctctgacttc aggaacaggg gcatgactgc cctgctgaaa gtctccagct gtgacaagaa   3120
```

-continued

```
cactggggac tactatgagg acagctatga ggacatctct gcctacctgc tgagcaagaa   3180
caatgccatt gagcccagga gcttcagcca gaaccccca gtgctgaaga ggcaccagag   3240
ggagatcacc aggaccaccc tgcagtctga ccaggaggag attgactatg atgacaccat   3300
ctctgtggag atgaagaagg aggactttga catctacgac gaggacgaga accagagccc   3360
caggagcttc cagaagaaga ccaggcacta cttcattgct gctgtggaga ggctgtggga   3420
ctatggcatg agcagcagcc cccatgtgct gaggaacagg gcccagtctg gctctgtgcc   3480
ccagttcaag aaggtggtgt tccaggagtt cactgatggc agcttcaccc agcccctgta   3540
cagaggggag ctgaatgagc acctgggcct gctgggcccc tacatcaggg ctgaggtgga   3600
ggacaacatc atggtgacct tcaggaacca ggccagcagg ccctacagct tctacagcag   3660
cctgatcagc tatgaggagg accagaggca gggggctgag cccaggaaga actttgtgaa   3720
gcccaatgaa accaagacct acttctggaa ggtgcagcac cacatggccc ccaccaagga   3780
tgagtttgac tgcaaggcct gggcctactt ctctgatgtg gacctggaga aggatgtgca   3840
ctctggcctg attggccccc tgctggtgtg ccacaccaac accctgaacc ctgcccatgg   3900
caggcaggtg actgtgcagg agtttgccct gttcttcacc atctttgatg aaaccaagag   3960
ctggtacttc actgagaaca tggagaggaa ctgcagggcc ccctgcaaca tccagatgga   4020
ggaccccacc ttcaaggaga actacaggtt ccatgccatc aatggctaca tcatggacac   4080
cctgcctggc ctggtgatgg cccaggacca gaggatcagg tggtacctgc tgagcatggg   4140
cagcaatgag aacatccaca gcatccactt ctctggccat gtgttcactg tgaggaagaa   4200
ggaggagtac aagatggccc tgtacaacct gtaccctggg gtgtttgaga ctgtggagat   4260
gctgcccagc aaggctggca tctggagggt ggagtgcctg attggggagc acctgcatgc   4320
tggcatgagc accctgttcc tggtgtacag caacaagtgc cagacccccc tgggcatggc   4380
ctctggccac atcagggact tccagatcac tgcctctggc cagtatggcc agtgggcccc   4440
caagctggcc aggctgcact actctggcag catcaatgcc tggagcacca aggagccctt   4500
cagctggatc aaggtggacc tgctggcccc catgatcatc catggcatca agacccaggg   4560
ggccaggcag aagttcagca gcctgtacat cagccagttc atcatcatgt acagcctgga   4620
tggcaagaag tggcagacct acaggggcaa cagcactggc accctgatgg tgttctttgg   4680
caatgtggac agctctggca tcaagcacaa catcttcaac cccccatca ttgccagata   4740
catcaggctg caccccaccc actacagcat caggagcacc ctgaggatgg agctgatggg   4800
ctgtgacctg aacagctgca gcatgcccct gggcatggag agcaaggcca tctctgatgc   4860
ccagatcact gccagcagct acttcaccaa catgtttgcc acctggagcc ccagcaaggc   4920
caggctgcac ctgcagggca ggagcaatgc ctggaggccc caggtcaaca accccaagga   4980
gtggctgcag gtggacttcc agaagaccat gaaggtgact ggggtgacca cccagggggt   5040
gaagagcctg ctgaccagca tgtatgtgaa ggagttcctg atcagcagca gccaggatgg   5100
ccaccagtgg accctgttct tccagaatgg caaggtgaag gtgttccagg gcaaccagga   5160
cagcttcacc cctgtggtga acagcctgga cccccccctg ctgaccagat acctgaggat   5220
tcacccccag agctgggtgc accagattgc cctgaggatg gaggtgctgg gctgtgaggc   5280
ccaggacctg tactgacctc gaggcactgt cctttcctaa taaaatgagg aaattgcatc   5340
gcattgtctg agtaggtgtc attctattct ggggggtggg gtggggcagg acagcaaggg   5400
ggaggattgg gaagacaata gcaggcatgc tggggatgcg gtgggctcta tgggcacgtg   5460
gcggccgcag gaacccctag tgatggagtt ggccactccc tctctgcgcg ctcgctcgct   5520
```

cactgaggcc gggcgaccaa aggtcgcccg acgcccgggc tttgcccggg cggcctcagt 5580
gagcgagcga gcgcgcagag agggagtggc caa 5613

<210> SEQ ID NO 12
<211> LENGTH: 5362
<212> TYPE: DNA
<213> ORGANISM: Adeno-Associated Virus 2

<400> SEQUENCE: 12
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgactg tttgctgttt 180
gctgcttgca atgtttgccc attttaggga catgtttgct gtttgctgct tgcaatgttt 240
gcccatttta gggacatgtt tgctgtttgc tgcttgcaat gtttgcccat tttagggaca 300
tgtttgctgt ttgctgcttg caatgtttgc ccattttagg gacaacgcga aacgtcgact 360
ggacacagga cgctgtggtt tctgagccag ggggcgactc agatcccagc cagtggactt 420
agcccctgtt tgctcctccg ataactgggg tgaccttggt taatattcac cagcagcctc 480
ccccgttgcc cctctggatc cactgcttaa atacggacga ggacagggcc ctgtctcctc 540
agcttcaggc accaccactg acctgggaca gtgaatcgta agtactagca gctacaatcc 600
agctaccatt ctgcttttat tttatggttg ggataaggct ggattattct gagtccaagc 660
taggcccttt tgctaatcat gttcatacct cttatcttcc tcccacagct cctgggcaac 720
gtgctggtct gtgtgctggc ccatcacttt ggcaaagaat tgcgatcgcc accatgcaga 780
ttgagctgag cacctgcttc ttcctgtgcc tgctgaggtt ctgcttctct gccaccagga 840
gatactacct gggggctgtg gagctgagct gggactacat gcagtctgac ctgggggagc 900
tgcctgtgga tgccaggttc ccccccagag tgcccaagag cttccccttc aacacctctg 960
tggtgtacaa gaagaccctg tttgtggagt tcactgacca cctgttcaac attgccaagc 1020
ccaggccccc ctggatgggc ctgctgggcc ccaccatcca ggctgaggtg tatgacactg 1080
tggtgatcac cctgaagaac atggccagcc accctgtgag cctgcatgct gtgggggtga 1140
gctactggaa ggcctctgag gggctgagt atgatgacca gaccagccag agggagaagg 1200
aggatgacaa ggtgttccct gggggcagcc acacctatgt gtggcaggtg ctgaaggaga 1260
atggccccat ggcctctgac cccctgtgcc tgacctacag ctacctgagc catgtggacc 1320
tggtgaagga cctgaactct ggcctgattg gggccctgct ggtgtgcagg gagggcagcc 1380
tggccaagga gaagacccag accctgcaca agttcatcct gctgtttgct gtgtttgatg 1440
agggcaagag ctggcactct gaaaccaaga acagcctgat gcaggacagg gatgctgcct 1500
ctgccagggc ctggcccaag atgcacactg tgaatggcta tgtgaacagg agcctgcctg 1560
gcctgattgg ctgccacagg aagtctgtgt actggcatgt gattggcatg ggcaccaccc 1620
ctgaggtgca cagcatcttc ctggagggcc acaccttcct ggtcaggaac cacaggcagg 1680
ccagcctgga gatcagcccc atcaccttcc tgactgccca gaccctgctg atggacctgg 1740
gccagttcct gctgttctgc cacatcagca gccaccagca tgatggcatg gaggcctatg 1800
tgaaggtgga cagctgccct gaggagcccc agctgaggat gaagaacaat gaggaggctg 1860
aggactatga tgatgacctg actgactctg agatggatgt ggtgaggttt gatgatgaca 1920
acagccccag cttcatccag atcaggtctg tggccaagaa gcaccccaag acctgggtgc 1980

-continued

```
actacattgc tgctgaggag gaggactggg actatgcccc cctggtgctg gcccctgatg   2040
acaggagcta caagagccag tacctgaaca atggccccca gaggattggc aggaagtaca   2100
agaaggtcag gttcatggcc tacactgatg aaaccttcaa gaccagggag gccatccagc   2160
atgagtctgg catcctgggc cccctgctgt atggggaggt gggggacacc ctgctgatca   2220
tcttcaagaa ccaggccagc aggccctaca acatctaccc ccatggcatc actgatgtga   2280
ggcccctgta cagcaggagg ctgcccaagg gggtgaagca cctgaaggac ttccccatcc   2340
tgcctgggga gatcttcaag tacaagtgga ctgtgactgt ggaggatggc cccaccaagt   2400
ctgaccccag gtgcctgacc agatactaca gcagctttgt gaacatggag agggacctgg   2460
cctctggcct gattggcccc ctgctgatct gctacaagga gtctgtggac cagaggggca   2520
accagatcat gtctgacaag aggaatgtga tcctgttctc tgtgtttgat gagaacagga   2580
gctggtacct gactgagaac atccagaggt tcctgcccaa ccctgctggg gtgcagctgg   2640
aggaccctga gttccaggcc agcaacatca tgcacagcat caatggctat gtgtttgaca   2700
gcctgcagct gtctgtgtgc ctgcatgagg tggcctactg gtacatcctg agcattgggg   2760
cccagactga cttcctgtct gtgttcttct ctggctacac cttcaagcac aagatggtgt   2820
atgaggacac cctgaccctg ttccccttct ctggggagac tgtgttcatg agcatggaga   2880
accctggcct gtggattctg ggctgccaca actctgactt caggaacagg ggcatgactg   2940
ccctgctgaa agtctccagc tgtgacaaga acactgggga ctactatgag gacagctatg   3000
aggacatctc tgcctacctg ctgagcaaga acaatgccat tgagcccagg agcttcagcc   3060
agaacccccc agtgctgaag aggcaccaga gggagatcac caggaccacc ctgcagtctg   3120
accaggagga gattgactat gatgacacca tctctgtgga gatgaagaag gaggactttg   3180
acatctacga cgaggacgag aaccagagcc ccaggagctt ccagaagaag accaggcact   3240
acttcattgc tgctgtggag aggctgtggg actatggcat gagcagcagc ccccatgtgc   3300
tgaggaacag ggcccagtct ggctctgtgc cccagttcaa gaaggtggtg ttccaggagt   3360
tcactgatgg cagcttcacc cagcccctgt acagagggga gctgaatgag cacctgggcc   3420
tgctgggccc ctacatcagg gctgaggtgg aggacaacat catggtgacc ttcaggaacc   3480
aggccagcag gccctacagc ttctacagca gcctgatcag ctatgaggag gaccagaggc   3540
agggggctga gcccaggaag aactttgtga agcccaatga aaccaagacc tacttctgga   3600
aggtgcagca ccacatggcc cccaccaagg atgagtttga ctgcaaggcc tgggcctact   3660
tctctgatgt ggacctggag aaggatgtgc actctggcct gattggcccc ctgctggtgt   3720
gccacaccaa caccctgaac cctgcccatg gcaggcaggt gactgtgcag gagtttgccc   3780
tgttcttcac catctttgat gaaaccaaga gctggtactt cactgagaac atggagagga   3840
actgcagggc cccctgcaac atccagatgg aggaccccac cttcaaggag aactacaggt   3900
tccatgccat caatggctac atcatggaca ccctgcctgg cctggtgatg gcccaggacc   3960
agaggatcag gtggtacctg ctgagcatgg gcagcaatga gaacatccac agcatccact   4020
tctctggcca tgtgttcact gtgaggaaga aggaggagta caagatggcc ctgtacaacc   4080
tgtaccctgg ggtgtttgag actgtggaga tgctgcccag caaggctggc atctggaggg   4140
tggagtgcct gattggggag cacctgcatg ctggcatgag caccctgttc ctggtgtaca   4200
gcaacaagtg ccagaccccc ctgggcatgg cctctggcca catcagggac ttccagatca   4260
ctgcctctgg ccagtatggc cagtgggccc ccaagctggc caggctgcac tactctggca   4320
gcatcaatgc ctggagcacc aaggagccct tcagctggat caaggtggac ctgctggccc   4380
```

```
ccatgatcat ccatggcatc aagacccagg gggccaggca gaagttcagc agcctgtaca   4440
tcagccagtt catcatcatg tacagcctgg atggcaagaa gtggcagacc tacaggggca   4500
acagcactgg caccctgatg gtgttctttg gcaatgtgga cagctctggc atcaagcaca   4560
acatcttcaa cccccccatc attgccagat acatcaggct gcaccccacc cactacagca   4620
tcaggagcac cctgaggatg gagctgatgg gctgtgacct gaacagctgc agcatgcccc   4680
tgggcatgga gagcaaggcc atctctgatg cccagatcac tgccagcagc tacttcacca   4740
acatgtttgc cacctggagc cccagcaagg ccaggctgca cctgcagggc aggagcaatg   4800
cctggaggcc ccaggtcaac aaccccaagg agtggctgca ggtggacttc cagaagacca   4860
tgaaggtgac tggggtgacc acccaggggg tgaagagcct gctgaccagc atgtatgtga   4920
aggagttcct gatcagcagc agccaggatg gccaccagtg gaccctgttc ttccagaatg   4980
gcaaggtgaa ggtgttccag ggcaaccagg acagcttcac ccctgtggtg aacagcctgg   5040
acccccccct gctgaccaga tacctgagga ttcaccccca gagctgggtg caccagattg   5100
ccctgaggat ggaggtgctg ggctgtgagg cccaggacct gtactgacct cgaggaataa   5160
aggaaattta ttttcattgc aatagtgtgt tggttttttg tgtcacgtgg cggccgcagg   5220
aacccctagt gatggagttg gccactccct ctctgcgcgc tcgctcgctc actgaggccg   5280
ggcgaccaaa ggtcgcccga cgcccgggct ttgcccgggc ggcctcagtg agcgagcgag   5340
cgcgcagaga gggagtggcc aa                                            5362
```

<210> SEQ ID NO 13
<211> LENGTH: 5464
<212> TYPE: DNA
<213> ORGANISM: Adeno-Associated Virus 2

<400> SEQUENCE: 13

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc ccattttagg gacaacgcga aacgtcgact    360
ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgta agtactagca gctacaatcc    600
agctaccatt ctgcttttat tttatggttg ggataaggct ggattattct gagtccaagc    660
taggcccttt tgctaatcat gttcatacct cttatcttcc tcccacagct cctgggcaac    720
gtgctggtct gtgtgctggc ccatcacttt ggcaaagaat tgcgatcgcc accatgcaga    780
ttgagctgag cacctgcttc ttcctgtgcc tgctgaggtt ctgcttctct gccaccagga    840
gatactacct gggggctgtg gagctgagct gggactacat gcagtctgac ctgggggagc    900
tgcctgtgga tgccaggttc ccccccagag tgcccaagag cttccccttc aacacctctg    960
tggtgtacaa gaagaccctg tttgtggagt tcactgacca cctgttcaac attgccaagc   1020
ccaggccccc ctggatgggc ctgctgggcc ccaccatcca ggctgaggtg tatgacactg   1080
```

-continued

```
tggtgatcac cctgaagaac atggccagcc accctgtgag cctgcatgct gtgggggtga   1140
gctactggaa ggcctctgag gggggctgagt atgatgacca gaccagccag agggagaagg   1200
aggatgacaa ggtgttccct gggggcagcc acacctatgt gtggcaggtg ctgaaggaga   1260
atggccccat ggcctctgac cccctgtgcc tgacctacag ctacctgagc catgtggacc   1320
tggtgaagga cctgaactct ggcctgattg gggccctgct ggtgtgcagg gagggcagcc   1380
tggccaagga gaagacccag accctgcaca agttcatcct gctgtttgct gtgtttgatg   1440
agggcaagag ctggcactct gaaaccaaga acagcctgat gcaggacagg gatgctgcct   1500
ctgccagggc ctggcccaag atgcacactg tgaatggcta tgtgaacagg agcctgcctg   1560
gcctgattgg ctgccacagg aagtctgtgt actggcatgt gattggcatg ggcaccaccc   1620
ctgaggtgca cagcatcttc ctggagggcc acaccttcct ggtcaggaac cacaggcagg   1680
ccagcctgga gatcagcccc atcaccttcc tgactgccca gaccctgctg atggacctgg   1740
gccagttcct gctgttctgc cacatcagca gccaccagca tgatggcatg gaggcctatg   1800
tgaaggtgga cagctgccct gaggagcccc agctgaggat gaagaacaat gaggaggctg   1860
aggactatga tgatgacctg actgactctg agatggatgt ggtgaggttt gatgatgaca   1920
acagccccag cttcatccag atcaggtctg tggccaagaa gcaccccaag acctgggtgc   1980
actacattgc tgctgaggag gaggactggg actatgcccc cctggtgctg gcccctgatg   2040
acaggagcta caagagccag tacctgaaca atggccccca gaggattggc aggaagtaca   2100
agaaggtcag gttcatggcc tacactgatg aaaccttcaa gaccagggag gccatccagc   2160
atgagtctgg catcctgggc cccctgctgt atggggaggt gggggacacc ctgctgatca   2220
tcttcaagaa ccaggccagc aggccctaca acatctaccc ccatggcatc actgatgtga   2280
ggcccctgta cagcaggagg ctgcccaagg gggtgaagca cctgaaggac ttccccatcc   2340
tgcctgggga gatcttcaag tacaagtgga ctgtgactgt ggaggatggc cccaccaagt   2400
ctgaccccag gtgcctgacc agatactaca gcagctttgt gaacatggag agggacctgg   2460
cctctggcct gattggcccc ctgctgatct gctacaagga gtctgtggac cagaggggca   2520
accagatcat gtctgacaag aggaatgtga tcctgttctc tgtgtttgat gagaacagga   2580
gctggtacct gactgagaac atccagaggt tcctgcccaa ccctgctggg gtgcagctgg   2640
aggaccctga gttccaggcc agcaacatca tgcacagcat caatggctat gtgtttgaca   2700
gcctgcagct gtctgtgtgc ctgcatgagg tggcctactg gtacatcctg agcattgggg   2760
cccagactga cttcctgtct gtgttcttct ctggctacac cttcaagcac aagatggtgt   2820
atgaggacac cctgaccctg ttccccttct ctggggagac tgtgttcatg agcatggaga   2880
accctggcct gtggattctg ggctgccaca actctgactt caggaacagg ggcatgactg   2940
ccctgctgaa agtctccagc tgtgacaaga acactgggga ctactatgag gacagctatg   3000
aggacatctc tgcctacctg ctgagcaaga acaatgccat tgagcccagg agcttcagcc   3060
agaacccccc agtgctgaag aggcaccaga gggagatcac caggaccacc ctgcagtctg   3120
accaggagga gattgactat gatgacacca tctctgtgga gatgaagaag gaggactttg   3180
acatctacga cgaggacgag aaccagagcc ccaggagctt ccagaagaag accaggcact   3240
acttcattgc tgctgtggag aggctgtggg actatggcat gagcagcagc ccccatgtgc   3300
tgaggaacag ggcccagtct ggctctgtgc cccagttcaa gaaggtggtg ttccaggagt   3360
tcactgatgg cagcttcacc cagcccctgt acagagggga gctgaatgag cacctgggcc   3420
tgctgggccc ctacatcagg gctgaggtgg aggacaacat catggtgacc ttcaggaacc   3480
```

-continued

```
aggccagcag gccctacagc ttctacagca gcctgatcag ctatgaggag gaccagaggc   3540
agggggctga gcccaggaag aactttgtga agcccaatga aaccaagacc tacttctgga   3600
aggtgcagca ccacatggcc cccaccaagg atgagtttga ctgcaaggcc tgggcctact   3660
tctctgatgt ggacctggag aaggatgtgc actctggcct gattggcccc ctgctggtgt   3720
gccacaccaa caccctgaac cctgcccatg gcaggcaggt gactgtgcag gagtttgccc   3780
tgttcttcac catctttgat gaaaccaaga gctggtactt cactgagaac atggagagga   3840
actgcagggc cccctgcaac atccagatgg aggaccccac cttcaaggag aactacaggt   3900
tccatgccat caatggctac atcatggaca ccctgcctgg cctggtgatg gcccaggacc   3960
agaggatcag gtggtacctg ctgagcatgg gcagcaatga gaacatccac agcatccact   4020
tctctggcca tgtgttcact gtgaggaaga aggaggagta caagatggcc ctgtacaacc   4080
tgtaccctgg ggtgtttgag actgtggaga tgctgcccag caaggctggc atctggaggg   4140
tggagtgcct gattggggag cacctgcatg ctggcatgag caccctgttc ctggtgtaca   4200
gcaacaagtg ccagaccccc ctgggcatgg cctctggcca catcagggac ttccagatca   4260
ctgcctctgg ccagtatggc cagtgggccc ccaagctggc caggctgcac tactctggca   4320
gcatcaatgc ctggagcacc aaggagccct tcagctggat caaggtggac ctgctggccc   4380
ccatgatcat ccatggcatc aagacccagg gggccaggca gaagttcagc agcctgtaca   4440
tcagccagtt catcatcatg tacagcctgg atggcaagaa gtggcagacc tacaggggca   4500
acagcactgg caccctgatg gtgttctttg gcaatgtgga cagctctggc atcaagcaca   4560
acatcttcaa cccccccatc attgccagat acatcaggct gcaccccacc cactacagca   4620
tcaggagcac cctgaggatg gagctgatgg gctgtgacct gaacagctgc agcatgcccc   4680
tgggcatgga gagcaaggcc atctctgatg cccagatcac tgccagcagc tacttcacca   4740
acatgtttgc cacctggagc cccagcaagg ccaggctgca cctgcagggc aggagcaatg   4800
cctggaggcc ccaggtcaac aaccccaagg agtggctgca ggtggacttc cagaagacca   4860
tgaaggtgac tggggtgacc acccaggggg tgaagagcct gctgaccagc atgtatgtga   4920
aggagttcct gatcagcagc agccaggatg gccaccagtg gaccctgttc ttccagaatg   4980
gcaaggtgaa ggtgttccag ggcaaccagg acagcttcac ccctgtggtg aacagcctgg   5040
accccccccct gctgaccaga tacctgagga ttcacccccca gagctgggtg caccagattg   5100
ccctgaggat ggaggtgctg ggctgtgagg cccaggacct gtactgacct cgaggcactg   5160
tcctttccta ataaaatgag gaaattgcat cgcattgtct gagtaggtgt cattctattc   5220
tggggggtgg ggtggggcag gacagcaagg gggaggattg ggaagacaat agcaggcatg   5280
ctggggatgc ggtgggctct atgggcacgt ggcggccgca ggaaccccta gtgatggagt   5340
tggccactcc ctctctgcgc gctcgctcgc tcactgaggc cgggcgacca aaggtcgccc   5400
gacgcccggg ctttgcccgg gcggcctcag tgagcgagcg agcgcgcaga gagggagtgg   5460
ccaa                                                                5464
```

<210> SEQ ID NO 14
<211> LENGTH: 6354
<212> TYPE: DNA
<213> ORGANISM: Adeno-Associated Virus 2

<400> SEQUENCE: 14

```
ttggccactc cctctctgcg cgctcgctcg ctcactgagg ccgcccgggc aaagcccggg     60
```

-continued

```
cgtcgggcga cctttggtcg cccggcctca gtgagcgagc gagcgcgcag agagggagtg    120
gccaactcca tcactagggg ttcctgcggc cgcacgcgtg tttaaacgtc gacaggttaa    180
tttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa tttttaaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg gacacaggac gctgtggttt    540
ctgagccagg gggcgactca gatcccagcc agtggactta gcccctgttt gctcctccga    600
taactggggt gaccttggtt aatattcacc agcagcctcc cccgttgccc ctctggatcc    660
actgcttaaa tacggacgag gacagggccc tgtctcctca gcttcaggca ccaccactga    720
cctgggacag tgaatcgtaa gtactagcag ctacaatcca gctaccattc tgcttttatt    780
ttatggttgg gataaggctg gattattctg agtccaagct aggccctttt gctaatcatg    840
ttcatacctc ttatcttcct cccacagctc ctgggcaacg tgctggtctg tgtgctggcc    900
catcactttg gcaaagaatt gcgatcgcca ccatgcagat tgagctgagc acctgcttct    960
tcctgtgcct gctgaggttc tgcttctctg ccaccaggag atactacctg gggctgtgg   1020
agctgagctg ggactacatg cagtctgacc tgggggagct gcctgtggat gccaggttcc   1080
cccccagagt gcccaagagc ttccccttca acacctctgt ggtgtacaag aagaccctgt   1140
ttgtggagtt cactgaccac ctgttcaaca ttgccaagcc caggcccccc tggatgggcc   1200
tgctgggccc caccatccag gctgaggtgt atgacactgt ggtgatcacc ctgaagaaca   1260
tggccagcca ccctgtgagc ctgcatgctg tgggggtgag ctactggaag gcctctgagg   1320
gggctgagta tgatgaccag accagccaga gggagaagga ggatgacaag gtgttccctg   1380
ggggcagcca cacctatgtg tggcaggtgc tgaaggagaa tggccccatg gcctctgacc   1440
ccctgtgcct gacctacagc tacctgagcc atgtggacct ggtgaaggac ctgaactctg   1500
gcctgattgg ggccctgctg gtgtgcaggg agggcagcct ggccaaggag aagacccaga   1560
ccctgcacaa gttcatcctg ctgtttgctg tgtttgatga gggcaagagc tggcactctg   1620
aaaccaagaa cagcctgatg caggacaggg atgctgcctc tgccagggcc tggcccaaga   1680
tgcacactgt gaatggctat gtgaacagga gcctgcctgg cctgattggc tgccacagga   1740
agtctgtgta ctggcatgtg attggcatgg gcaccacccc tgaggtgcac agcatcttcc   1800
tggagggcca caccttcctg gtcaggaacc acaggcaggc cagcctggag atcagcccca   1860
tcaccttcct gactgcccag accctgctga tggacctggg ccagttcctg ctgttctgcc   1920
acatcagcag ccaccagcat gatggcatgg aggcctatgt gaaggtggac agctgccctg   1980
aggagcccca gctgaggatg aagaacaatg aggaggctga ggactatgat gatgacctga   2040
ctgactctga gatggatgtg gtgaggtttg atgatgacaa cagccccagc ttcatccaga   2100
tcaggtctgt ggccaagaag caccccaaga cctgggtgca ctacattgct gctgaggagg   2160
aggactggga ctatgccccc ctggtgctgg cccctgatga caggagctac aagagccagt   2220
acctgaacaa tggcccccag aggattggca ggaagtacaa gaaggtcagg ttcatggcct   2280
acactgatga aaccttcaag accagggagg ccatccagca tgagtctggc atcctgggcc   2340
ccctgctgta tggggaggtg ggggacaccc tgctgatcat cttcaagaac caggccagca   2400
ggccctacaa catctacccc catggcatca ctgatgtgag gcccctgtac agcaggaggc   2460
```

-continued

```
tgcccaaggg ggtgaagcac ctgaaggact tccccatcct gcctggggag atcttcaagt   2520
acaagtggac tgtgactgtg gaggatggcc ccaccaagtc tgaccccagg tgcctgacca   2580
gatactacag cagctttgtg aacatggaga gggacctggc ctctggcctg attggccccc   2640
tgctgatctg ctacaaggag tctgtggacc agaggggcaa ccagatcatg tctgacaaga   2700
ggaatgtgat cctgttctct gtgtttgatg agaacaggag ctggtacctg actgagaaca   2760
tccagaggtt cctgcccaac cctgctgggg tgcagctgga ggaccctgag ttccaggcca   2820
gcaacatcat gcacagcatc aatggctatg tgtttgacag cctgcagctg tctgtgtgcc   2880
tgcatgaggt ggcctactgg tacatcctga gcattggggc ccagactgac ttcctgtctg   2940
tgttcttctc tggctacacc ttcaagcaca agatggtgta tgaggacacc ctgaccctgt   3000
tccccttctc tggggagact gtgttcatga gcatggagaa ccctggcctg tggattctgg   3060
gctgccacaa ctctgacttc aggaacaggg gcatgactgc cctgctgaaa gtctccagct   3120
gtgacaagaa cactggggac tactatgagg acagctatga ggacatctct gcctacctgc   3180
tgagcaagaa caatgccatt gagcccagga gcttcagcca gaaccccccca gtgctgaaga   3240
ggcaccagag ggagatcacc aggaccaccc tgcagtctga ccaggaggag attgactatg   3300
atgacaccat ctctgtggag atgaagaagg aggactttga catctacgac gaggacgaga   3360
accagagccc caggagcttc cagaagaaga ccaggcacta cttcattgct gctgtggaga   3420
ggctgtggga ctatggcatg agcagcagcc cccatgtgct gaggaacagg gcccagtctg   3480
gctctgtgcc ccagttcaag aaggtggtgt tccaggagtt cactgatggc agcttcaccc   3540
agcccctgta cagaggggag ctgaatgagc acctgggcct gctgggcccc tacatcaggg   3600
ctgaggtgga ggacaacatc atggtgacct tcaggaacca ggccagcagg ccctacagct   3660
tctacagcag cctgatcagc tatgaggagg accagaggca gggggctgag cccaggaaga   3720
actttgtgaa gcccaatgaa accaagacct acttctggaa ggtgcagcac cacatggccc   3780
ccaccaagga tgagtttgac tgcaaggcct gggcctactt ctctgatgtg gacctggaga   3840
aggatgtgca ctctggcctg attggccccc tgctggtgtg ccacaccaac accctgaacc   3900
ctgcccatgg caggcaggtg actgtgcagg agtttgccct gttcttcacc atctttgatg   3960
aaaccaagag ctggtacttc actgagaaca tggagaggaa ctgcagggcc ccctgcaaca   4020
tccagatgga ggaccccacc ttcaaggaga actacaggtt ccatgccatc aatggctaca   4080
tcatggacac cctgcctggc ctggtgatgg cccaggacca gaggatcagg tggtacctgc   4140
tgagcatggg cagcaatgag aacatccaca gcatccactt ctctggccat gtgttcactg   4200
tgaggaagaa ggaggagtac aagatggccc tgtacaacct gtaccctggg gtgtttgaga   4260
ctgtggagat gctgcccagc aaggctggca tctggagggt ggagtgcctg attggggagc   4320
acctgcatgc tggcatgagc accctgttcc tggtgtacag caacaagtgc cagacccccc   4380
tgggcatggc ctctggccac atcagggact tccagatcac tgcctctggc cagtatggcc   4440
agtgggcccc caagctggcc aggctgcact actctggcag catcaatgcc tggagcacca   4500
aggagccctt cagctggatc aaggtggacc tgctggcccc catgatcatc catggcatca   4560
agacccaggg ggccaggcag aagttcagca gcctgtacat cagccagttc atcatcatgt   4620
acagcctgga tggcaagaag tggcagacct acaggggcaa cagcactggc accctgatgg   4680
tgttctttgg caatgtggac agctctggca tcaagcacaa catcttcaac ccccccatca   4740
ttgccagata catcaggctg caccccaccc actacagcat caggagcacc ctgaggatgg   4800
```

agctgatggg ctgtgacctg aacagctgca gcatgcccct gggcatggag agcaaggcca 4860
tctctgatgc ccagatcact gccagcagct acttcaccaa catgtttgcc acctggagcc 4920
ccagcaaggc caggctgcac ctgcagggca ggagcaatgc ctggaggccc caggtcaaca 4980
accccaagga gtggctgcag gtggacttcc agaagaccat gaaggtgact ggggtgacca 5040
cccagggggt gaagagcctg ctgaccagca tgtatgtgaa ggagttcctg atcagcagca 5100
gccaggatgg ccaccagtgg accctgttct tccagaatgg caaggtgaag gtgttccagg 5160
gcaaccagga cagcttcacc cctgtggtga acagcctgga cccccccctg ctgaccagat 5220
acctgaggat tcacccccag agctgggtgc accagattgc cctgaggatg gaggtgctgg 5280
gctgtgaggc ccaggacctg tactgacctc gaggtgtgcc ttctagttgc cagccatctg 5340
ttgtttgccc ctcccccgtg ccttccttga ccctggaagg tgccactccc actgtccttt 5400
cctaataaaa tgaggaaatt gcatcgcatt gtctgagtag gtgtcattct attctggggg 5460
gtggggtggg gcaggacagc aagggggagg attgggaaga caatagcagg catgctgggg 5520
atgcggtggg ctctatgggc acgtgccctc tcacactacc taaaccacgc caggacaacc 5580
tctgctcctc tccaccgaaa ttccaagggg tcgagtggat gttggaggtg gcatgggccc 5640
agagaggtct ctgacctctg ccccagctcc aaggtcagca ggcagggagg gctgtgtgtt 5700
tgctgtttgc tgcttgcaat gtttgcccat tttagggaca tgagtaggct gaagtttgtt 5760
cagtgtggac ttcagaggca gcacacaaac agctgctgga ggatgggaac tgaggggttg 5820
gaagggggca gggtgagccc agaaactcct gtgtgcctct gagcctgcag ccctctcaca 5880
ctacctaaac cacgccagga caacctctgc tcctctccac cgaaattcca aggggtcgag 5940
tggatgttgg aggtggcatg ggcccagaga ggtctctgac ctctgcccca gctccaaggt 6000
cagcaggcag ggagggctgt gtgtttgctg tttgctgctt gcaatgtttg cccattttag 6060
ggacatgagt aggctgaagt ttgttcagtg tggacttcag aggcagcaca caaacagctg 6120
ctggaggatg ggaactgagg ggttggaagg gggcagggtg agcccagaaa ctcctgtgtg 6180
cctctgagcc tgcagcacgt ggcggccgca ggaaccccta gtgatggagt tggccactcc 6240
ctctctgcgc gctcgctcgc tcactgaggc cgggcgacca aaggtcgccc gacgcccggg 6300
ctttgcccgg gcggcctcag tgagcgagcg agcgcgcaga gagggagtgg ccaa 6354

<210> SEQ ID NO 15
<211> LENGTH: 6308
<212> TYPE: DNA
<213> ORGANISM: Adeno-Associated Virus 2

<400> SEQUENCE: 15
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttaattttta aaaagcagtc 180
aaaagtccaa gtggcccttg gcagcattta ctctctctgt ttgctctggt taataatctc 240
aggagcacaa acattcctgg aggcaggaga agaaatcaac atcctggact tatcctctgg 300
gcctgttaat ttttaaaaag cagtcaaaag tccaagtggc ccttggcagc atttactctc 360
tctgtttgct ctggttaata atctcaggag cacaaacatt cctggaggca ggagaagaaa 420
tcaacatcct ggacttatcc tctgggccta ggcctgaggc tggtcaaaat tgaacctcct 480
cctgctctga gcagcctggg gggcagacta agcagagggc tgtgcagacc cacataaaga 540
gcctactgtg tgccaggcac ttcacccgag gcacttcaca agcatgcttg ggaatgaaac 600

-continued

```
ttccaactct ttgggatgca ggtgaaacag ttcctggttc agagaggtga agcggcctgc    660
ctgaggcagc acagctcttc tttacagatg tgcttcccca cctctaccct gtctcacggc    720
cccccatgcc agcctgacgg ttgtgtctgc ctcagtcatg ctccattttt ccatcgggac    780
catcaagagg gtgtttgtgt ctaaggctga ctgggtaact ttggatgagc ggtctctccg    840
ctctgagcct gtttcctcat ctgtcaaatg ggctctaacc cactctgatc tcccagggcg    900
gcagtaagtc ttcagcatca ggcattttgg ggtgactcag taaatggtag atcttgctac    960
cagtggaaca gccactaagg attctgcagt gagagcagag ggccagctaa gtggtactct   1020
cccagagact gtctgactca cgccaccccc tccaccttgg acacaggacg ctgtggtttc   1080
tgagccaggt acaatgactc ctttcggtaa gtgcagtgga agctgtacac tgcccaggca   1140
aagcgtccgg gcagcgtagg cgggcgactc agatcccagc cagtggactt agcccctgtt   1200
tgctcctccg ataactgggg tgaccttggt taatattcac cagcagcctc ccccgttgcc   1260
cctctggatc cactgcttaa atacggacga ggacagggcc ctgtctcctc agcttcaggc   1320
accaccactg acctgggaca gtgaatcgta agtactagca gctacaatcc agctaccatt   1380
ctgcttttat tttatggttg ggataaggct ggattattct gagtccaagc taggcccttt   1440
tgctaatcat gttcatacct cttatcttcc tcccacagct cctgggcaac gtgctggtct   1500
gtgtgctggc ccatcacttt ggcaaagaat tgcgatcgcc accatgcaga ttgagctgag   1560
cacctgcttc ttcctgtgcc tgctgaggtt ctgcttctct gccaccagga gatactacct   1620
gggggctgtg gagctgagct gggactacat gcagtctgac ctgggggagc tgcctgtgga   1680
tgccaggttc ccccccagag tgcccaagag cttccccttc aacacctctg tggtgtacaa   1740
gaagaccctg tttgtggagt tcactgacca cctgttcaac attgccaagc ccaggccccc   1800
ctggatgggc ctgctgggcc ccaccatcca ggctgaggtg tatgacactg tggtgatcac   1860
cctgaagaac atggccagcc accctgtgag cctgcatgct gtgggggtga gctactggaa   1920
ggcctctgag gggg ctgagt atgatgacca gaccagccag agggagaagg aggatgacaa   1980
ggtgttccct gggggcagcc acacctatgt gtggcaggtg ctgaaggaga atggccccat   2040
ggcctctgac cccctgtgcc tgacctacag ctacctgagc catgtggacc tggtgaagga   2100
cctgaactct ggcctgattg ggccctgct ggtgtgcagg gagggcagcc tggccaagga   2160
gaagacccag accctgcaca agttcatcct gctgtttgct gtgtttgatg agggcaagag   2220
ctggcactct gaaaccaaga acagcctgat gcaggacagg gatgctgcct ctgccagggc   2280
ctggcccaag atgcacactg tgaatggcta tgtgaacagg agcctgcctg gcctgattgg   2340
ctgccacagg aagtctgtgt actggcatgt gattggcatg ggcaccaccc ctgaggtgca   2400
cagcatcttc ctggagggcc acaccttcct ggtcaggaac cacaggcagg ccagcctgga   2460
gatcagcccc atcaccttcc tgactgccca gaccctgctg atggacctgg gccagttcct   2520
gctgttctgc cacatcagca gccaccagca tgatggcatg gaggcctatg tgaaggtgga   2580
cagctgccct gaggagcccc agctgaggat gaagaacaat gaggaggctg aggactatga   2640
tgatgacctg actgactctg agatggatgt ggtgaggttt gatgatgaca acagccccag   2700
cttcatccag atcaggtctg tggccaagaa gcaccccaag acctgggtgc actacattgc   2760
tgctgaggag gaggactggg actatgcccc cctggtgctg gcccctgatg acaggagcta   2820
caagagccag tacctgaaca atggccccca gaggattggc aggaagtaca agaaggtcag   2880
gttcatggcc tacactgatg aaaccttcaa gaccagggag gccatccagc atgagtctgg   2940
```

-continued

```
catcctgggc cccctgctgt atggggaggt gggggacacc ctgctgatca tcttcaagaa   3000

ccaggccagc aggccctaca acatctaccc ccatggcatc actgatgtga ggcccctgta   3060

cagcaggagg ctgcccaagg gggtgaagca cctgaaggac ttccccatcc tgcctgggga   3120

gatcttcaag tacaagtgga ctgtgactgt ggaggatggc cccaccaagt ctgaccccag   3180

gtgcctgacc agatactaca gcagctttgt gaacatggag agggacctgg cctctggcct   3240

gattggcccc ctgctgatct gctacaagga gtctgtggac cagaggggca accagatcat   3300

gtctgacaag aggaatgtga tcctgttctc tgtgtttgat gagaacagga gctggtacct   3360

gactgagaac atccagaggt tcctgcccaa ccctgctggg gtgcagctgg aggaccctga   3420

gttccaggcc agcaacatca tgcacagcat caatggctat gtgtttgaca gcctgcagct   3480

gtctgtgtgc ctgcatgagg tggcctactg gtacatcctg agcattgggg cccagactga   3540

cttcctgtct gtgttcttct ctggctacac cttcaagcac aagatggtgt atgaggacac   3600

cctgaccctg ttccccttct ctggggagac tgtgttcatg agcatggaga accctggcct   3660

gtggattctg ggctgccaca actctgactt caggaacagg ggcatgactg ccctgctgaa   3720

agtctccagc tgtgacaaga acactgggga ctactatgag gacagctatg aggacatctc   3780

tgcctacctg ctgagcaaga acaatgccat tgagcccagg agcttcagcc agaacccccc   3840

agtgctgaag aggcaccaga gggagatcac caggaccacc ctgcagtctg accaggagga   3900

gattgactat gatgacacca tctctgtgga gatgaagaag gaggactttg acatctacga   3960

cgaggacgag aaccagagcc ccaggagctt ccagaagaag accaggcact acttcattgc   4020

tgctgtggag aggctgtggg actatggcat gagcagcagc ccccatgtgc tgaggaacag   4080

ggcccagtct ggctctgtgc cccagttcaa gaaggtggtg ttccaggagt tcactgatgg   4140

cagcttcacc cagcccctgt acagagggga gctgaatgag cacctgggcc tgctgggccc   4200

ctacatcagg gctgaggtgg aggacaacat catggtgacc ttcaggaacc aggccagcag   4260

gccctacagc ttctacagca gcctgatcag ctatgaggag gaccagaggc agggggctga   4320

gcccaggaag aactttgtga agcccaatga aaccaagacc tacttctgga aggtgcagca   4380

ccacatggcc cccaccaagg atgagtttga ctgcaaggcc tgggcctact tctctgatgt   4440

ggacctggag aaggatgtgc actctggcct gattggcccc ctgctggtgt gccacaccaa   4500

caccctgaac cctgcccatg gcaggcaggt gactgtgcag gagtttgccc tgttcttcac   4560

catctttgat gaaaccaaga gctggtactt cactgagaac atggagagga actgcagggc   4620

cccctgcaac atccagatgg aggaccccac cttcaaggag aactacaggt tccatgccat   4680

caatggctac atcatggaca ccctgcctgg cctggtgatg gcccaggacc agaggatcag   4740

gtggtacctg ctgagcatgg gcagcaatga gaacatccac agcatccact tctctggcca   4800

tgtgttcact gtgaggaaga aggaggagta caagatggcc ctgtacaacc tgtaccctgg   4860

ggtgtttgag actgtggaga tgctgcccag caaggctggc atctggaggg tggagtgcct   4920

gattggggag cacctgcatg ctggcatgag caccctgttc ctggtgtaca gcaacaagtg   4980

ccagaccccc ctgggcatgg cctctggcca catcagggac ttccagatca ctgcctctgg   5040

ccagtatggc cagtgggccc ccaagctggc caggctgcac tactctggca gcatcaatgc   5100

ctggagcacc aaggagccct tcagctggat caaggtggac ctgctggccc ccatgatcat   5160

ccatggcatc aagacccagg gggccaggca gaagttcagc agcctgtaca tcagccagtt   5220

catcatcatg tacagcctgg atggcaagaa gtggcagacc tacaggggca acagcactgg   5280

caccctgatg gtgttctttg gcaatgtgga cagctctggc atcaagcaca acatcttcaa   5340
```

```
ccccccccatc attgccagat acatcaggct gcaccccacc cactacagca tcaggagcac   5400

cctgaggatg gagctgatgg gctgtgacct gaacagctgc agcatgcccc tgggcatgga   5460

gagcaaggcc atctctgatg cccagatcac tgccagcagc tacttcacca acatgtttgc   5520

cacctggagc cccagcaagg ccaggctgca cctgcagggc aggagcaatg cctggaggcc   5580

ccaggtcaac aaccccaagg agtggctgca ggtggacttc cagaagacca tgaaggtgac   5640

tggggtgacc acccaggggg tgaagagcct gctgaccagc atgtatgtga aggagttcct   5700

gatcagcagc agccaggatg gccaccagtg gaccctgttc ttccagaatg gcaaggtgaa   5760

ggtgttccag ggcaaccagg acagcttcac ccctgtggtg aacagcctgg acccccccct   5820

gctgaccaga tacctgagga ttcacccccca gagctgggtg caccagattg ccctgaggat   5880

ggaggtgctg ggctgtgagg cccaggacct gtactgacct cgagctgtgc cttctagttg   5940

ccagccatct gttgtttgcc cctcccccgt gccttccttg accctggaag gtgccactcc   6000

cactgtcctt tcctaataaa atgaggaaat tgcatcgcat tgtctgagta ggtgtcattc   6060

tattctgggg ggtggggtgg ggcaggacag caagggggag gattgggaag acaatagcag   6120

gcatgctggg gatgcggtgg gctctatgga ccggtgcggc cgcaggaacc cctagtgatg   6180

gagttggcca ctccctctct gcgcgctcgc tcgctcactg aggccgggcg accaaaggtc   6240

gcccgacgcc cgggctttgc ccgggcggcc tcagtgagcg agcgagcgcg cagagaggga   6300

gtggccaa                                                            6308
```

<210> SEQ ID NO 16
<211> LENGTH: 5635
<212> TYPE: DNA
<213> ORGANISM: Adeno-Associate Virus 2

<400> SEQUENCE: 16

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttaattttta aaaagcagtc    180

aaaagtccaa gtggcccttg gcagcattta ctctctctgt ttgctctggt taataatctc    240

aggagcacaa acattcctgg aggcaggaga agaaatcaac atcctggact tatcctctgg    300

gcctgttaat ttttaaaaag cagtcaaaag tccaagtggc ccttggcagc atttactctc    360

tctgtttgct ctggttaata atctcaggag cacaaacatt cctggaggca ggagaagaaa    420

tcaacatcct ggacttatcc tctgggccta gtcgactgga cacaggacgc tgtggtttct    480

gagccagggg gcgactcaga tcccagccag tggacttagc ccctgtttgc tcctccgata    540

actggggtga ccttggttaa tattcaccag cagcctcccc cgttgcccct ctggatccac    600

tgcttaaata cggacgagga cagggccctg tctcctcagc ttcaggcacc accactgacc    660

tgggacagtg aatcgtaagt actagcagct acaatccagc taccattctg cttttatttt    720

atggttggga taaggctgga ttattctgag tccaagctag gcccttttgc taatcatgtt    780

catacctctt atcttcctcc cacagctcct gggcaacgtg ctggtctgtg tgctggccca    840

tcactttggc aaagaattgc gatcgccacc atgcagattg agctgagcac ctgcttcttc    900

ctgtgcctgc tgaggttctg cttctctgcc accaggagat actacctggg ggctgtggag    960

ctgagctggg actacatgca gtctgacctg gggggagctgc ctgtggatgc caggttcccc   1020

cccagagtgc ccaagagctt ccccttcaac acctctgtgg tgtacaagaa gaccctgttt   1080
```

-continued

```
gtggagttca ctgaccacct gttcaacatt gccaagccca ggcccccctg gatgggcctg   1140
ctgggcccca ccatccaggc tgaggtgtat gacactgtgg tgatcaccct gaagaacatg   1200
gccagccacc ctgtgagcct gcatgctgtg gggtgagct actggaaggc ctctgagggg   1260
gctgagtatg atgaccagac cagccagagg gagaaggagg atgacaaggt gttccctggg   1320
ggcagccaca cctatgtgtg gcaggtgctg aaggagaatg gccccatggc ctctgacccc   1380
ctgtgcctga cctacagcta cctgagccat gtggacctgg tgaaggacct gaactctggc   1440
ctgattgggg ccctgctggt gtgcagggag ggcagcctgg ccaaggagaa gacccagacc   1500
ctgcacaagt tcatcctgct gtttgctgtg tttgatgagg gcaagagctg gcactctgaa   1560
accaagaaca gcctgatgca ggacagggat gctgcctctg ccagggcctg gcccaagatg   1620
cacactgtga atggctatgt gaacaggagc ctgcctggcc tgattggctg ccacaggaag   1680
tctgtgtact ggcatgtgat tggcatgggc accacccctg aggtgcacag catcttcctg   1740
gagggccaca ccttcctggt caggaaccac aggcaggcca gcctggagat cagccccatc   1800
accttcctga ctgcccagac cctgctgatg gacctgggcc agttcctgct gttctgccac   1860
atcagcagcc accagcatga tggcatggag gcctatgtga aggtggacag ctgccctgag   1920
gagccccagc tgaggatgaa gaacaatgag gaggctgagg actatgatga tgacctgact   1980
gactctgaga tggatgtggt gaggtttgat gatgacaaca gccccagctt catccagatc   2040
aggtctgtgg ccaagaagca ccccaagacc tgggtgcact acattgctgc tgaggaggag   2100
gactgggact atgcccccct ggtgctggcc cctgatgaca ggagctacaa gagccagtac   2160
ctgaacaatg gcccccagag gattggcagg aagtacaaga aggtcaggtt catggcctac   2220
actgatgaaa ccttcaagac cagggaggcc atccagcatg agtctggcat cctgggcccc   2280
ctgctgtatg gggaggtggg ggacaccctg ctgatcatct tcaagaacca ggccagcagg   2340
ccctacaaca tctacccccca tggcatcact gatgtgaggc ccctgtacag caggaggctg   2400
cccaaggggg tgaagcacct gaaggacttc cccatcctgc ctggggagat cttcaagtac   2460
aagtggactg tgactgtgga ggatggcccc accaagtctg accccaggtg cctgaccaga   2520
tactacagca gctttgtgaa catggagagg gacctggcct ctggcctgat tggcccccctg   2580
ctgatctgct acaaggagtc tgtggaccag aggggcaacc agatcatgtc tgacaagagg   2640
aatgtgatcc tgttctctgt gtttgatgag aacaggagct ggtacctgac tgagaacatc   2700
cagaggttcc tgcccaaccc tgctggggtg cagctggagg accctgagtt ccaggccagc   2760
aacatcatgc acagcatcaa tggctatgtg tttgacagcc tgcagctgtc tgtgtgcctg   2820
catgaggtgg cctactggta catcctgagc attggggccc agactgactt cctgtctgtg   2880
ttcttctctg gctacacctt caagcacaag atggtgtatg aggacaccct gaccctgttc   2940
cccttctctg ggagactgt gttcatgagc atggagaacc ctggcctgtg gattctgggc   3000
tgccacaact ctgacttcag gaacaggggc atgactgccc tgctgaaagt ctccagctgt   3060
gacaagaaca ctggggacta ctatgaggac agctatgagg acatctctgc ctacctgctg   3120
agcaagaaca atgccattga gcccaggagc ttcagccaga accccccagt gctgaagagg   3180
caccagaggg agatcaccag gaccaccctg cagtctgacc aggaggagat tgactatgat   3240
gacaccatct ctgtggagat gaagaaggag gactttgaca tctacgacga ggacgagaac   3300
cagagcccca ggagcttcca gaagaagacc aggcactact tcattgctgc tgtggagagg   3360
ctgtgggact atggcatgag cagcagcccc catgtgctga ggaacagggc ccagtctggc   3420
tctgtgcccc agttcaagaa ggtggtgttc caggagttca ctgatggcag cttcacccag   3480
```

```
cccctgtaca gaggggagct gaatgagcac ctgggcctgc tgggccccta catcagggct   3540
gaggtggagg acaacatcat ggtgaccttc aggaaccagg ccagcaggcc ctacagcttc   3600
tacagcagcc tgatcagcta tgaggaggac cagaggcagg gggctgagcc caggaagaac   3660
tttgtgaagc ccaatgaaac caagacctac ttctggaagg tgcagcacca catggccccc   3720
accaaggatg agtttgactg caaggcctgg gcctacttct ctgatgtgga cctggagaag   3780
gatgtgcact ctggcctgat tggcccccctg ctggtgtgcc acaccaacac cctgaaccct   3840
gcccatggca ggcaggtgac tgtgcaggag tttgccctgt tcttcaccat ctttgatgaa   3900
accaagagct ggtacttcac tgagaacatg gagaggaact gcagggcccc ctgcaacatc   3960
cagatggagg accccacctt caaggagaac tacaggttcc atgccatcaa tggctacatc   4020
atggacaccc tgcctggcct ggtgatggcc caggaccaga ggatcaggtg gtacctgctg   4080
agcatgggca gcaatgagaa catccacagc atccacttct ctggccatgt gttcactgtg   4140
aggaagaagg aggagtacaa gatggccctg tacaacctgt accctggggt gtttgagact   4200
gtggagatgc tgcccagcaa ggctggcatc tggagggtgg agtgcctgat tggggagcac   4260
ctgcatgctg gcatgagcac cctgttcctg gtgtacagca acaagtgcca gacccccctg   4320
ggcatggcct ctggccacat cagggacttc cagatcactg cctctggcca gtatggccag   4380
tgggccccca agctggccag gctgcactac tctggcagca tcaatgcctg gagcaccaag   4440
gagcccttca gctggatcaa ggtggacctg ctggccccca tgatcatcca tggcatcaag   4500
acccaggggg ccaggcagaa gttcagcagc ctgtacatca gccagttcat catcatgtac   4560
agcctggatg gcaagaagtg gcagacctac aggggcaaca gcactggcac cctgatggtg   4620
ttctttggca atgtggacag ctctggcatc aagcacaaca tcttcaaccc ccccatcatt   4680
gccagataca tcaggctgca ccccacccac tacagcatca ggagcaccct gaggatggag   4740
ctgatgggct gtgacctgaa cagctgcagc atgcccctgg gcatggagag caaggccatc   4800
tctgatgccc agatcactgc cagcagctac ttcaccaaca tgtttgccac ctggagcccc   4860
agcaaggcca ggctgcacct gcagggcagg agcaatgcct ggaggcccca ggtcaacaac   4920
cccaaggagt ggctgcaggt ggacttccag aagaccatga aggtgactgg ggtgaccacc   4980
cagggggtga agagcctgct gaccagcatg tatgtgaagg agttcctgat cagcagcagc   5040
caggatggcc accagtggac cctgttcttc cagaatggca aggtgaaggt gttccagggc   5100
aaccaggaca gcttcacccc tgtggtgaac agcctggacc ccccccctgct gaccagatac   5160
ctgaggattc acccccagag ctgggtgcac cagattgccc tgaggatgga ggtgctgggc   5220
tgtgaggccc aggacctgta ctgacctcga gctgtgcctt ctagttgcca gccatctgtt   5280
gtttgcccct cccccgtgcc ttccttgacc ctggaaggtg ccactcccac tgtcctttcc   5340
taataaaatg aggaaattgc atcgcattgt ctgagtaggt gtcattctat tctggggggt   5400
ggggtggggc aggacagcaa gggggaggat tgggaagaca atagcaggca tgctggggat   5460
gcggtgggct ctatggaccg gtgcggccgc aggaacccct agtgatggag ttggccactc   5520
cctctctgcg cgctcgctcg ctcactgagg ccgggcgacc aaaggtcgcc cgacgcccgg   5580
gctttgcccg ggcggcctca gtgagcgagc gagcgcgcag agagggagtg gccaa        5635
```

<210> SEQ ID NO 17
<211> LENGTH: 6962
<212> TYPE: DNA
<213> ORGANISM: Adeno-Associated Virus 2

<400> SEQUENCE: 17
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgta ggctcagagg cacacaggag 180
tttctgggct caccctgccc ccttccaacc cctcagttcc catcctccag cagctgtttg 240
tgtgctgcct ctgaagtcca cactgaacaa acttcagcct actcatgtcc ctaaaatggg 300
caaacattgc aagcagcaaa cagcaaacac acagccctcc ctgcctgctg accttggagc 360
tggggcagag gtcagagacc tctctgggcc catgccacct ccaacatcca ctcgacccct 420
tggaatttcg gtggagagga gcagaggttg tcctggcgtg gtttaggtag tgtgagaggg 480
gtcgacaggc tcagaggcac acaggagttt ctgggctcac cctgccccct tccaacccct 540
cagttcccat cctccagcag ctgtttgtgt gctgcctctg aagtccacac tgaacaaact 600
tcagcctact catgtcccta aaatgggcaa acattgcaag cagcaaacag caaacacaca 660
gccctccctg cctgctgacc ttggagctgg ggcagaggtc agagacctct ctgggcccat 720
gccacctcca acatccactc gaccccttgg aatttcggtg gagaggagca gaggttgtcc 780
tggcgtggtt taggtagtgt gagaggggtc gacgttaatt tttaaaaagc agtcaaaagt 840
ccaagtggcc cttggcagca tttactctct ctgtttgctc tggttaataa tctcaggagc 900
acaaacattc ctggaggcag gagaagaaat caacatcctg gacttatcct ctgggcctgt 960
taatttttaa aaagcagtca aaagtccaag tggcccttgg cagcatttac tctctctgtt 1020
tgctctggtt aataatctca ggagcacaaa cattcctgga ggcaggagaa gaaatcaaca 1080
tcctggactt atcctctggg cctaggcctg aggctggtca aaattgaacc tcctcctgct 1140
ctgagcagcc tgggggggcag actaagcaga gggctgtgca gacccacata aagagcctac 1200
tgtgtgccag gcacttcacc cgaggcactt cacaagcatg cttgggaatg aaacttccaa 1260
ctctttggga tgcaggtgaa acagttcctg gttcagagag gtgaagcggc ctgcctgagg 1320
cagcacagct cttctttaca gatgtgcttc cccacctcta ccctgtctca cggcccccca 1380
tgccagcctg acggttgtgt ctgcctcagt catgctccat tttccatcg ggaccatcaa 1440 gagggtgttt gtgtctaagg ctgactgggt aactttggat gagcggtctc tccgctctga 1500
gcctgtttcc tcatctgtca aatgggctct aacccactct gatctcccag ggcggcagta 1560
agtcttcagc atcaggcatt ttggggtgac tcagtaaatg gtagatcttg ctaccagtgg 1620
aacagccact aaggattctg cagtgagagc agagggccag ctaagtggta ctctcccaga 1680
gactgtctga ctcacgccac cccctccacc ttggacacag gacgctgtgg tttctgagcc 1740
aggtacaatg actcctttcg gtaagtgcag tggaagctgt acactgccca ggcaaagcgt 1800
ccgggcagcg taggcgggcg actcagatcc cagccagtgg acttagcccc tgtttgctcc 1860
tccgataact ggggtgacct tggttaatat tcaccagcag cctcccccgt tgcccctctg 1920
gatccactgc ttaaatacgg acgaggacag ggccctgtct cctcagcttc aggcaccacc 1980
actgacctgg gacagtgaat cgtaagtact agcagctaca atccagctac cattctgctt 2040
ttattttatg gttgggataa ggctggatta ttctgagtcc aagctaggcc cttttgctaa 2100
tcatgttcat acctcttatc ttcctcccac agctcctggg caacgtgctg gtctgtgtgc 2160
tggcccatca ctttggcaaa gaattgcgat cgccaccatg cagattgagc tgagcacctg 2220
cttcttcctg tgcctgctga ggttctgctt ctctgccacc aggagatact acctgggggc 2280
tgtggagctg agctgggact acatgcagtc tgacctgggg gagctgcctg tggatgccag 2340

```
gttccccccc agagtgccca agagcttccc cttcaacacc tctgtggtgt acaagaagac   2400
cctgtttgtg gagttcactg accacctgtt caacattgcc aagcccaggc ccccctggat   2460
gggcctgctg ggccccacca tccaggctga ggtgtatgac actgtggtga tcaccctgaa   2520
gaacatggcc agccaccctg tgagcctgca tgctgtgggg gtgagctact ggaaggcctc   2580
tgagggggct gagtatgatg accagaccag ccagagggag aaggaggatg acaaggtgtt   2640
ccctgggggc agccacacct atgtgtggca ggtgctgaag gagaatggcc ccatggcctc   2700
tgaccccctg tgcctgacct acagctacct gagccatgtg gacctggtga aggacctgaa   2760
ctctggcctg attggggccc tgctggtgtg cagggagggc agcctggcca aggagaagac   2820
ccagaccctg cacaagttca tcctgctgtt tgctgtgttt gatgagggca agagctggca   2880
ctctgaaacc aagaacagcc tgatgcagga cagggatgct gcctctgcca gggcctggcc   2940
caagatgcac actgtgaatg gctatgtgaa caggagcctg cctggcctga ttggctgcca   3000
caggaagtct gtgtactggc atgtgattgg catgggcacc acccctgagg tgcacagcat   3060
cttcctggag ggccacacct tcctggtcag gaaccacagg caggccagcc tggagatcag   3120
ccccatcacc ttcctgactg cccagaccct gctgatggac ctgggccagt tcctgctgtt   3180
ctgccacatc agcagccacc agcatgatgg catggaggcc tatgtgaagg tggacagctg   3240
ccctgaggag ccccagctga ggatgaagaa caatgaggag gctgaggact atgatgatga   3300
cctgactgac tctgagatgg atgtggtgag gtttgatgat gacaacagcc ccagcttcat   3360
ccagatcagg tctgtggcca agaagcaccc caagacctgg gtgcactaca ttgctgctga   3420
ggaggaggac tgggactatg ccccccctggt gctggcccct gatgacagga gctacaagag   3480
ccagtacctg aacaatggcc cccagaggat tggcaggaag tacaagaagg tcaggttcat   3540
ggcctacact gatgaaacct tcaagaccag ggaggccatc cagcatgagt ctggcatcct   3600
gggcccccctg ctgtatgggg aggtggggga caccctgctg atcatcttca agaaccaggc   3660
cagcaggccc tacaacatct acccccatgg catcactgat gtgaggcccc tgtacagcag   3720
gaggctgccc aagggggtga agcacctgaa ggacttcccc atcctgcctg ggagatctt    3780
caagtacaag tggactgtga ctgtggagga tggccccacc aagtctgacc ccaggtgcct   3840
gaccagatac tacagcagct ttgtgaacat ggagagggac ctggcctctg gcctgattgg   3900
ccccctgctg atctgctaca aggagtctgt ggaccagagg ggcaaccaga tcatgtctga   3960
caagaggaat gtgatcctgt tctctgtgtt tgatgagaac aggagctggt acctgactga   4020
gaacatccag aggttcctgc ccaaccctgc tggggtgcag ctggaggacc ctgagttcca   4080
ggccagcaac atcatgcaca gcatcaatgg ctatgtgttt gacagcctgc agctgtctgt   4140
gtgcctgcat gaggtggcct actggtacat cctgagcatt ggggcccaga ctgacttcct   4200
gtctgtgttc ttctctggct acaccttcaa gcacaagatg gtgtatgagg acaccctgac   4260
cctgttcccc ttctctgggg agactgtgtt catgagcatg gagaaccctg gcctgtggat   4320
tctgggctgc cacaactctg acttcaggaa caggggcatg actgccctgc tgaaagtctc   4380
cagctgtgac aagaacactg gggactacta tgaggacagc tatgaggaca tctctgccta   4440
cctgctgagc aagaacaatg ccattgagcc caggagcttc agccagaacc ccccagtgct   4500
gaagaggcac cagagggaga tcaccaggac caccctgcag tctgaccagg aggagattga   4560
ctatgatgac accatctctg tggagatgaa gaaggaggac tttgacatct acgacgagga   4620
cgagaaccag agccccagga gcttccagaa gaagaccagg cactacttca ttgctgctgt   4680
```

-continued

```
ggagaggctg tgggactatg gcatgagcag cagcccccat gtgctgagga acagggccca   4740
gtctggctct gtgccccagt tcaagaaggt ggtgttccag gagttcactg atggcagctt   4800
cacccagccc ctgtacagag gggagctgaa tgagcacctg ggcctgctgg gcccctacat   4860
cagggctgag gtggaggaca acatcatggt gaccttcagg aaccaggcca gcaggcccta   4920
cagcttctac agcagcctga tcagctatga ggaggaccag aggcaggggg ctgagcccag   4980
gaagaacttt gtgaagccca atgaaaccaa gacctacttc tggaaggtgc agcaccacat   5040
ggcccccacc aaggatgagt ttgactgcaa ggcctgggcc tacttctctg atgtggacct   5100
ggagaaggat gtgcactctg gcctgattgg cccccctgctg gtgtgccaca ccaacaccct   5160
gaaccctgcc catggcaggc aggtgactgt gcaggagttt gccctgttct tcaccatctt   5220
tgatgaaacc aagagctggt acttcactga gaacatggag aggaactgca gggcccccctg   5280
caacatccag atggaggacc ccaccttcaa ggagaactac aggttccatg ccatcaatgg   5340
ctacatcatg gacaccctgc ctggcctggt gatggcccag gaccagagga tcaggtggta   5400
cctgctgagc atgggcagca atgagaacat ccacagcatc cacttctctg gccatgtgtt   5460
cactgtgagg aagaaggagg agtacaagat ggccctgtac aacctgtacc ctggggtgtt   5520
tgagactgtg gagatgctgc ccagcaaggc tggcatctgg agggtggagt gcctgattgg   5580
ggagcacctg catgctggca tgagcaccct gttcctggtg tacagcaaca agtgccagac   5640
ccccctgggc atggcctctg gccacatcag ggacttccag atcactgcct ctggccagta   5700
tggccagtgg gcccccaagc tggccaggct gcactactct ggcagcatca atgcctggag   5760
caccaaggag cccttcagct ggatcaaggt ggacctgctg gcccccatga tcatccatgg   5820
catcaagacc cagggggcca ggcagaagtt cagcagcctg tacatcagcc agttcatcat   5880
catgtacagc ctggatggca agaagtggca gacctacagg ggcaacagca ctggcaccct   5940
gatggtgttc tttggcaatg tggacagctc tggcatcaag cacaacatct tcaacccccc   6000
catcattgcc agatacatca ggctgcaccc cacccactac agcatcagga gcaccctgag   6060
gatggagctg atgggctgtg acctgaacag ctgcagcatg cccctgggca tggagagcaa   6120
ggccatctct gatgcccaga tcactgccag cagctacttc accaacatgt ttgccacctg   6180
gagccccagc aaggccaggc tgcacctgca gggcaggagc aatgcctgga ggccccaggt   6240
caacaacccc aaggagtggc tgcaggtgga cttccagaag accatgaagg tgactggggt   6300
gaccacccag gggtgaaga gcctgctgac cagcatgtat gtgaaggagt tcctgatcag   6360
cagcagccag gatggccacc agtggaccct gttcttccag aatggcaagg tgaaggtgtt   6420
ccagggcaac caggacagct tcacccctgt ggtgaacagc ctggaccccc ccctgctgac   6480
cagatacctg aggattcacc cccagagctg ggtgcaccag attgccctga ggatggaggt   6540
gctgggctgt gaggcccagg acctgtactg acctcgagct gtgccttcta gttgccagcc   6600
atctgttgtt tgcccctccc ccgtgccttc cttgaccctg gaaggtgcca ctcccactgt   6660
cctttcctaa taaaatgagg aaattgcatc gcattgtctg agtaggtgtc attctattct   6720
ggggggtggg gtggggcagg acagcaaggg ggaggattgg gaagacaata gcaggcatgc   6780
tggggatgcg gtgggctcta tggaccggtg cggccgcagg aacccctagt gatggagttg   6840
gccactccct ctctgcgcgc tcgctcgctc actgaggccg ggcgaccaaa ggtcgcccga   6900
cgcccgggct ttgcccgggc ggcctcagtg agcgagcgag cgcgcagaga gggagtggcc   6960
aa                                                                  6962
```

-continued

<210> SEQ ID NO 18
<211> LENGTH: 6289
<212> TYPE: DNA
<213> ORGANISM: Adeno-Associated Virus 2

<400> SEQUENCE: 18
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgta ggctcagagg cacacaggag 180
tttctgggct caccctgccc ccttccaacc cctcagttcc catcctccag cagctgtttg 240
tgtgctgcct ctgaagtcca cactgaacaa acttcagcct actcatgtcc ctaaaatggg 300
caaacattgc aagcagcaaa cagcaaacac acagccctcc ctgcctgctg accttggagc 360
tggggcagag gtcagagacc tctctgggcc catgccacct ccaacatcca ctcgacccct 420
tggaatttcg gtggagagga gcagaggttg tcctggcgtg gtttaggtag tgtgagaggg 480
gtcgacaggc tcagaggcac acaggagttt ctgggctcac cctgccccct tccaacccct 540
cagttcccat cctccagcag ctgtttgtgt gctgcctctg aagtccacac tgaacaaact 600
tcagcctact catgtcccta aaatgggcaa acattgcaag cagcaaacag caaacacaca 660
gccctccctg cctgctgacc ttggagctgg ggcagaggtc agagacctct ctgggcccat 720
gccacctcca acatccactc gaccccttgg aatttcggtg gagaggagca gaggttgtcc 780
tggcgtggtt taggtagtgt gagaggggtc gacgttaatt tttaaaaagc agtcaaaagt 840
ccaagtggcc cttggcagca tttactctct ctgtttgctc tggttaataa tctcaggagc 900
acaaacattc ctggaggcag gagaagaaat caacatcctg gacttatcct ctgggcctgt 960
taatttttaa aaagcagtca aaagtccaag tggcccttgg cagcatttac tctctctgtt 1020
tgctctggtt aataatctca ggagcacaaa cattcctgga ggcaggagaa gaaatcaaca 1080
tcctggactt atcctctggg cctagtcgac tggacacagg acgctgtggt ttctgagcca 1140
gggggcgact cagatcccag ccagtggact tagcccctgt ttgctcctcc gataactggg 1200
gtgaccttgg ttaatattca ccagcagcct cccccgttgc cctctggat ccactgctta 1260 aatacggacg aggacagggc cctgtctcct cagcttcagg caccaccact gacctgggac 1320
agtgaatcgt aagtactagc agctacaatc cagctaccat tctgctttta ttttatggtt 1380
gggataaggc tggattattc tgagtccaag ctaggccctt ttgctaatca tgttcatacc 1440
tcttatcttc ctcccacagc tcctgggcaa cgtgctggtc tgtgtgctgg cccatcactt 1500
tggcaaagaa ttgcgatcgc caccatgcag attgagctga gcacctgctt cttcctgtgc 1560
ctgctgaggt tctgcttctc tgccaccagg agatactacc tgggggctgt ggagctgagc 1620
tgggactaca tgcagtctga cctgggggag ctgcctgtgg atgccaggtt cccccccaga 1680
gtgcccaaga gcttcccctt caacacctct gtggtgtaca agaagaccct gtttgtggag 1740
ttcactgacc acctgttcaa cattgccaag cccaggcccc cctggatggg cctgctgggc 1800
cccaccatcc aggctgaggt gtatgacact gtggtgatca ccctgaagaa catggccagc 1860
caccctgtga gcctgcatgc tgtgggggtg agctactgga aggcctctga gggggctgag 1920
tatgatgacc agaccagcca gagggagaag gaggatgaca aggtgttccc tgggggcagc 1980
cacacctatg tgtggcaggt gctgaaggag aatggcccca tggcctctga ccccctgtgc 2040
ctgacctaca gctacctgag ccatgtggac ctggtgaagg acctgaactc tggcctgatt 2100
ggggccctgc tggtgtgcag ggagggcagc ctggccaagg agaagaccca gaccctgcac 2160

-continued

```
aagttcatcc tgctgtttgc tgtgtttgat gagggcaaga gctggcactc tgaaaccaag   2220
aacagcctga tgcaggacag ggatgctgcc tctgccaggg cctggcccaa gatgcacact   2280
gtgaatggct atgtgaacag gagcctgcct ggcctgattg gctgccacag gaagtctgtg   2340
tactggcatg tgattggcat gggcaccacc cctgaggtgc acagcatctt cctggagggc   2400
cacaccttcc tggtcaggaa ccacaggcag gccagcctgg agatcagccc catcaccttc   2460
ctgactgccc agaccctgct gatggacctg ggccagttcc tgctgttctg ccacatcagc   2520
agccaccagc atgatggcat ggaggcctat gtgaaggtgg acagctgccc tgaggagccc   2580
cagctgagga tgaagaacaa tgaggaggct gaggactatg atgatgacct gactgactct   2640
gagatggatg tggtgaggtt tgatgatgac aacagcccca gcttcatcca gatcaggtct   2700
gtggccaaga agcaccccaa gacctgggtg cactacattg ctgctgagga ggaggactgg   2760
gactatgccc ccctggtgct ggcccctgat gacaggagct acaagagcca gtacctgaac   2820
aatggccccc agaggattgg caggaagtac aagaaggtca ggttcatggc ctacactgat   2880
gaaaccttca agaccaggga ggccatccag catgagtctg gcatcctggg cccccctgctg   2940
tatggggagg tgggggacac cctgctgatc atcttcaaga accaggccag caggccctac   3000
aacatctacc cccatggcat cactgatgtg aggcccctgt acagcaggag gctgcccaag   3060
ggggtgaagc acctgaagga cttccccatc ctgcctgggg agatcttcaa gtacaagtgg   3120
actgtgactg tggaggatgg ccccaccaag tctgacccca ggtgcctgac cagatactac   3180
agcagctttg tgaacatgga gagggacctg gcctctggcc tgattggccc cctgctgatc   3240
tgctacaagg agtctgtgga ccagaggggc aaccagatca tgtctgacaa gaggaatgtg   3300
atcctgttct ctgtgtttga tgagaacagg agctggtacc tgactgagaa catccagagg   3360
ttcctgccca accctgctgg ggtgcagctg gaggaccctg agttccaggc cagcaacatc   3420
atgcacagca tcaatggcta tgtgtttgac agcctgcagc tgtctgtgtg cctgcatgag   3480
gtggcctact ggtacatcct gagcattggg gcccagactg acttcctgtc tgtgttcttc   3540
tctggctaca ccttcaagca caagatggtg tatgaggaca ccctgaccct gttccccttc   3600
tctggggaga ctgtgttcat gagcatggag aaccctggcc tgtggattct gggctgccac   3660
aactctgact tcaggaacag ggcatgact gccctgctga aagtctccag ctgtgacaag   3720
aacactgggg actactatga ggacagctat gaggacatct ctgcctacct gctgagcaag   3780
aacaatgcca ttgagcccag gagcttcagc cagaaccccc cagtgctgaa gaggcaccag   3840
agggagatca ccaggaccac cctgcagtct gaccaggagg agattgacta tgatgacacc   3900
atctctgtgg agatgaagaa ggaggacttt gacatctacg acgaggacga gaaccagagc   3960
cccaggagct tccagaagaa gaccaggcac tacttcattg ctgctgtgga gaggctgtgg   4020
gactatggca tgagcagcag cccccatgtg ctgaggaaca gggcccagtc tggctctgtg   4080
ccccagttca agaaggtggt gttccaggag ttcactgatg gcagcttcac ccagcccctg   4140
tacagagggg agctgaatga gcacctgggc ctgctgggcc cctacatcag ggctgaggtg   4200
gaggacaaca tcatggtgac cttcaggaac caggccagca ggccctacag cttctacagc   4260
agcctgatca gctatgagga ggaccagagg caggggggctg agcccaggaa gaactttgtg   4320
aagcccaatg aaaccaagac ctacttctgg aaggtgcagc accacatggc cccccaccaag   4380
gatgagtttg actgcaaggc ctgggcctac ttctctgatg tggacctgga gaaggatgtg   4440
cactctggcc tgattggccc cctgctggtg tgccacacca acaccctgaa ccctgcccat   4500
ggcaggcagg tgactgtgca ggagtttgcc ctgttcttca ccatctttga tgaaaccaag   4560
```

-continued agctggtact tcactgagaa catggagagg aactgcaggg ccccctgcaa catccagatg 4620
gaggacccca ccttcaagga gaactacagg ttccatgcca tcaatggcta catcatggac 4680
accctgcctg gcctggtgat ggcccaggac cagaggatca ggtggtacct gctgagcatg 4740
ggcagcaatg agaacatcca cagcatccac ttctctggcc atgtgttcac tgtgaggaag 4800
aaggaggagt acaagatggc cctgtacaac ctgtaccctg ggtgtttga gactgtggag 4860 atgctgccca gcaaggctgg catctggagg gtggagtgcc tgattgggga gcacctgcat 4920
gctggcatga gcaccctgtt cctggtgtac agcaacaagt gccagacccc cctgggcatg 4980
gcctctggcc acatcaggga cttccagatc actgcctctg gccagtatgg ccagtgggcc 5040
cccaagctgg ccaggctgca ctactctggc agcatcaatg cctggagcac caaggagccc 5100
ttcagctgga tcaaggtgga cctgctggcc cccatgatca tccatggcat caagacccag 5160
ggggccaggc agaagttcag cagcctgtac atcagccagt tcatcatcat gtacagcctg 5220
gatggcaaga agtggcagac ctacaggggc aacagcactg gcaccctgat ggtgttcttt 5280
ggcaatgtgg acagctctgg catcaagcac aacatcttca acccccccat cattgccaga 5340
tacatcaggc tgcaccccac ccactacagc atcaggagca ccctgaggat ggagctgatg 5400
ggctgtgacc tgaacagctg cagcatgccc ctgggcatgg agagcaaggc catctctgat 5460
gcccagatca ctgccagcag ctacttcacc aacatgtttg ccacctggag ccccagcaag 5520
gccaggctgc acctgcaggg caggagcaat gcctggaggc cccaggtcaa caaccccaag 5580
gagtggctgc aggtggactt ccagaagacc atgaaggtga ctggggtgac cacccagggg 5640
gtgaagagcc tgctgaccag catgtatgtg aaggagttcc tgatcagcag cagccaggat 5700
ggccaccagt ggaccctgtt cttccagaat ggcaaggtga aggtgttcca gggcaaccag 5760
gacagcttca cccctgtggt gaacagcctg gacccccccc tgctgaccag atacctgagg 5820
attcaccccc agagctgggt gcaccagatt gccctgagga tggaggtgct gggctgtgag 5880
gcccaggacc tgtactgacc tcgagctgtg ccttctagtt gccagccatc tgttgtttgc 5940
ccctcccccg tgccttcctt gaccctggaa ggtgccactc ccactgtcct ttcctaataa 6000
aatgaggaaa ttgcatcgca ttgtctgagt aggtgtcatt ctattctggg gggtggggtg 6060
gggcaggaca gcaaggggga ggattgggaa gacaatagca ggcatgctgg ggatgcggtg 6120
ggctctatgg accggtgcgg ccgcaggaac ccctagtgat ggagttggcc actccctctc 6180
tgcgcgctcg ctcgctcact gaggccgggc gaccaaaggt cgcccgacgc ccgggctttg 6240
cccgggcggc ctcagtgagc gagcgagcgc gcagagaggg agtggccaa 6289

<210> SEQ ID NO 19
<211> LENGTH: 5430
<212> TYPE: DNA
<213> ORGANISM: Adeno-Associated Virus 2

<400> SEQUENCE: 19
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgacgt ggacttagcc 180
cctgtttgct cctccgataa ctggggtgac cttggttaat attcaccagc agcctccccg 240
tggacttagc ccctgtttgc tcctccgata actggggtga ccttggttaa tattcaccag 300
cagcctcccc acgcgaaacg tcgactggac acaggacgct gtggtttctg agccaggggg 360

-continued

```
cgactcagat cccagccagt ggacttagcc cctgtttgct cctccgataa ctggggtgac    420
cttggttaat attcaccagc agcctccccc gttgcccctc tggatccact gcttaaatac    480
ggacgaggac agggccctgt ctcctcagct tcaggcacca ccactgacct gggacagtga    540
atcgtaagta ctagcagcta caatccagct accattctgc ttttatttta tggttgggat    600
aaggctggat tattctgagt ccaagctagg cccttttgct aatcatgttc atacctctta    660
tcttcctccc acagctcctg ggcaacgtgc tggtctgtgt gctggcccat cactttggca    720
aagaattgcg atcgccacca tgcagattga gctgagcacc tgcttcttcc tgtgcctgct    780
gaggttctgc ttctctgcca ccaggagata ctacctgggg gctgtggagc tgagctggga    840
ctacatgcag tctgacctgg gggagctgcc tgtggatgcc aggttccccc ccagagtgcc    900
caagagcttc cccttcaaca cctctgtggt gtacaagaag accctgtttg tggagttcac    960
tgaccacctg ttcaacattg ccaagcccag gccccccctgg atgggcctgc tgggccccac   1020
catccaggct gaggtgtatg acactgtggt gatcaccctg aagaacatgg ccagccaccc   1080
tgtgagcctg catgctgtgg gggtgagcta ctggaaggcc tctgaggggg ctgagtatga   1140
tgaccagacc agccagaggg agaaggagga tgacaaggtg ttccctgggg gcagccacac   1200
ctatgtgtgg caggtgctga aggagaatgg ccccatggcc tctgaccccc tgtgcctgac   1260
ctacagctac ctgagccatg tggacctggt gaaggacctg aactctggcc tgattggggc   1320
cctgctggtg tgcagggagg gcagcctggc caaggagaag acccagaccc tgcacaagtt   1380
catcctgctg tttgctgtgt ttgatgaggg caagagctgg cactctgaaa ccaagaacag   1440
cctgatgcag gacagggatg ctgcctctgc cagggcctgg cccaagatgc acactgtgaa   1500
tggctatgtg aacaggagcc tgcctggcct gattggctgc cacaggaagt ctgtgtactg   1560
gcatgtgatt ggcatgggca ccacccctga ggtgcacagc atcttcctgg agggccacac   1620
cttcctggtc aggaaccaca ggcaggccag cctggagatc agccccatca ccttcctgac   1680
tgcccagacc ctgctgatgg acctgggcca gttcctgctg ttctgccaca tcagcagcca   1740
ccagcatgat ggcatggagg cctatgtgaa ggtggacagc tgccctgagg agccccagct   1800
gaggatgaag aacaatgagg aggctgagga ctatgatgat gacctgactg actctgagat   1860
ggatgtggtg aggtttgatg atgacaacag ccccagcttc atccagatca ggtctgtggc   1920
caagaagcac cccaagacct gggtgcacta cattgctgct gaggaggagg actgggacta   1980
tgccccccctg gtgctggccc ctgatgacag gagctacaag agccagtacc tgaacaatgg   2040
cccccagagg attggcagga agtacaagaa ggtcaggttc atggcctaca ctgatgaaac   2100
cttcaagacc agggaggcca tccagcatga gtctggcatc ctgggccccc tgctgtatgg   2160
ggaggtgggg gacaccctgc tgatcatctt caagaaccag gccagcaggc cctacaacat   2220
ctacccccat ggcatcactg atgtgaggcc cctgtacagc aggaggctgc ccaagggggt   2280
gaagcacctg aaggacttcc ccatcctgcc tggggagatc ttcaagtaca agtggactgt   2340
gactgtggag gatggcccca ccaagtctga ccccaggtgc ctgaccagat actacagcag   2400
ctttgtgaac atggagaggg acctggcctc tggcctgatt ggccccctgc tgatctgcta   2460
caaggagtct gtggaccaga ggggcaacca gatcatgtct gacaagagga atgtgatcct   2520
gttctctgtg tttgatgaga acaggagctg gtacctgact gagaacatcc agaggttcct   2580
gcccaaccct gctggggtgc agctggagga ccctgagttc caggccagca acatcatgca   2640
cagcatcaat ggctatgtgt ttgacagcct gcagctgtct gtgtgcctgc atgaggtggc   2700
ctactggtac atcctgagca ttggggccca gactgacttc ctgtctgtgt tcttctctgg   2760
```

ctacaccttc aagcacaaga tggtgtatga ggacaccctg accctgttcc ccttctctgg 2820
ggagactgtg ttcatgagca tggagaaccc tggcctgtgg attctgggct gccacaactc 2880
tgacttcagg aacaggggca tgactgccct gctgaaagtc tccagctgtg acaagaacac 2940
tggggactac tatgaggaca gctatgagga catctctgcc tacctgctga gcaagaacaa 3000
tgccattgag cccaggagct tcagccagaa ccccccagtg ctgaagaggc accagaggga 3060
gatcaccagg accaccctgc agtctgacca ggaggagatt gactatgatg acaccatctc 3120
tgtggagatg aagaaggagg actttgacat ctacgacgag gacgagaacc agagccccag 3180
gagcttccag aagaagacca ggcactactt cattgctgct gtggagaggc tgtgggacta 3240
tggcatgagc agcagccccc atgtgctgag gaacagggcc cagtctggct ctgtgcccca 3300
gttcaagaag gtggtgttcc aggagttcac tgatggcagc ttcacccagc ccctgtacag 3360
aggggagctg aatgagcacc tgggcctgct gggcccctac atcagggctg aggtggagga 3420
caacatcatg gtgaccttca ggaaccaggc cagcaggccc tacagcttct acagcagcct 3480
gatcagctat gaggaggacc agaggcaggg ggctgagccc aggaagaact ttgtgaagcc 3540
caatgaaacc aagacctact tctggaaggt gcagcaccac atggccccca ccaaggatga 3600
gtttgactgc aaggcctggg cctacttctc tgatgtggac ctggagaagg atgtgcactc 3660
tggcctgatt ggcccccctgc tggtgtgcca caccaacacc ctgaaccctg cccatggcag 3720
gcaggtgact gtgcaggagt ttgccctgtt cttcaccatc tttgatgaaa ccaagagctg 3780
gtacttcact gagaacatgg agaggaactg cagggccccc tgcaacatcc agatggagga 3840
ccccaccttc aaggagaact acaggttcca tgccatcaat ggctacatca tggacaccct 3900
gcctggcctg gtgatggccc aggaccagag gatcaggtgg tacctgctga gcatgggcag 3960
caatgagaac atccacagca tccacttctc tggccatgtg ttcactgtga ggaagaagga 4020
ggagtacaag atggccctgt acaacctgta ccctggggtg tttgagactg tggagatgct 4080
gcccagcaag gctggcatct ggagggtgga gtgcctgatt ggggagcacc tgcatgctgg 4140
catgagcacc ctgttcctgg tgtacagcaa caagtgccag accccccctgg gcatggcctc 4200 tggccacatc agggacttcc agatcactgc ctctggccag tatggccagt gggcccccaa 4260
gctggccagg ctgcactact ctggcagcat caatgcctgg agcaccaagg agcccttcag 4320
ctggatcaag gtggacctgc tggcccccat gatcatccat ggcatcaaga cccagggggc 4380
caggcagaag ttcagcagcc tgtacatcag ccagttcatc atcatgtaca gcctggatgg 4440
caagaagtgg cagacctaca ggggcaacag cactggcacc ctgatggtgt tctttggcaa 4500
tgtggacagc tctggcatca agcacaacat cttcaacccc cccatcattg ccagatacat 4560
caggctgcac cccacccact acagcatcag gagcaccctg aggatggagc tgatgggctg 4620
tgacctgaac agctgcagca tgcccctggg catggagagc aaggccatct ctgatgccca 4680
gatcactgcc agcagctact tcaccaacat gtttgccacc tggagcccca gcaaggccag 4740
gctgcacctg cagggcagga gcaatgcctg gaggccccag gtcaacaacc ccaaggagtg 4800
gctgcaggtg gacttccaga agaccatgaa ggtgactggg gtgaccaccc agggggtgaa 4860
gagcctgctg accagcatgt atgtgaagga gttcctgatc agcagcagcc aggatggcca 4920
ccagtggacc ctgttcttcc agaatggcaa ggtgaaggtg ttccagggca accaggacag 4980
cttcacccct gtggtgaaca gcctggaccc cccccctgctg accagatacc tgaggattca 5040
cccccagagc tgggtgcacc agattgccct gaggatggag gtgctgggct gtgaggccca 5100

-continued

```
ggacctgtac tgacctcgag gcactgtcct ttcctaataa aatgaggaaa ttgcatcgca   5160

ttgtctgagt aggtgtcatt ctattctggg gggtggggtg gggcaggaca gcaaggggga   5220

ggattgggaa gacaatagca ggcatgctgg ggatgcggtg ggctctatgg gcacgtggcg   5280

gccgcaggaa cccctagtga tggagttggc cactccctct ctgcgcgctc gctcgctcac   5340

tgaggccggg cgaccaaagg tcgcccgacg cccgggcttt gcccgggcgg cctcagtgag   5400

cgagcgagcg cgcagagagg gagtggccaa                                     5430
```

```
<210> SEQ ID NO 20
<211> LENGTH: 5779
<212> TYPE: DNA
<213> ORGANISM: Adeno-Associated Virus 2

<400> SEQUENCE: 20

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgacgt ggacttagcc    180

cctgtttgct cctccgataa ctggggtgac cttggttaat attcaccagc agcctccccg    240

tggacttagc ccctgtttgc tcctccgata actggggtga ccttggttaa tattcaccag    300

cagcctcccc acgcgaaacg tcgactggac acaggacgct gtggtttctg agccaggggg    360

cgactcagat cccagccagt ggacttagcc cctgtttgct cctccgataa ctggggtgac    420

cttggttaat attcaccagc agcctccccc gttgcccctc tggatccact gcttaaatac    480

ggacgaggac agggccctgt ctcctcagct tcaggcacca ccactgacct gggacagtga    540

atcgtaagta ctagcagcta caatccagct accattctgc ttttatttta tggttgggat    600

aaggctggat tattctgagt ccaagctagg cccttttgct aatcatgttc atacctctta    660

tcttcctccc acagctcctg ggcaacgtgc tggtctgtgt gctggcccat cactttggca    720

aagaattgcg atcgccacca tgcagattga gctgagcacc tgcttcttcc tgtgcctgct    780

gaggttctgc ttctctgcca ccaggagata ctacctgggg gctgtggagc tgagctggga    840

ctacatgcag tctgacctgg gggagctgcc tgtggatgcc aggttccccc ccagagtgcc    900

caagagcttc cccttcaaca cctctgtggt gtacaagaag accctgtttg tggagttcac    960

tgaccacctg ttcaacattg ccaagcccag gccccccctgg atgggcctgc tgggccccac   1020

catccaggct gaggtgtatg acactgtggt gatcaccctg aagaacatgg ccagccaccc   1080

tgtgagcctg catgctgtgg gggtgagcta ctggaaggcc tctgaggggg ctgagtatga   1140

tgaccagacc agccagaggg agaaggagga tgacaaggtg ttccctgggg gcagccacac   1200

ctatgtgtgg caggtgctga aggagaatgg ccccatggcc tctgaccccc tgtgcctgac   1260

ctacagctac ctgagccatg tggacctggt gaaggacctg aactctggcc tgattggggc   1320

cctgctggtg tgcagggagg gcagcctggc caaggagaag acccagaccc tgcacaagtt   1380

catcctgctg tttgctgtgt ttgatgaggg caagagctgg cactctgaaa ccaagaacag   1440

cctgatgcag gacagggatg ctgcctctgc cagggcctgg cccaagatgc acactgtgaa   1500

tggctatgtg aacaggagcc tgcctggcct gattggctgc cacaggaagt ctgtgtactg   1560

gcatgtgatt ggcatgggca ccacccctga ggtgcacagc atcttcctgg agggccacac   1620

cttcctggtc aggaaccaca ggcaggccag cctggagatc agccccatca ccttcctgac   1680

tgcccagacc ctgctgatgg acctgggcca gttcctgctg ttctgccaca tcagcagcca   1740

ccagcatgat ggcatggagg cctatgtgaa ggtggacagc tgccctgagg agccccagct   1800
```

-continued

```
gaggatgaag aacaatgagg aggctgagga ctatgatgat gacctgactg actctgagat   1860
ggatgtggtg aggtttgatg atgacaacag ccccagcttc atccagatca ggtctgtggc   1920
caagaagcac cccaagacct gggtgcacta cattgctgct gaggaggagg actgggacta   1980
tgccccccctg gtgctggccc ctgatgacag gagctacaag agccagtacc tgaacaatgg   2040
cccccagagg attggcagga agtacaagaa ggtcaggttc atggcctaca ctgatgaaac   2100
cttcaagacc agggaggcca tccagcatga gtctggcatc ctgggccccc tgctgtatgg   2160
ggaggtgggg gacaccctgc tgatcatctt caagaaccag gccagcaggc cctacaacat   2220
ctacccccat ggcatcactg atgtgaggcc cctgtacagc aggaggctgc ccaagggggt   2280
gaagcacctg aaggacttcc ccatcctgcc tggggagatc ttcaagtaca agtggactgt   2340
gactgtggag gatggcccca ccaagtctga ccccaggtgc ctgaccagat actacagcag   2400
ctttgtgaac atggagaggg acctggcctc tggcctgatt ggccccctgc tgatctgcta   2460
caaggagtct gtggaccaga ggggcaacca gatcatgtct gacaagagga atgtgatcct   2520
gttctctgtg tttgatgaga acaggagctg gtacctgact gagaacatcc agaggttcct   2580
gcccaaccct gctggggtgc agctggagga ccctgagttc caggccagca acatcatgca   2640
cagcatcaat ggctatgtgt ttgacagcct gcagctgtct gtgtgcctgc atgaggtggc   2700
ctactggtac atcctgagca ttggggccca gactgacttc ctgtctgtgt tcttctctgg   2760
ctacaccttc aagcacaaga tggtgtatga ggacaccctg accctgttcc ccttctctgg   2820
ggagactgtg ttcatgagca tggagaaccc tggcctgtgg attctgggct gccacaactc   2880
tgacttcagg aacaggggca tgactgccct gctgaaagtc tccagctgtg acaagaacac   2940
tggggactac tatgaggaca gctatgagga catctctgcc tacctgctga gcaagaacaa   3000
tgccattgag cccaggagct tcagccagaa ccccccagtg ctgaagaggc accagaggga   3060
gatcaccagg accaccctgc agtctgacca ggaggagatt gactatgatg acaccatctc   3120
tgtggagatg aagaaggagg actttgacat ctacgacgag gacgagaacc agagccccag   3180
gagcttccag aagaagacca ggcactactt cattgctgct gtggagaggc tgtgggacta   3240
tggcatgagc agcagccccc atgtgctgag gaacagggcc cagtctggct ctgtgcccca   3300
gttcaagaag gtggtgttcc aggagttcac tgatggcagc ttcacccagc ccctgtacag   3360
aggggagctg aatgagcacc tgggcctgct gggcccctac atcagggctg aggtggagga   3420
caacatcatg gtgaccttca ggaaccaggc cagcaggccc tacagcttct acagcagcct   3480
gatcagctat gaggaggacc agaggcaggg ggctgagccc aggaagaact ttgtgaagcc   3540
caatgaaacc aagacctact tctggaaggt gcagcaccac atggccccca ccaaggatga   3600
gtttgactgc aaggcctggg cctacttctc tgatgtggac ctggagaagg atgtgcactc   3660
tggcctgatt ggcccccctgc tggtgtgcca caccaacacc ctgaaccctg cccatggcag   3720
gcaggtgact gtgcaggagt ttgccctgtt cttcaccatc tttgatgaaa ccaagagctg   3780
gtacttcact gagaacatgg agaggaactg cagggccccc tgcaacatcc agatggagga   3840
ccccaccttc aaggagaact acaggttcca tgccatcaat ggctacatca tggacaccct   3900
gcctggcctg gtgatggccc aggaccagag gatcaggtgg tacctgctga gcatgggcag   3960
caatgagaac atccacagca tccacttctc tggccatgtg ttcactgtga ggaagaagga   4020
ggagtacaag atggccctgt acaacctgta ccctggggtg tttgagactg tggagatgct   4080
gcccagcaag gctggcatct ggagggtgga gtgcctgatt ggggagcacc tgcatgctgg   4140
```

catgagcacc ctgttcctgg tgtacagcaa caagtgccag accccccctgg gcatggcctc 4200 tggccacatc agggacttcc agatcactgc ctctggccag tatggccagt gggcccccaa 4260
gctggccagg ctgcactact ctggcagcat caatgcctgg agcaccaagg agcccttcag 4320
ctggatcaag gtggacctgc tggcccccat gatcatccat ggcatcaaga cccagggggc 4380
caggcagaag ttcagcagcc tgtacatcag ccagttcatc atcatgtaca gcctggatgg 4440
caagaagtgg cagacctaca ggggcaacag cactggcacc ctgatggtgt tctttggcaa 4500
tgtggacagc tctggcatca agcacaacat cttcaacccc cccatcattg ccagatacat 4560
caggctgcac ccccacccact acagcatcag gagcaccctg aggatggagc tgatgggctg 4620
tgacctgaac agctgcagca tgcccctggg catggagagc aaggccatct ctgatgccca 4680
gatcactgcc agcagctact tcaccaacat gtttgccacc tggagcccca gcaaggccag 4740
gctgcacctg cagggcagga gcaatgcctg gaggccccag gtcaacaacc ccaaggagtg 4800
gctgcaggtg gacttccaga agaccatgaa ggtgactggg gtgaccaccc agggggtgaa 4860
gagcctgctg accagcatgt atgtgaagga gttcctgatc agcagcagcc aggatggcca 4920
ccagtggacc ctgttcttcc agaatggcaa ggtgaaggtg ttccagggca accaggacag 4980
cttcacccct gtggtgaaca gcctggaccc cccccctgctg accagatacc tgaggattca 5040
cccccagagc tgggtgcacc agattgccct gaggatggag gtgctgggct gtgaggccca 5100
ggacctgtac tgacctcgag gcactgtcct ttcctaataa aatgaggaaa ttgcatcgca 5160
ttgtctgagt aggtgtcatt ctattctggg gggtggggtg gggcaggaca gcaaggggga 5220
ggattgggaa gacaatagca ggcatgctgg ggatgcggtg ggctctatgg gcactcgaca 5280
ggttaatttt taaaaagcag tcaaaagtcc aagtggccct tggcagcatt tactctctct 5340
gtttgctctg gttaataatc tcaggagcac aaacattcct ggaggcagga gaagaaatca 5400
acatcctgga cttatcctct gggcctctcc ccaccccccag gagaggctca ggttaatttt 5460
taaaaagcag tcaaaagtcc aagtggccct tggcagcatt tactctctct gtttgctctg 5520
gttaataatc tcaggagcac aaacattcct ggaggcagga gaagaaatca acatcctgga 5580
cttatcctct gggcctctcc ccaccccccag gagaggctgt cgagtggcgg ccgcaggaac 5640
ccctagtgat ggagttggcc actccctctc tgcgcgctcg ctcgctcact gaggccgggc 5700
gaccaaaggt cgcccgacgc ccgggctttg cccgggcggc ctcagtgagc gagcgagcgc 5760
gcagagaggg agtggccaa 5779

<210> SEQ ID NO 21
<211> LENGTH: 5962
<212> TYPE: DNA
<213> ORGANISM: Adeno-Associated Virus 2

<400> SEQUENCE: 21
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgaccc ctctcacact 180
acctaaacca cgccaggaca acctctgctc ctctccaccg aaattccaag gggtcgagtg 240
gatgttggag gtggcatggg cccagagagg tctctgacct ctgccccagc tccaaggtca 300
gcaggcaggg agggctgtgt gtttgctgtt tgctgcttgc aatgtttgcc cattttaggg 360
acatgagtag gctgaagttt gttcagtgtg gacttcagag gcagcacaca aacagctgct 420
ggaggatggg aactgagggg ttggaagggg gcagggtgag cccagaaact cctgtgtgcc 480

-continued

```
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggccctttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca acacctctgt ggtgtacaag aagaccctgt ttgtggagtt   1140
cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tgggggtgag ctactggaag gcctctgagg gggctgagta   1320
tgatgaccag accagccaga gggagaagga ggatgacaag gtgttccctg gggggcagcca   1380
cacctatgtg tggcaggtgc tgaaggagaa tggccccatg gcctctgacc ccctgtgcct   1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgaccccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
```

-continued

```
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
tggctacacc ttcaagcaca agatggtgta tgaggacacc ctgaccctgt tccccttctc   3000
tggggagact gtgttcatga gcatggagaa ccctggcctg tggattctgg gctgccacaa   3060
ctctgacttc aggaacaggg gcatgactgc cctgctgaaa gtctccagct gtgacaagaa   3120
cactggggac tactatgagg acagctatga ggacatctct gcctacctgc tgagcaagaa   3180
caatgccatt gagcccagga gcttcagcca gaaccccccca gtgctgaaga ggcaccagag   3240
ggagatcacc aggaccaccc tgcagtctga ccaggaggag attgactatg atgacaccat   3300
ctctgtggag atgaagaagg aggactttga catctacgac gaggacgaga accagagccc   3360
caggagcttc cagaagaaga ccaggcacta cttcattgct gctgtggaga ggctgtggga   3420
ctatggcatg agcagcagcc cccatgtgct gaggaacagg gcccagtctg gctctgtgcc   3480
ccagttcaag aaggtggtgt tccaggagtt cactgatggc agcttcaccc agcccctgta   3540
cagaggggag ctgaatgagc acctgggcct gctgggcccc tacatcaggg ctgaggtgga   3600
ggacaacatc atggtgacct tcaggaacca ggccagcagg ccctacagct tctacagcag   3660
cctgatcagc tatgaggagg accagaggca gggggctgag cccaggaaga actttgtgaa   3720
gcccaatgaa accaagacct acttctggaa ggtgcagcac cacatggccc ccaccaagga   3780
tgagtttgac tgcaaggcct gggcctactt ctctgatgtg gacctggaga aggatgtgca   3840
ctctggcctg attggccccc tgctggtgtg ccacaccaac accctgaacc ctgcccatgg   3900
caggcaggtg actgtgcagg agtttgccct gttcttcacc atctttgatg aaaccaagag   3960
ctggtacttc actgagaaca tggagaggaa ctgcagggcc ccctgcaaca tccagatgga   4020
ggaccccacc ttcaaggaga actacaggtt ccatgccatc aatggctaca tcatggacac   4080
cctgcctggc ctggtgatgg cccaggacca gaggatcagg tggtacctgc tgagcatggg   4140
cagcaatgag aacatccaca gcatccactt ctctggccat gtgttcactg tgaggaagaa   4200
ggaggagtac aagatggccc tgtacaacct gtaccctggg gtgtttgaga ctgtggagat   4260
gctgcccagc aaggctggca tctggagggt ggagtgcctg attggggagc acctgcatgc   4320
tggcatgagc accctgttcc tggtgtacag caacaagtgc cagacccccc tgggcatggc   4380
ctctggccac atcagggact tccagatcac tgcctctggc cagtatggcc agtgggcccc   4440
caagctggcc aggctgcact actctggcag catcaatgcc tggagcacca aggagccctt   4500
cagctggatc aaggtggacc tgctggcccc catgatcatc catggcatca agacccaggg   4560
ggccaggcag aagttcagca gcctgtacat cagccagttc atcatcatgt acagcctgga   4620
tggcaagaag tggcagacct acaggggcaa cagcactggc accctgatgg tgttctttgg   4680
caatgtggac agctctggca tcaagcacaa catcttcaac cccccccatca ttgccagata   4740
catcaggctg caccccaccc actacagcat caggagcacc ctgaggatgg agctgatggg   4800
ctgtgacctg aacagctgca gcatgcccct gggcatggag agcaaggcca tctctgatgc   4860
ccagatcact gccagcagct acttcaccaa catgtttgcc acctggagcc ccagcaaggc   4920
caggctgcac ctgcagggca ggagcaatgc ctggaggccc caggtcaaca accccaagga   4980
gtggctgcag gtggacttcc agaagaccat gaaggtgact ggggtgacca cccagggggt   5040
gaagagcctg ctgaccagca tgtatgtgaa ggagttcctg atcagcagca gccaggatgg   5100
ccaccagtgg accctgttct tccagaatgg caaggtgaag gtgttccagg gcaaccagga   5160
cagcttcacc cctgtggtga acagcctgga cccccccctg ctgaccagat acctgaggat   5220
```

```
tcacccccag agctgggtgc accagattgc cctgaggatg gaggtgctgg gctgtgaggc   5280
ccaggacctg tactgacctc gaggcactgt cctttcctaa taaaatgagg aaattgcatc   5340
gcattgtctg agtaggtgtc attctattct ggggggtggg gtggggcagg acagcaaggg   5400
ggaggattgg gaagacaata gcaggcatgc tggggatgcg gtgggctcta tgggcactcg   5460
acaggttaat ttttaaaaag cagtcaaaag tccaagtggc ccttggcagc atttactctc   5520
tctgtttgct ctggttaata atctcaggag cacaaacatt cctggaggca ggagaagaaa   5580
tcaacatcct ggacttatcc tctgggcctc tccccacccc caggagaggc tcaggttaat   5640
ttttaaaaag cagtcaaaag tccaagtggc ccttggcagc atttactctc tctgtttgct   5700
ctggttaata atctcaggag cacaaacatt cctggaggca ggagaagaaa tcaacatcct   5760
ggacttatcc tctgggcctc tccccacccc caggagaggc tgtcgagtgg cggccgcagg   5820
aacccctagt gatggagttg gccactccct ctctgcgcgc tcgctcgctc actgaggccg   5880
ggcgaccaaa ggtcgcccga cgcccgggct ttgcccgggc ggcctcagtg agcgagcgag   5940
cgcgcagaga gggagtggcc aa                                            5962
```

<210> SEQ ID NO 22
<211> LENGTH: 5919
<212> TYPE: DNA
<213> ORGANISM: Adeno-Associated Virus 2

<400> SEQUENCE: 22

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgta ggctcagagg cacacaggag    180
tttctgggct caccctgccc ccttccaacc cctcagttcc catcctccag cagctgtttg    240
tgtgctgcct ctgaagtcca cactgaacaa acttcagcct actcatgtcc ctaaaatggg    300
caaacattgc aagcagcaaa cagcaaacac acagccctcc ctgcctgctg accttggagc    360
tggggcagag gtcagagacc tctctgggcc catgccacct ccaacatcca ctcgacccct    420
tggaatttcg gtggagagga gcagaggttg tcctggcgtg gtttaggtag tgtgagaggg    480
gtcgacgatc ttgctaccag tggaacagcc actaaggatt ctgcagtgag agcagagggc    540
cagctaagtg gtactctccc agagactgtc tgactcacgc cacccccctcc accttggaca    600
caggacgctg tggtttctga gccaggtaca atgactcctt tcggtaagtg cagtggaagc    660
tgtacactgc ccaggcaaag cgtccgggca gcgtaggcgg gcgactcaga tcccagccag    720
tggacttagc ccctgtttgc tcctccgata actggggtga ccttggttaa tattcaccag    780
cagcctcccc cgttgcccct ctggatccac tgcttaaata cggacgagga cagggccctg    840
tctcctcagc ttcaggcacc accactgacc tgggacagtg aatcgtaagt atgcctttca    900
ctgcgagagg ttctggagag gcttctgagc tccccatggc ccaggcaggc agcaggtctg    960
gggcaggagg ggggttgtgg agtgggtatc cgcctgctga ggtgcagggc agatcatcat   1020
gtgccttgac tcggggcctg gcccccccat ctctgtcttg caggacaatt gccgtcttct   1080
gtctcgtggg gcatcctcct gctggcaggc ctgtgctgcc tggtccctgt ctccctggct   1140
gaggaccggc caccatgcag attgagctga gcacctgctt cttcctgtgc ctgctgaggt   1200
tctgcttctc tgccaccagg agatactacc tgggggctgt ggagctgagc tgggactaca   1260
tgcagtctga cctgggggag ctgcctgtgg atgccaggtt cccccccaga gtgcccaaga   1320
```

-continued

```
gcttcccctt caacacctct gtggtgtaca agaagaccct gtttgtggag ttcactgacc   1380
acctgttcaa cattgccaag cccaggcccc cctggatggg cctgctgggc cccaccatcc   1440
aggctgaggt gtatgacact gtggtgatca ccctgaagaa catggccagc caccctgtga   1500
gcctgcatgc tgtgggggtg agctactgga aggcctctga gggggctgag tatgatgacc   1560
agaccagcca gagggagaag gaggatgaca aggtgttccc tgggggcagc cacacctatg   1620
tgtggcaggt gctgaaggag aatggcccca tggcctctga ccccctgtgc ctgacctaca   1680
gctacctgag ccatgtggac ctggtgaagg acctgaactc tggcctgatt ggggccctgc   1740
tggtgtgcag ggagggcagc ctggccaagg agaagaccca gaccctgcac aagttcatcc   1800
tgctgtttgc tgtgtttgat gagggcaaga gctggcactc tgaaaccaag aacagcctga   1860
tgcaggacag ggatgctgcc tctgccaggg cctggcccaa gatgcacact gtgaatggct   1920
atgtgaacag gagcctgcct ggcctgattg gctgccacag gaagtctgtg tactggcatg   1980
tgattggcat gggcaccacc cctgaggtgc acagcatctt cctggagggc cacaccttcc   2040
tggtcaggaa ccacaggcag gccagcctgg agatcagccc catcaccttc ctgactgccc   2100
agaccctgct gatggacctg ggccagttcc tgctgttctg ccacatcagc agccaccagc   2160
atgatggcat ggaggcctat gtgaaggtgg acagctgccc tgaggagccc cagctgagga   2220
tgaagaacaa tgaggaggct gaggactatg atgatgacct gactgactct gagatggatg   2280
tggtgaggtt tgatgatgac aacagcccca gcttcatcca gatcaggtct gtggccaaga   2340
agcaccccaa gacctgggtg cactacattg ctgctgagga ggaggactgg gactatgccc   2400
ccctggtgct ggcccctgat gacaggagct acaagagcca gtacctgaac aatggccccc   2460
agaggattgg caggaagtac aagaaggtca ggttcatggc ctacactgat gaaaccttca   2520
agaccaggga ggccatccag catgagtctg gcatcctggg cccccctgctg tatggggagg   2580
tgggggacac cctgctgatc atcttcaaga accaggccag caggccctac aacatctacc   2640
cccatggcat cactgatgtg aggcccctgt acagcaggag gctgcccaag gggtgaagc    2700
acctgaagga cttccccatc ctgcctgggg agatcttcaa gtacaagtgg actgtgactg   2760
tggaggatgg ccccaccaag tctgacccca ggtgcctgac cagatactac agcagctttg   2820
tgaacatgga gagggacctg gcctctggcc tgattggccc cctgctgatc tgctacaagg   2880
agtctgtgga ccagaggggc aaccagatca tgtctgacaa gaggaatgtg atcctgttct   2940
ctgtgtttga tgagaacagg agctggtacc tgactgagaa catccagagg ttcctgccca   3000
accctgctgg ggtgcagctg gaggaccctg agttccaggc cagcaacatc atgcacagca   3060
tcaatggcta tgtgtttgac agcctgcagc tgtctgtgtg cctgcatgag gtggcctact   3120
ggtacatcct gagcattggg gcccagactg acttcctgtc tgtgttcttc tctggctaca   3180
ccttcaagca caagatggtg tatgaggaca ccctgaccct gttccccttc tctggggaga   3240
ctgtgttcat gagcatggag aaccctggcc tgtggattct gggctgccac aactctgact   3300
tcaggaacag gggcatgact gccctgctga aagtctccag ctgtgacaag aacactgggg   3360
actactatga ggacagctat gaggacatct ctgcctacct gctgagcaag aacaatgcca   3420
ttgagcccag gagcttcagc cagaaccccc cagtgctgaa gaggcaccag agggagatca   3480
ccaggaccac cctgcagtct gaccaggagg agattgacta tgatgacacc atctctgtgg   3540
agatgaagaa ggaggacttt gacatctacg acgaggacga gaaccagagc cccaggagct   3600
tccagaagaa gaccaggcac tacttcattg ctgctgtgga gaggctgtgg gactatggca   3660
tgagcagcag cccccatgtg ctgaggaaca gggcccagtc tggctctgtg ccccagttca   3720
```

agaaggtggt gttccaggag ttcactgatg gcagcttcac ccagcccctg tacagagggg 3780
agctgaatga gcacctgggc ctgctgggcc cctacatcag ggctgaggtg gaggacaaca 3840
tcatggtgac cttcaggaac caggccagca ggccctacag cttctacagc agcctgatca 3900
gctatgagga ggaccagagg caggggggctg agcccaggaa gaactttgtg aagcccaatg 3960
aaaccaagac ctacttctgg aaggtgcagc accacatggc ccccaccaag gatgagtttg 4020
actgcaaggc ctgggcctac ttctctgatg tggacctgga gaaggatgtg cactctggcc 4080
tgattggccc cctgctggtg tgccacacca acaccctgaa ccctgcccat ggcaggcagg 4140
tgactgtgca ggagtttgcc ctgttcttca ccatctttga tgaaaccaag agctggtact 4200
tcactgagaa catggagagg aactgcaggg ccccctgcaa catccagatg gaggacccca 4260
ccttcaagga gaactacagg ttccatgcca tcaatggcta catcatggac accctgcctg 4320
gcctggtgat ggcccaggac cagaggatca ggtggtacct gctgagcatg ggcagcaatg 4380
agaacatcca cagcatccac ttctctggcc atgtgttcac tgtgaggaag aaggaggagt 4440
acaagatggc cctgtacaac ctgtaccctg ggtgtttga gactgtggag atgctgccca 4500
gcaaggctgg catctggagg gtggagtgcc tgattgggga gcacctgcat gctggcatga 4560
gcaccctgtt cctggtgtac agcaacaagt gccagacccc cctgggcatg gcctctggcc 4620
acatcaggga cttccagatc actgcctctg gccagtatgg ccagtgggcc cccaagctgg 4680
ccaggctgca ctactctggc agcatcaatg cctggagcac caaggagccc ttcagctgga 4740
tcaaggtgga cctgctggcc cccatgatca tccatggcat caagacccag gggccaggc 4800 agaagttcag cagcctgtac atcagccagt tcatcatcat gtacagcctg gatggcaaga 4860
agtggcagac ctacaggggc aacagcactg gcaccctgat ggtgttcttt ggcaatgtgg 4920
acagctctgg catcaagcac aacatcttca acccccccat cattgccaga tacatcaggc 4980
tgcaccccac ccactacagc atcaggagca ccctgaggat ggagctgatg ggctgtgacc 5040
tgaacagctg cagcatgccc ctgggcatgg agagcaaggc catctctgat gcccagatca 5100
ctgccagcag ctacttcacc aacatgtttg ccacctggag ccccagcaag gccaggctgc 5160
acctgcaggg caggagcaat gcctggaggc cccaggtcaa caaccccaag gagtggctgc 5220
aggtggactt ccagaagacc atgaaggtga ctggggtgac cacccagggg gtgaagagcc 5280
tgctgaccag catgtatgtg aaggagttcc tgatcagcag cagccaggat ggccaccagt 5340
ggaccctgtt cttccagaat ggcaaggtga aggtgttcca gggcaaccag gacagcttca 5400
cccctgtggt gaacagcctg gacccccccc tgctgaccag atacctgagg attcaccccc 5460
agagctgggt gcaccagatt gccctgagga tggaggtgct gggctgtgag gcccaggacc 5520
tgtactgagc tcgagctgtg ccttctagtt gccagccatc tgttgtttgc ccctcccccg 5580
tgccttcctt gaccctggaa ggtgccactc ccactgtcct ttcctaataa aatgaggaaa 5640
ttgcatcgca ttgtctgagt aggtgtcatt ctattctggg gggtggggtg gggcaggaca 5700
gcaaggggga ggattgggaa gacaatagca ggcatgctgg ggatgcggtg ggctctatgg 5760
accggtgcgg ccgcaggaac ccctagtgat ggagttggcc actccctctc tgcgcgctcg 5820
ctcgctcact gaggccgggc gaccaaaggt cgcccgacgc ccgggctttg cccgggcggc 5880
ctcagtgagc gagcgagcgc gcagagaggg agtggccaa 5919

<210> SEQ ID NO 23
<211> LENGTH: 5306
<212> TYPE: DNA

-continued

<213> ORGANISM: Adeno-Associated Virus 2

<400> SEQUENCE: 23

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttaaacgt cgaccctaaa    180
atgggcaaac attgcaagca gcaaacagca aactgacctt ggagctgggg cagaggtcag    240
agacctctct gggcactcga ccccttggaa tttcggtgga gaggagcaga ggtacacagc    300
cctccctgcc tgccccatgc cacctccaac atctgtcctg gcgtggttta ggtagtgtga    360
gaggggaatg actcctttcg gtaagtgcag tggaagctgt acactgccca ggcaaagcgt    420
ccgggcagcg taggcgggcg actcagatcc cagccagtgg acttagcccc tgtttgctcc    480
tccgataact ggggtgacct tggttaatat tcaccagcag cctcccccgt tgcccctctg    540
gatccactgc ttaaatacgg acgaggacag ggccctgtct cctcagcttc aggcaccacc    600
actgacctgg gacagtgaat cgcgatcgca ctgcttaaat acggacgagg acagggccct    660
gtctcctcag cttcaggcac caccactgac ctgggacagt gaatcgcgat cgccaccatg    720
cagattgagc tgagcacctg cttcttcctg tgcctgctga ggttctgctt ctctgccacc    780
aggagatact acctgggggc tgtggagctg agctgggact acatgcagtc tgacctgggg    840
gagctgcctg tggatgccag gttccccccc agagtgccca agagcttccc cttcaacacc    900
tctgtggtgt acaagaagac cctgtttgtg gagttcactg accacctgtt caacattgcc    960
aagcccaggc ccccctggat gggcctgctg ggccccacca tccaggctga ggtgtatgac   1020
actgtggtga tcaccctgaa gaacatggcc agccaccctg tgagcctgca tgctgtgggg   1080
gtgagctact ggaaggcctc tgagggggct gagtatgatg accagaccag ccagagggag   1140
aaggaggatg acaaggtgtt ccctgggggc agccacacct atgtgtggca ggtgctgaag   1200
gagaatggcc ccatggcctc tgacccccctg tgcctgacct acagctacct gagccatgtg   1260
gacctggtga aggacctgaa ctctggcctg attggggccc tgctggtgtg cagggagggc   1320
agcctggcca aggagaagac ccagaccctg cacaagttca tcctgctgtt tgctgtgttt   1380
gatgagggca agagctggca ctctgaaacc aagaacagcc tgatgcagga cagggatgct   1440
gcctctgcca gggcctggcc caagatgcac actgtgaatg gctatgtgaa caggagcctg   1500
cctggcctga ttggctgcca caggaagtct gtgtactggc atgtgattgg catgggcacc   1560
acccctgagg tgcacagcat cttcctggag ggccacacct tcctggtcag gaaccacagg   1620
caggccagcc tggagatcag ccccatcacc ttcctgactg cccagaccct gctgatggac   1680
ctgggccagt tcctgctgtt ctgccacatc agcagccacc agcatgatgg catggaggcc   1740
tatgtgaagg tggacagctg ccctgaggag ccccagctga ggatgaagaa caatgaggag   1800
gctgaggact atgatgatga cctgactgac tctgagatgg atgtggtgag gtttgatgat   1860
gacaacagcc ccagcttcat ccagatcagg tctgtggcca agaagcaccc caagacctgg   1920
gtgcactaca ttgctgctga ggaggaggac tgggactatg ccccccctggt gctggcccct   1980
gatgacagga gctacaagag ccagtacctg aacaatggcc cccagaggat tggcaggaag   2040
tacaagaagg tcaggttcat ggcctacact gatgaaacct tcaagaccag ggaggccatc   2100
cagcatgagt ctggcatcct gggcccccctg ctgtatgggg aggtggggga caccctgctg   2160
atcatcttca agaaccaggc cagcaggccc tacaacatct acccccatgg catcactgat   2220
gtgaggcccc tgtacagcag gaggctgccc aagggggtga agcacctgaa ggacttcccc   2280
```

-continued

```
atcctgcctg gggagatctt caagtacaag tggactgtga ctgtggagga tggccccacc   2340
aagtctgacc ccaggtgcct gaccagatac tacagcagct ttgtgaacat ggagagggac   2400
ctggcctctg gcctgattgg ccccctgctg atctgctaca aggagtctgt ggaccagagg   2460
ggcaaccaga tcatgtctga caagaggaat gtgatcctgt tctctgtgtt tgatgagaac   2520
aggagctggt acctgactga gaacatccag aggttcctgc ccaaccctgc tggggtgcag   2580
ctggaggacc ctgagttcca ggccagcaac atcatgcaca gcatcaatgg ctatgtgttt   2640
gacagcctgc agctgtctgt gtgcctgcat gaggtggcct actggtacat cctgagcatt   2700
ggggcccaga ctgacttcct gtctgtgttc ttctctggct acaccttcaa gcacaagatg   2760
gtgtatgagg acaccctgac cctgttcccc ttctctgggg agactgtgtt catgagcatg   2820
gagaaccctg gcctgtggat tctgggctgc cacaactctg acttcaggaa caggggcatg   2880
actgccctgc tgaaagtctc cagctgtgac aagaacactg gggactacta tgaggacagc   2940
tatgaggaca tctctgccta cctgctgagc aagaacaatg ccattgagcc caggagcttc   3000
agccagaacc ccccagtgct gaagaggcac cagagggaga tcaccaggac caccctgcag   3060
tctgaccagg aggagattga ctatgatgac accatctctg tggagatgaa gaaggaggac   3120
tttgacatct acgacgagga cgagaaccag agccccagga gcttccagaa gaagaccagg   3180
cactacttca ttgctgctgt ggagaggctg tgggactatg gcatgagcag cagcccccat   3240
gtgctgagga acagggccca gtctggctct gtgccccagt tcaagaaggt ggtgttccag   3300
gagttcactg atggcagctt cacccagccc ctgtacagag gggagctgaa tgagcacctg   3360
ggcctgctgg gcccctacat cagggctgag gtggaggaca acatcatggt gaccttcagg   3420
aaccaggcca gcaggcccta cagcttctac agcagcctga tcagctatga ggaggaccag   3480
aggcaggggg ctgagcccag gaagaacttt gtgaagccca atgaaaccaa gacctacttc   3540
tggaaggtgc agcaccacat ggcccccacc aaggatgagt ttgactgcaa ggcctgggcc   3600
tacttctctg atgtggacct ggagaaggat gtgcactctg gcctgattgg cccccctgctg   3660
gtgtgccaca ccaacaccct gaaccctgcc catggcaggc aggtgactgt gcaggagttt   3720
gccctgttct tcaccatctt tgatgaaacc aagagctggt acttcactga gaacatggag   3780
aggaactgca gggccccctg caacatccag atggaggacc ccaccttcaa ggagaactac   3840
aggttccatg ccatcaatgg ctacatcatg gacaccctgc ctggcctggt gatggcccag   3900
gaccagagga tcaggtggta cctgctgagc atgggcagca atgagaacat ccacagcatc   3960
cacttctctg gccatgtgtt cactgtgagg aagaaggagg agtacaagat ggccctgtac   4020
aacctgtacc ctgggggtgtt tgagactgtg gagatgctgc ccagcaaggc tggcatctgg   4080
agggtggagt gcctgattgg ggagcacctg catgctggca tgagcaccct gttcctggtg   4140
tacagcaaca agtgccagac ccccctgggc atggcctctg gccacatcag ggacttccag   4200
atcactgcct ctggccagta tggccagtgg gcccccaagc tggccaggct gcactactct   4260
ggcagcatca atgcctggag caccaaggag cccttcagct ggatcaaggt ggacctgctg   4320
gcccccatga tcatccatgg catcaagacc caggggggcca ggcagaagtt cagcagcctg   4380
tacatcagcc agttcatcat catgtacagc ctggatggca agaagtggca gacctacagg   4440
ggcaacagca ctggcaccct gatggtgttc tttggcaatg tggacagctc tggcatcaag   4500
cacaacatct tcaacccccc catcattgcc agatacatca ggctgcaccc cacccactac   4560
agcatcagga gcaccctgag gatggagctg atgggctgtg acctgaacag ctgcagcatg   4620
```

```
cccctgggca tggagagcaa ggccatctct gatgcccaga tcactgccag cagctacttc   4680
accaacatgt ttgccacctg gagccccagc aaggccaggc tgcacctgca gggcaggagc   4740
aatgcctgga ggccccaggt caacaacccc aaggagtggc tgcaggtgga cttccagaag   4800
accatgaagg tgactggggt gaccacccag gggtgaaga gcctgctgac cagcatgtat   4860
gtgaaggagt tcctgatcag cagcagccag gatggccacc agtggaccct gttcttccag   4920
aatggcaagg tgaaggtgtt ccagggcaac caggacagct tcacccctgt ggtgaacagc   4980
ctggaccccc ccctgctgac cagatacctg aggattcacc cccagagctg ggtgcaccag   5040
attgccctga ggatggaggt gctgggctgt gaggcccagg acctgtactg acctcgagga   5100
ataaaggaaa tttattttca ttgcaatagt gtgttggttt tttgtgtcac gtggcggccg   5160
caggaacccc tagtgatgga gttggccact ccctctctgc gcgctcgctc gctcactgag   5220
gccgggcgac caaaggtcgc ccgacgcccg ggctttgccc gggcggcctc agtgagcgag   5280
cgagcgcgca gagagggagt ggccaa                                         5306
```

<210> SEQ ID NO 24
<211> LENGTH: 5461
<212> TYPE: DNA
<213> ORGANISM: Adeno-Associated Virus 2

<400> SEQUENCE: 24

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgactt tatttgccac    180
aaaaacccta tcagatgggc gtctttatca tttccattgt acagatgggg aaacaggctt    240
cggggtcggg gcatagccac ttactgacga ctccccaccc agcaagtggt tttgaacccg    300
gaccctctca cactacctaa accacgccag gacaacctct gctcctctcc accgaaattc    360
caaggggtcg agtggatgtt ggaggtggca tgggcccaga gaggtctctg acctctgccc    420
cagctccaag gtcagcaggc agggagggct gtgtgtttgc tgtttgctgc ttgcaatgtt    480
tgcccatttt agggacatga gtaggctgaa gtttgttcag tgtggacttc agaggcagca    540
cacaaacagc tgctggagga tgggaactga ggggttggaa gggggcaggg tgagcccaga    600
aactcctgtg tgcctctgag cctgcagacg cgaaacgtcg actggacaca ggacgctgtg    660
gtttctgagc caggggggcga ctcagatccc agccagtgga cttagcccct gtttgctcct    720
ccgataactg gggtgacctt ggttaatatt caccagcagc ctcccccgtt gcccctctgg    780
atccactgct taaatacgga cgaggacagg gccctgtctc ctcagcttca ggcaccacca    840
ctgacctggg acagtgaatc gcgatcgcca ccatgcagat tgagctgagc acctgcttct    900
tcctgtgcct gctgaggttc tgcttctctg ccaccaggag atactacctg gggctgtgg    960
agctgagctg ggactacatg cagtctgacc tgggggagct gcctgtggat gccaggttcc   1020
cccccagagt gcccaagagc ttccccttca acacctctgt ggtgtacaag aagaccctgt   1080
ttgtggagtt cactgaccac ctgttcaaca ttgccaagcc caggcccccc tggatgggcc   1140
tgctgggccc caccatccag gctgaggtgt atgacactgt ggtgatcacc ctgaagaaca   1200
tggccagcca ccctgtgagc ctgcatgctg tgggggtgag ctactggaag gcctctgagg   1260
gggctgagta tgatgaccag accagccaga gggagaagga ggatgacaag gtgttccctg   1320
gggcagcca cacctatgtg tggcaggtgc tgaaggagaa tggccccatg gcctctgacc   1380
ccctgtgcct gacctacagc tacctgagcc atgtggacct ggtgaaggac ctgaactctg   1440
```

-continued

```
gcctgattgg ggccctgctg gtgtgcaggg agggcagcct ggccaaggag aagacccaga   1500
ccctgcacaa gttcatcctg ctgtttgctg tgtttgatga gggcaagagc tggcactctg   1560
aaaccaagaa cagcctgatg caggacaggg atgctgcctc tgccagggcc tggcccaaga   1620
tgcacactgt gaatggctat gtgaacagga gcctgcctgg cctgattggc tgccacagga   1680
agtctgtgta ctggcatgtg attggcatgg gcaccacccc tgaggtgcac agcatcttcc   1740
tggagggcca caccttcctg gtcaggaacc acaggcaggc cagcctggag atcagcccca   1800
tcaccttcct gactgcccag accctgctga tggacctggg ccagttcctg ctgttctgcc   1860
acatcagcag ccaccagcat gatggcatgg aggcctatgt gaaggtggac agctgccctg   1920
aggagcccca gctgaggatg aagaacaatg aggaggctga ggactatgat gatgacctga   1980
ctgactctga gatggatgtg gtgaggtttg atgatgacaa cagccccagc ttcatccaga   2040
tcaggtctgt ggccaagaag caccccaaga cctgggtgca ctacattgct gctgaggagg   2100
aggactggga ctatgccccc ctggtgctgg cccctgatga caggagctac aagagccagt   2160
acctgaacaa tggcccccag aggattggca ggaagtacaa gaaggtcagg ttcatggcct   2220
acactgatga aaccttcaag accagggagg ccatccagca tgagtctggc atcctgggcc   2280
ccctgctgta tggggaggtg gggacaccc tgctgatcat cttcaagaac caggccagca   2340
ggccctacaa catctacccc catggcatca ctgatgtgag gcccctgtac agcaggaggc   2400
tgcccaaggg ggtgaagcac ctgaaggact tccccatcct gcctggggag atcttcaagt   2460
acaagtggac tgtgactgtg gaggatggcc ccaccaagtc tgaccccagg tgcctgacca   2520
gatactacag cagctttgtg aacatggaga gggacctggc ctctggcctg attggccccc   2580
tgctgatctg ctacaaggag tctgtggacc agaggggcaa ccagatcatg tctgacaaga   2640
ggaatgtgat cctgttctct gtgtttgatg agaacaggag ctggtacctg actgagaaca   2700
tccagaggtt cctgcccaac cctgctgggg tgcagctgga ggaccctgag ttccaggcca   2760
gcaacatcat gcacagcatc aatggctatg tgtttgacag cctgcagctg tctgtgtgcc   2820
tgcatgaggt ggcctactgg tacatcctga gcattggggc ccagactgac ttcctgtctg   2880
tgttcttctc tggctacacc ttcaagcaca agatggtgta tgaggacacc ctgaccctgt   2940
tccccttctc tggggagact gtgttcatga gcatggagaa ccctggcctg tggattctgg   3000
gctgccacaa ctctgacttc aggaacaggg gcatgactgc cctgctgaaa gtctccagct   3060
gtgacaagaa cactggggac tactatgagg acagctatga ggacatctct gcctacctgc   3120
tgagcaagaa caatgccatt gagcccagga gcttcagcca gaaccccccca gtgctgaaga   3180
ggcaccagag ggagatcacc aggaccaccc tgcagtctga ccaggaggag attgactatg   3240
atgacaccat ctctgtggag atgaagaagg aggactttga catctacgac gaggacgaga   3300
accagagccc caggagcttc cagaagaaga ccaggcacta cttcattgct gctgtggaga   3360
ggctgtggga ctatggcatg agcagcagcc cccatgtgct gaggaacagg gcccagtctg   3420
gctctgtgcc ccagttcaag aaggtggtgt tccaggagtt cactgatggc agcttcaccc   3480
agcccctgta cagaggggag ctgaatgagc acctgggcct gctgggcccc tacatcaggg   3540
ctgaggtgga ggacaacatc atggtgacct tcaggaacca ggccagcagg ccctacagct   3600
tctacagcag cctgatcagc tatgaggagg accagaggca gggggctgag cccaggaaga   3660
actttgtgaa gcccaatgaa accaagacct acttctggaa ggtgcagcac cacatggccc   3720
ccaccaagga tgagtttgac tgcaaggcct gggcctactt ctctgatgtg gacctggaga   3780
```

-continued

```
aggatgtgca ctctggcctg attggccccc tgctggtgtg ccacaccaac accctgaacc   3840
ctgcccatgg caggcaggtg actgtgcagg agtttgccct gttcttcacc atctttgatg   3900
aaaccaagag ctggtacttc actgagaaca tggagaggaa ctgcagggcc ccctgcaaca   3960
tccagatgga ggaccccacc ttcaaggaga actacaggtt ccatgccatc aatggctaca   4020
tcatggacac cctgcctggc ctggtgatgg cccaggacca gaggatcagg tggtacctgc   4080
tgagcatggg cagcaatgag aacatccaca gcatccactt ctctggccat gtgttcactg   4140
tgaggaagaa ggaggagtac aagatggccc tgtacaacct gtaccctggg gtgtttgaga   4200
ctgtggagat gctgcccagc aaggctggca tctggagggt ggagtgcctg attggggagc   4260
acctgcatgc tggcatgagc accctgttcc tggtgtacag caacaagtgc cagacccccc   4320
tgggcatggc ctctggccac atcagggact tccagatcac tgcctctggc cagtatggcc   4380
agtgggcccc caagctggcc aggctgcact actctggcag catcaatgcc tggagcacca   4440
aggagccctt cagctggatc aaggtggacc tgctggcccc catgatcatc catggcatca   4500
agacccaggg ggccaggcag aagttcagca gcctgtacat cagccagttc atcatcatgt   4560
acagcctgga tggcaagaag tggcagacct acaggggcaa cagcactggc accctgatgg   4620
tgttctttgg caatgtggac agctctggca tcaagcacaa catcttcaac cccccccatca   4680
ttgccagata catcaggctg caccccaccc actacagcat caggagcacc ctgaggatgg   4740
agctgatggg ctgtgacctg aacagctgca gcatgcccct gggcatggag agcaaggcca   4800
tctctgatgc ccagatcact gccagcagct acttcaccaa catgtttgcc acctggagcc   4860
ccagcaaggc caggctgcac ctgcagggca ggagcaatgc ctggaggccc caggtcaaca   4920
accccaagga gtggctgcag gtggacttcc agaagaccat gaaggtgact ggggtgacca   4980
cccagggggt gaagagcctg ctgaccagca tgtatgtgaa ggagttcctg atcagcagca   5040
gccaggatgg ccaccagtgg accctgttct tccagaatgg caaggtgaag gtgttccagg   5100
gcaaccagga cagcttcacc cctgtggtga acagcctgga cccccccctg ctgaccagat   5160
acctgaggat tcacccccag agctgggtgc accagattgc cctgaggatg gaggtgctgg   5220
gctgtgaggc ccaggacctg tactgacctc gaggaataaa ggaaatttat tttcattgca   5280
atagtgtgtt ggtttttttgt gtcacgtggc ggccgcagga acccctagtg atggagttgg   5340
ccactccctc tctgcgcgct cgctcgctca ctgaggccgg gcgaccaaag gtcgcccgac   5400
gcccgggctt tgcccgggcg gcctcagtga gcgagcgagc gcgcagagag ggagtggcca   5460
a                                                                   5461
```

<210> SEQ ID NO 25
<211> LENGTH: 5327
<212> TYPE: DNA
<213> ORGANISM: Adeno-Associated Virus 2

<400> SEQUENCE: 25

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag ggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
```

-continued

```
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttcccccc cagagtgccc    900
aagagcttcc ccttcaacac ctctgtggtg tacaagaaga ccctgtttgt ggagttcact    960
gaccacctgt tcaacattgc caagcccagg ccccccctgga tgggcctgct gggccccacc  1020
atccaggctg aggtgtatga cactgtggtg atcaccctga agaacatggc cagccaccct   1080
gtgagcctgc atgctgtggg ggtgagctac tggaaggcct ctgagggggc tgagtatgat   1140
gaccagacca gccagaggga gaaggaggat gacaaggtgt tccctggggg cagccacacc   1200
tatgtgtggc aggtgctgaa ggagaatggc cccatggcct ctgacccccct gtgcctgacc  1260
tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc ccaagatgca cactgtgaat   1500
ggctatgtga acaggagcct gcctggcctg attggctgcc acaggaagtc tgtgtactgg   1560
catgtgattg gcatgggcac cacccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagct gccctgagga gccccagctg   1800
aggatgaaga acaatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980
gccccccctgg tgctggcccc tgatgacagg agctacaaga gccagtacct gaacaatggc  2040
ccccagagga ttggcaggaa gtacaagaag gtcaggttca tggcctacac tgatgaaacc   2100
ttcaagacca gggaggccat ccagcatgag tctggcatcc tgggccccct gctgtatggg   2160
gaggtggggg acaccctgct gatcatcttc aagaaccagg ccagcaggcc ctacaacatc   2220
tacccccatg gcatcactga tgtgaggccc ctgtacagca ggaggctgcc caagggggtg   2280
aagcacctga aggacttccc catcctgcct ggggagatct tcaagtacaa gtggactgtg   2340
actgtggagg atggccccac caagtctgac cccaggtgcc tgaccagata ctacagcagc   2400
tttgtgaaca tggagaggga cctggcctct ggcctgattg gcccccctgct gatctgctac  2460
aaggagtctg tggaccagag gggcaaccag atcatgtctg acaagaggaa tgtgatcctg   2520
ttctctgtgt ttgatgagaa caggagctgg tacctgactg agaacatcca gaggttcctg   2580
cccaaccctg ctggggtgca gctggaggac cctgagttcc aggccagcaa catcatgcac   2640
agcatcaatg gctatgtgtt tgacagcctg cagctgtctg tgtgcctgca tgaggtggcc   2700
tactggtaca tcctgagcat tggggcccag actgacttcc tgtctgtgtt cttctctggc   2760
```

-continued

```
tacaccttca agcacaagat ggtgtatgag gacaccctga ccctgttccc cttctctggg   2820
gagactgtgt tcatgagcat ggagaaccct ggcctgtgga ttctgggctg ccacaactct   2880
gacttcagga acaggggcat gactgccctg ctgaaagtct ccagctgtga caagaacact   2940
ggggactact atgaggacag ctatgaggac atctctgcct acctgctgag caagaacaat   3000
gccattgagc ccaggagctt cagccagaac cccccagtgc tgaagaggca ccagagggag   3060
atcaccagga ccaccctgca gtctgaccag gaggagattg actatgatga caccatctct   3120
gtggagatga agaaggagga ctttgacatc tacgacgagg acgagaacca gagccccagg   3180
agcttccaga agaagaccag gcactacttc attgctgctg tggagaggct gtgggactat   3240
ggcatgagca gcagccccca tgtgctgagg aacagggccc agtctggctc tgtgccccag   3300
ttcaagaagg tggtgttcca ggagttcact gatggcagct tcacccagcc cctgtacaga   3360
ggggagctga atgagcacct gggcctgctg ggcccctaca tcagggctga ggtggaggac   3420
aacatcatgg tgaccttcag gaaccaggcc agcaggccct acagcttcta cagcagcctg   3480
atcagctatg aggaggacca gaggcagggg gctgagccca ggaagaactt tgtgaagccc   3540
aatgaaacca agacctactt ctggaaggtg cagcaccaca tggcccccac caaggatgag   3600
tttgactgca aggcctgggc ctacttctct gatgtggacc tggagaagga tgtgcactct   3660
ggcctgattg gcccccctgct ggtgtgccac accaacaccc tgaaccctgc ccatggcagg   3720
caggtgactg tgcaggagtt tgccctgttc ttcaccatct ttgatgaaac caagagctgg   3780
tacttcactg agaacatgga gaggaactgc agggcccccct gcaacatcca gatggaggac   3840
cccaccttca aggagaacta caggttccat gccatcaatg gctacatcat ggacaccctg   3900
cctggcctgg tgatggccca ggaccagagg atcaggtggt acctgctgag catgggcagc   3960
aatgagaaca tccacagcat ccacttctct ggccatgtgt tcactgtgag gaagaaggag   4020
gagtacaaga tggccctgta caacctgtac cctggggtgt ttgagactgt ggagatgctg   4080
cccagcaagg ctggcatctg gagggtggag tgcctgattg gggagcacct gcatgctggc   4140
atgagcaccc tgttcctggt gtacagcaac aagtgccaga cccccctggg catggcctct   4200
ggccacatca gggacttcca gatcactgcc tctggccagt atggccagtg ggcccccaag   4260
ctggccaggc tgcactactc tggcagcatc aatgcctgga gcaccaagga gcccttcagc   4320
tggatcaagg tggacctgct ggcccccatg atcatccatg gcatcaagac ccagggggcc   4380
aggcagaagt tcagcagcct gtacatcagc cagttcatca tcatgtacag cctggatggc   4440
aagaagtggc agacctacag gggcaacagc actggcaccc tgatggtgtt ctttggcaat   4500
gtggacagct ctggcatcaa gcacaacatc ttcaaccccc ccatcattgc cagatacatc   4560
aggctgcacc ccacccacta cagcatcagg agcaccctga ggatggagct gatgggctgt   4620
gacctgaaca gctgcagcat gcccctgggc atggagagca aggccatctc tgatgcccag   4680
atcactgcca gcagctactt caccaacatg tttgccacct ggagccccag caaggccagg   4740
ctgcacctgc agggcaggag caatgcctgg aggccccagg tcaacaaccc caaggagtgg   4800
ctgcaggtgg acttccagaa gaccatgaag gtgactgggg tgaccaccca gggggtgaag   4860
agcctgctga ccagcatgta tgtgaaggag ttcctgatca gcagcagcca ggatggccac   4920
cagtggaccc tgttcttcca gaatggcaag gtgaaggtgt tccagggcaa ccaggacagc   4980
ttcacccctg tggtgaacag cctggacccc cccctgctga ccagatacct gaggattcac   5040
ccccagagct gggtgcacca gattgccctg aggatggagg tgctgggctg tgaggcccag   5100
gacctgtact gacctcgagg aataaaggaa atttattttc attgcaatag tgtgttggtt   5160
```

```
ttttgtgtca cgtggcggcc gcaggaaccc ctagtgatgg agttggccac tccctctctg   5220

cgcgctcgct cgctcactga ggccgggcga ccaaaggtcg cccgacgccc gggctttgcc   5280

cgggcggcct cagtgagcga gcgagcgcgc agagagggag tggccaa                 5327
```

<210> SEQ ID NO 26
<211> LENGTH: 5309
<212> TYPE: DNA
<213> ORGANISM: Adeno-Associated Virus 2

<400> SEQUENCE: 26

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtc tgcaggctca gaggcacaca    180

ggagtttctg ggctcaccct gccccccttcc aaccccctcag ttcccatcct ccagcagctg    240

tttgtgtgct gcctctgaag tccacactga acaaacttca gcctactcat gtccctaaaa    300

tgggcaaaca ttgcaagcag caaacagcaa acacacagcc ctccctgcct gctgaccttg    360

gagctggggc agaggtcaga gacctctctg ggcccatgcc acctccaaca tccactcgac    420

cccttggaat ttcggtggag aggagcagag gttgtcctgg cgtggtttag gtagtgtgag    480

aggggtcgac tggacacagg acgctgtggt ttctgagcca gggggcgact cagatcccag    540

ccagtggact tagcccctgt ttgctcctcc gataactggg gtgaccttgg ttaatattca    600

ccagcagcct cccccgttgc cctctggat ccactgctta aatacggacg aggacagggc    660

cctgtctcct cagcttcagg caccaccact gacctgggac agtgaatcgc gatcgccacc    720

atgcagattg agctgagcac ctgcttcttc ctgtgcctgc tgaggttctg cttctctgcc    780

accaggagat actacctggg ggctgtggag ctgagctggg actacatgca gtctgacctg    840

ggggagctgc ctgtggatgc caggttcccc cccagagtgc ccaagagctt ccccttcaac    900

acctctgtgg tgtacaagaa gaccctgttt gtggagttca ctgaccacct gttcaacatt    960

gccaagccca ggccccccctg gatgggcctg ctgggcccca ccatccaggc tgaggtgtat   1020

gacactgtgg tgatcaccct gaagaacatg gccagccacc ctgtgagcct gcatgctgtg   1080

ggggtgagct actggaaggc ctctgagggg gctgagtatg atgaccagac cagccagagg   1140

gagaaggagg atgacaaggt gttccctggg ggcagccaca cctatgtgtg gcaggtgctg   1200

aaggagaatg gccccatggc ctctgacccc ctgtgcctga cctacagcta cctgagccat   1260

gtggacctgg tgaaggacct gaactctggc ctgattgggg ccctgctggt gtgcagggag   1320

ggcagcctgg ccaaggagaa gacccagacc ctgcacaagt tcatcctgct gtttgctgtg   1380

tttgatgagg gcaagagctg gcactctgaa accaagaaca gcctgatgca ggacagggat   1440

gctgcctctg ccagggcctg gcccaagatg cacactgtga atggctatgt gaacaggagc   1500

ctgcctggcc tgattggctg ccacaggaag tctgtgtact ggcatgtgat tggcatgggc   1560

accacccctg aggtgcacag catcttcctg gagggccaca ccttcctggt caggaaccac   1620

aggcaggcca gcctggagat cagccccatc accttcctga ctgcccagac cctgctgatg   1680

gacctgggcc agttcctgct gttctgccac atcagcagcc accagcatga tggcatggag   1740

gcctatgtga aggtggacag ctgccctgag gagccccagc tgaggatgaa gaacaatgag   1800

gaggctgagg actatgatga tgacctgact gactctgaga tggatgtggt gaggtttgat   1860

gatgacaaca gcccccagctt catccagatc aggtctgtgg ccaagaagca ccccaagacc   1920
```

-continued

```
tgggtgcact acattgctgc tgaggaggag gactgggact atgcccccct ggtgctggcc   1980
cctgatgaca ggagctacaa gagccagtac ctgaacaatg gcccccagag gattggcagg   2040
aagtacaaga aggtcaggtt catggcctac actgatgaaa ccttcaagac cagggaggcc   2100
atccagcatg agtctggcat cctgggcccc ctgctgtatg gggaggtggg ggacaccctg   2160
ctgatcatct tcaagaacca ggccagcagg ccctacaaca tctaccccca tggcatcact   2220
gatgtgaggc ccctgtacag caggaggctg cccaaggggg tgaagcacct gaaggacttc   2280
cccatcctgc ctggggagat cttcaagtac aagtggactg tgactgtgga ggatggcccc   2340
accaagtctg accccaggtg cctgaccaga tactacagca gctttgtgaa catggagagg   2400
gacctggcct ctggcctgat tggccccctg ctgatctgct acaaggagtc tgtggaccag   2460
aggggcaacc agatcatgtc tgacaagagg aatgtgatcc tgttctctgt gtttgatgag   2520
aacaggagct ggtacctgac tgagaacatc cagaggttcc tgcccaaccc tgctggggtg   2580
cagctggagg accctgagtt ccaggccagc aacatcatgc acagcatcaa tggctatgtg   2640
tttgacagcc tgcagctgtc tgtgtgcctg catgaggtgg cctactggta catcctgagc   2700
attggggccc agactgactt cctgtctgtg ttcttctctg gctacacctt caagcacaag   2760
atggtgtatg aggacaccct gaccctgttc cccttctctg ggagactgt gttcatgagc   2820
atggagaacc ctggcctgtg gattctgggc tgccacaact ctgacttcag gaacaggggc   2880
atgactgccc tgctgaaagt ctccagctgt gacaagaaca ctggggacta ctatgaggac   2940
agctatgagg acatctctgc ctacctgctg agcaagaaca atgccattga gcccaggagc   3000
ttcagccaga accccccagt gctgaagagg caccagaggg agatcaccag gaccaccctg   3060
cagtctgacc aggaggagat tgactatgat gacaccatct ctgtggagat gaagaaggag   3120
gactttgaca tctacgacga ggacgagaac cagagcccca ggagcttcca gaagaagacc   3180
aggcactact tcattgctgc tgtggagagg ctgtgggact atggcatgag cagcagcccc   3240
catgtgctga ggaacagggc ccagtctggc tctgtgcccc agttcaagaa ggtggtgttc   3300
caggagttca ctgatggcag cttcacccag cccctgtaca gaggggagct gaatgagcac   3360
ctgggcctgc tgggccccta catcagggct gaggtggagg acaacatcat ggtgaccttc   3420
aggaaccagg ccagcaggcc ctacagcttc tacagcagcc tgatcagcta tgaggaggac   3480
cagaggcagg gggctgagcc caggaagaac tttgtgaagc ccaatgaaac caagacctac   3540
ttctggaagg tgcagcacca catggccccc accaaggatg agtttgactg caaggcctgg   3600
gcctacttct ctgatgtgga cctggagaag gatgtgcact ctggcctgat tggccccctg   3660
ctggtgtgcc acaccaacac cctgaaccct gcccatggca ggcaggtgac tgtgcaggag   3720
tttgccctgt tcttcaccat ctttgatgaa accaagagct ggtacttcac tgagaacatg   3780
gagaggaact gcagggcccc ctgcaacatc cagatggagg accccacctt caaggagaac   3840
tacaggttcc atgccatcaa tggctacatc atggacaccc tgcctggcct ggtgatggcc   3900
caggaccaga ggatcaggtg gtacctgctg agcatgggca gcaatgagaa catccacagc   3960
atccacttct ctggccatgt gttcactgtg aggaagaagg aggagtacaa gatggccctg   4020
tacaacctgt accctggggt gtttgagact gtggagatgc tgcccagcaa ggctggcatc   4080
tggagggtgg agtgcctgat tggggagcac ctgcatgctg gcatgagcac cctgttcctg   4140
gtgtacagca acaagtgcca gacccccctg ggcatggcct ctggccacat cagggacttc   4200
cagatcactg cctctggcca gtatggccag tgggccccca agctggccag gctgcactac   4260
tctggcagca tcaatgcctg gagcaccaag gagcccttca gctggatcaa ggtggacctg   4320
```

-continued

```
ctggccccca tgatcatcca tggcatcaag acccaggggg ccaggcagaa gttcagcagc   4380
ctgtacatca gccagttcat catcatgtac agcctggatg gcaagaagtg gcagacctac   4440
aggggcaaca gcactggcac cctgatggtg ttctttggca atgtggacag ctctggcatc   4500
aagcacaaca tcttcaaccc ccccatcatt gccagataca tcaggctgca ccccacccac   4560
tacagcatca ggagcaccct gaggatggag ctgatgggct gtgacctgaa cagctgcagc   4620
atgcccctgg gcatggagag caaggccatc tctgatgccc agatcactgc cagcagctac   4680
ttcaccaaca tgtttgccac ctggagcccc agcaaggcca ggctgcacct gcagggcagg   4740
agcaatgcct ggaggcccca ggtcaacaac cccaaggagt ggctgcaggt ggacttccag   4800
aagaccatga aggtgactgg ggtgaccacc cagggggtga agagcctgct gaccagcatg   4860
tatgtgaagg agttcctgat cagcagcagc caggatggcc accagtggac cctgttcttc   4920
cagaatggca aggtgaaggt gttccagggc aaccaggaca gcttcacccc tgtggtgaac   4980
agcctggacc ccccccctgct gaccagatac ctgaggattc acccccagag ctgggtgcac   5040
cagattgccc tgaggatgga ggtgctgggc tgtgaggccc aggacctgta ctgacctcga   5100
ggaataaagg aaatttattt tcattgcaat agtgtgttgg tttttttgtgt cacgtggcgg   5160
ccgcaggaac ccctagtgat ggagttggcc actccctctc tgcgcgctcg ctcgctcact   5220
gaggccgggc gaccaaaggt cgcccgacgc ccgggctttg cccgggcggc ctcagtgagc   5280
gagcgagcgc gcagagaggg agtggccaa                                    5309
```

<210> SEQ ID NO 27
<211> LENGTH: 5532
<212> TYPE: DNA
<213> ORGANISM: Adeno-Associated Virus 2

<400> SEQUENCE: 27

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgtaa gtatgccttt cactgcgaga ggttctggag aggcttctga gctccccatg    780
gcccaggcag gcagcaggtc tggggcagga ggggggttgt ggagtgcctt gactcggggc    840
ctggcccccc catctctgtc ttgcaggaca attgccgtct tctgtctcgt ggggcatcct    900
cctgctggca ggcctgtgct gcctggtccc tgcgatcgcc accatgcaga ttgagctgag    960
cacctgcttc ttcctgtgcc tgctgaggtt ctgcttctct gccaccagga gatactacct   1020
gggggctgtg gagctgagct gggactacat gcagtctgac ctgggggagc tgcctgtgga   1080
```

-continued

```
tgccaggttc ccccccagag tgcccaagag cttccccttc aacacctctg tggtgtacaa   1140
gaagaccctg tttgtggagt tcactgacca cctgttcaac attgccaagc ccaggccccc   1200
ctggatgggc ctgctgggcc ccaccatcca ggctgaggtg tatgacactg tggtgatcac   1260
cctgaagaac atggccagcc accctgtgag cctgcatgct gtgggggtga gctactggaa   1320
ggcctctgag gggggctgagt atgatgacca gaccagccag agggagaagg aggatgacaa  1380
ggtgttccct gggggcagcc acacctatgt gtggcaggtg ctgaaggaga atggccccat   1440
ggcctctgac cccctgtgcc tgacctacag ctacctgagc catgtggacc tggtgaagga   1500
cctgaactct ggcctgattg ggcccctgct ggtgtgcagg gagggcagcc tggccaagga   1560
gaagacccag accctgcaca agttcatcct gctgtttgct gtgtttgatg agggcaagag   1620
ctggcactct gaaaccaaga acagcctgat gcaggacagg gatgctgcct ctgccagggc   1680
ctggcccaag atgcacactg tgaatggcta tgtgaacagg agcctgcctg gcctgattgg   1740
ctgccacagg aagtctgtgt actggcatgt gattggcatg ggcaccaccc ctgaggtgca   1800
cagcatcttc ctggagggcc acaccttcct ggtcaggaac cacaggcagg ccagcctgga   1860
gatcagcccc atcaccttcc tgactgccca gaccctgctg atggacctgg gccagttcct   1920
gctgttctgc cacatcagca gccaccagca tgatggcatg gaggcctatg tgaaggtgga   1980
cagctgccct gaggagcccc agctgaggat gaagaacaat gaggaggctg aggactatga   2040
tgatgacctg actgactctg agatggatgt ggtgaggttt gatgatgaca acagccccag   2100
cttcatccag atcaggtctg tggccaagaa gcaccccaag acctgggtgc actacattgc   2160
tgctgaggag gaggactggg actatgcccc cctggtgctg gcccctgatg acaggagcta   2220
caagagccag tacctgaaca atggccccca gaggattggc aggaagtaca agaaggtcag   2280
gttcatggcc tacactgatg aaaccttcaa gaccagggag gccatccagc atgagtctgg   2340
catcctgggc cccctgctgt atggggaggt gggggacacc ctgctgatca tcttcaagaa   2400
ccaggccagc aggccctaca acatctaccc ccatggcatc actgatgtga ggcccctgta   2460
cagcaggagg ctgcccaagg gggtgaagca cctgaaggac ttccccatcc tgcctgggga   2520
gatcttcaag tacaagtgga ctgtgactgt ggaggatggc cccaccaagt ctgaccccag   2580
gtgcctgacc agatactaca gcagctttgt gaacatggag agggacctgg cctctggcct   2640
gattggcccc ctgctgatct gctacaagga gtctgtggac cagaggggca accagatcat   2700
gtctgacaag aggaatgtga tcctgttctc tgtgtttgat gagaacagga gctggtacct   2760
gactgagaac atccagaggt tcctgcccaa ccctgctggg gtgcagctgg aggaccctga   2820
gttccaggcc agcaacatca tgcacagcat caatggctat gtgtttgaca gcctgcagct   2880
gtctgtgtgc ctgcatgagg tggcctactg gtacatcctg agcattgggg cccagactga   2940
cttcctgtct gtgttcttct ctggctacac cttcaagcac aagatggtgt atgaggacac   3000
cctgaccctg ttccccttct ctggggagac tgtgttcatg agcatggaga accctggcct   3060
gtggattctg ggctgccaca actctgactt caggaacagg ggcatgactg ccctgctgaa   3120
agtctccagc tgtgacaaga acactgggga ctactatgag gacagctatg aggacatctc   3180
tgcctacctg ctgagcaaga acaatgccat tgagcccagg agcttcagcc agaacccccc   3240
agtgctgaag aggcaccaga gggagatcac caggaccacc ctgcagtctg accaggagga   3300
gattgactat gatgacacca tctctgtgga gatgaagaag gaggactttg acatctacga   3360
cgaggacgag aaccagagcc ccaggagctt ccagaagaag accaggcact acttcattgc   3420
tgctgtggag aggctgtggg actatggcat gagcagcagc ccccatgtgc tgaggaacag   3480
```

-continued

```
ggcccagtct ggctctgtgc cccagttcaa gaaggtggtg ttccaggagt tcactgatgg   3540
cagcttcacc cagcccctgt acagagggga gctgaatgag cacctgggcc tgctgggccc   3600
ctacatcagg gctgaggtgg aggacaacat catggtgacc ttcaggaacc aggccagcag   3660
gccctacagc ttctacagca gcctgatcag ctatgaggag gaccagaggc agggggctga   3720
gcccaggaag aactttgtga agcccaatga aaccaagacc tacttctgga aggtgcagca   3780
ccacatggcc cccaccaagg atgagtttga ctgcaaggcc tgggcctact tctctgatgt   3840
ggacctggag aaggatgtgc actctggcct gattggcccc ctgctggtgt gccacaccaa   3900
caccctgaac cctgcccatg gcaggcaggt gactgtgcag gagtttgccc tgttcttcac   3960
catctttgat gaaaccaaga gctggtactt cactgagaac atggagagga actgcagggc   4020
cccctgcaac atccagatgg aggaccccac cttcaaggag aactacaggt tccatgccat   4080
caatggctac atcatggaca ccctgcctgg cctggtgatg gcccaggacc agaggatcag   4140
gtggtacctg ctgagcatgg gcagcaatga gaacatccac agcatccact tctctggcca   4200
tgtgttcact gtgaggaaga aggaggagta caagatggcc ctgtacaacc tgtaccctgg   4260
ggtgtttgag actgtggaga tgctgcccag caaggctggc atctggaggg tggagtgcct   4320
gattggggag cacctgcatg ctggcatgag caccctgttc ctggtgtaca gcaacaagtg   4380
ccagaccccc ctgggcatgg cctctggcca catcagggac ttccagatca ctgcctctgg   4440
ccagtatggc cagtgggccc ccaagctggc caggctgcac tactctggca gcatcaatgc   4500
ctggagcacc aaggagccct tcagctggat caaggtggac ctgctggccc ccatgatcat   4560
ccatggcatc aagacccagg gggccaggca gaagttcagc agcctgtaca tcagccagtt   4620
catcatcatg tacagcctgg atggcaagaa gtggcagacc tacaggggca acagcactgg   4680
caccctgatg gtgttctttg gcaatgtgga cagctctggc atcaagcaca acatcttcaa   4740
cccccccatc attgccagat acatcaggct gcaccccacc cactacagca tcaggagcac   4800
cctgaggatg gagctgatgg gctgtgacct gaacagctgc agcatgcccc tgggcatgga   4860
gagcaaggcc atctctgatg cccagatcac tgccagcagc tacttcacca acatgtttgc   4920
cacctggagc cccagcaagg ccaggctgca cctgcagggc aggagcaatg cctggaggcc   4980
ccaggtcaac aaccccaagg agtggctgca ggtggacttc cagaagacca tgaaggtgac   5040
tggggtgacc acccaggggg tgaagagcct gctgaccagc atgtatgtga aggagttcct   5100
gatcagcagc agccaggatg gccaccagtg gaccctgttc ttccagaatg gcaaggtgaa   5160
ggtgttccag ggcaaccagg acagcttcac ccctgtggtg aacagcctgg acccccccct   5220
gctgaccaga tacctgagga ttcaccccca gagctgggtg caccagattg ccctgaggat   5280
ggaggtgctg ggctgtgagg cccaggacct gtactgacct cgaggaataa aggaaattta   5340
ttttcattgc aatagtgtgt tggttttttg tgtcacgtgg cggccgcagg aacccctagt   5400
gatggagttg gccactccct ctctgcgcgc tcgctcgctc actgaggccg ggcgaccaaa   5460
ggtcgcccga cgcccgggct ttgcccgggc ggcctcagtg agcgagcgag cgcgcagaga   5520
gggagtggcc aa                                                       5532
```

<210> SEQ ID NO 28
<211> LENGTH: 5877
<212> TYPE: DNA
<213> ORGANISM: Adeno-Associated Virus 2

<400> SEQUENCE: 28

-continued

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag ggtcgagtg     240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgacag gttaattttt aaaaagcagt caaaagtcca    540
agtggccctt ggcagcattt actctctctg tttgctctgg ttaataatct caggagcaca    600
aacattcctg gaggcaggag aagaaatcaa catcctggac ttatcctctg ggcctctccc    660
cacccccagg agaggctcag gttaattttt aaaaagcagt caaaagtcca agtggccctt    720
ggcagcattt actctctctg tttgctctgg ttaataatct caggagcaca aacattcctg    780
gaggcaggag aagaaatcaa catcctggac ttatcctctg ggcctctccc cacccccagg    840
agaggctgtc gactggacac aggacgctgt ggtttctgag ccagggggcg actcagatcc    900
cagccagtgg acttagcccc tgtttgctcc tccgataact ggggtgacct tggttaatat    960
tcaccagcag cctcccccgt tgcccctctg gatccactgc ttaaatacgg acgaggacag   1020
ggccctgtct cctcagcttc aggcaccacc actgacctgg gacagtgaat cgtaagtatg   1080
cctttcactg cgagaggttc tggagaggct tctgagctcc ccatggccca ggcaggcagc   1140
aggtctgggg caggaggggg gttgtggagt gccttgactc ggggcctggc ccccccatct   1200
ctgtcttgca ggacaattgc cgtcttctgt ctcgtggggc atcctcctgc tggcaggcct   1260
gtgctgcctg gtccctgcga tcgccaccat gcagattgag ctgagcacct gcttcttcct   1320
gtgcctgctg aggttctgct tctctgccac caggagatac tacctggggg ctgtggagct   1380
gagctgggac tacatgcagt ctgacctggg ggagctgcct gtggatgcca ggttcccccc   1440
cagagtgccc aagagcttcc ccttcaacac ctctgtggtg tacaagaaga ccctgtttgt   1500
ggagttcact gaccacctgt tcaacattgc caagcccagg ccccccctgga tgggcctgct   1560
gggccccacc atccaggctg aggtgtatga cactgtggtg atcaccctga agaacatggc   1620
cagccaccct gtgagcctgc atgctgtggg ggtgagctac tggaaggcct ctgagggggc   1680
tgagtatgat gaccagacca gccagaggga gaaggaggat gacaaggtgt tccctggggg   1740
cagccacacc tatgtgtggc aggtgctgaa ggagaatggc cccatggcct ctgacccccct  1800
gtgcctgacc tacagctacc tgagccatgt ggacctggtg aaggacctga actctggcct   1860
gattggggcc ctgctggtgt gcagggaggg cagcctggcc aaggagaaga cccagaccct   1920
gcacaagttc atcctgctgt ttgctgtgtt tgatgagggc aagagctggc actctgaaac   1980
caagaacagc ctgatgcagg acagggatgc tgcctctgcc agggcctggc ccaagatgca   2040
cactgtgaat ggctatgtga acaggagcct gcctggcctg attggctgcc acaggaagtc   2100
tgtgtactgg catgtgattg gcatgggcac caccccctgag gtgcacagca tcttcctgga   2160
gggccacacc ttcctggtca ggaaccacag gcaggccagc ctggagatca gccccatcac   2220
cttcctgact gcccagaccc tgctgatgga cctgggccag ttcctgctgt tctgccacat   2280
cagcagccac cagcatgatg gcatggaggc ctatgtgaag gtggacagct gccctgagga   2340
gccccagctg aggatgaaga acaatgagga ggctgaggac tatgatgatg acctgactga   2400
```

-continued

```
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
ctgggactat gccccctgg tgctggcccc tgatgacagg agctacaaga gccagtacct   2580
gaacaatggc ccccagagga ttggcaggaa gtacaagaag gtcaggttca tggcctacac   2640
tgatgaaacc ttcaagacca gggaggccat ccagcatgag tctggcatcc tgggcccct   2700
gctgtatggg gaggtggggg acaccctgct gatcatcttc aagaaccagg ccagcaggcc   2760
ctacaacatc tacccccatg gcatcactga tgtgaggccc ctgtacagca ggaggctgcc   2820
caagggggtg aagcacctga aggacttccc catcctgcct ggggagatct tcaagtacaa   2880
gtggactgtg actgtggagg atggccccac caagtctgac cccaggtgcc tgaccagata   2940
ctacagcagc tttgtgaaca tggagaggga cctggcctct ggcctgattg gcccctgct   3000
gatctgctac aaggagtctg tggaccagag gggcaaccag atcatgtctg acaagaggaa   3060
tgtgatcctg ttctctgtgt ttgatgagaa caggagctgg tacctgactg agaacatcca   3120
gaggttcctg cccaaccctg ctggggtgca gctggaggac cctgagttcc aggccagcaa   3180
catcatgcac agcatcaatg gctatgtgtt tgacagcctg cagctgtctg tgtgcctgca   3240
tgaggtggcc tactggtaca tcctgagcat tggggcccag actgacttcc tgtctgtgtt   3300
cttctctggc tacaccttca agcacaagat ggtgtatgag gacaccctga ccctgttccc   3360
cttctctggg gagactgtgt tcatgagcat ggagaaccct ggcctgtgga ttctgggctg   3420
ccacaactct gacttcagga acaggggcat gactgccctg ctgaaagtct ccagctgtga   3480
caagaacact ggggactact atgaggacag ctatgaggac atctctgcct acctgctgag   3540
caagaacaat gccattgagc ccaggagctt cagccagaac cccccagtgc tgaagaggca   3600
ccagagggag atcaccagga ccaccctgca gtctgaccag gaggagattg actatgatga   3660
caccatctct gtggagatga agaaggagga ctttgacatc tacgacgagg acgagaacca   3720
gagccccagg agcttccaga agaagaccag gcactacttc attgctgctg tggagaggct   3780
gtgggactat ggcatgagca gcagccccca tgtgctgagg aacagggccc agtctggctc   3840
tgtgccccag ttcaagaagg tggtgttcca ggagttcact gatggcagct tcacccagcc   3900
cctgtacaga ggggagctga atgagcacct gggcctgctg ggcccctaca tcagggctga   3960
ggtggaggac aacatcatgg tgaccttcag gaaccaggcc agcaggccct acagcttcta   4020
cagcagcctg atcagctatg aggaggacca gaggcagggg gctgagccca ggaagaactt   4080
tgtgaagccc aatgaaacca agacctactt ctggaaggtg cagcaccaca tggcccccac   4140
caaggatgag tttgactgca aggcctgggc ctacttctct gatgtggacc tggagaagga   4200
tgtgcactct ggcctgattg gcccctgct ggtgtgccac accaacaccc tgaaccctgc   4260
ccatggcagg caggtgactg tgcaggagtt tgccctgttc ttcaccatct ttgatgaaac   4320
caagagctgg tacttcactg agaacatgga gaggaactgc agggccccct gcaacatcca   4380
gatggaggac cccaccttca aggagaacta caggttccat gccatcaatg gctacatcat   4440
ggacaccctg cctggcctgg tgatggccca ggaccagagg atcaggtggt acctgctgag   4500
catgggcagc aatgagaaca tccacagcat ccacttctct ggccatgtgt tcactgtgag   4560
gaagaaggag gagtacaaga tggccctgta caacctgtac cctggggtgt ttgagactgt   4620
ggagatgctg cccagcaagg ctggcatctg gagggtggag tgcctgattg gggagcacct   4680
gcatgctggc atgagcaccc tgttcctggt gtacagcaac aagtgccaga cccccctggg   4740
```

-continued

```
catggcctct ggccacatca gggacttcca gatcactgcc tctggccagt atggccagtg   4800
ggcccccaag ctggccaggc tgcactactc tggcagcatc aatgcctgga gcaccaagga   4860
gcccttcagc tggatcaagg tggacctgct ggcccccatg atcatccatg gcatcaagac   4920
ccagggggcc aggcagaagt tcagcagcct gtacatcagc cagttcatca tcatgtacag   4980
cctggatggc aagaagtggc agacctacag gggcaacagc actggcaccc tgatggtgtt   5040
ctttggcaat gtggacagct ctggcatcaa gcacaacatc ttcaaccccc ccatcattgc   5100
cagatacatc aggctgcacc ccacccacta cagcatcagg agcaccctga ggatggagct   5160
gatgggctgt gacctgaaca gctgcagcat gcccctgggc atggagagca aggccatctc   5220
tgatgcccag atcactgcca gcagctactt caccaacatg tttgccacct ggagccccag   5280
caaggccagg ctgcacctgc agggcaggag caatgcctgg aggccccagg tcaacaaccc   5340
caaggagtgg ctgcaggtgg acttccagaa gaccatgaag gtgactgggg tgaccaccca   5400
gggggtgaag agcctgctga ccagcatgta tgtgaaggag ttcctgatca gcagcagcca   5460
ggatggccac cagtggaccc tgttcttcca gaatggcaag gtgaaggtgt tccagggcaa   5520
ccaggacagc ttcacccctg tggtgaacag cctggacccc cccctgctga ccagatacct   5580
gaggattcac ccccagagct gggtgcacca gattgccctg aggatggagg tgctgggctg   5640
tgaggcccag gacctgtact gacctcgagg aataaaggaa atttattttc attgcaatag   5700
tgtgttggtt ttttgtgtca cgtggcggcc gcaggaaccc ctagtgatgg agttggccac   5760
tccctctctg cgcgctcgct cgctcactga ggccgggcga ccaaaggtcg cccgacgccc   5820
gggctttgcc cgggcggcct cagtgagcga gcgagcgcgc agagagggag tggccaa      5877
```

<210> SEQ ID NO 29
<211> LENGTH: 6054
<212> TYPE: DNA
<213> ORGANISM: Adeno-Associated Virus 2

<400> SEQUENCE: 29

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag ggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgacag gttaattttt aaaaagcagt caaaagtcca    540
agtggccctt ggcagcattt actctctctg tttgctctgg ttaataatct caggagcaca    600
aacattcctg gaggcaggag aagaaatcaa catcctggac ttatcctctg ggcctctccc    660
cacccccagg agaggctcag gttaattttt aaaaagcagt caaaagtcca agtggccctt    720
ggcagcattt actctctctg tttgctctgg ttaataatct caggagcaca aacattcctg    780
gaggcaggag aagaaatcaa catcctggac ttatcctctg ggcctctccc cacccccagg    840
agaggctgtc gactggacac aggacgctgt ggtttctgag ccagggggcg actcagatcc    900
cagccagtgg acttagcccc tgtttgctcc tccgataact ggggtgacct tggttaatat    960
tcaccagcag cctcccccgt tgcccctctg gatccactgc ttaaatacgg acgaggacag   1020
```

-continued

```
ggccctgtct cctcagcttc aggcaccacc actgacctgg gacagtgaat cgtaagtatg   1080
cctttcactg cgagaggttc tggagaggct tctgagctcc ccatggccca ggcaggcagc   1140
aggtctgggg caggaggggg gttgtggagt gccttgactc ggggcctggc ccccccatct   1200
ctgtcttgca ggacaattgc cgtcttctgt ctcgtggggc atcctcctgc tggcaggcct   1260
gtgctgcctg gtccctgcga tcgccaccat gcagattgag ctgagcacct gcttcttcct   1320
gtgcctgctg aggttctgct tctctgccac caggagatac tacctggggg ctgtggagct   1380
gagctgggac tacatgcagt ctgacctggg ggagctgcct gtggatgcca ggttcccccc   1440
cagagtgccc aagagcttcc ccttcaacac ctctgtggtg tacaagaaga ccctgtttgt   1500
ggagttcact gaccacctgt tcaacattgc caagcccagg ccccccctgga tgggcctgct   1560
gggcccccacc atccaggctg aggtgtatga cactgtggtg atcaccctga agaacatggc   1620
cagccaccct gtgagcctgc atgctgtggg ggtgagctac tggaaggcct ctgagggggc   1680
tgagtatgat gaccagacca gccagaggga gaaggaggat gacaaggtgt tccctggggg   1740
cagccacacc tatgtgtggc aggtgctgaa ggagaatggc cccatggcct ctgacccccct   1800
gtgcctgacc tacagctacc tgagccatgt ggacctggtg aaggacctga actctggcct   1860
gattggggcc ctgctggtgt gcagggaggg cagcctggcc aaggagaaga cccagaccct   1920
gcacaagttc atcctgctgt ttgctgtgtt tgatgagggc aagagctggc actctgaaac   1980
caagaacagc ctgatgcagg acagggatgc tgcctctgcc agggcctggc ccaagatgca   2040
cactgtgaat ggctatgtga acaggagcct gcctggcctg attggctgcc acaggaagtc   2100
tgtgtactgg catgtgattg gcatgggcac caccccctgag gtgcacagca tcttcctgga   2160
gggccacacc ttcctggtca ggaaccacag gcaggccagc ctggagatca gccccatcac   2220
cttcctgact gcccagaccc tgctgatgga cctgggccag ttcctgctgt tctgccacat   2280
cagcagccac cagcatgatg gcatggaggc ctatgtgaag gtggacagct gccctgagga   2340
gccccagctg aggatgaaga acaatgagga ggctgaggac tatgatgatg acctgactga   2400
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
ctgggactat gcccccctgg tgctggcccc tgatgacagg agctacaaga gccagtacct   2580
gaacaatggc ccccagagga ttggcaggaa gtacaagaag gtcaggttca tggcctacac   2640
tgatgaaacc ttcaagacca gggaggccat ccagcatgag tctggcatcc tgggcccccct   2700
gctgtatggg gaggtggggg acaccctgct gatcatcttc aagaaccagg ccagcaggcc   2760
ctacaacatc tacccccatg gcatcactga tgtgaggccc ctgtacagca ggaggctgcc   2820
caagggggtg aagcacctga aggacttccc catcctgcct ggggagatct tcaagtacaa   2880
gtggactgtg actgtggagg atggccccac caagtctgac cccaggtgcc tgaccagata   2940
ctacagcagc tttgtgaaca tggagaggga cctggcctct ggcctgattg gcccccctgct   3000
gatctgctac aaggagtctg tggaccagag gggcaaccag atcatgtctg acaagaggaa   3060
tgtgatcctg ttctctgtgt ttgatgagaa caggagctgg tacctgactg agaacatcca   3120
gaggttcctg cccaaccctg ctggggtgca gctggaggac cctgagttcc aggccagcaa   3180
catcatgcac agcatcaatg gctatgtgtt tgacagcctg cagctgtctg tgtgcctgca   3240
tgaggtggcc tactggtaca tcctgagcat tggggcccag actgacttcc tgtctgtgtt   3300
cttctctggc tacaccttca agcacaagat ggtgtatgag gacaccctga ccctgttccc   3360
```

-continued

```
cttctctggg gagactgtgt tcatgagcat ggagaaccct ggcctgtgga ttctgggctg   3420
ccacaactct gacttcagga acaggggcat gactgccctg ctgaaagtct ccagctgtga   3480
caagaacact ggggactact atgaggacag ctatgaggac atctctgcct acctgctgag   3540
caagaacaat gccattgagc ccaggagctt cagccagaac cccccagtgc tgaagaggca   3600
ccagagggag atcaccagga ccaccctgca gtctgaccag gaggagattg actatgatga   3660
caccatctct gtggagatga agaaggagga ctttgacatc tacgacgagg acgagaacca   3720
gagccccagg agcttccaga agaagaccag gcactacttc attgctgctg tggagaggct   3780
gtgggactat ggcatgagca gcagccccca tgtgctgagg aacagggccc agtctggctc   3840
tgtgccccag ttcaagaagg tggtgttcca ggagttcact gatggcagct tcacccagcc   3900
cctgtacaga ggggagctga atgagcacct gggcctgctg ggcccctaca tcagggctga   3960
ggtggaggac aacatcatgg tgaccttcag gaaccaggcc agcaggccct acagcttcta   4020
cagcagcctg atcagctatg aggaggacca gaggcagggg gctgagccca ggaagaactt   4080
tgtgaagccc aatgaaacca agacctactt ctggaaggtg cagcaccaca tggcccccac   4140
caaggatgag tttgactgca aggcctgggc ctacttctct gatgtggacc tggagaagga   4200
tgtgcactct ggcctgattg gccccctgct ggtgtgccac accaacaccc tgaaccctgc   4260
ccatggcagg caggtgactg tgcaggagtt tgccctgttc ttcaccatct ttgatgaaac   4320
caagagctgg tacttcactg agaacatgga gaggaactgc agggcccccct gcaacatcca   4380
gatggaggac cccaccttca aggagaacta caggttccat gccatcaatg gctacatcat   4440
ggacaccctg cctggcctgg tgatggccca ggaccagagg atcaggtggt acctgctgag   4500
catgggcagc aatgagaaca tccacagcat ccacttctct ggccatgtgt tcactgtgag   4560
gaagaaggag gagtacaaga tggccctgta caacctgtac cctggggtgt ttgagactgt   4620
ggagatgctg cccagcaagg ctggcatctg gagggtggag tgcctgattg gggagcacct   4680
gcatgctggc atgagcaccc tgttcctggt gtacagcaac aagtgccaga ccccccctggg   4740
catggcctct ggccacatca gggacttcca gatcactgcc tctggccagt atggccagtg   4800
ggcccccaag ctggccaggc tgcactactc tggcagcatc aatgcctgga gcaccaagga   4860
gcccttcagc tggatcaagg tggacctgct ggcccccatg atcatccatg gcatcaagac   4920
ccagggggcc aggcagaagt tcagcagcct gtacatcagc cagttcatca tcatgtacag   4980
cctggatggc aagaagtggc agacctacag gggcaacagc actggcaccc tgatggtgtt   5040
ctttggcaat gtggacagct ctggcatcaa gcacaacatc ttcaaccccc ccatcattgc   5100
cagatacatc aggctgcacc ccacccacta cagcatcagg agcaccctga ggatggagct   5160
gatgggctgt gacctgaaca gctgcagcat gcccctgggc atggagagca aggccatctc   5220
tgatgcccag atcactgcca gcagctactt caccaacatg tttgccacct ggagccccag   5280
caaggccagg ctgcacctgc agggcaggag caatgcctgg aggccccagg tcaacaaccc   5340
caaggagtgg ctgcaggtgg acttccagaa gaccatgaag gtgactgggg tgaccaccca   5400
gggggtgaag agcctgctga ccagcatgta tgtgaaggag ttcctgatca gcagcagcca   5460
ggatggccac cagtggaccc tgttcttcca gaatggcaag gtgaaggtgt tccagggcaa   5520
ccaggacagc ttcacccctg tggtgaacag cctggacccc cccctgctga ccagatacct   5580
gaggattcac ccccagagct gggtgcacca gattgccctg aggatggagg tgctgggctg   5640
tgaggcccag gacctgtact gacctcgagg tgtgccttct agttgccagc catctgttgt   5700
ttgcccctcc cccgtgcctt ccttgaccct ggaaggtgcc actcccactg tcctttccta   5760
```

```
ataaaatgag gaaattgcat cgcattgtct gagtaggtgt cattctattc tggggggtgg   5820

ggtggggcag gacagcaagg gggaggattg ggaagacaat agcaggcatg ctggggatgc   5880

ggtgggctct atgggcacgt ggcggccgca ggaacccta gtgatggagt tggccactcc   5940

ctctctgcgc gctcgctcgc tcactgaggc cgggcgacca aaggtcgccc gacgcccggg   6000

ctttgcccgg gcggcctcag tgagcgagcg agcgcgcaga gagggagtgg ccaa         6054
```

<210> SEQ ID NO 30
<211> LENGTH: 6054
<212> TYPE: DNA
<213> ORGANISM: Adeno-Associated Virus 2

<400> SEQUENCE: 30

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgaccc ctctcacact    180

acctaaacca cgccaggaca acctctgctc ctctccaccg aaattccaag ggtcgagtg     240

gatgttggag gtggcatggg cccagagagg tctctgacct ctgccccagc tccaaggtca    300

gcaggcaggg agggctgtgt gtttgctgtt tgctgcttgc aatgtttgcc cattttaggg    360

acatgagtag gctgaagttt gttcagtgtg gacttcagag gcagcacaca aacagctgct    420

ggaggatggg aactgagggg ttggaagggg gcagggtgag cccagaaact cctgtgtgcc    480

tctgagcctg cagacgcgaa acgtcgaagc ctctcctggg ggtggggaga ggcccagagg    540

ataagtccag gatgttgatt tcttctcctg cctccaggaa tgtttgtgct cctgagatta    600

ttaaccagag caaacagaga gagtaaatgc tgccaagggc cacttggact tttgactgct    660

ttttaaaaat taacctgagc ctctcctggg ggtggggaga ggcccagagg ataagtccag    720

gatgttgatt tcttctcctg cctccaggaa tgtttgtgct cctgagatta ttaaccagag    780

caaacagaga gagtaaatgc tgccaagggc cacttggact tttgactgct ttttaaaaat    840

taacctggtc gactggacac aggacgctgt ggtttctgag ccagggggcg actcagatcc    900

cagccagtgg acttagcccc tgtttgctcc tccgataact ggggtgacct tggttaatat    960

tcaccagcag cctcccccgt tgcccctctg gatccactgc ttaaatacgg acgaggacag   1020

ggccctgtct cctcagcttc aggcaccacc actgacctgg gacagtgaat cgtaagtatg   1080

cctttcactg cgagaggttc tggagaggct tctgagctcc ccatggccca ggcaggcagc   1140

aggtctgggg caggaggggg gttgtggagt gccttgactc ggggcctggc ccccccatct   1200

ctgtcttgca ggacaattgc cgtcttctgt ctcgtggggc atcctcctgc tggcaggcct   1260

gtgctgcctg gtccctgcga tcgccaccat gcagattgag ctgagcacct gcttcttcct   1320

gtgcctgctg aggttctgct tctctgccac caggagatac tacctggggg ctgtggagct   1380

gagctgggac tacatgcagt ctgacctggg ggagctgcct gtggatgcca ggttcccccc   1440

cagagtgccc aagagcttcc ccttcaacac ctctgtggtg tacaagaaga ccctgtttgt   1500

ggagttcact gaccacctgt tcaacattgc caagcccagg ccccccctgga tgggcctgct   1560

gggccccacc atccaggctg aggtgtatga cactgtggtg atcaccctga agaacatggc   1620

cagccaccct gtgagcctgc atgctgtggg ggtgagctac tggaaggcct ctgagggggc   1680

tgagtatgat gaccagacca gccagaggga gaaggaggat gacaaggtgt tccctggggg   1740

cagccacacc tatgtgtggc aggtgctgaa ggagaatggc cccatggcct ctgacccccct   1800
```

-continued

```
gtgcctgacc tacagctacc tgagccatgt ggacctggtg aaggacctga actctggcct   1860
gattggggcc ctgctggtgt gcagggaggg cagcctggcc aaggagaaga cccagaccct   1920
gcacaagttc atcctgctgt ttgctgtgtt tgatgagggc aagagctggc actctgaaac   1980
caagaacagc ctgatgcagg acagggatgc tgcctctgcc agggcctggc ccaagatgca   2040
cactgtgaat ggctatgtga acaggagcct gcctggcctg attggctgcc acaggaagtc   2100
tgtgtactgg catgtgattg gcatgggcac cacccctgag gtgcacagca tcttcctgga   2160
gggccacacc ttcctggtca ggaaccacag gcaggccagc ctggagatca gccccatcac   2220
cttcctgact gcccagaccc tgctgatgga cctgggccag ttcctgctgt tctgccacat   2280
cagcagccac cagcatgatg gcatggaggc ctatgtgaag gtggacagct gccctgagga   2340
gccccagctg aggatgaaga acaatgagga ggctgaggac tatgatgatg acctgactga   2400
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
ctgggactat gccccccctgg tgctggcccc tgatgacagg agctacaaga gccagtacct   2580
gaacaatggc ccccagagga ttggcaggaa gtacaagaag gtcaggttca tggcctacac   2640
tgatgaaacc ttcaagacca gggaggccat ccagcatgag tctggcatcc tgggcccccct   2700
gctgtatggg gaggtggggg acaccctgct gatcatcttc aagaaccagg ccagcaggcc   2760
ctacaacatc taccccccatg gcatcactga tgtgaggccc ctgtacagca ggaggctgcc   2820
caagggggtg aagcacctga aggacttccc catcctgcct ggggagatct tcaagtacaa   2880
gtggactgtg actgtggagg atggccccac caagtctgac cccaggtgcc tgaccagata   2940
ctacagcagc tttgtgaaca tggagaggga cctggcctct ggcctgattg gcccccctgct   3000
gatctgctac aaggagtctg tggaccagag gggcaaccag atcatgtctg acaagaggaa   3060
tgtgatcctg ttctctgtgt ttgatgagaa caggagctgg tacctgactg agaacatcca   3120
gaggttcctg cccaaccctg ctggggtgca gctggaggac cctgagttcc aggccagcaa   3180
catcatgcac agcatcaatg gctatgtgtt tgacagcctg cagctgtctg tgtgcctgca   3240
tgaggtggcc tactggtaca tcctgagcat tggggcccag actgacttcc tgtctgtgtt   3300
cttctctggc tacaccttca agcacaagat ggtgtatgag gacaccctga ccctgttccc   3360
cttctctggg gagactgtgt tcatgagcat ggagaaccct ggcctgtgga ttctgggctg   3420
ccacaactct gacttcagga acaggggcat gactgccctg ctgaaagtct ccagctgtga   3480
caagaacact ggggactact atgaggacag ctatgaggac atctctgcct acctgctgag   3540
caagaacaat gccattgagc ccaggagctt cagccagaac ccccccagtgc tgaagaggca   3600
ccagagggag atcaccagga ccaccctgca gtctgaccag gaggagattg actatgatga   3660
caccatctct gtggagatga agaaggagga ctttgacatc tacgacgagg acgagaacca   3720
gagccccagg agcttccaga agaagaccag gcactacttc attgctgctg tggagaggct   3780
gtgggactat ggcatgagca gcagccccca tgtgctgagg aacagggccc agtctggctc   3840
tgtgccccag ttcaagaagg tggtgttcca ggagttcact gatggcagct tcacccagcc   3900
cctgtacaga ggggagctga atgagcacct gggcctgctg ggcccctaca tcagggctga   3960
ggtggaggac aacatcatgg tgaccttcag gaaccaggcc agcaggccct acagcttcta   4020
cagcagcctg atcagctatg aggaggacca gaggcagggg gctgagccca ggaagaactt   4080
tgtgaagccc aatgaaacca agacctactt ctggaaggtg cagcaccaca tggcccccac   4140
caaggatgag tttgactgca aggcctgggc ctacttctct gatgtggacc tggagaagga   4200
```

-continued

```
tgtgcactct ggcctgattg gccccctgct ggtgtgccac accaacaccc tgaaccctgc   4260

ccatggcagg caggtgactg tgcaggagtt tgccctgttc ttcaccatct ttgatgaaac   4320

caagagctgg tacttcactg agaacatgga gaggaactgc agggccccct gcaacatcca   4380

gatggaggac cccaccttca aggagaacta caggttccat gccatcaatg gctacatcat   4440

ggacaccctg cctggcctgg tgatggccca ggaccagagg atcaggtggt acctgctgag   4500

catgggcagc aatgagaaca tccacagcat ccacttctct ggccatgtgt tcactgtgag   4560

gaagaaggag gagtacaaga tggccctgta caacctgtac cctggggtgt ttgagactgt   4620

ggagatgctg cccagcaagg ctggcatctg gagggtggag tgcctgattg gggagcacct   4680

gcatgctggc atgagcaccc tgttcctggt gtacagcaac aagtgccaga ccccccctggg   4740

catggcctct ggccacatca gggacttcca gatcactgcc tctggccagt atggccagtg   4800

ggcccccaag ctggccaggc tgcactactc tggcagcatc aatgcctgga gcaccaagga   4860

gcccttcagc tggatcaagg tggacctgct ggcccccatg atcatccatg gcatcaagac   4920

ccagggggcc aggcagaagt tcagcagcct gtacatcagc cagttcatca tcatgtacag   4980

cctggatggc aagaagtggc agacctacag gggcaacagc actggcaccc tgatggtgtt   5040

ctttggcaat gtggacagct ctggcatcaa gcacaacatc ttcaaccccc ccatcattgc   5100

cagatacatc aggctgcacc ccacccacta cagcatcagg agcaccctga ggatggagct   5160

gatgggctgt gacctgaaca gctgcagcat gcccctgggc atggagagca aggccatctc   5220

tgatgcccag atcactgcca gcagctactt caccaacatg tttgccacct ggagccccag   5280

caaggccagg ctgcacctgc agggcaggag caatgcctgg aggccccagg tcaacaaccc   5340

caaggagtgg ctgcaggtgg acttccagaa gaccatgaag gtgactgggg tgaccaccca   5400

gggggtgaag agcctgctga ccagcatgta tgtgaaggag ttcctgatca gcagcagcca   5460

ggatggccac cagtggaccc tgttcttcca gaatggcaag gtgaaggtgt tccagggcaa   5520

ccaggacagc ttcacccctg tggtgaacag cctggacccc cccctgctga ccagatacct   5580

gaggattcac ccccagagct gggtgcacca gattgccctg aggatggagg tgctgggctg   5640

tgaggcccag gacctgtact gacctcgagg tgtgccttct agttgccagc catctgttgt   5700

ttgcccctcc cccgtgcctt ccttgaccct ggaaggtgcc actcccactg tcctttccta   5760

ataaaatgag gaaattgcat cgcattgtct gagtaggtgt cattctattc tggggggtgg   5820

ggtggggcag gacagcaagg gggaggattg ggaagacaat agcaggcatg ctggggatgc   5880

ggtgggctct atgggcacgt ggcggccgca ggaaccccta gtgatggagt tggccactcc   5940

ctctctgcgc gctcgctcgc tcactgaggc cgggcgacca aaggtcgccc gacgcccggg   6000

ctttgcccgg gcggcctcag tgagcgagcg agcgcgcaga gagggagtgg ccaa         6054
```

<210> SEQ ID NO 31
<211> LENGTH: 5504
<212> TYPE: DNA
<213> ORGANISM: Adeno-Associated Virus 2

<400> SEQUENCE: 31

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgaccc ctctcacact    180

acctaaacca cgccaggaca acctctgctc ctctccaccg aaattccaag ggtcgagtg    240
```

```
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttcccccc cagagtgccc    900
aagagcttcc ccttcaacac ctctgtggtg tacaagaaga ccctgtttgt ggagttcact    960
gaccacctgt tcaacattgc caagcccagg ccccccctgga tgggcctgct gggccccacc   1020
atccaggctg aggtgtatga cactgtggtg atcaccctga agaacatggc cagccaccct   1080
gtgagcctgc atgctgtggg ggtgagctac tggaaggcct ctgagggggc tgagtatgat   1140
gaccagacca gccagaggga gaaggaggat gacaaggtgt tccctggggg cagccacacc   1200
tatgtgtggc aggtgctgaa ggagaatggc cccatggcct ctgacccccct gtgcctgacc   1260
tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc ccaagatgca cactgtgaat   1500
ggctatgtga acaggagcct gcctggcctg attggctgcc acaggaagtc tgtgtactgg   1560
catgtgattg gcatgggcac cacccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagct gccctgagga gccccagctg   1800
aggatgaaga acaatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980
gcccccctgg tgctggcccc tgatgacagg agctacaaga gccagtacct gaacaatggc   2040
ccccagagga ttggcaggaa gtacaagaag gtcaggttca tggcctacac tgatgaaacc   2100
ttcaagacca gggaggccat ccagcatgag tctggcatcc tgggcccccct gctgtatggg   2160
gaggtggggg acaccctgct gatcatcttc aagaaccagg ccagcaggcc ctacaacatc   2220
tacccccatg gcatcactga tgtgaggccc ctgtacagca ggaggctgcc caagggggtg   2280
aagcacctga aggacttccc catcctgcct ggggagatct tcaagtacaa gtggactgtg   2340
actgtggagg atggccccac caagtctgac cccaggtgcc tgaccagata ctacagcagc   2400
tttgtgaaca tggagaggga cctggcctct ggcctgattg gcccccctgct gatctgctac   2460
aaggagtctg tggaccagag gggcaaccag atcatgtctg acaagaggaa tgtgatcctg   2520
ttctctgtgt ttgatgagaa caggagctgg tacctgactg agaacatcca gaggttcctg   2580
cccaaccctg ctggggtgca gctggaggac cctgagttcc aggccagcaa catcatgcac   2640
```

-continued agcatcaatg gctatgtgtt tgacagcctg cagctgtctg tgtgcctgca tgaggtggcc 2700
tactggtaca tcctgagcat tggggcccag actgacttcc tgtctgtgtt cttctctggc 2760
tacaccttca agcacaagat ggtgtatgag gacaccctga ccctgttccc cttctctggg 2820
gagactgtgt tcatgagcat ggagaaccct ggcctgtgga ttctgggctg ccacaactct 2880
gacttcagga acaggggcat gactgccctg ctgaaagtct ccagctgtga caagaacact 2940
ggggactact atgaggacag ctatgaggac atctctgcct acctgctgag caagaacaat 3000
gccattgagc ccaggagctt cagccagaac cccccagtgc tgaagaggca ccagagggag 3060
atcaccagga ccaccctgca gtctgaccag gaggagattg actatgatga caccatctct 3120
gtggagatga agaaggagga ctttgacatc tacgacgagg acgagaacca gagccccagg 3180
agcttccaga agaagaccag gcactacttc attgctgctg tggagaggct gtgggactat 3240
ggcatgagca gcagccccca tgtgctgagg aacagggccc agtctggctc tgtgccccag 3300
ttcaagaagg tggtgttcca ggagttcact gatggcagct tcacccagcc cctgtacaga 3360
ggggagctga atgagcacct gggcctgctg ggcccctaca tcagggctga ggtggaggac 3420
aacatcatgg tgaccttcag gaaccaggcc agcaggccct acagcttcta cagcagcctg 3480
atcagctatg aggaggacca gaggcagggg gctgagccca ggaagaactt tgtgaagccc 3540
aatgaaacca agacctactt ctggaaggtg cagcaccaca tggcccccac caaggatgag 3600
tttgactgca aggcctgggc ctacttctct gatgtggacc tggagaagga tgtgcactct 3660
ggcctgattg gcccccctgct ggtgtgccac accaacaccc tgaaccctgc ccatggcagg 3720
caggtgactg tgcaggagtt tgccctgttc ttcaccatct ttgatgaaac caagagctgg 3780
tacttcactg agaacatgga gaggaactgc agggcccccct gcaacatcca gatggaggac 3840
cccaccttca aggagaacta caggttccat gccatcaatg gctacatcat ggacaccctg 3900
cctggcctgg tgatggccca ggaccagagg atcaggtggt acctgctgag catgggcagc 3960
aatgagaaca tccacagcat ccacttctct ggccatgtgt tcactgtgag gaagaaggag 4020
gagtacaaga tggccctgta caacctgtac cctggggtgt ttgagactgt ggagatgctg 4080
cccagcaagg ctggcatctg gagggtggag tgcctgattg gggagcacct gcatgctggc 4140
atgagcaccc tgttcctggt gtacagcaac aagtgccaga ccccccctgggg catggcctct 4200
ggccacatca gggacttcca gatcactgcc tctggccagt atggccagtg ggcccccaag 4260
ctggccaggc tgcactactc tggcagcatc aatgcctgga gcaccaagga gcccttcagc 4320
tggatcaagg tggacctgct ggcccccatg atcatccatg gcatcaagac ccaggggggcc 4380
aggcagaagt tcagcagcct gtacatcagc cagttcatca tcatgtacag cctggatggc 4440
aagaagtggc agacctacag gggcaacagc actggcaccc tgatggtgtt ctttggcaat 4500
gtggacagct ctggcatcaa gcacaacatc ttcaaccccc ccatcattgc cagatacatc 4560
aggctgcacc ccacccacta cagcatcagg agcaccctga ggatggagct gatgggctgt 4620
gacctgaaca gctgcagcat gcccctgggc atggagagca aggccatctc tgatgcccag 4680
atcactgcca gcagctactt caccaacatg tttgccacct ggagccccag caaggccagg 4740
ctgcacctgc agggcaggag caatgcctgg aggccccagg tcaacaaccc caaggagtgg 4800
ctgcaggtgg acttccagaa gaccatgaag gtgactgggg tgaccaccca gggggtgaag 4860
agcctgctga ccagcatgta tgtgaaggag ttcctgatca gcagcagcca ggatggccac 4920
cagtggaccc tgttcttcca gaatggcaag gtgaaggtgt tccagggcaa ccaggacagc 4980

```
ttcacccctg tggtgaacag cctggacccc cccctgctga ccagatacct gaggattcac   5040
ccccagagct gggtgcacca gattgccctg aggatggagg tgctgggctg tgaggcccag   5100
gacctgtact gacctcgagg tgtgccttct agttgccagc catctgttgt ttgcccctcc   5160
cccgtgcctt ccttgaccct ggaaggtgcc actcccactg tcctttccta ataaaatgag   5220
gaaattgcat cgcattgtct gagtaggtgt cattctattc tggggggtgg ggtggggcag   5280
gacagcaagg gggaggattg ggaagacaat agcaggcatg ctggggatgc ggtgggctct   5340
atgggcacgt ggcggccgca ggaaccccta gtgatggagt tggccactcc ctctctgcgc   5400
gctcgctcgc tcactgaggc cgggcgacca aaggtcgccc gacgcccggg ctttgcccgg   5460
gcggcctcag tgagcgagcg agcgcgcaga gagggagtgg ccaa                    5504
```

<210> SEQ ID NO 32
<211> LENGTH: 5507
<212> TYPE: DNA
<213> ORGANISM: Adeno-Associated Virus 2

<400> SEQUENCE: 32

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag ggtcgagtg     240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgacga tcttgctacc agtggaacag ccactaagga    540
ttctgcagtg agagcagagg gccagctaag tggtactctc ccagagactg tctgactcac    600
gccacccct ccaccttgga cacaggacgc tgtggtttct gagccaggta caatgactcc    660
tttcggtaag tgcagtggaa gctgtacact gcccaggcaa agcgtccggg cagcgtaggc    720
gggcgactca gatcccagcc agtggactta gcccctgttt gctcctccga taactggggt    780
gaccttggtt aatattcacc agcagcctcc cccgttgccc ctctggatcc actgcttaaa    840
tacggacgag gacagggccc tgtctcctca gcttcaggca ccaccactga cctgggacag    900
tgaatcgcga tcgccaccat gcagattgag ctgagcacct gcttcttcct gtgcctgctg    960
aggttctgct tctctgccac caggagatac tacctggggg ctgtggagct gagctgggac   1020
tacatgcagt ctgacctggg ggagctgcct gtggatgcca ggttcccccc cagagtgccc   1080
aagagcttcc ccttcaacac ctctgtggtg tacaagaaga ccctgtttgt ggagttcact   1140
gaccacctgt tcaacattgc caagcccagg ccccccctgga tgggcctgct gggccccacc  1200
atccaggctg aggtgtatga cactgtggtg atcaccctga agaacatggc cagccaccct   1260
gtgagcctgc atgctgtggg ggtgagctac tggaaggcct ctgagggggc tgagtatgat   1320
gaccagacca gccagaggga gaaggaggat gacaaggtgt tccctggggg cagccacacc   1380
tatgtgtggc aggtgctgaa ggagaatggc cccatggcct ctgacccccct gtgcctgacc  1440
tacagctacc tgagccatgt ggacctggtg aaggacctga actctggcct gattggggcc   1500
ctgctggtgt gcagggaggg cagcctggcc aaggagaaga cccagaccct gcacaagttc   1560
atcctgctgt ttgctgtgtt tgatgagggc aagagctggc actctgaaac caagaacagc   1620
```

-continued

```
ctgatgcagg acagggatgc tgcctctgcc agggcctggc ccaagatgca cactgtgaat   1680
ggctatgtga acaggagcct gcctggcctg attggctgcc acaggaagtc tgtgtactgg   1740
catgtgattg gcatgggcac cacccctgag gtgcacagca tcttcctgga gggccacacc   1800
ttcctggtca ggaaccacag gcaggccagc ctggagatca gccccatcac cttcctgact   1860
gcccagaccc tgctgatgga cctgggccag ttcctgctgt tctgccacat cagcagccac   1920
cagcatgatg gcatggaggc ctatgtgaag gtggacagct gccctgagga gccccagctg   1980
aggatgaaga acaatgagga ggctgaggac tatgatgatg acctgactga ctctgagatg   2040
gatgtggtga ggtttgatga tgacaacagc cccagcttca tccagatcag gtctgtggcc   2100
aagaagcacc ccaagacctg ggtgcactac attgctgctg aggaggagga ctgggactat   2160
gccccccctgg tgctggcccc tgatgacagg agctacaaga gccagtacct gaacaatggc   2220
ccccagagga ttggcaggaa gtacaagaag gtcaggttca tggcctacac tgatgaaacc   2280
ttcaagacca gggaggccat ccagcatgag tctggcatcc tgggccccct gctgtatggg   2340
gaggtggggg acaccctgct gatcatcttc aagaaccagg ccagcaggcc ctacaacatc   2400
tacccccatg gcatcactga tgtgaggccc ctgtacagca ggaggctgcc caagggggtg   2460
aagcacctga aggacttccc catcctgcct ggggagatct tcaagtacaa gtggactgtg   2520
actgtggagg atggccccac caagtctgac cccaggtgcc tgaccagata ctacagcagc   2580
tttgtgaaca tggagaggga cctggcctct ggcctgattg gcccccctgct gatctgctac   2640
aaggagtctg tggaccagag gggcaaccag atcatgtctg acaagaggaa tgtgatcctg   2700
ttctctgtgt ttgatgagaa caggagctgg tacctgactg agaacatcca gaggttcctg   2760
cccaaccctg ctggggtgca gctggaggac cctgagttcc aggccagcaa catcatgcac   2820
agcatcaatg gctatgtgtt tgacagcctg cagctgtctg tgtgcctgca tgaggtggcc   2880
tactggtaca tcctgagcat tggggcccag actgacttcc tgtctgtgtt cttctctggc   2940
tacaccttca agcacaagat ggtgtatgag gacaccctga ccctgttccc cttctctggg   3000
gagactgtgt tcatgagcat ggagaaccct ggcctgtgga ttctgggctg ccacaactct   3060
gacttcagga acaggggcat gactgccctg ctgaaagtct ccagctgtga caagaacact   3120
ggggactact atgaggacag ctatgaggac atctctgcct acctgctgag caagaacaat   3180
gccattgagc ccaggagctt cagccagaac ccccccagtgc tgaagaggca ccagagggag   3240
atcaccagga ccaccctgca gtctgaccag gaggagattg actatgatga caccatctct   3300
gtggagatga agaaggagga ctttgacatc tacgacgagg acgagaacca gagccccagg   3360
agcttccaga agaagaccag gcactacttc attgctgctg tggagaggct gtgggactat   3420
ggcatgagca gcagccccca tgtgctgagg aacagggccc agtctggctc tgtgccccag   3480
ttcaagaagg tggtgttcca ggagttcact gatggcagct tcacccagcc cctgtacaga   3540
ggggagctga atgagcacct gggcctgctg ggcccctaca tcagggctga ggtggaggac   3600
aacatcatgg tgaccttcag gaaccaggcc agcaggccct acagcttcta cagcagcctg   3660
atcagctatg aggaggacca gaggcagggg gctgagccca ggaagaactt tgtgaagccc   3720
aatgaaacca agacctactt ctggaaggtg cagcaccaca tggcccccac caaggatgag   3780
tttgactgca aggcctgggc ctacttctct gatgtggacc tggagaagga tgtgcactct   3840
ggcctgattg gcccccctgct ggtgtgccac accaacaccc tgaaccctgc ccatggcagg   3900
caggtgactg tgcaggagtt tgccctgttc ttcaccatct ttgatgaaac caagagctgg   3960
```

-continued

```
tacttcactg agaacatgga gaggaactgc agggcccccct gcaacatcca gatggaggac   4020

cccaccttca aggagaacta caggttccat gccatcaatg gctacatcat ggacaccctg   4080

cctggcctgg tgatggccca ggaccagagg atcaggtggt acctgctgag catgggcagc   4140

aatgagaaca tccacagcat ccacttctct ggccatgtgt tcactgtgag gaagaaggag   4200

gagtacaaga tggccctgta caacctgtac cctggggtgt ttgagactgt ggagatgctg   4260

cccagcaagg ctggcatctg gagggtggag tgcctgattg gggagcacct gcatgctggc   4320

atgagcaccc tgttcctggt gtacagcaac aagtgccaga ccccccctggg catggcctct   4380

ggccacatca gggacttcca gatcactgcc tctggccagt atggccagtg ggcccccaag   4440

ctggccaggc tgcactactc tggcagcatc aatgcctgga gcaccaagga gcccttcagc   4500

tggatcaagg tggacctgct ggcccccatg atcatccatg gcatcaagac ccagggggcc   4560

aggcagaagt tcagcagcct gtacatcagc cagttcatca tcatgtacag cctggatggc   4620

aagaagtggc agacctacag gggcaacagc actggcaccc tgatggtgtt ctttggcaat   4680

gtggacagct ctggcatcaa gcacaacatc ttcaaccccc ccatcattgc cagatacatc   4740

aggctgcacc ccacccacta cagcatcagg agcaccctga ggatggagct gatgggctgt   4800

gacctgaaca gctgcagcat gcccctgggc atggagagca aggccatctc tgatgcccag   4860

atcactgcca gcagctactt caccaacatg tttgccacct ggagccccag caaggccagg   4920

ctgcacctgc agggcaggag caatgcctgg aggccccagg tcaacaaccc caaggagtgg   4980

ctgcaggtgg acttccagaa gaccatgaag gtgactgggg tgaccaccca gggggtgaag   5040

agcctgctga ccagcatgta tgtgaaggag ttcctgatca gcagcagcca ggatggccac   5100

cagtggaccc tgttcttcca gaatggcaag gtgaaggtgt tccagggcaa ccaggacagc   5160

ttcacccctg tggtgaacag cctggacccc cccctgctga ccagatacct gaggattcac   5220

ccccagagct gggtgcacca gattgccctg aggatggagg tgctgggctg tgaggcccag   5280

gacctgtact gacctcgagg aataaaggaa atttattttc attgcaatag tgtgttggtt   5340

ttttgtgtca cgtggcggcc gcaggaaccc ctagtgatgg agttggccac tccctctctg   5400

cgcgctcgct cgctcactga ggccgggcga ccaaaggtcg cccgacgccc gggctttgcc   5460

cgggcggcct cagtgagcga gcgagcgcgc agagagggag tggccaa                 5507
```

```
<210> SEQ ID NO 33
<211> LENGTH: 5311
<212> TYPE: DNA
<213> ORGANISM: Adeno-Associated Virus 2

<400> SEQUENCE: 33
```

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgacgc agagaggtct    180

ctgacctctg ccccagctcc aaggtcagca ggcagggagg gctgtgtgtt tgctgtttgc    240

tgcttgcaat gtttgcccat tttagggaca tgagtaggct gaagtttgtt cagtgtggac    300

ttcagaggca gcacacaaac agccagagag gtctctgacc tctgccccag ctccaaggtc    360

agcaggcagg gagggctgtg tgtttgctgt ttgctgcttg caatgtttgc ccattttagg    420

gacatgagta ggctgaagtt tgttcagtgt ggacttcaga ggcagcacac aaacagcacg    480

cgaaacgtcg actggacaca ggacgctgtg gtttctgagc caggggggcga ctcagatccc    540

agccagtgga cttagcccct gtttgctcct ccgataactg gggtgacctt ggttaatatt    600
```

-continued

```
caccagcagc ctcccccgtt gcccctctgg atccactgct taaatacgga cgaggacagg    660
gccctgtctc ctcagcttca ggcaccacca ctgacctggg acagtgaatc gcgatcgcca    720
ccatgcagat tgagctgagc acctgcttct tcctgtgcct gctgaggttc tgcttctctg    780
ccaccaggag atactacctg ggggctgtgg agctgagctg ggactacatg cagtctgacc    840
tgggggagct gcctgtggat gccaggttcc cccccagagt gcccaagagc ttccccttca    900
acacctctgt ggtgtacaag aagaccctgt ttgtggagtt cactgaccac ctgttcaaca    960
ttgccaagcc caggcccccc tggatgggcc tgctgggccc caccatccag gctgaggtgt   1020
atgacactgt ggtgatcacc ctgaagaaca tggccagcca ccctgtgagc ctgcatgctg   1080
tgggggtgag ctactggaag gcctctgagg gggctgagta tgatgaccag accagccaga   1140
gggagaagga ggatgacaag gtgttccctg gggcagcca cacctatgtg tggcaggtgc   1200
tgaaggagaa tggccccatg gcctctgacc ccctgtgcct gacctacagc tacctgagcc   1260
atgtggacct ggtgaaggac ctgaactctg gcctgattgg ggccctgctg gtgtgcaggg   1320
agggcagcct ggccaaggag aagacccaga ccctgcacaa gttcatcctg ctgtttgctg   1380
tgtttgatga gggcaagagc tggcactctg aaaccaagaa cagcctgatg caggacaggg   1440
atgctgcctc tgccagggcc tggcccaaga tgcacactgt gaatggctat gtgaacagga   1500
gcctgcctgg cctgattggc tgccacagga agtctgtgta ctggcatgtg attggcatgg   1560
gcaccacccc tgaggtgcac agcatcttcc tggagggcca caccttcctg gtcaggaacc   1620
acaggcaggc cagcctggag atcagcccca tcaccttcct gactgcccag accctgctga   1680
tggacctggg ccagttcctg ctgttctgcc acatcagcag ccaccagcat gatggcatgg   1740
aggcctatgt gaaggtggac agctgccctg aggagcccca gctgaggatg aagaacaatg   1800
aggaggctga ggactatgat gatgacctga ctgactctga gatggatgtg gtgaggtttg   1860
atgatgacaa cagccccagc ttcatccaga tcaggtctgt ggccaagaag caccccaaga   1920
cctgggtgca ctacattgct gctgaggagg aggactggga ctatgccccc ctggtgctgg   1980
cccctgatga caggagctac aagagccagt acctgaacaa tggcccccag aggattggca   2040
ggaagtacaa gaaggtcagg ttcatggcct acactgatga aaccttcaag accagggagg   2100
ccatccagca tgagtctggc atcctgggcc ccctgctgta tggggaggtg ggggacaccc   2160
tgctgatcat cttcaagaac caggccagca ggccctacaa catctacccc catggcatca   2220
ctgatgtgag gcccctgtac agcaggaggc tgcccaaggg ggtgaagcac ctgaaggact   2280
tccccatcct gcctggggag atcttcaagt acaagtggac tgtgactgtg gaggatggcc   2340
ccaccaagtc tgaccccagg tgcctgacca gatactacag cagctttgtg aacatggaga   2400
gggacctggc ctctggcctg attggccccc tgctgatctg ctacaaggag tctgtggacc   2460
agaggggcaa ccagatcatg tctgacaaga ggaatgtgat cctgttctct gtgtttgatg   2520
agaacaggag ctggtacctg actgagaaca tccagaggtt cctgcccaac cctgctgggg   2580
tgcagctgga ggaccctgag ttccaggcca gcaacatcat gcacagcatc aatggctatg   2640
tgtttgacag cctgcagctg tctgtgtgcc tgcatgaggt ggcctactgg tacatcctga   2700
gcattggggc ccagactgac ttcctgtctg tgttcttctc tggctacacc ttcaagcaca   2760
agatggtgta tgaggacacc ctgaccctgt tccccttctc tggggagact gtgttcatga   2820
gcatggagaa ccctggcctg tggattctgg gctgccacaa ctctgacttc aggaacaggg   2880
gcatgactgc cctgctgaaa gtctccagct gtgacaagaa cactggggac tactatgagg   2940
```

-continued

```
acagctatga ggacatctct gcctacctgc tgagcaagaa caatgccatt gagcccagga   3000
gcttcagcca gaacccccca gtgctgaaga ggcaccagag ggagatcacc aggaccaccc   3060
tgcagtctga ccaggaggag attgactatg atgacaccat ctctgtggag atgaagaagg   3120
aggactttga catctacgac gaggacgaga accagagccc caggagcttc cagaagaaga   3180
ccaggcacta cttcattgct gctgtggaga ggctgtggga ctatggcatg agcagcagcc   3240
cccatgtgct gaggaacagg gcccagtctg gctctgtgcc ccagttcaag aaggtggtgt   3300
tccaggagtt cactgatggc agcttcaccc agcccctgta cagaggggag ctgaatgagc   3360
acctgggcct gctgggcccc tacatcaggg ctgaggtgga ggacaacatc atggtgacct   3420
tcaggaacca ggccagcagg ccctacagct tctacagcag cctgatcagc tatgaggagg   3480
accagaggca gggggctgag cccaggaaga actttgtgaa gcccaatgaa accaagacct   3540
acttctggaa ggtgcagcac cacatggccc ccaccaagga tgagtttgac tgcaaggcct   3600
gggcctactt ctctgatgtg gacctggaga aggatgtgca ctctggcctg attggccccc   3660
tgctggtgtg ccacaccaac accctgaacc ctgcccatgg caggcaggtg actgtgcagg   3720
agtttgccct gttcttcacc atctttgatg aaaccaagag ctggtacttc actgagaaca   3780
tggagaggaa ctgcagggcc ccctgcaaca tccagatgga ggaccccacc ttcaaggaga   3840
actacaggtt ccatgccatc aatggctaca tcatggacac cctgcctggc ctggtgatgg   3900
cccaggacca gaggatcagg tggtacctgc tgagcatggg cagcaatgag aacatccaca   3960
gcatccactt ctctggccat gtgttcactg tgaggaagaa ggaggagtac aagatggccc   4020
tgtacaacct gtaccctggg gtgtttgaga ctgtggagat gctgcccagc aaggctggca   4080
tctggagggt ggagtgcctg attggggagc acctgcatgc tggcatgagc accctgttcc   4140
tggtgtacag caacaagtgc cagacccccc tgggcatggc ctctggccac atcagggact   4200
tccagatcac tgcctctggc cagtatggcc agtgggcccc caagctggcc aggctgcact   4260
actctggcag catcaatgcc tggagcacca aggagccctt cagctggatc aaggtggacc   4320
tgctggcccc catgatcatc catggcatca agacccaggg ggccaggcag aagttcagca   4380
gcctgtacat cagccagttc atcatcatgt acagcctgga tggcaagaag tggcagacct   4440
acaggggcaa cagcactggc accctgatgg tgttctttgg caatgtggac agctctggca   4500
tcaagcacaa catcttcaac ccccccatca ttgccagata catcaggctg caccccaccc   4560
actacagcat caggagcacc ctgaggatgg agctgatggg ctgtgacctg aacagctgca   4620
gcatgcccct gggcatggag agcaaggcca tctctgatgc ccagatcact gccagcagct   4680
acttcaccaa catgtttgcc acctggagcc ccagcaaggc caggctgcac ctgcagggca   4740
ggagcaatgc ctggaggccc caggtcaaca accccaagga gtggctgcag gtggacttcc   4800
agaagaccat gaaggtgact ggggtgacca cccagggggt gaagagcctg ctgaccagca   4860
tgtatgtgaa ggagttcctg atcagcagca gccaggatgg ccaccagtgg accctgttct   4920
tccagaatgg caaggtgaag gtgttccagg gcaaccagga cagcttcacc cctgtggtga   4980
acagcctgga cccccccctg ctgaccagat acctgaggat tcacccccag agctgggtgc   5040
accagattgc cctgaggatg gaggtgctgg gctgtgaggc ccaggacctg tactgacctc   5100
gaggaataaa ggaaatttat tttcattgca atagtgtgtt ggttttttgt gtcacgtggc   5160
ggccgcagga acccctagtg atggagttgg ccactccctc tctgcgcgct cgctcgctca   5220
ctgaggccgg gcgaccaaag gtcgcccgac gcccgggctt tgcccgggcg gcctcagtga   5280
gcgagcgagc gcgcagagag ggagtggcca a                                  5311
```

<210> SEQ ID NO 34
<211> LENGTH: 5156
<212> TYPE: DNA
<213> ORGANISM: Adeno-Associated Virus 2

<400> SEQUENCE: 34
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgacca gagaggtctc 180
tgacctctgc cccagctcca aggtcagcag gcagggaggg ctgtgtgttt gctgtttgct 240
gcttgcaatg tttgcccatt ttagggacat gagtaggctg aagtttgttc agtgtggact 300
tcagaggcag cacacaaaca gcacgcgaaa cgtcgactgg acacaggacg ctgtggtttc 360
tgagccaggg ggcgactcag atcccagcca gtggacttag cccctgtttg ctcctccgat 420
aactggggtg accttggtta atattcacca gcagcctccc ccgttgcccc tctggatcca 480
ctgcttaaat acggacgagg acagggccct gtctcctcag cttcaggcac caccactgac 540
ctgggacagt gaatcgcgat cgccaccatg cagattgagc tgagcacctg cttcttcctg 600
tgcctgctga ggttctgctt ctctgccacc aggagatact acctgggggc tgtggagctg 660
agctgggact acatgcagtc tgacctgggg gagctgcctg tggatgccag gttccccccc 720
agagtgccca agagcttccc cttcaacacc tctgtggtgt acaagaagac cctgtttgtg 780
gagttcactg accacctgtt caacattgcc aagcccaggc ccccctggat gggcctgctg 840
ggccccacca tccaggctga ggtgtatgac actgtggtga tcaccctgaa gaacatggcc 900
agccaccctg tgagcctgca tgctgtgggg gtgagctact ggaaggcctc tgagggggct 960
gagtatgatg accagaccag ccagagggag aaggaggatg acaaggtgtt ccctgggggc 1020
agccacacct atgtgtggca ggtgctgaag gagaatggcc ccatggcctc tgacccccctg 1080 tgcctgacct acagctacct gagccatgtg gacctggtga aggacctgaa ctctggcctg 1140
attggggccc tgctggtgtg cagggagggc agcctggcca aggagaagac ccagaccctg 1200
cacaagttca tcctgctgtt tgctgtgttt gatgagggca agagctggca ctctgaaacc 1260
aagaacagcc tgatgcagga cagggatgct gcctctgcca gggcctggcc caagatgcac 1320
actgtgaatg gctatgtgaa caggagcctg cctggcctga ttggctgcca caggaagtct 1380
gtgtactggc atgtgattgg catgggcacc acccctgagg tgcacagcat cttcctggag 1440
ggccacacct tcctggtcag gaaccacagg caggccagcc tggagatcag ccccatcacc 1500
ttcctgactg cccagaccct gctgatggac ctgggccagt tcctgctgtt ctgccacatc 1560
agcagccacc agcatgatgg catggaggcc tatgtgaagg tggacagctg ccctgaggag 1620
ccccagctga ggatgaagaa caatgaggag gctgaggact atgatgatga cctgactgac 1680
tctgagatgg atgtggtgag gtttgatgat gacaacagcc ccagcttcat ccagatcagg 1740
tctgtggcca agaagcaccc caagacctgg gtgcactaca ttgctgctga ggaggaggac 1800
tgggactatg ccccccctggt gctggcccct gatgacagga gctacaagag ccagtacctg 1860
aacaatggcc cccagaggat tggcaggaag tacaagaagg tcaggttcat ggcctacact 1920
gatgaaacct tcaagaccag ggaggccatc cagcatgagt ctggcatcct gggcccccctg 1980 ctgtatgggg aggtggggga caccctgctg atcatcttca agaaccaggc cagcaggccc 2040
tacaacatct acccccatgg catcactgat gtgaggcccc tgtacagcag gaggctgccc 2100

-continued

```
aagggggtga agcacctgaa ggacttcccc atcctgcctg gggagatctt caagtacaag   2160
tggactgtga ctgtggagga tggccccacc aagtctgacc ccaggtgcct gaccagatac   2220
tacagcagct ttgtgaacat ggagagggac ctggcctctg gcctgattgg cccccctgctg   2280
atctgctaca aggagtctgt ggaccagagg ggcaaccaga tcatgtctga caagaggaat   2340
gtgatcctgt tctctgtgtt tgatgagaac aggagctggt acctgactga gaacatccag   2400
aggttcctgc ccaaccctgc tggggtgcag ctggaggacc ctgagttcca ggccagcaac   2460
atcatgcaca gcatcaatgg ctatgtgttt gacagcctgc agctgtctgt gtgcctgcat   2520
gaggtggcct actggtacat cctgagcatt ggggcccaga ctgacttcct gtctgtgttc   2580
ttctctggct acaccttcaa gcacaagatg gtgtatgagg acaccctgac cctgttcccc   2640
ttctctgggg agactgtgtt catgagcatg gagaaccctg gcctgtggat tctgggctgc   2700
cacaactctg acttcaggaa caggggcatg actgccctgc tgaaagtctc cagctgtgac   2760
aagaacactg ggactactta tgaggacagc tatgaggaca tctctgccta cctgctgagc   2820
aagaacaatg ccattgagcc caggagcttc agccagaacc ccccagtgct gaagaggcac   2880
cagagggaga tcaccaggac caccctgcag tctgaccagg aggagattga ctatgatgac   2940
accatctctg tggagatgaa gaaggaggac tttgacatct acgacgagga cgagaaccag   3000
agccccagga gcttccagaa gaagaccagg cactacttca ttgctgctgt ggagaggctg   3060
tgggactatg gcatgagcag cagcccccat gtgctgagga acagggccca gtctggctct   3120
gtgccccagt tcaagaaggt ggtgttccag gagttcactg atggcagctt cacccagccc   3180
ctgtacagag gggagctgaa tgagcacctg ggcctgctgg gcccctacat cagggctgag   3240
gtggaggaca acatcatggt gaccttcagg aaccaggcca gcaggcccta cagcttctac   3300
agcagcctga tcagctatga ggaggaccag aggcaggggg ctgagcccag gaagaacttt   3360
gtgaagccca atgaaaccaa gacctacttc tggaaggtgc agcaccacat ggccccccacc   3420
aaggatgagt ttgactgcaa ggcctgggcc tacttctctg atgtggacct ggagaaggat   3480
gtgcactctg gcctgattgg cccccctgctg gtgtgccaca ccaacaccct gaaccctgcc   3540
catggcaggc aggtgactgt gcaggagttt gccctgttct tcaccatctt tgatgaaacc   3600
aagagctggt acttcactga gaacatggag aggaactgca gggccccctg caacatccag   3660
atggaggacc ccaccttcaa ggagaactac aggttccatg ccatcaatgg ctacatcatg   3720
gacaccctgc ctggcctggt gatggcccag gaccagagga tcaggtggta cctgctgagc   3780
atgggcagca atgagaacat ccacagcatc cacttctctg gccatgtgtt cactgtgagg   3840
aagaaggagg agtacaagat ggccctgtac aacctgtacc ctggggtgtt tgagactgtg   3900
gagatgctgc ccagcaaggc tggcatctgg agggtggagt gcctgattgg ggagcacctg   3960
catgctggca tgagcaccct gttcctggtg tacagcaaca agtgccagac cccccctgggc   4020
atggcctctg gccacatcag ggacttccag atcactgcct ctggccagta tggccagtgg   4080
gcccccaagc tggccaggct gcactactct ggcagcatca atgcctggag caccaaggag   4140
cccttcagct ggatcaaggt ggacctgctg gcccccatga tcatccatgg catcaagacc   4200
cagggggcca ggcagaagtt cagcagcctg tacatcagcc agttcatcat catgtacagc   4260
ctggatggca agaagtggca gacctacagg ggcaacagca ctggcaccct gatggtgttc   4320
tttggcaatg tggacagctc tggcatcaag cacaacatct tcaacccccc catcattgcc   4380
agatacatca ggctgcaccc cacccactac agcatcagga gcaccctgag gatggagctg   4440
atgggctgtg acctgaacag ctgcagcatg cccctgggca tggagagcaa ggccatctct   4500
```

gatgcccaga tcactgccag cagctacttc accaacatgt ttgccacctg gagccccagc 4560
aaggccaggc tgcacctgca gggcaggagc aatgcctgga ggccccaggt caacaacccc 4620
aaggagtggc tgcaggtgga cttccagaag accatgaagg tgactggggt gaccacccag 4680
ggggtgaaga gcctgctgac cagcatgtat gtgaaggagt tcctgatcag cagcagccag 4740
gatggccacc agtggaccct gttcttccag aatggcaagg tgaaggtgtt ccagggcaac 4800
caggacagct tcacccctgt ggtgaacagc ctggaccccc ccctgctgac cagatacctg 4860
aggattcacc cccagagctg ggtgcaccag attgccctga ggatggaggt gctgggctgt 4920
gaggcccagg acctgtactg acctcgagga ataaaggaaa tttattttca ttgcaatagt 4980
gtgttggttt tttgtgtcac gtggcggccg caggaacccc tagtgatgga gttggccact 5040
ccctctctgc gcgctcgctc gctcactgag gccgggcgac caaaggtcgc ccgacgcccg 5100
ggctttgccc gggcggcctc agtgagcgag cgagcgcgca gagagggagt ggccaa 5156

<210> SEQ ID NO 35
<211> LENGTH: 5178
<212> TYPE: DNA
<213> ORGANISM: Adeno-Associated Virus 2

<400> SEQUENCE: 35
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgactg tttgctgttt 180
gctgcttgca atgtttgccc attttaggga catgtttgct gtttgctgct tgcaatgttt 240
gcccatttta gggacatgtt tgctgtttgc tgcttgcaat gtttgcccat tttagggaca 300
tgtttgctgt ttgctgcttg caatgtttgc ccattttagg gacaacgcga aacgtcgact 360
ggacacagga cgctgtggtt tctgagccag ggggcgactc agatcccagc cagtggactt 420
agcccctgtt tgctcctccg ataactgggg tgaccttggt taatattcac cagcagcctc 480
ccccgttgcc cctctggatc cactgcttaa atacggacga ggacagggcc ctgtctcctc 540
agcttcaggc accaccactg acctgggaca gtgaatcgcg atcgccacca tgcagattga 600
gctgagcacc tgcttcttcc tgtgcctgct gaggttctgc ttctctgcca ccaggagata 660
ctacctgggg gctgtggagc tgagctggga ctacatgcag tctgacctgg gggagctgcc 720
tgtggatgcc aggttccccc ccagagtgcc caagagcttc cccttcaaca cctctgtggt 780
gtacaagaag accctgtttg tggagttcac tgaccacctg ttcaacattg ccaagcccag 840 gccccccctgg atgggcctgc tgggccccac catccaggct gaggtgtatg acactgtggt 900
gatcaccctg aagaacatgg ccagccaccc tgtgagcctg catgctgtgg gggtgagcta 960
ctggaaggcc tctgaggggg ctgagtatga tgaccagacc agccagaggg agaaggagga 1020
tgacaaggtg ttccctgggg gcagccacac ctatgtgtgg caggtgctga aggagaatgg 1080
ccccatggcc tctgaccccc tgtgcctgac ctacagctac ctgagccatg tggacctggt 1140
gaaggacctg aactctggcc tgattggggc cctgctggtg tgcagggagg gcagcctggc 1200
caaggagaag acccagaccc tgcacaagtt catcctgctg tttgctgtgt ttgatgaggg 1260
caagagctgg cactctgaaa ccaagaacag cctgatgcag gacagggatg ctgcctctgc 1320
cagggcctgg cccaagatgc acactgtgaa tggctatgtg aacaggagcc tgcctggcct 1380
gattggctgc cacaggaagt ctgtgtactg gcatgtgatt ggcatgggca ccacccctga 1440

-continued

```
ggtgcacagc atcttcctgg agggccacac cttcctggtc aggaaccaca ggcaggccag   1500
cctggagatc agccccatca ccttcctgac tgcccagacc ctgctgatgg acctgggcca   1560
gttcctgctg ttctgccaca tcagcagcca ccagcatgat ggcatggagg cctatgtgaa   1620
ggtggacagc tgccctgagg agccccagct gaggatgaag aacaatgagg aggctgagga   1680
ctatgatgat gacctgactg actctgagat ggatgtggtg aggtttgatg atgacaacag   1740
ccccagcttc atccagatca ggtctgtggc caagaagcac cccaagacct gggtgcacta   1800
cattgctgct gaggaggagg actgggacta tgcccccctg gtgctggccc ctgatgacag   1860
gagctacaag agccagtacc tgaacaatgg cccccagagg attggcagga agtacaagaa   1920
ggtcaggttc atggcctaca ctgatgaaac cttcaagacc agggaggcca tccagcatga   1980
gtctggcatc ctgggccccc tgctgtatgg ggaggtgggg gacaccctgc tgatcatctt   2040
caagaaccag gccagcaggc cctacaacat ctacccccat ggcatcactg atgtgaggcc   2100
cctgtacagc aggaggctgc ccaagggggt gaagcacctg aaggacttcc ccatcctgcc   2160
tggggagatc ttcaagtaca agtggactgt gactgtggag gatggcccca ccaagtctga   2220
ccccaggtgc ctgaccagat actacagcag ctttgtgaac atggagaggg acctggcctc   2280
tggcctgatt ggcccccctgc tgatctgcta caaggagtct gtggaccaga ggggcaacca   2340
gatcatgtct gacaagagga atgtgatcct gttctctgtg tttgatgaga acaggagctg   2400
gtacctgact gagaacatcc agaggttcct gcccaaccct gctggggtgc agctggagga   2460
ccctgagttc caggccagca acatcatgca cagcatcaat ggctatgtgt ttgacagcct   2520
gcagctgtct gtgtgcctgc atgaggtggc ctactggtac atcctgagca ttggggccca   2580
gactgacttc ctgtctgtgt tcttctctgg ctacaccttc aagcacaaga tggtgtatga   2640
ggacaccctg accctgttcc ccttctctgg ggagactgtg ttcatgagca tggagaaccc   2700
tggcctgtgg attctgggct gccacaactc tgacttcagg aacaggggca tgactgccct   2760
gctgaaagtc tccagctgtg acaagaacac tggggactac tatgaggaca gctatgagga   2820
catctctgcc tacctgctga gcaagaacaa tgccattgag cccaggagct tcagccagaa   2880
ccccccagtg ctgaagaggc accagaggga gatcaccagg accaccctgc agtctgacca   2940
ggaggagatt gactatgatg acaccatctc tgtggagatg aagaaggagg actttgacat   3000
ctacgacgag gacgagaacc agagccccag gagcttccag aagaagacca ggcactactt   3060
cattgctgct gtggagaggc tgtgggacta tggcatgagc agcagccccc atgtgctgag   3120
gaacagggcc cagtctggct ctgtgcccca gttcaagaag gtggtgttcc aggagttcac   3180
tgatggcagc ttcacccagc cctgtacag aggggagctg aatgagcacc tgggcctgct   3240
gggcccctac atcagggctg aggtggagga caacatcatg gtgaccttca ggaaccaggc   3300
cagcaggccc tacagcttct acagcagcct gatcagctat gaggaggacc agaggcaggg   3360
ggctgagccc aggaagaact ttgtgaagcc caatgaaacc aagacctact tctggaaggt   3420
gcagcaccac atggccccca ccaaggatga gtttgactgc aaggcctggg cctacttctc   3480
tgatgtggac ctggagaagg atgtgcactc tggcctgatt ggcccccctgc tggtgtgcca   3540
caccaacacc ctgaaccctg cccatggcag gcaggtgact gtgcaggagt ttgccctgtt   3600
cttcaccatc tttgatgaaa ccaagagctg gtacttcact gagaacatgg agaggaactg   3660
cagggccccc tgcaacatcc agatggagga ccccaccttc aaggagaact acaggttcca   3720
tgccatcaat ggctacatca tggacaccct gcctggcctg gtgatggccc aggaccagag   3780
gatcaggtgg tacctgctga gcatgggcag caatgagaac atccacagca tccacttctc   3840
```

```
tggccatgtg ttcactgtga ggaagaagga ggagtacaag atggccctgt acaacctgta   3900
ccctggggtg tttgagactg tggagatgct gcccagcaag gctggcatct ggagggtgga   3960
gtgcctgatt ggggagcacc tgcatgctgg catgagcacc ctgttcctgg tgtacagcaa   4020
caagtgccag acccccctgg gcatggcctc tggccacatc agggacttcc agatcactgc   4080
ctctggccag tatggccagt gggcccccaa gctggccagg ctgcactact ctggcagcat   4140
caatgcctgg agcaccaagg agcccttcag ctggatcaag gtggacctgc tggcccccat   4200
gatcatccat ggcatcaaga cccagggggc caggcagaag ttcagcagcc tgtacatcag   4260
ccagttcatc atcatgtaca gcctggatgg caagaagtgg cagacctaca ggggcaacag   4320
cactggcacc ctgatggtgt tctttggcaa tgtggacagc tctggcatca agcacaacat   4380
cttcaacccc cccatcattg ccagatacat caggctgcac ccccacccact acagcatcag   4440
gagcaccctg aggatggagc tgatgggctg tgacctgaac agctgcagca tgcccctggg   4500
catggagagc aaggccatct ctgatgccca gatcactgcc agcagctact tcaccaacat   4560
gtttgccacc tggagcccca gcaaggccag gctgcacctg cagggcagga gcaatgcctg   4620
gaggccccag gtcaacaacc ccaaggagtg gctgcaggtg gacttccaga agaccatgaa   4680
ggtgactggg gtgaccaccc agggggtgaa gagcctgctg accagcatgt atgtgaagga   4740
gttcctgatc agcagcagcc aggatggcca ccagtggacc ctgttcttcc agaatggcaa   4800
ggtgaaggtg ttccagggca accaggacag cttcacccct gtggtgaaca gcctggaccc   4860
cccccctgctg accagatacc tgaggattca cccccagagc tgggtgcacc agattgccct   4920
gaggatggag gtgctgggct gtgaggccca ggacctgtac tgacctcgag gaataaagga   4980
aatttatttt cattgcaata gtgtgttggt tttttgtgtc acgtggcggc cgcaggaacc   5040
cctagtgatg gagttggcca ctccctctct gcgcgctcgc tcgctcactg aggccgggcg   5100
accaaaggtc gcccgacgcc cgggctttgc ccgggcggcc tcagtgagcg agcgagcgcg   5160
cagagaggga gtggccaa                                                 5178
```

```
<210> SEQ ID NO 36
<211> LENGTH: 5160
<212> TYPE: DNA
<213> ORGANISM: Adeno-Associated Virus 2

<400> SEQUENCE: 36

ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtt gtccctaaaa tgggcaaaca    180
ttgcaagcag caaacagcaa acatgtccct aaaatgggca aacattgcaa gcagcaaaca    240
gcaaacatgt ccctaaaatg ggcaaacatt gcaagcagca aacagcaaac atgtccctaa    300
aatgggcaaa cattgcaagc agcaaacagc aaacagtcga ctggacacag gacgctgtgg    360
tttctgagcc agggggcgac tcagatccca gccagtggac ttagcccctg tttgctcctc    420
cgataactgg ggtgaccttg gttaatattc accagcagcc tcccccgttg cccctctgga    480
tccactgctt aaatacggac gaggacaggg ccctgtctcc tcagcttcag gcaccaccac    540
tgacctggga cagtgaatcg cgatcgccac catgcagatt gagctgagca cctgcttctt    600
cctgtgcctg ctgaggttct gcttctctgc caccaggaga tactacctgg gggctgtgga    660
gctgagctgg gactacatgc agtctgacct gggggagctg cctgtggatg ccaggttccc    720
```

-continued

```
ccccagagtg cccaagagct tccccttcaa cacctctgtg gtgtacaaga agaccctgtt    780
tgtggagttc actgaccacc tgttcaacat tgccaagccc aggcccccct ggatgggcct    840
gctgggcccc accatccagg ctgaggtgta tgacactgtg gtgatcaccc tgaagaacat    900
ggccagccac cctgtgagcc tgcatgctgt gggggtgagc tactggaagg cctctgaggg    960
ggctgagtat gatgaccaga ccagccagag ggagaaggag gatgacaagg tgttccctgg   1020
gggcagccac acctatgtgt ggcaggtgct gaaggagaat ggccccatgg cctctgaccc   1080
cctgtgcctg acctacagct acctgagcca tgtggacctg gtgaaggacc tgaactctgg   1140
cctgattggg gccctgctgg tgtgcaggga gggcagcctg gccaaggaga agacccagac   1200
cctgcacaag ttcatcctgc tgtttgctgt gtttgatgag ggcaagagct ggcactctga   1260
aaccaagaac agcctgatgc aggacaggga tgctgcctct gccagggcct ggcccaagat   1320
gcacactgtg aatggctatg tgaacaggag cctgcctggc ctgattggct gccacaggaa   1380
gtctgtgtac tggcatgtga ttggcatggg caccacccct gaggtgcaca gcatcttcct   1440
ggagggccac accttcctgg tcaggaacca caggcaggcc agcctggaga tcagccccat   1500
caccttcctg actgcccaga ccctgctgat ggacctgggc cagttcctgc tgttctgcca   1560
catcagcagc caccagcatg atggcatgga ggcctatgtg aaggtggaca gctgccctga   1620
ggagccccag ctgaggatga agaacaatga ggaggctgag gactatgatg atgacctgac   1680
tgactctgag atggatgtgg tgaggtttga tgatgacaac agccccagct tcatccagat   1740
caggtctgtg gccaagaagc accccaagac ctgggtgcac tacattgctg ctgaggagga   1800
ggactgggac tatgcccccc tggtgctggc cctgatgac aggagctaca agagccagta    1860
cctgaacaat ggcccccaga ggattggcag gaagtacaag aaggtcaggt tcatggccta   1920
cactgatgaa accttcaaga ccagggaggc catccagcat gagtctggca tcctgggccc   1980
cctgctgtat ggggaggtgg gggacaccct gctgatcatc ttcaagaacc aggccagcag   2040
gccctacaac atctaccccc atggcatcac tgatgtgagg cccctgtaca gcaggaggct   2100
gcccaagggg gtgaagcacc tgaaggactt ccccatcctg cctggggaga tcttcaagta   2160
caagtggact gtgactgtgg aggatggccc caccaagtct gaccccaggt gcctgaccag   2220
atactacagc agctttgtga acatggagag ggacctggcc tctggcctga ttggcccccct  2280
gctgatctgc tacaaggagt ctgtggacca gaggggcaac cagatcatgt ctgacaagag   2340
gaatgtgatc ctgttctctg tgtttgatga gaacaggagc tggtacctga ctgagaacat   2400
ccagaggttc ctgcccaacc ctgctggggt gcagctggag gaccctgagt tccaggccag   2460
caacatcatg cacagcatca atggctatgt gtttgacagc ctgcagctgt ctgtgtgcct   2520
gcatgaggtg gcctactggt acatcctgag cattggggcc cagactgact tcctgtctgt   2580
gttcttctct ggctacacct tcaagcacaa gatggtgtat gaggacaccc tgaccctgtt   2640
ccccttctct ggggagactg tgttcatgag catggagaac cctggcctgt ggattctggg   2700
ctgccacaac tctgacttca ggaacagggg catgactgcc ctgctgaaag tctccagctg   2760
tgacaagaac actggggact actatgagga cagctatgag gacatctctg cctacctgct   2820
gagcaagaac aatgccattg agcccaggag cttcagccag aacccccccag tgctgaagag  2880
gcaccagagg gagatcacca ggaccaccct gcagtctgac caggaggaga ttgactatga   2940
tgacaccatc tctgtggaga tgaagaagga ggactttgac atctacgacg aggacgagaa   3000
ccagagcccc aggagcttcc agaagaagac caggcactac ttcattgctg ctgtggagag   3060
gctgtgggac tatggcatga gcagcagccc ccatgtgctg aggaacaggg cccagtctgg   3120
```

```
ctctgtgccc cagttcaaga aggtggtgtt ccaggagttc actgatggca gcttcaccca   3180

gcccctgtac agaggggagc tgaatgagca cctgggcctg ctgggcccct acatcagggc   3240

tgaggtggag gacaacatca tggtgacctt caggaaccag gccagcaggc cctacagctt   3300

ctacagcagc ctgatcagct atgaggagga ccagaggcag gggctgagc ccaggaagaa   3360

ctttgtgaag cccaatgaaa ccaagaccta cttctggaag gtgcagcacc acatggcccc   3420

caccaaggat gagtttgact gcaaggcctg ggcctacttc tctgatgtgg acctggagaa   3480

ggatgtgcac tctggcctga ttggccccct gctggtgtgc cacaccaaca ccctgaaccc   3540

tgcccatggc aggcaggtga ctgtgcagga gtttgccctg ttcttcacca tctttgatga   3600

aaccaagagc tggtacttca ctgagaacat ggagaggaac tgcagggccc cctgcaacat   3660

ccagatggag gaccccacct tcaaggagaa ctacaggttc catgccatca atggctacat   3720

catggacacc ctgcctggcc tggtgatggc ccaggaccag aggatcaggt ggtacctgct   3780

gagcatgggc agcaatgaga acatccacag catccacttc tctggccatg tgttcactgt   3840

gaggaagaag gaggagtaca agatggccct gtacaacctg taccctgggg tgtttgagac   3900

tgtggagatg ctgcccagca aggctggcat ctggagggtg gagtgcctga ttggggagca   3960

cctgcatgct ggcatgagca ccctgttcct ggtgtacagc aacaagtgcc agacccccct   4020

gggcatggcc tctggccaca tcagggactt ccagatcact gcctctggcc agtatggcca   4080

gtgggccccc aagctggcca ggctgcacta ctctggcagc atcaatgcct ggagcaccaa   4140

ggagcccttc agctggatca aggtggacct gctggccccc atgatcatcc atggcatcaa   4200

gacccagggg gccaggcaga agttcagcag cctgtacatc agccagttca tcatcatgta   4260

cagcctggat ggcaagaagt ggcagaccta caggggcaac agcactggca ccctgatggt   4320

gttctttggc aatgtggaca gctctggcat caagcacaac atcttcaacc cccccatcat   4380

tgccagatac atcaggctgc accccaccca ctacagcatc aggagcaccc tgaggatgga   4440

gctgatgggc tgtgacctga acagctgcag catgcccctg ggcatggaga gcaaggccat   4500

ctctgatgcc cagatcactg ccagcagcta cttcaccaac atgtttgcca cctggagccc   4560

cagcaaggcc aggctgcacc tgcagggcag gagcaatgcc tggaggcccc aggtcaacaa   4620

ccccaaggag tggctgcagg tggacttcca gaagaccatg aaggtgactg gggtgaccac   4680

ccagggggtg aagagcctgc tgaccagcat gtatgtgaag gagttcctga tcagcagcag   4740

ccaggatggc caccagtgga ccctgttctt ccagaatggc aaggtgaagg tgttccaggg   4800

caaccaggac agcttcaccc ctgtggtgaa cagcctggac ccccccctgc tgaccagata   4860

cctgaggatt cacccccaga gctgggtgca ccagattgcc ctgaggatgg aggtgctggg   4920

ctgtgaggcc caggacctgt actgacctcg aggaataaag gaaatttatt ttcattgcaa   4980

tagtgtgttg gtttttgtg tcacgtggcg gccgcaggaa cccctagtga tggagttggc   5040

cactccctct ctgcgcgctc gctcgctcac tgaggccggg cgaccaaagg tcgcccgacg   5100

cccgggcttt gcccgggcgg cctcagtgag cgagcgagcg cgcagagagg gagtggccaa   5160
```

<210> SEQ ID NO 37
<211> LENGTH: 5383
<212> TYPE: DNA
<213> ORGANISM: Adeno-Associated Virus 2

<400> SEQUENCE: 37

```
ttggccactc cctctctgcg cgctcgctcg ctcactgagg ccgcccgggc aaagcccggg     60
```

-continued

```
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc ccattttagg gacaacgcga aacgtcgact    360
ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgta agtatgcctt tcactgcgag    600
aggttctgga gaggcttctg agctccccat ggcccaggca ggcagcaggt ctggggcagg    660
agggggggttg tggagtgcct tgactcgggg cctggccccc ccatctctgt cttgcaggac    720
aattgccgtc ttctgtctcg tggggcatcc tcctgctggc aggcctgtgc tgcctggtcc    780
ctgcgatcgc caccatgcag attgagctga gcacctgctt cttcctgtgc ctgctgaggt    840
tctgcttctc tgccaccagg agatactacc tgggggctgt ggagctgagc tgggactaca    900
tgcagtctga cctgggggag ctgcctgtgg atgccaggtt cccccccaga gtgcccaaga    960
gcttcccctt caacacctct gtggtgtaca agaagaccct gtttgtggag ttcactgacc   1020
acctgttcaa cattgccaag cccaggcccc cctggatggg cctgctgggc cccaccatcc   1080
aggctgaggt gtatgacact gtggtgatca ccctgaagaa catggccagc caccctgtga   1140
gcctgcatgc tgtgggggtg agctactgga aggcctctga gggggctgag tatgatgacc   1200
agaccagcca gagggagaag gaggatgaca aggtgttccc tgggggcagc cacacctatg   1260
tgtggcaggt gctgaaggag aatggcccca tggcctctga ccccctgtgc ctgacctaca   1320
gctacctgag ccatgtggac ctggtgaagg acctgaactc tggcctgatt ggggccctgc   1380
tggtgtgcag ggagggcagc ctggccaagg agaagaccca gaccctgcac aagttcatcc   1440
tgctgtttgc tgtgtttgat gagggcaaga gctggcactc tgaaaccaag aacagcctga   1500
tgcaggacag ggatgctgcc tctgccaggg cctggcccaa gatgcacact gtgaatggct   1560
atgtgaacag gagcctgcct ggcctgattg gctgccacag gaagtctgtg tactggcatg   1620
tgattggcat gggcaccacc cctgaggtgc acagcatctt cctggagggc cacaccttcc   1680
tggtcaggaa ccacaggcag gccagcctgg agatcagccc catcaccttc ctgactgccc   1740
agaccctgct gatggacctg ggccagttcc tgctgttctg ccacatcagc agccaccagc   1800
atgatggcat ggaggcctat gtgaaggtgg acagctgccc tgaggagccc cagctgagga   1860
tgaagaacaa tgaggaggct gaggactatg atgatgacct gactgactct gagatggatg   1920
tggtgaggtt tgatgatgac aacagcccca gcttcatcca gatcaggtct gtggccaaga   1980
agcaccccaa gacctgggtg cactacattg ctgctgagga ggaggactgg gactatgccc   2040
ccctggtgct ggcccctgat gacaggagct acaagagcca gtacctgaac aatggccccc   2100
agaggattgg caggaagtac aagaaggtca ggttcatggc ctacactgat gaaaccttca   2160
agaccaggga ggccatccag catgagtctg gcatcctggg cccccctgctg tatggggagg   2220
tgggggacac cctgctgatc atcttcaaga accaggccag caggccctac aacatctacc   2280
cccatggcat cactgatgtg aggcccctgt acagcaggag gctgcccaag gggggtgaagc   2340
acctgaagga cttccccatc ctgcctgggg agatcttcaa gtacaagtgg actgtgactg   2400
tggaggatgg ccccaccaag tctgacccca ggtgcctgac cagatactac agcagctttg   2460
```

-continued

```
tgaacatgga gagggacctg gcctctggcc tgattggccc cctgctgatc tgctacaagg   2520
agtctgtgga ccagaggggc aaccagatca tgtctgacaa gaggaatgtg atcctgttct   2580
ctgtgtttga tgagaacagg agctggtacc tgactgagaa catccagagg ttcctgccca   2640
accctgctgg ggtgcagctg gaggaccctg agttccaggc cagcaacatc atgcacagca   2700
tcaatggcta tgtgtttgac agcctgcagc tgtctgtgtg cctgcatgag gtggcctact   2760
ggtacatcct gagcattggg gcccagactg acttcctgtc tgtgttcttc tctggctaca   2820
ccttcaagca caagatggtg tatgaggaca ccctgaccct gttccccttc tctggggaga   2880
ctgtgttcat gagcatggag aaccctggcc tgtggattct gggctgccac aactctgact   2940
tcaggaacag gggcatgact gccctgctga aagtctccag ctgtgacaag aacactgggg   3000
actactatga ggacagctat gaggacatct ctgcctacct gctgagcaag aacaatgcca   3060
ttgagcccag gagcttcagc cagaaccccc cagtgctgaa gaggcaccag agggagatca   3120
ccaggaccac cctgcagtct gaccaggagg agattgacta tgatgacacc atctctgtgg   3180
agatgaagaa ggaggacttt gacatctacg acgaggacga gaaccagagc cccaggagct   3240
tccagaagaa gaccaggcac tacttcattg ctgctgtgga gaggctgtgg gactatggca   3300
tgagcagcag cccccatgtg ctgaggaaca gggcccagtc tggctctgtg ccccagttca   3360
agaaggtggt gttccaggag ttcactgatg gcagcttcac ccagcccctg tacagagggg   3420
agctgaatga gcacctgggc ctgctgggcc cctacatcag ggctgaggtg gaggacaaca   3480
tcatggtgac cttcaggaac caggccagca ggccctacag cttctacagc agcctgatca   3540
gctatgagga ggaccagagg caggggcctg agcccaggaa gaactttgtg aagcccaatg   3600
aaaccaagac ctacttctgg aaggtgcagc accacatggc ccccaccaag gatgagtttg   3660
actgcaaggc ctgggcctac ttctctgatg tggacctgga gaaggatgtg cactctggcc   3720
tgattggccc cctgctggtg tgccacacca acaccctgaa ccctgcccat ggcaggcagg   3780
tgactgtgca ggagtttgcc ctgttcttca ccatctttga tgaaaccaag agctggtact   3840
tcactgagaa catggagagg aactgcaggg ccccctgcaa catccagatg gaggacccca   3900
ccttcaagga gaactacagg ttccatgcca tcaatggcta catcatggac accctgcctg   3960
gcctggtgat ggcccaggac cagaggatca ggtggtacct gctgagcatg ggcagcaatg   4020
agaacatcca cagcatccac ttctctggcc atgtgttcac tgtgaggaag aaggaggagt   4080
acaagatggc cctgtacaac ctgtaccctg ggtgtttga gactgtggag atgctgccca   4140
gcaaggctgg catctggagg gtggagtgcc tgattgggga gcacctgcat gctggcatga   4200
gcaccctgtt cctggtgtac agcaacaagt gccagacccc cctgggcatg gcctctggcc   4260
acatcaggga cttccagatc actgcctctg gccagtatgg ccagtgggcc cccaagctgg   4320
ccaggctgca ctactctggc agcatcaatg cctggagcac caaggagccc ttcagctgga   4380
tcaaggtgga cctgctggcc cccatgatca tccatggcat caagacccag gggccaggc    4440
agaagttcag cagcctgtac atcagccagt tcatcatcat gtacagcctg gatggcaaga   4500
agtggcagac ctacaggggc aacagcactg gcaccctgat ggtgttcttt ggcaatgtgg   4560
acagctctgg catcaagcac aacatcttca acccccccat cattgccaga tacatcaggc   4620
tgcaccccac ccactacagc atcaggagca ccctgaggat ggagctgatg ggctgtgacc   4680
tgaacagctg cagcatgccc ctgggcatgg agagcaaggc catctctgat gcccagatca   4740
ctgccagcag ctacttcacc aacatgtttg ccacctggag ccccagcaag gccaggctgc   4800
```

-continued acctgcaggg caggagcaat gcctggaggc cccaggtcaa caaccccaag gagtggctgc 4860
aggtggactt ccagaagacc atgaaggtga ctggggtgac cacccagggg gtgaagagcc 4920
tgctgaccag catgtatgtg aaggagttcc tgatcagcag cagccaggat ggccaccagt 4980
ggaccctgtt cttccagaat ggcaaggtga aggtgttcca gggcaaccag gacagcttca 5040
cccctgtggt gaacagcctg gacccccccc tgctgaccag atacctgagg attcaccccc 5100
agagctgggt gcaccagatt gccctgagga tggaggtgct gggctgtgag gcccaggacc 5160
tgtactgacc tcgaggaata aaggaaattt attttcattg caatagtgtg ttggtttttt 5220
gtgtcacgtg gcggccgcag gaacccctag tgatggagtt ggccactccc tctctgcgcg 5280
ctcgctcgct cactgaggcc gggcgaccaa aggtcgcccg acgcccgggc tttgcccggg 5340
cggcctcagt gagcgagcga gcgcgcagag agggagtggc caa 5383

<210> SEQ ID NO 38
<211> LENGTH: 5728
<212> TYPE: DNA
<213> ORGANISM: Adeno-Associated Virus 2

<400> SEQUENCE: 38
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg ttttcgactg tttgctgttt 180
gctgcttgca atgtttgccc attttaggga catgtttgct gtttgctgct tgcaatgttt 240
gcccatttta gggacatgtt tgctgtttgc tgcttgcaat gtttgcccat tttagggaca 300
tgtttgctgt ttgctgcttg caatgtttgc ccattttagg gacaacgcga aacgtcgaca 360
ggttaatttt taaaaagcag tcaaaagtcc aagtggccct tggcagcatt tactctctct 420
gtttgctctg gttaataatc tcaggagcac aaacattcct ggaggcagga gaagaaatca 480
acatcctgga cttatcctct gggcctctcc ccacccccag gagaggctca ggttaatttt 540
taaaaagcag tcaaaagtcc aagtggccct tggcagcatt tactctctct gtttgctctg 600
gttaataatc tcaggagcac aaacattcct ggaggcagga gaagaaatca acatcctgga 660
cttatcctct gggcctctcc ccacccccag gagaggctgt cgactggaca caggacgctg 720
tggtttctga gccagggggc gactcagatc ccagccagtg gacttagccc ctgtttgctc 780
ctccgataac tggggtgacc ttggttaata ttcaccagca gcctcccccg ttgcccctct 840
ggatccactg cttaaatacg gacgaggaca gggccctgtc tcctcagctt caggcaccac 900
cactgacctg ggacagtgaa tcgtaagtat gcctttcact gcgagaggtt ctggagaggc 960
ttctgagctc cccatggccc aggcaggcag caggtctggg gcaggagggg ggttgtggag 1020
tgccttgact cggggcctgg cccccccatc tctgtcttgc aggacaattg ccgtcttctg 1080
tctcgtgggg catcctcctg ctggcaggcc tgtgctgcct ggtccctgcg atcgccacca 1140
tgcagattga gctgagcacc tgcttcttcc tgtgcctgct gaggttctgc ttctctgcca 1200
ccaggagata ctacctgggg gctgtggagc tgagctggga ctacatgcag tctgacctgg 1260
gggagctgcc tgtggatgcc aggttccccc ccagagtgcc caagagcttc cccttcaaca 1320
cctctgtggt gtacaagaag accctgtttg tggagttcac tgaccacctg ttcaacattg 1380
ccaagcccag gccccccctgg atgggcctgc tgggccccac catccaggct gaggtgtatg 1440
acactgtggt gatcaccctg aagaacatgg ccagccaccc tgtgagcctg catgctgtgg 1500
gggtgagcta ctggaaggcc tctgaggggg ctgagtatga tgaccagacc agccagaggg 1560

-continued

```
agaaggagga tgacaaggtg ttccctgggg gcagccacac ctatgtgtgg caggtgctga   1620
aggagaatgg ccccatggcc tctgaccccc tgtgcctgac ctacagctac ctgagccatg   1680
tggacctggt gaaggacctg aactctggcc tgattggggc cctgctggtg tgcagggagg   1740
gcagcctggc caaggagaag acccagaccc tgcacaagtt catcctgctg tttgctgtgt   1800
ttgatgaggg caagagctgg cactctgaaa ccaagaacag cctgatgcag gacagggatg   1860
ctgcctctgc cagggcctgg cccaagatgc acactgtgaa tggctatgtg aacaggagcc   1920
tgcctggcct gattggctgc cacaggaagt ctgtgtactg gcatgtgatt ggcatgggca   1980
ccacccctga ggtgcacagc atcttcctgg agggccacac cttcctggtc aggaaccaca   2040
ggcaggccag cctggagatc agccccatca ccttcctgac tgcccagacc ctgctgatgg   2100
acctgggcca gttcctgctg ttctgccaca tcagcagcca ccagcatgat ggcatggagg   2160
cctatgtgaa ggtggacagc tgccctgagg agccccagct gaggatgaag aacaatgagg   2220
aggctgagga ctatgatgat gacctgactg actctgagat ggatgtggtg aggtttgatg   2280
atgacaacag ccccagcttc atccagatca ggtctgtggc caagaagcac cccaagacct   2340
gggtgcacta cattgctgct gaggaggagg actgggacta tgcccccctg gtgctggccc   2400
ctgatgacag gagctacaag agccagtacc tgaacaatgg cccccagagg attggcagga   2460
agtacaagaa ggtcaggttc atggcctaca ctgatgaaac cttcaagacc agggaggcca   2520
tccagcatga gtctggcatc ctgggccccc tgctgtatgg ggaggtgggg gacaccctgc   2580
tgatcatctt caagaaccag gccagcaggc cctacaacat ctacccccat ggcatcactg   2640
atgtgaggcc cctgtacagc aggaggctgc ccaagggggt gaagcacctg aaggacttcc   2700
ccatcctgcc tggggagatc ttcaagtaca agtggactgt gactgtggag gatggcccca   2760
ccaagtctga ccccaggtgc ctgaccagat actacagcag ctttgtgaac atggagaggg   2820
acctggcctc tggcctgatt ggccccctgc tgatctgcta caaggagtct gtggaccaga   2880
ggggcaacca gatcatgtct gacaagagga atgtgatcct gttctctgtg tttgatgaga   2940
acaggagctg gtacctgact gagaacatcc agaggttcct gcccaaccct gctggggtgc   3000
agctggagga ccctgagttc caggccagca acatcatgca cagcatcaat ggctatgtgt   3060
ttgacagcct gcagctgtct gtgtgcctgc atgaggtggc ctactggtac atcctgagca   3120
ttggggccca gactgacttc ctgtctgtgt tcttctctgg ctacaccttc aagcacaaga   3180
tggtgtatga ggacaccctg accctgttcc ccttctctgg ggagactgtg ttcatgagca   3240
tggagaaccc tggcctgtgg attctgggct gccacaactc tgacttcagg aacaggggca   3300
tgactgccct gctgaaagtc tccagctgtg acaagaacac tggggactac tatgaggaca   3360
gctatgagga catctctgcc tacctgctga gcaagaacaa tgccattgag cccaggagct   3420
tcagccagaa cccccccagtg ctgaagaggc accagaggga gatcaccagg accaccctgc   3480
agtctgacca ggaggagatt gactatgatg acaccatctc tgtggagatg aagaaggagg   3540
actttgacat ctacgacgag gacgagaacc agagccccag gagcttccag aagaagacca   3600
ggcactactt cattgctgct gtggagaggc tgtgggacta tggcatgagc agcagccccc   3660
atgtgctgag gaacagggcc cagtctggct ctgtgcccca gttcaagaag gtggtgttcc   3720
aggagttcac tgatggcagc ttcacccagc ccctgtacag aggggagctg aatgagcacc   3780
tgggcctgct gggcccctac atcagggctg aggtggagga caacatcatg gtgaccttca   3840
ggaaccaggc cagcaggccc tacagcttct acagcagcct gatcagctat gaggaggacc   3900
```

-continued

```
agaggcaggg ggctgagccc aggaagaact ttgtgaagcc caatgaaacc aagacctact   3960

tctggaaggt gcagcaccac atggccccca ccaaggatga gtttgactgc aaggcctggg   4020

cctacttctc tgatgtggac ctggagaagg atgtgcactc tggcctgatt ggcccccctgc   4080

tggtgtgcca caccaacacc ctgaaccctg cccatggcag gcaggtgact gtgcaggagt   4140

ttgccctgtt cttcaccatc tttgatgaaa ccaagagctg gtacttcact gagaacatgg   4200

agaggaactg cagggccccc tgcaacatcc agatggagga ccccaccttc aaggagaact   4260

acaggttcca tgccatcaat ggctacatca tggacaccct gcctggcctg gtgatggccc   4320

aggaccagag gatcaggtgg tacctgctga gcatgggcag caatgagaac atccacagca   4380

tccacttctc tggccatgtg ttcactgtga ggaagaagga ggagtacaag atggccctgt   4440

acaacctgta ccctggggtg tttgagactg tggagatgct gcccagcaag gctggcatct   4500

ggagggtgga gtgcctgatt ggggagcacc tgcatgctgg catgagcacc ctgttcctgg   4560

tgtacagcaa caagtgccag accccccctgg gcatggcctc tggccacatc agggacttcc   4620

agatcactgc ctctggccag tatggccagt gggcccccaa gctggccagg ctgcactact   4680

ctggcagcat caatgcctgg agcaccaagg agcccttcag ctggatcaag gtggacctgc   4740

tggcccccat gatcatccat ggcatcaaga cccagggggc caggcagaag ttcagcagcc   4800

tgtacatcag ccagttcatc atcatgtaca gcctggatgg caagaagtgg cagacctaca   4860

ggggcaacag cactggcacc ctgatggtgt tctttggcaa tgtggacagc tctggcatca   4920

agcacaacat cttcaacccc cccatcattg ccagatacat caggctgcac cccacccact   4980

acagcatcag gagcaccctg aggatggagc tgatgggctg tgacctgaac agctgcagca   5040

tgcccctggg catggagagc aaggccatct ctgatgccca gatcactgcc agcagctact   5100

tcaccaacat gtttgccacc tggagcccca gcaaggccag gctgcacctg cagggcagga   5160

gcaatgcctg gaggccccag gtcaacaacc ccaaggagtg gctgcaggtg gacttccaga   5220

agaccatgaa ggtgactggg gtgaccaccc agggggtgaa gagcctgctg accagcatgt   5280

atgtgaagga gttcctgatc agcagcagcc aggatggcca ccagtggacc ctgttcttcc   5340

agaatggcaa ggtgaaggtg ttccagggca accaggacag cttcacccct gtggtgaaca   5400

gcctggaccc ccccctgctg accagatacc tgaggattca cccccagagc tgggtgcacc   5460

agattgccct gaggatggag gtgctgggct gtgaggccca ggacctgtac tgacctcgag   5520

gaataaagga aatttatttt cattgcaata gtgtgttggt tttttgtgtc acgtggcggc   5580

cgcaggaacc cctagtgatg gagttggcca ctccctctct gcgcgctcgc tcgctcactg   5640

aggccgggcg accaaaggtc gcccgacgcc cgggctttgc ccgggcggcc tcagtgagcg   5700

agcgagcgcg cagagaggga gtggccaa                                      5728
```

<210> SEQ ID NO 39
<211> LENGTH: 5905
<212> TYPE: DNA
<213> ORGANISM: Adeno-Associated Virus 2

<400> SEQUENCE: 39

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgactg tttgctgttt    180

gctgcttgca atgtttgccc attttaggga catgtttgct gtttgctgct tgcaatgttt    240

gcccatttta gggacatgtt tgctgtttgc tgcttgcaat gtttgcccat tttagggaca    300
```

-continued

```
tgtttgctgt ttgctgcttg caatgtttgc ccattttagg gacaacgcga aacgtcgaca    360
ggttaatttt taaaaagcag tcaaaagtcc aagtggccct tggcagcatt tactctctct    420
gtttgctctg gttaataatc tcaggagcac aaacattcct ggaggcagga gaagaaatca    480
acatcctgga cttatcctct gggcctctcc ccacccccag gagaggctca ggttaatttt    540
taaaaagcag tcaaaagtcc aagtggccct tggcagcatt tactctctct gtttgctctg    600
gttaataatc tcaggagcac aaacattcct ggaggcagga gaagaaatca acatcctgga    660
cttatcctct gggcctctcc ccacccccag gagaggctgt cgactggaca caggacgctg    720
tggtttctga gccagggggc gactcagatc ccagccagtg gacttagccc ctgtttgctc    780
ctccgataac tggggtgacc ttggttaata ttcaccagca gcctcccccg ttgcccctct    840
ggatccactg cttaaatacg gacgaggaca gggccctgtc tcctcagctt caggcaccac    900
cactgacctg ggacagtgaa tcgtaagtat gcctttcact gcgagaggtt ctggagaggc    960
ttctgagctc cccatggccc aggcaggcag caggtctggg gcaggagggg ggttgtggag   1020
tgccttgact cggggcctgg ccccccatc tctgtcttgc aggacaattg ccgtcttctg   1080
tctcgtgggg catcctcctg ctggcaggcc tgtgctgcct ggtccctgcg atcgccacca   1140
tgcagattga gctgagcacc tgcttcttcc tgtgcctgct gaggttctgc ttctctgcca   1200
ccaggagata ctacctgggg gctgtggagc tgagctggga ctacatgcag tctgacctgg   1260
gggagctgcc tgtggatgcc aggttccccc ccagagtgcc caagagcttc cccttcaaca   1320
cctctgtggt gtacaagaag accctgtttg tggagttcac tgaccacctg ttcaacattg   1380
ccaagcccag gccccccctgg atgggcctgc tgggccccac catccaggct gaggtgtatg   1440
acactgtggt gatcaccctg aagaacatgg ccagccaccc tgtgagcctg catgctgtgg   1500
gggtgagcta ctggaaggcc tctgaggggg ctgagtatga tgaccagacc agccagaggg   1560
agaaggagga tgacaaggtg ttccctgggg gcagccacac ctatgtgtgg caggtgctga   1620
aggagaatgg ccccatggcc tctgaccccc tgtgcctgac ctacagctac ctgagccatg   1680
tggacctggt gaaggacctg aactctggcc tgattggggc cctgctggtg tgcagggagg   1740
gcagcctggc caaggagaag acccagaccc tgcacaagtt catcctgctg tttgctgtgt   1800
ttgatgaggg caagagctgg cactctgaaa ccaagaacag cctgatgcag gacagggatg   1860
ctgcctctgc cagggcctgg cccaagatgc acactgtgaa tggctatgtg aacaggagcc   1920
tgcctggcct gattggctgc cacaggaagt ctgtgtactg gcatgtgatt ggcatgggca   1980
ccacccctga ggtgcacagc atcttcctgg agggccacac cttcctggtc aggaaccaca   2040
ggcaggccag cctggagatc agccccatca ccttcctgac tgcccagacc ctgctgatgg   2100
acctgggcca gttcctgctg ttctgccaca tcagcagcca ccagcatgat ggcatggagg   2160
cctatgtgaa ggtggacagc tgccctgagg agccccagct gaggatgaag aacaatgagg   2220
aggctgagga ctatgatgat gacctgactg actctgagat ggatgtggtg aggtttgatg   2280
atgacaacag ccccagcttc atccagatca ggtctgtggc caagaagcac cccaagacct   2340
gggtgcacta cattgctgct gaggaggagg actgggacta tgccccccctg gtgctggccc   2400
ctgatgacag gagctacaag agccagtacc tgaacaatgg cccccagagg attggcagga   2460
agtacaagaa ggtcaggttc atggcctaca ctgatgaaac cttcaagacc agggaggcca   2520
tccagcatga gtctggcatc ctgggccccc tgctgtatgg ggaggtgggg gacaccctgc   2580
tgatcatctt caagaaccag gccagcaggc cctacaacat ctacccccat ggcatcactg   2640
```

-continued

```
atgtgaggcc cctgtacagc aggaggctgc ccaagggggt gaagcacctg aaggacttcc   2700
ccatcctgcc tggggagatc ttcaagtaca agtggactgt gactgtggag gatggcccca   2760
ccaagtctga ccccaggtgc ctgaccagat actacagcag ctttgtgaac atggagaggg   2820
acctggcctc tggcctgatt ggccccctgc tgatctgcta caaggagtct gtggaccaga   2880
ggggcaacca gatcatgtct gacaagagga atgtgatcct gttctctgtg tttgatgaga   2940
acaggagctg gtacctgact gagaacatcc agaggttcct gcccaaccct gctggggtgc   3000
agctggagga ccctgagttc caggccagca acatcatgca cagcatcaat ggctatgtgt   3060
ttgacagcct gcagctgtct gtgtgcctgc atgaggtggc ctactggtac atcctgagca   3120
ttggggccca gactgacttc ctgtctgtgt tcttctctgg ctacaccttc aagcacaaga   3180
tggtgtatga ggacaccctg accctgttcc ccttctctgg ggagactgtg ttcatgagca   3240
tggagaaccc tggcctgtgg attctgggct gccacaactc tgacttcagg aacaggggca   3300
tgactgccct gctgaaagtc tccagctgtg acaagaacac tggggactac tatgaggaca   3360
gctatgagga catctctgcc tacctgctga gcaagaacaa tgccattgag cccaggagct   3420
tcagccagaa ccccccagtg ctgaagaggc accagaggga gatcaccagg accaccctgc   3480
agtctgacca ggaggagatt gactatgatg acaccatctc tgtggagatg aagaaggagg   3540
actttgacat ctacgacgag gacgagaacc agagccccag gagcttccag aagaagacca   3600
ggcactactt cattgctgct gtggagaggc tgtgggacta tggcatgagc agcagccccc   3660
atgtgctgag gaacagggcc cagtctggct ctgtgcccca gttcaagaag gtggtgttcc   3720
aggagttcac tgatggcagc ttcacccagc ccctgtacag aggggagctg aatgagcacc   3780
tgggcctgct gggcccctac atcagggctg aggtggagga caacatcatg gtgaccttca   3840
ggaaccaggc cagcaggccc tacagcttct acagcagcct gatcagctat gaggaggacc   3900
agaggcaggg ggctgagccc aggaagaact ttgtgaagcc caatgaaacc aagacctact   3960
tctggaaggt gcagcaccac atggccccca ccaaggatga gtttgactgc aaggcctggg   4020
cctacttctc tgatgtggac ctggagaagg atgtgcactc tggcctgatt ggccccctgc   4080
tggtgtgcca caccaacacc ctgaaccctg cccatggcag gcaggtgact gtgcaggagt   4140
ttgccctgtt cttcaccatc tttgatgaaa ccaagagctg gtacttcact gagaacatgg   4200
agaggaactg cagggccccc tgcaacatcc agatggagga ccccaccttc aaggagaact   4260
acaggttcca tgccatcaat ggctacatca tggacaccct gcctggcctg gtgatggccc   4320
aggaccagag gatcaggtgg tacctgctga gcatgggcag caatgagaac atccacagca   4380
tccacttctc tggccatgtg ttcactgtga ggaagaagga ggagtacaag atggccctgt   4440
acaacctgta ccctggggtg tttgagactg tggagatgct gcccagcaag gctggcatct   4500
ggagggtgga gtgcctgatt ggggagcacc tgcatgctgg catgagcacc ctgttcctgg   4560
tgtacagcaa caagtgccag accccctgg gcatggcctc tggccacatc agggacttcc   4620
agatcactgc ctctggccag tatggccagt gggcccccaa gctggccagg ctgcactact   4680
ctggcagcat caatgcctgg agcaccaagg agcccttcag ctggatcaag gtggacctgc   4740
tggcccccat gatcatccat ggcatcaaga cccagggggc caggcagaag ttcagcagcc   4800
tgtacatcag ccagttcatc atcatgtaca gcctggatgg caagaagtgg cagacctaca   4860
ggggcaacag cactggcacc ctgatggtgt tctttggcaa tgtggacagc tctggcatca   4920
agcacaacat cttcaacccc cccatcattg ccagatacat caggctgcac cccacccact   4980
acagcatcag gagcaccctg aggatggagc tgatgggctg tgacctgaac agctgcagca   5040
```

```
tgcccctggg catggagagc aaggccatct ctgatgccca gatcactgcc agcagctact   5100

tcaccaacat gtttgccacc tggagcccca gcaaggccag gctgcacctg cagggcagga   5160

gcaatgcctg gaggccccag gtcaacaacc ccaaggagtg gctgcaggtg gacttccaga   5220

agaccatgaa ggtgactggg gtgaccaccc agggggtgaa gagcctgctg accagcatgt   5280

atgtgaagga gttcctgatc agcagcagcc aggatggcca ccagtggacc ctgttcttcc   5340

agaatggcaa ggtgaaggtg ttccagggca accaggacag cttcacccct gtggtgaaca   5400

gcctggaccc ccccctgctg accagatacc tgaggattca cccccagagc tgggtgcacc   5460

agattgccct gaggatggag gtgctgggct gtgaggccca ggacctgtac tgacctcgag   5520

gtgtgccttc tagttgccag ccatctgttg tttgcccctc ccccgtgcct tccttgaccc   5580

tggaaggtgc cactcccact gtcctttcct aataaaatga ggaaattgca tcgcattgtc   5640

tgagtaggtg tcattctatt ctggggggtg gggtggggca ggacagcaag ggggaggatt   5700

gggaagacaa tagcaggcat gctggggatg cggtgggctc tatgggcacg tggcggccgc   5760

aggaacccct agtgatggag ttggccactc cctctctgcg cgctcgctcg ctcactgagg   5820

ccgggcgacc aaaggtcgcc cgacgcccgg gctttgcccg ggcggcctca gtgagcgagc   5880

gagcgcgcag agagggagtg gccaa                                         5905
```

```
<210> SEQ ID NO 40
<211> LENGTH: 5355
<212> TYPE: DNA
<213> ORGANISM: Adeno-Associated Virus 2

<400> SEQUENCE: 40

ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgactg tttgctgttt    180

gctgcttgca atgtttgccc attttaggga catgtttgct gtttgctgct tgcaatgttt    240

gcccatttta gggacatgtt tgctgtttgc tgcttgcaat gtttgcccat tttagggaca    300

tgtttgctgt ttgctgcttg caatgtttgc ccattttagg gacaacgcga aacgtcgact    360

ggacacagga cgctgtggtt tctgagccag gggcgactc agatcccagc cagtggactt     420

agcccctgtt tgctcctccg ataactgggg tgaccttggt taatattcac cagcagcctc    480

ccccgttgcc cctctggatc cactgcttaa atacggacga ggacagggcc ctgtctcctc    540

agcttcaggc accaccactg acctgggaca gtgaatcgcg atcgccacca tgcagattga    600

gctgagcacc tgcttcttcc tgtgcctgct gaggttctgc ttctctgcca ccaggagata    660

ctacctgggg gctgtggagc tgagctggga ctacatgcag tctgacctgg gggagctgcc    720

tgtggatgcc aggttccccc ccagagtgcc caagagcttc cccttcaaca cctctgtggt    780

gtacaagaag accctgtttg tggagttcac tgaccacctg ttcaacattg ccaagcccag    840

gccccccctgg atgggcctgc tgggccccac catccaggct gaggtgtatg acactgtggt    900

gatcaccctg aagaacatgg ccagccaccc tgtgagcctg catgctgtgg gggtgagcta    960

ctggaaggcc tctgaggggg ctgagtatga tgaccagacc agccagaggg agaaggagga   1020

tgacaaggtg ttccctgggg gcagccacac ctatgtgtgg caggtgctga aggagaatgg   1080

ccccatggcc tctgaccccc tgtgcctgac ctacagctac ctgagccatg tggacctggt   1140

gaaggacctg aactctggcc tgattggggc cctgctggtg tgcagggagg gcagcctggc   1200
```

-continued caaggagaag acccagaccc tgcacaagtt catcctgctg tttgctgtgt ttgatgaggg 1260
caagagctgg cactctgaaa ccaagaacag cctgatgcag gacagggatg ctgcctctgc 1320
cagggcctgg cccaagatgc acactgtgaa tggctatgtg aacaggagcc tgcctggcct 1380
gattggctgc cacaggaagt ctgtgtactg gcatgtgatt ggcatgggca ccacccctga 1440
ggtgcacagc atcttcctgg agggccacac cttcctggtc aggaaccaca ggcaggccag 1500
cctggagatc agccccatca ccttcctgac tgcccagacc ctgctgatgg acctgggcca 1560
gttcctgctg ttctgccaca tcagcagcca ccagcatgat ggcatggagg cctatgtgaa 1620
ggtggacagc tgccctgagg agccccagct gaggatgaag aacaatgagg aggctgagga 1680
ctatgatgat gacctgactg actctgagat ggatgtggtg aggtttgatg atgacaacag 1740
ccccagcttc atccagatca ggtctgtggc caagaagcac cccaagacct gggtgcacta 1800
cattgctgct gaggaggagg actgggacta tgccccccctg gtgctggccc ctgatgacag 1860
gagctacaag agccagtacc tgaacaatgg cccccagagg attggcagga agtacaagaa 1920
ggtcaggttc atggcctaca ctgatgaaac cttcaagacc agggaggcca tccagcatga 1980
gtctggcatc ctgggccccc tgctgtatgg ggaggtgggg gacaccctgc tgatcatctt 2040
caagaaccag gccagcaggc cctacaacat ctacccccat ggcatcactg atgtgaggcc 2100
cctgtacagc aggaggctgc ccaagggggt gaagcacctg aaggacttcc ccatcctgcc 2160
tggggagatc ttcaagtaca agtggactgt gactgtggag gatggcccca ccaagtctga 2220
ccccaggtgc ctgaccagat actacagcag ctttgtgaac atggagaggg acctggcctc 2280
tggcctgatt ggcccccctgc tgatctgcta caaggagtct gtggaccaga ggggcaacca 2340
gatcatgtct gacaagagga atgtgatcct gttctctgtg tttgatgaga acaggagctg 2400
gtacctgact gagaacatcc agaggttcct gcccaaccct gctggggtgc agctggagga 2460
ccctgagttc caggccagca acatcatgca cagcatcaat ggctatgtgt ttgacagcct 2520
gcagctgtct gtgtgcctgc atgaggtggc ctactggtac atcctgagca ttggggccca 2580
gactgacttc ctgtctgtgt tcttctctgg ctacaccttc aagcacaaga tggtgtatga 2640
ggacaccctg accctgttcc ccttctctgg ggagactgtg ttcatgagca tggagaaccc 2700
tggcctgtgg attctgggct gccacaactc tgacttcagg aacaggggca tgactgccct 2760
gctgaaagtc tccagctgtg acaagaacac tggggactac tatgaggaca gctatgagga 2820
catctctgcc tacctgctga gcaagaacaa tgccattgag cccaggagct tcagccagaa 2880
ccccccagtg ctgaagaggc accagaggga gatcaccagg accaccctgc agtctgacca 2940
ggaggagatt gactatgatg acaccatctc tgtggagatg aagaaggagg actttgacat 3000
ctacgacgag gacgagaacc agagccccag gagcttccag aagaagacca ggcactactt 3060
cattgctgct gtggagaggc tgtgggacta tggcatgagc agcagccccc atgtgctgag 3120
gaacagggcc cagtctggct ctgtgcccca gttcaagaag gtggtgttcc aggagttcac 3180
tgatggcagc ttcacccagc ccctgtacag aggggagctg aatgagcacc tgggcctgct 3240
gggcccctac atcagggctg aggtggagga caacatcatg gtgaccttca ggaaccaggc 3300
cagcaggccc tacagcttct acagcagcct gatcagctat gaggaggacc agaggcaggg 3360
ggctgagccc aggaagaact ttgtgaagcc caatgaaacc aagacctact tctggaaggt 3420
gcagcaccac atggcccccca ccaaggatga gtttgactgc aaggcctggg cctacttctc 3480
tgatgtggac ctggagaagg atgtgcactc tggcctgatt ggcccccctgc tggtgtgcca 3540 caccaacacc ctgaaccctg cccatggcag gcaggtgact gtgcaggagt ttgccctgtt 3600

```
cttcaccatc tttgatgaaa ccaagagctg gtacttcact gagaacatgg agaggaactg   3660

cagggccccc tgcaacatcc agatggagga ccccaccttc aaggagaact acaggttcca   3720

tgccatcaat ggctacatca tggacaccct gcctggcctg gtgatggccc aggaccagag   3780

gatcaggtgg tacctgctga gcatgggcag caatgagaac atccacagca tccacttctc   3840

tggccatgtg ttcactgtga ggaagaagga ggagtacaag atggccctgt acaacctgta   3900

ccctggggtg tttgagactg tggagatgct gcccagcaag gctggcatct ggagggtgga   3960

gtgcctgatt ggggagcacc tgcatgctgg catgagcacc ctgttcctgg tgtacagcaa   4020

caagtgccag accccctgg gcatggcctc tggccacatc agggacttcc agatcactgc   4080

ctctggccag tatggccagt gggcccccaa gctggccagg ctgcactact ctggcagcat   4140

caatgcctgg agcaccaagg agcccttcag ctggatcaag gtggacctgc tggcccccat   4200

gatcatccat ggcatcaaga cccagggggc caggcagaag ttcagcagcc tgtacatcag   4260

ccagttcatc atcatgtaca gcctggatgg caagaagtgg cagacctaca ggggcaacag   4320

cactggcacc ctgatggtgt tctttggcaa tgtggacagc tctggcatca agcacaacat   4380

cttcaacccc cccatcattg ccagatacat caggctgcac ccccacccact acagcatcag   4440

gagcaccctg aggatggagc tgatgggctg tgacctgaac agctgcagca tgcccctggg   4500

catggagagc aaggccatct ctgatgccca gatcactgcc agcagctact tcaccaacat   4560

gtttgccacc tggagcccca gcaaggccag gctgcacctg cagggcagga gcaatgcctg   4620

gaggccccag gtcaacaacc ccaaggagtg gctgcaggtg gacttccaga agaccatgaa   4680

ggtgactggg gtgaccaccc agggggtgaa gagcctgctg accagcatgt atgtgaagga   4740

gttcctgatc agcagcagcc aggatggcca ccagtggacc ctgttcttcc agaatggcaa   4800

ggtgaaggtg ttccagggca accaggacag cttcacccct gtggtgaaca gcctggaccc   4860

ccccctgctg accagatacc tgaggattca cccccagagc tgggtgcacc agattgccct   4920

gaggatggag gtgctgggct gtgaggccca ggacctgtac tgacctcgag gtgtgccttc   4980

tagttgccag ccatctgttg tttgcccctc ccccgtgcct tccttgaccc tggaaggtgc   5040

cactcccact gtcctttcct aataaaatga ggaaattgca tcgcattgtc tgagtaggtg   5100

tcattctatt ctggggggtg gggtggggca ggacagcaag ggggaggatt gggaagacaa   5160

tagcaggcat gctggggatg cggtgggctc tatgggcacg tggcggccgc aggaacccct   5220

agtgatggag ttggccactc cctctctgcg cgctcgctcg ctcactgagg ccgggcgacc   5280

aaaggtcgcc cgacgcccgg gctttgcccg ggcggcctca gtgagcgagc gagcgcgcag   5340

agagggagtg gccaa                                                    5355
```

<210> SEQ ID NO 41
<211> LENGTH: 5618
<212> TYPE: DNA
<213> ORGANISM: Adeno-Associated Virus 2

<400> SEQUENCE: 41

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ttttcgacca gagaggtctc    180

tgacctctgc cccagctcca aggtcagcag gcagggaggg ctgtgtgttt gctgtttgct    240

gcttgcaatg tttgcccatt ttagggacat gagtaggctg aagtttgttc agtgtggact    300
```

-continued

```
tcagaggcag cacacaaaca gccagagagg tctctgacct ctgccccagc tccaaggtca    360
gcaggcaggg agggctgtgt gtttgctgtt tgctgcttgc aatgtttgcc cattttaggg    420
acatgagtag gctgaagttt gttcagtgtg gacttcagag gcagcacaca aacagccaga    480
gaggtctctg acctctgccc cagctccaag gtcagcaggc agggagggct gtgtgtttgc    540
tgtttgctgc ttgcaatgtt tgcccatttt agggacatga gtaggctgaa gtttgttcag    600
tgtggacttc agaggcagca cacaaacagc cagagaggtc tctgacctct gccccagctc    660
caaggtcagc aggcagggag ggctgtgtgt ttgctgtttg ctgcttgcaa tgtttgccca    720
ttttagggac atgagtaggc tgaagtttgt tcagtgtgga cttcagaggc agcacacaaa    780
cagcacgcga aacgtcgact ggacacagga cgctgtggtt tctgagccag gggcgactc     840
agatcccagc cagtggactt agcccctgtt tgctcctccg ataactgggg tgaccttggt    900
taatattcac cagcagcctc ccccgttgcc cctctggatc cactgcttaa atacggacga    960
ggacagggcc ctgtctcctc agcttcaggc accaccactg acctgggaca gtgaatcgcg   1020
atcgccacca tgcagattga gctgagcacc tgcttcttcc tgtgcctgct gaggttctgc   1080
ttctctgcca ccaggagata ctacctgggg gctgtggagc tgagctggga ctacatgcag   1140
tctgacctgg gggagctgcc tgtggatgcc aggttccccc ccagagtgcc caagagcttc   1200
cccttcaaca cctctgtggt gtacaagaag accctgtttg tggagttcac tgaccacctg   1260
ttcaacattg ccaagcccag gccccccctgg atgggcctgc tgggccccac catccaggct   1320
gaggtgtatg acactgtggt gatcaccctg aagaacatgg ccagccaccc tgtgagcctg   1380
catgctgtgg gggtgagcta ctggaaggcc tctgaggggg ctgagtatga tgaccagacc   1440
agccagaggg agaaggagga tgacaaggtg ttccctgggg gcagccacac ctatgtgtgg   1500
caggtgctga aggagaatgg ccccatggcc tctgaccccc tgtgcctgac ctacagctac   1560
ctgagccatg tggacctggt gaaggacctg aactctggcc tgattggggc cctgctggtg   1620
tgcagggagg gcagcctggc caaggagaag acccagaccc tgcacaagtt catcctgctg   1680
tttgctgtgt ttgatgaggg caagagctgg cactctgaaa ccaagaacag cctgatgcag   1740
gacagggatg ctgcctctgc cagggcctgg cccaagatgc acactgtgaa tggctatgtg   1800
aacaggagcc tgcctggcct gattggctgc cacaggaagt ctgtgtactg gcatgtgatt   1860
ggcatgggca ccacccctga ggtgcacagc atcttcctgg agggccacac cttcctggtc   1920
aggaaccaca ggcaggccag cctggagatc agccccatca ccttcctgac tgcccagacc   1980
ctgctgatgg acctgggcca gttcctgctg ttctgccaca tcagcagcca ccagcatgat   2040
ggcatggagg cctatgtgaa ggtggacagc tgccctgagg agccccagct gaggatgaag   2100
aacaatgagg aggctgagga ctatgatgat gacctgactg actctgagat ggatgtggtg   2160
aggtttgatg atgacaacag ccccagcttc atccagatca ggtctgtggc caagaagcac   2220
cccaagacct gggtgcacta cattgctgct gaggaggagg actgggacta tgccccccctg  2280
gtgctggccc ctgatgacag gagctacaag agccagtacc tgaacaatgg cccccagagg   2340
attggcagga agtacaagaa ggtcaggttc atggcctaca ctgatgaaac cttcaagacc   2400
agggaggcca tccagcatga gtctggcatc ctgggccccc tgctgtatgg ggaggtgggg   2460
gacaccctgc tgatcatctt caagaaccag gccagcaggc cctacaacat ctacccccat   2520
ggcatcactg atgtgaggcc cctgtacagc aggaggctgc ccaagggggt gaagcacctg   2580
aaggacttcc ccatcctgcc tggggagatc ttcaagtaca agtggactgt gactgtggag   2640
gatggcccca ccaagtctga ccccaggtgc ctgaccagat actacagcag ctttgtgaac   2700
```

-continued

```
atggagaggg acctggcctc tggcctgatt ggccccctgc tgatctgcta caaggagtct   2760
gtggaccaga ggggcaacca gatcatgtct gacaagagga atgtgatcct gttctctgtg   2820
tttgatgaga acaggagctg gtacctgact gagaacatcc agaggttcct gcccaaccct   2880
gctggggtgc agctggagga ccctgagttc caggccagca acatcatgca cagcatcaat   2940
ggctatgtgt ttgacagcct gcagctgtct gtgtgcctgc atgaggtggc ctactggtac   3000
atcctgagca ttggggccca gactgacttc ctgtctgtgt tcttctctgg ctacaccttc   3060
aagcacaaga tggtgtatga ggacaccctg accctgttcc ccttctctgg ggagactgtg   3120
ttcatgagca tggagaaccc tggcctgtgg attctgggct gccacaactc tgacttcagg   3180
aacaggggca tgactgccct gctgaaagtc tccagctgtg acaagaacac tggggactac   3240
tatgaggaca gctatgagga catctctgcc tacctgctga gcaagaacaa tgccattgag   3300
cccaggagct tcagccagaa ccccccagtg ctgaagaggc accagaggga gatcaccagg   3360
accaccctgc agtctgacca ggaggagatt gactatgatg acaccatctc tgtggagatg   3420
aagaaggagg actttgacat ctacgacgag gacgagaacc agagccccag gagcttccag   3480
aagaagacca ggcactactt cattgctgct gtggagaggc tgtgggacta tggcatgagc   3540
agcagccccc atgtgctgag gaacagggcc cagtctggct ctgtgcccca gttcaagaag   3600
gtggtgttcc aggagttcac tgatggcagc ttcacccagc cctgtacag aggggagctg   3660
aatgagcacc tgggcctgct gggcccctac atcagggctg aggtggagga caacatcatg   3720
gtgaccttca ggaaccaggc cagcaggccc tacagcttct acagcagcct gatcagctat   3780
gaggaggacc agaggcaggg ggctgagccc aggaagaact ttgtgaagcc caatgaaacc   3840
aagacctact tctggaaggt gcagcaccac atggccccca ccaaggatga gtttgactgc   3900
aaggcctggg cctacttctc tgatgtggac ctggagaagg atgtgcactc tggcctgatt   3960
ggccccctgc tggtgtgcca caccaacacc ctgaaccctg cccatggcag gcaggtgact   4020
gtgcaggagt ttgccctgtt cttcaccatc tttgatgaaa ccaagagctg gtacttcact   4080
gagaacatgg agaggaactg cagggccccc tgcaacatcc agatggagga ccccaccttc   4140
aaggagaact acaggttcca tgccatcaat ggctacatca tggacaccct gcctggcctg   4200
gtgatggccc aggaccagag gatcaggtgg tacctgctga gcatgggcag caatgagaac   4260
atccacagca tccacttctc tggccatgtg ttcactgtga ggaagaagga ggagtacaag   4320
atggccctgt acaacctgta ccctggggtg tttgagactg tggagatgct gcccagcaag   4380
gctggcatct ggagggtgga gtgcctgatt ggggagcacc tgcatgctgg catgagcacc   4440
ctgttcctgg tgtacagcaa caagtgccag accccccctgg gcatggcctc tggccacatc   4500
agggacttcc agatcactgc ctctggccag tatggccagt gggcccccaa gctggccagg   4560
ctgcactact ctggcagcat caatgcctgg agcaccaagg agcccttcag ctggatcaag   4620
gtggacctgc tggcccccat gatcatccat ggcatcaaga cccagggggc caggcagaag   4680
ttcagcagcc tgtacatcag ccagttcatc atcatgtaca gcctggatgg caagaagtgg   4740
cagacctaca ggggcaacag cactggcacc ctgatggtgt tctttggcaa tgtggacagc   4800
tctggcatca agcacaacat cttcaacccc cccatcattg ccagatacat caggctgcac   4860
cccacccact acagcatcag gagcaccctg aggatggagc tgatgggctg tgacctgaac   4920
agctgcagca tgcccctggg catggagagc aaggccatct ctgatgccca gatcactgcc   4980
agcagctact tcaccaacat gtttgccacc tggagcccca gcaaggccag gctgcacctg   5040
```

-continued

```
cagggcagga gcaatgcctg gaggccccag gtcaacaacc ccaaggagtg gctgcaggtg   5100
gacttccaga agaccatgaa ggtgactggg gtgaccaccc agggggtgaa gagcctgctg   5160
accagcatgt atgtgaagga gttcctgatc agcagcagcc aggatggcca ccagtggacc   5220
ctgttcttcc agaatggcaa ggtgaaggtg ttccagggca accaggacag cttcacccct   5280
gtggtgaaca gcctggaccc ccccctgctg accagatacc tgaggattca cccccagagc   5340
tgggtgcacc agattgccct gaggatggag gtgctgggct gtgaggccca ggacctgtac   5400
tgacctcgag gaataaagga aatttatttt cattgcaata gtgtgttggt tttttgtgtc   5460
acgtggcggc cgcaggaacc cctagtgatg gagttggcca ctccctctct gcgcgctcgc   5520
tcgctcactg aggccgggcg accaaaggtc gcccgacgcc cgggctttgc ccgggcggcc   5580
tcagtgagcg agcgagcgcg cagagaggga gtggccaa                           5618
```

<210> SEQ ID NO 42
<211> LENGTH: 5993
<212> TYPE: DNA
<213> ORGANISM: Adeno-Associated Virus 2

<400> SEQUENCE: 42

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg tttaaacgtc gacaggttaa    180
tttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa tttttaaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg gacacaggac gctgtggttt    540
ctgagccagg gggcgactca gatcccagcc agtggactta gcccctgttt gctcctccga    600
taactggggt gaccttggtt aatattcacc agcagcctcc cccgttgccc ctctggatcc    660
actgcttaaa tacggacgag gacagggccc tgtctcctca gcttcaggca ccaccactga    720
cctgggacag tgaatcgcga tcgccaccat gcagattgag ctgagcacct gcttcttcct    780
gtgcctgctg aggttctgct tctctgccac caggagatac tacctggggg ctgtggagct    840
gagctgggac tacatgcagt ctgacctggg ggagctgcct gtggatgcca ggttcccccc    900
cagagtgccc aagagcttcc ccttcaacac ctctgtggtg tacaagaaga ccctgtttgt    960
ggagttcact gaccacctgt tcaacattgc caagcccagg ccccccctgga tgggcctgct   1020
gggccccacc atccaggctg aggtgtatga cactgtggtg atcaccctga agaacatggc   1080
cagccaccct gtgagcctgc atgctgtggg ggtgagctac tggaaggcct ctgaggggc   1140
tgagtatgat gaccagacca gccagaggga gaaggaggat gacaaggtgt tccctggggg   1200
cagccacacc tatgtgtggc aggtgctgaa ggagaatggc cccatggcct ctgacccccct   1260
gtgcctgacc tacagctacc tgagccatgt ggacctggtg aaggacctga actctggcct   1320
gattggggcc ctgctggtgt gcagggaggg cagcctggcc aaggagaaga cccagaccct   1380
gcacaagttc atcctgctgt ttgctgtgtt tgatgagggc aagagctggc actctgaaac   1440
caagaacagc ctgatgcagg acagggatgc tgcctctgcc agggcctggc ccaagatgca   1500
cactgtgaat ggctatgtga acaggagcct gcctggcctg attggctgcc acaggaagtc   1560
```

-continued

```
tgtgtactgg catgtgattg gcatgggcac cacccctgag gtgcacagca tcttcctgga   1620
gggccacacc ttcctggtca ggaaccacag gcaggccagc ctggagatca gccccatcac   1680
cttcctgact gcccagaccc tgctgatgga cctgggccag ttcctgctgt tctgccacat   1740
cagcagccac cagcatgatg gcatggaggc ctatgtgaag gtggacagct gccctgagga   1800
gccccagctg aggatgaaga acaatgagga ggctgaggac tatgatgatg acctgactga   1860
ctctgagatg gatgtggtga ggtttgatga tgacaacagc cccagcttca tccagatcag   1920
gtctgtggcc aagaagcacc ccaagacctg ggtgcactac attgctgctg aggaggagga   1980
ctgggactat gccccccctgg tgctggcccc tgatgacagg agctacaaga gccagtacct   2040
gaacaatggc ccccagagga ttggcaggaa gtacaagaag gtcaggttca tggcctacac   2100
tgatgaaacc ttcaagacca gggaggccat ccagcatgag tctggcatcc tgggcccccct   2160
gctgtatggg gaggtggggg acaccctgct gatcatcttc aagaaccagg ccagcaggcc   2220
ctacaacatc taccccccatg gcatcactga tgtgaggccc ctgtacagca ggaggctgcc   2280
caagggggtg aagcacctga aggacttccc catcctgcct ggggagatct tcaagtacaa   2340
gtggactgtg actgtggagg atggccccac caagtctgac cccaggtgcc tgaccagata   2400
ctacagcagc tttgtgaaca tggagaggga cctggcctct ggcctgattg gcccccctgct   2460
gatctgctac aaggagtctg tggaccagag gggcaaccag atcatgtctg acaagaggaa   2520
tgtgatcctg ttctctgtgt ttgatgagaa caggagctgg tacctgactg agaacatcca   2580
gaggttcctg cccaaccctg ctggggtgca gctggaggac cctgagttcc aggccagcaa   2640
catcatgcac agcatcaatg gctatgtgtt tgacagcctg cagctgtctg tgtgcctgca   2700
tgaggtggcc tactggtaca tcctgagcat tggggcccag actgacttcc tgtctgtgtt   2760
cttctctggc tacaccttca agcacaagat ggtgtatgag gacaccctga ccctgttccc   2820
cttctctggg gagactgtgt tcatgagcat ggagaaccct ggcctgtgga ttctgggctg   2880
ccacaactct gacttcagga acaggggcat gactgccctg ctgaaagtct ccagctgtga   2940
caagaacact ggggactact atgaggacag ctatgaggac atctctgcct acctgctgag   3000
caagaacaat gccattgagc ccaggagctt cagccagaac cccccagtgc tgaagaggca   3060
ccagagggag atcaccagga ccaccctgca gtctgaccag gaggagattg actatgatga   3120
caccatctct gtggagatga agaaggagga ctttgacatc tacgacgagg acgagaacca   3180
gagccccagg agcttccaga agaagaccag gcactacttc attgctgctg tggagaggct   3240
gtgggactat ggcatgagca gcagccccca tgtgctgagg aacagggccc agtctggctc   3300
tgtgccccag ttcaagaagg tggtgttcca ggagttcact gatggcagct tcacccagcc   3360
cctgtacaga ggggagctga atgagcacct gggcctgctg ggcccctaca tcagggctga   3420
ggtggaggac aacatcatgg tgaccttcag gaaccaggcc agcaggccct acagcttcta   3480
cagcagcctg atcagctatg aggaggacca gaggcagggg gctgagccca ggaagaactt   3540
tgtgaagccc aatgaaacca agacctactt ctggaaggtg cagcaccaca tggcccccac   3600
caaggatgag tttgactgca aggcctgggc ctacttctct gatgtggacc tggagaagga   3660
tgtgcactct ggcctgattg gcccccctgct ggtgtgccac accaacaccc tgaaccctgc   3720
ccatggcagg caggtgactg tgcaggagtt tgccctgttc ttcaccatct ttgatgaaac   3780
caagagctgg tacttcactg agaacatgga gaggaactgc agggccccct gcaacatcca   3840
gatggaggac cccaccttca aggagaacta caggttccat gccatcaatg gctacatcat   3900
```

```
ggacaccctg cctggcctgg tgatggccca ggaccagagg atcaggtggt acctgctgag   3960

catgggcagc aatgagaaca tccacagcat ccacttctct ggccatgtgt tcactgtgag   4020

gaagaaggag gagtacaaga tggccctgta caacctgtac cctggggtgt ttgagactgt   4080

ggagatgctg cccagcaagg ctggcatctg gagggtggag tgcctgattg gggagcacct   4140

gcatgctggc atgagcaccc tgttcctggt gtacagcaac aagtgccaga ccccccctggg  4200

catggcctct ggccacatca gggacttcca gatcactgcc tctggccagt atggccagtg   4260

ggcccccaag ctggccaggc tgcactactc tggcagcatc aatgcctgga gcaccaagga   4320

gcccttcagc tggatcaagg tggacctgct ggcccccatg atcatccatg gcatcaagac   4380

ccagggggcc aggcagaagt tcagcagcct gtacatcagc cagttcatca tcatgtacag   4440

cctggatggc aagaagtggc agacctacag gggcaacagc actggcaccc tgatggtgtt   4500

ctttggcaat gtggacagct ctggcatcaa gcacaacatc ttcaaccccc ccatcattgc   4560

cagatacatc aggctgcacc ccacccacta cagcatcagg agcaccctga ggatggagct   4620

gatgggctgt gacctgaaca gctgcagcat gcccctgggc atggagagca aggccatctc   4680

tgatgcccag atcactgcca gcagctactt caccaacatg tttgccacct ggagccccag   4740

caaggccagg ctgcacctgc agggcaggag caatgcctgg aggccccagg tcaacaaccc   4800

caaggagtgg ctgcaggtgg acttccagaa gaccatgaag gtgactgggg tgaccaccca   4860

gggggtgaag agcctgctga ccagcatgta tgtgaaggag ttcctgatca gcagcagcca   4920

ggatggccac cagtggaccc tgttcttcca gaatggcaag gtgaaggtgt tccagggcaa   4980

ccaggacagc ttcacccctg tggtgaacag cctggacccc cccctgctga ccagatacct   5040

gaggattcac ccccagagct gggtgcacca gattgccctg aggatggagg tgctgggctg   5100

tgaggcccag gacctgtact gacctcgagg aataaaggaa atttattttc attgcaatag   5160

tgtgttggtt ttttgtgtca cgtgccctct cacactacct aaaccacgcc aggacaacct   5220

ctgctcctct ccaccgaaat tccaaggggt cgagtggatg ttggaggtgg catgggccca   5280

gagaggtctc tgacctctgc cccagctcca aggtcagcag gcagggaggg ctgtgtgttt   5340

gctgtttgct gcttgcaatg tttgcccatt ttagggacat gagtaggctg aagtttgttc   5400

agtgtggact tcagaggcag cacacaaaca gctgctggag gatgggaact gaggggttgg   5460

aagggggcag ggtgagccca gaaactcctg tgtgcctctg agcctgcagc cctctcacac   5520

tacctaaacc acgccaggac aacctctgct cctctccacc gaaattccaa ggggtcgagt   5580

ggatgttgga ggtggcatgg gcccagagag gtctctgacc tctgccccag ctccaaggtc   5640

agcaggcagg gagggctgtg tgtttgctgt ttgctgcttg caatgtttgc ccattttagg   5700

gacatgagta ggctgaagtt tgttcagtgt ggacttcaga ggcagcacac aaacagctgc   5760

tggaggatgg gaactgaggg gttggaaggg ggcagggtga gcccagaaac tcctgtgtgc   5820

ctctgagcct gcagcacgtg gcggccgcag gaacccctag tgatggagtt ggccactccc   5880

tctctgcgcg ctcgctcgct cactgaggcc gggcgaccaa aggtcgcccg acgcccgggc   5940

tttgcccggg cggcctcagt gagcgagcga gcgcgcagag agggagtggc caa          5993
```

<210> SEQ ID NO 43
<211> LENGTH: 5337
<212> TYPE: DNA
<213> ORGANISM: Adeno-Associated Virus 2

<400> SEQUENCE: 43

```
ttggccactc cctctctgcg cgctcgctcg ctcactgagg ccgcccgggc aaagcccggg     60
```

-continued

```
cgtcgggcga cctttggtcg cccggcctca gtgagcgagc gagcgcgcag agagggagtg    120
gccaactcca tcactagggg ttcctgcggc cgcacgcgtg tttaaacgtc gacaggttaa    180
tttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa tttttaaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg gacacaggac gctgtggttt    540
ctgagccagg gggcgactca gatcccagcc agtggactta gcccctgttt gctcctccga    600
taactggggt gaccttggtt aatattcacc agcagcctcc cccgttgccc ctctggatcc    660
actgcttaaa tacggacgag gacagggccc tgtctcctca gcttcaggca ccaccactga    720
cctgggacag tgaatcgcga tcgccaccat gcagattgag ctgagcacct gcttcttcct    780
gtgcctgctg aggttctgct tctctgccac caggagatac tacctggggg ctgtggagct    840
gagctgggac tacatgcagt ctgacctggg ggagctgcct gtggatgcca ggttcccccc    900
cagagtgccc aagagcttcc ccttcaacac ctctgtggtg tacaagaaga ccctgtttgt    960
ggagttcact gaccacctgt tcaacattgc caagcccagg ccccccctgga tgggcctgct   1020
gggccccacc atccaggctg aggtgtatga cactgtggtg atcaccctga agaacatggc   1080
cagccaccct gtgagcctgc atgctgtggg ggtgagctac tggaaggcct ctgagggggc   1140
tgagtatgat gaccagacca gccagaggga gaaggaggat gacaaggtgt tccctggggg   1200
cagccacacc tatgtgtggc aggtgctgaa ggagaatggc cccatggcct ctgacccccct   1260
gtgcctgacc tacagctacc tgagccatgt ggacctggtg aaggacctga actctggcct   1320
gattggggcc ctgctggtgt gcagggaggg cagcctggcc aaggagaaga cccagaccct   1380
gcacaagttc atcctgctgt ttgctgtgtt tgatgagggc aagagctggc actctgaaac   1440
caagaacagc ctgatgcagg acagggatgc tgcctctgcc agggcctggc ccaagatgca   1500
cactgtgaat ggctatgtga acaggagcct gcctggcctg attggctgcc acaggaagtc   1560
tgtgtactgg catgtgattg gcatgggcac cacccctgag gtgcacagca tcttcctgga   1620
gggccacacc ttcctggtca ggaaccacag gcaggccagc ctggagatca gccccatcac   1680
cttcctgact gcccagaccc tgctgatgga cctgggccag ttcctgctgt tctgccacat   1740
cagcagccac cagcatgatg gcatggaggc ctatgtgaag gtggacagct gccctgagga   1800
gccccagctg aggatgaaga acaatgagga ggctgaggac tatgatgatg acctgactga   1860
ctctgagatg gatgtggtga ggtttgatga tgacaacagc cccagcttca tccagatcag   1920
gtctgtggcc aagaagcacc ccaagacctg ggtgcactac attgctgctg aggaggagga   1980
ctgggactat gccccccctgg tgctggcccc tgatgacagg agctacaaga gccagtacct   2040
gaacaatggc ccccagagga ttggcaggaa gtacaagaag gtcaggttca tggcctacac   2100
tgatgaaacc ttcaagacca gggaggccat ccagcatgag tctggcatcc tgggccccct   2160
gctgtatggg gaggtggggg acaccctgct gatcatcttc aagaaccagg ccagcaggcc   2220
ctacaacatc taccccccatg gcatcactga tgtgaggccc ctgtacagca ggaggctgcc   2280
caagggggtg aagcacctga aggacttccc catcctgcct ggggagatct tcaagtacaa   2340
gtggactgtg actgtggagg atggccccac caagtctgac cccaggtgcc tgaccagata   2400
```

-continued

```
ctacagcagc tttgtgaaca tggagaggga cctggcctct ggcctgattg gcccccctgct   2460
gatctgctac aaggagtctg tggaccagag gggcaaccag atcatgtctg acaagaggaa   2520
tgtgatcctg ttctctgtgt ttgatgagaa caggagctgg tacctgactg agaacatcca   2580
gaggttcctg cccaaccctg ctggggtgca gctggaggac cctgagttcc aggccagcaa   2640
catcatgcac agcatcaatg gctatgtgtt tgacagcctg cagctgtctg tgtgcctgca   2700
tgaggtggcc tactggtaca tcctgagcat tggggcccag actgacttcc tgtctgtgtt   2760
cttctctggc tacaccttca agcacaagat ggtgtatgag gacaccctga ccctgttccc   2820
cttctctggg gagactgtgt tcatgagcat ggagaaccct ggcctgtgga ttctgggctg   2880
ccacaactct gacttcagga acaggggcat gactgccctg ctgaaagtct ccagctgtga   2940
caagaacact ggggactact atgaggacag ctatgaggac atctctgcct acctgctgag   3000
caagaacaat gccattgagc ccaggagctt cagccagaac cccccagtgc tgaagaggca   3060
ccagagggag atcaccagga ccaccctgca gtctgaccag gaggagattg actatgatga   3120
caccatctct gtggagatga agaaggagga ctttgacatc tacgacgagg acgagaacca   3180
gagccccagg agcttccaga agaagaccag gcactacttc attgctgctg tggagaggct   3240
gtgggactat ggcatgagca gcagccccca tgtgctgagg aacagggccc agtctggctc   3300
tgtgccccag ttcaagaagg tggtgttcca ggagttcact gatggcagct tcacccagcc   3360
cctgtacaga ggggagctga atgagcacct gggcctgctg ggcccctaca tcagggctga   3420
ggtggaggac aacatcatgg tgaccttcag gaaccaggcc agcaggccct acagcttcta   3480
cagcagcctg atcagctatg aggaggacca gaggcagggg gctgagccca ggaagaactt   3540
tgtgaagccc aatgaaacca agacctactt ctggaaggtg cagcaccaca tggcccccac   3600
caaggatgag tttgactgca aggcctgggc ctacttctct gatgtggacc tggagaagga   3660
tgtgcactct ggcctgattg gcccccctgct ggtgtgccac accaacaccc tgaaccctgc   3720
ccatggcagg caggtgactg tgcaggagtt tgccctgttc ttcaccatct ttgatgaaac   3780
caagagctgg tacttcactg agaacatgga gaggaactgc agggcccccct gcaacatcca   3840
gatggaggac cccaccttca aggagaacta caggttccat gccatcaatg gctacatcat   3900
ggacaccctg cctggcctgg tgatggccca ggaccagagg atcaggtggt acctgctgag   3960
catgggcagc aatgagaaca tccacagcat ccacttctct ggccatgtgt tcactgtgag   4020
gaagaaggag gagtacaaga tggccctgta caacctgtac cctggggtgt ttgagactgt   4080
ggagatgctg cccagcaagg ctggcatctg gagggtggag tgcctgattg gggagcacct   4140
gcatgctggc atgagcaccc tgttcctggt gtacagcaac aagtgccaga cccccctggg   4200
catggcctct ggccacatca gggacttcca gatcactgcc tctggccagt atggccagtg   4260
ggcccccaag ctggccaggc tgcactactc tggcagcatc aatgcctgga gcaccaagga   4320
gcccttcagc tggatcaagg tggacctgct ggcccccatg atcatccatg gcatcaagac   4380
ccagggggcc aggcagaagt tcagcagcct gtacatcagc cagttcatca tcatgtacag   4440
cctggatggc aagaagtggc agacctacag gggcaacagc actggcaccc tgatggtgtt   4500
ctttggcaat gtggacagct ctggcatcaa gcacaacatc ttcaaccccc ccatcattgc   4560
cagatacatc aggctgcacc ccacccacta cagcatcagg agcaccctga ggatggagct   4620
gatgggctgt gacctgaaca gctgcagcat gcccctgggc atggagagca aggccatctc   4680
tgatgcccag atcactgcca gcagctactt caccaacatg tttgccacct ggagccccag   4740
caaggccagg ctgcacctgc agggcaggag caatgcctgg aggccccagg tcaacaaccc   4800
```

caaggagtgg ctgcaggtgg acttccagaa gaccatgaag gtgactgggg tgaccaccca 4860
gggggtgaag agcctgctga ccagcatgta tgtgaaggag ttcctgatca gcagcagcca 4920
ggatggccac cagtggaccc tgttcttcca gaatggcaag gtgaaggtgt tccagggcaa 4980
ccaggacagc ttcacccctg tggtgaacag cctggacccc cccctgctga ccagatacct 5040
gaggattcac ccccagagct gggtgcacca gattgccctg aggatggagg tgctgggctg 5100
tgaggcccag gacctgtact gacctcgagg aataaaggaa atttattttc attgcaatag 5160
tgtgttggtt ttttgtgtca cgtggcggcc gcaggaaccc ctagtgatgg agttggccac 5220
tccctctctg cgcgctcgct cgctcactga ggccgggcga ccaaaggtcg cccgacgccc 5280
gggctttgcc cgggcggcct cagtgagcga gcgagcgcgc agagagggag tggccaa 5337

<210> SEQ ID NO 44
<211> LENGTH: 5542
<212> TYPE: DNA
<213> ORGANISM: Adeno-Associated Virus 2

<400> SEQUENCE: 44
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgcggc cgcacgcgtg tttaaacgtc gacaggttaa 180
tttttaaaaa gcagtcaaaa gtccaagtgg cccttggcag catttactct ctctgtttgc 240
tctggttaat aatctcagga gcacaaacat tcctggaggc aggagaagaa atcaacatcc 300
tggacttatc ctctgggcct ctccccaccc ccaggagagg ctcaggttaa tttttaaaaa 360
gcagtcaaaa gtccaagtgg cccttggcag catttactct ctctgtttgc tctggttaat 420
aatctcagga gcacaaacat tcctggaggc aggagaagaa atcaacatcc tggacttatc 480
ctctgggcct ctccccaccc ccaggagagg ctgtcgactg gacacaggac gctgtggttt 540
ctgagccagg gggcgactca gatcccagcc agtggactta gcccctgttt gctcctccga 600
taactggggt gaccttggtt aatattcacc agcagcctcc cccgttgccc ctctggatcc 660
actgcttaaa tacggacgag gacagggccc tgtctcctca gcttcaggca ccaccactga 720
cctgggacag tgaatcgtaa gtatgccttt cactgcgaga ggttctggag aggcttctga 780
gctccccatg gcccaggcag gcagcaggtc tggggcagga ggggggttgt ggagtgcctt 840
gactcggggc ctggcccccc catctctgtc ttgcaggaca attgccgtct tctgtctcgt 900
ggggcatcct cctgctggca ggcctgtgct gcctggtccc tgcgatcgcc accatgcaga 960
ttgagctgag cacctgcttc ttcctgtgcc tgctgaggtt ctgcttctct gccaccagga 1020
gatactacct gggggctgtg gagctgagct gggactacat gcagtctgac ctgggggagc 1080
tgcctgtgga tgccaggttc ccccccagag tgcccaagag cttccccttc aacacctctg 1140
tggtgtacaa gaagaccctg tttgtggagt tcactgacca cctgttcaac attgccaagc 1200
ccaggccccc ctggatgggc ctgctgggcc ccaccatcca ggctgaggtg tatgacactg 1260
tggtgatcac cctgaagaac atggccagcc accctgtgag cctgcatgct gtgggggtga 1320
gctactggaa ggcctctgag gggctgagt atgatgacca gaccagccag agggagaagg 1380
aggatgacaa ggtgttccct gggggcagcc acacctatgt gtggcaggtg ctgaaggaga 1440
atggccccat ggcctctgac cccctgtgcc tgacctacag ctacctgagc catgtggacc 1500
tggtgaagga cctgaactct ggcctgattg gggccctgct ggtgtgcagg gagggcagcc 1560

-continued tggccaagga gaagacccag accctgcaca agttcatcct gctgtttgct gtgtttgatg 1620
agggcaagag ctggcactct gaaaccaaga acagcctgat gcaggacagg gatgctgcct 1680
ctgccagggc ctggcccaag atgcacactg tgaatggcta tgtgaacagg agcctgcctg 1740
gcctgattgg ctgccacagg aagtctgtgt actggcatgt gattggcatg ggcaccaccc 1800
ctgaggtgca cagcatcttc ctggagggcc acaccttcct ggtcaggaac cacaggcagg 1860
ccagcctgga gatcagcccc atcaccttcc tgactgccca gaccctgctg atggacctgg 1920
gccagttcct gctgttctgc cacatcagca gccaccagca tgatggcatg gaggcctatg 1980
tgaaggtgga cagctgccct gaggagcccc agctgaggat gaagaacaat gaggaggctg 2040
aggactatga tgatgacctg actgactctg agatggatgt ggtgaggttt gatgatgaca 2100
acagccccag cttcatccag atcaggtctg tggccaagaa gcaccccaag acctgggtgc 2160
actacattgc tgctgaggag gaggactggg actatgcccc cctggtgctg gcccctgatg 2220
acaggagcta caagagccag tacctgaaca atggccccca gaggattggc aggaagtaca 2280
agaaggtcag gttcatggcc tacactgatg aaaccttcaa gaccagggag gccatccagc 2340
atgagtctgg catcctgggc cccctgctgt atggggaggt gggggacacc ctgctgatca 2400
tcttcaagaa ccaggccagc aggccctaca acatctaccc ccatggcatc actgatgtga 2460
ggcccctgta cagcaggagg ctgcccaagg gggtgaagca cctgaaggac ttccccatcc 2520
tgcctgggga gatcttcaag tacaagtgga ctgtgactgt ggaggatggc cccaccaagt 2580
ctgaccccag gtgcctgacc agatactaca gcagctttgt gaacatggag agggacctgg 2640
cctctggcct gattggcccc ctgctgatct gctacaagga gtctgtggac cagaggggca 2700
accagatcat gtctgacaag aggaatgtga tcctgttctc tgtgtttgat gagaacagga 2760
gctggtacct gactgagaac atccagaggt tcctgcccaa ccctgctggg gtgcagctgg 2820
aggaccctga gttccaggcc agcaacatca tgcacagcat caatggctat gtgtttgaca 2880
gcctgcagct gtctgtgtgc ctgcatgagg tggcctactg gtacatcctg agcattgggg 2940
cccagactga cttcctgtct gtgttcttct ctggctacac cttcaagcac aagatggtgt 3000
atgaggacac cctgaccctg ttccccttct ctggggagac tgtgttcatg agcatggaga 3060
accctggcct gtggattctg ggctgccaca actctgactt caggaacagg ggcatgactg 3120
ccctgctgaa agtctccagc tgtgacaaga acactgggga ctactatgag gacagctatg 3180
aggacatctc tgcctacctg ctgagcaaga acaatgccat tgagcccagg agcttcagcc 3240
agaacccccc agtgctgaag aggcaccaga gggagatcac caggaccacc ctgcagtctg 3300
accaggagga gattgactat gatgacacca tctctgtgga gatgaagaag gaggactttg 3360
acatctacga cgaggacgag aaccagagcc ccaggagctt ccagaagaag accaggcact 3420
acttcattgc tgctgtggag aggctgtggg actatggcat gagcagcagc ccccatgtgc 3480
tgaggaacag ggcccagtct ggctctgtgc cccagttcaa gaaggtggtg ttccaggagt 3540
tcactgatgg cagcttcacc cagcccctgt acagagggga gctgaatgag cacctgggcc 3600
tgctgggccc ctacatcagg gctgaggtgg aggacaacat catggtgacc ttcaggaacc 3660
aggccagcag gccctacagc ttctacagca gcctgatcag ctatgaggag gaccagaggc 3720
agggggctga gcccaggaag aactttgtga agcccaatga aaccaagacc tacttctgga 3780
aggtgcagca ccacatggcc cccaccaagg atgagtttga ctgcaaggcc tgggcctact 3840
tctctgatgt ggacctggag aaggatgtgc actctggcct gattggcccc ctgctggtgt 3900
gccacaccaa caccctgaac cctgcccatg gcaggcaggt gactgtgcag gagtttgccc 3960

-continued

```
tgttcttcac catctttgat gaaaccaaga gctggtactt cactgagaac atggagagga   4020

actgcagggc cccctgcaac atccagatgg aggaccccac cttcaaggag aactacaggt   4080

tccatgccat caatggctac atcatggaca ccctgcctgg cctggtgatg gcccaggacc   4140

agaggatcag gtggtacctg ctgagcatgg gcagcaatga gaacatccac agcatccact   4200

tctctggcca tgtgttcact gtgaggaaga aggaggagta caagatggcc ctgtacaacc   4260

tgtaccctgg ggtgtttgag actgtggaga tgctgcccag caaggctggc atctggaggg   4320

tggagtgcct gattggggag cacctgcatg ctggcatgag caccctgttc ctggtgtaca   4380

gcaacaagtg ccagaccccc ctgggcatgg cctctggcca catcagggac ttccagatca   4440

ctgcctctgg ccagtatggc cagtgggccc ccaagctggc caggctgcac tactctggca   4500

gcatcaatgc ctggagcacc aaggagccct tcagctggat caaggtggac ctgctggccc   4560

ccatgatcat ccatggcatc aagacccagg gggccaggca gaagttcagc agcctgtaca   4620

tcagccagtt catcatcatg tacagcctgg atggcaagaa gtggcagacc tacaggggca   4680

acagcactgg caccctgatg gtgttctttg gcaatgtgga cagctctggc atcaagcaca   4740

acatcttcaa cccccccatc attgccagat acatcaggct gcaccccacc cactacagca   4800

tcaggagcac cctgaggatg gagctgatgg gctgtgacct gaacagctgc agcatgcccc   4860

tgggcatgga gagcaaggcc atctctgatg cccagatcac tgccagcagc tacttcacca   4920

acatgtttgc cacctggagc cccagcaagg ccaggctgca cctgcagggc aggagcaatg   4980

cctggaggcc ccaggtcaac aaccccaagg agtggctgca ggtggacttc cagaagacca   5040

tgaaggtgac tggggtgacc acccaggggg tgaagagcct gctgaccagc atgtatgtga   5100

aggagttcct gatcagcagc agccaggatg gccaccagtg gaccctgttc ttccagaatg   5160

gcaaggtgaa ggtgttccag ggcaaccagg acagcttcac ccctgtggtg aacagcctgg   5220

accccccct gctgaccaga tacctgagga ttcaccccca gagctgggtg caccagattg   5280

ccctgaggat ggaggtgctg ggctgtgagg cccaggacct gtactgacct cgaggaataa   5340

aggaaattta ttttcattgc aatagtgtgt tggtttttg tgtcacgtgg cggccgcagg   5400

aacccctagt gatggagttg gccactccct ctctgcgcgc tcgctcgctc actgaggccg   5460

ggcgaccaaa ggtcgcccga cgcccgggct ttgcccgggc ggcctcagtg agcgagcgag   5520

cgcgcagaga gggagtggcc aa                                             5542
```

<210> SEQ ID NO 45
<211> LENGTH: 5126
<212> TYPE: DNA
<213> ORGANISM: Adeno-Associated Virus 2

<400> SEQUENCE: 45

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgcggc cgcacgcgtg ggaggctgct ggtgaatatt    180

aaccaaggtc accccagtta tcggaggagc aaacaggggc taagtccacg gggaggctgc    240

tggtgaatat taaccaaggt caccccagtt atcggaggag caaacagggg ctaagtccac    300

ggtcgactgg acacaggacg ctgtggtttc tgagccaggg ggcgactcag atcccagcca    360

gtggacttag cccctgtttg ctcctccgat aactggggtg accttggtta atattcacca    420

gcagcctccc ccgttgcccc tctggatcca ctgcttaaat acggacgagg acagggccct    480
```

```
gtctcctcag cttcaggcac caccactgac ctgggacagt gaatcgcgat cgccaccatg    540
cagattgagc tgagcacctg cttcttcctg tgcctgctga ggttctgctt ctctgccacc    600
aggagatact acctgggggc tgtggagctg agctgggact acatgcagtc tgacctgggg    660
gagctgcctg tggatgccag gttccccccc agagtgccca agagcttccc cttcaacacc    720
tctgtggtgt acaagaagac cctgtttgtg gagttcactg accacctgtt caacattgcc    780
aagcccaggc ccccctggat gggcctgctg ggccccacca tccaggctga ggtgtatgac    840
actgtggtga tcaccctgaa gaacatggcc agccaccctg tgagcctgca tgctgtgggg    900
gtgagctact ggaaggcctc tgagggggct gagtatgatg accagaccag ccagagggag    960
aaggaggatg acaaggtgtt ccctgggggc agccacacct atgtgtggca ggtgctgaag   1020
gagaatggcc ccatggcctc tgacccccctg tgcctgacct acagctacct gagccatgtg   1080
gacctggtga aggacctgaa ctctggcctg attggggccc tgctggtgtg cagggagggc   1140
agcctggcca aggagaagac ccagaccctg cacaagttca tcctgctgtt tgctgtgttt   1200
gatgagggca agagctggca ctctgaaacc aagaacagcc tgatgcagga cagggatgct   1260
gcctctgcca gggcctggcc caagatgcac actgtgaatg gctatgtgaa caggagcctg   1320
cctggcctga ttggctgcca caggaagtct gtgtactggc atgtgattgg catgggcacc   1380
acccctgagg tgcacagcat cttcctggag ggccacacct tcctggtcag gaaccacagg   1440
caggccagcc tggagatcag ccccatcacc ttcctgactg cccagaccct gctgatggac   1500
ctgggccagt tcctgctgtt ctgccacatc agcagccacc agcatgatgg catggaggcc   1560
tatgtgaagg tggacagctg ccctgaggag ccccagctga ggatgaagaa caatgaggag   1620
gctgaggact atgatgatga cctgactgac tctgagatgg atgtggtgag gtttgatgat   1680
gacaacagcc ccagcttcat ccagatcagg tctgtggcca agaagcaccc caagacctgg   1740
gtgcactaca ttgctgctga ggaggaggac tgggactatg ccccccctggt gctggcccct   1800
gatgacagga gctacaagag ccagtacctg aacaatggcc cccagaggat tggcaggaag   1860
tacaagaagg tcaggttcat ggcctacact gatgaaacct tcaagaccag ggaggccatc   1920
cagcatgagt ctggcatcct gggcccccctg ctgtatgggg aggtggggga caccctgctg   1980
atcatcttca agaaccaggc cagcaggccc tacaacatct acccccatgg catcactgat   2040
gtgaggcccc tgtacagcag gaggctgccc aagggggtga agcacctgaa ggacttcccc   2100
atcctgcctg ggagatcttt caagtacaag tggactgtga ctgtggagga tggccccacc   2160
aagtctgacc ccaggtgcct gaccagatac tacagcagct ttgtgaacat ggagagggac   2220
ctggcctctg gcctgattgg cccccctgctg atctgctaca aggagtctgt ggaccagagg   2280
ggcaaccaga tcatgtctga caagaggaat gtgatcctgt tctctgtgtt tgatgagaac   2340
aggagctggt acctgactga gaacatccag aggttcctgc ccaaccctgc tggggtgcag   2400
ctggaggacc ctgagttcca ggccagcaac atcatgcaca gcatcaatgg ctatgtgttt   2460
gacagcctgc agctgtctgt gtgcctgcat gaggtggcct actggtacat cctgagcatt   2520
ggggcccaga ctgacttcct gtctgtgttc ttctctggct acaccttcaa gcacaagatg   2580
gtgtatgagg acaccctgac cctgttcccc ttctctgggg agactgtgtt catgagcatg   2640
gagaaccctg gcctgtggat tctgggctgc cacaactctg acttcaggaa caggggcatg   2700
actgccctgc tgaaagtctc cagctgtgac aagaacactg gggactacta tgaggacagc   2760
tatgaggaca tctctgccta cctgctgagc aagaacaatg ccattgagcc caggagcttc   2820
agccagaacc ccccagtgct gaagaggcac cagagggaga tcaccaggac caccctgcag   2880
```

-continued

```
tctgaccagg aggagattga ctatgatgac accatctctg tggagatgaa gaaggaggac   2940
tttgacatct acgacgagga cgagaaccag agccccagga gcttccagaa gaagaccagg   3000
cactacttca ttgctgctgt ggagaggctg tgggactatg gcatgagcag cagcccccat   3060
gtgctgagga acagggccca gtctggctct gtgccccagt tcaagaaggt ggtgttccag   3120
gagttcactg atggcagctt cacccagccc ctgtacagag gggagctgaa tgagcacctg   3180
ggcctgctgg gcccctacat cagggctgag gtggaggaca acatcatggt gaccttcagg   3240
aaccaggcca gcaggcccta cagcttctac agcagcctga tcagctatga ggaggaccag   3300
aggcaggggg ctgagcccag gaagaacttt gtgaagccca atgaaaccaa gacctacttc   3360
tggaaggtgc agcaccacat ggcccccacc aaggatgagt ttgactgcaa ggcctgggcc   3420
tacttctctg atgtggacct ggagaaggat gtgcactctg gcctgattgg cccccctgctg   3480
gtgtgccaca ccaacaccct gaaccctgcc catggcaggc aggtgactgt gcaggagttt   3540
gccctgttct tcaccatctt tgatgaaacc aagagctggt acttcactga gaacatggag   3600
aggaactgca gggccccctg caacatccag atggaggacc ccaccttcaa ggagaactac   3660
aggttccatg ccatcaatgg ctacatcatg gacaccctgc ctggcctggt gatggcccag   3720
gaccagagga tcaggtggta cctgctgagc atgggcagca atgagaacat ccacagcatc   3780
cacttctctg gccatgtgtt cactgtgagg aagaaggagg agtacaagat ggccctgtac   3840
aacctgtacc ctggggtgtt tgagactgtg gagatgctgc ccagcaaggc tggcatctgg   3900
agggtggagt gcctgattgg ggagcacctg catgctggca tgagcaccct gttcctggtg   3960
tacagcaaca agtgccagac cccccctgggc atggcctctg gccacatcag ggacttccag   4020
atcactgcct ctggccagta tggccagtgg gcccccaagc tggccaggct gcactactct   4080
ggcagcatca atgcctggag caccaaggag cccttcagct ggatcaaggt ggacctgctg   4140
gcccccatga tcatccatgg catcaagacc caggggggcca ggcagaagtt cagcagcctg   4200
tacatcagcc agttcatcat catgtacagc ctggatggca agaagtggca gacctacagg   4260
ggcaacagca ctggcaccct gatggtgttc tttggcaatg tggacagctc tggcatcaag   4320
cacaacatct tcaacccccc catcattgcc agatacatca ggctgcaccc cacccactac   4380
agcatcagga gcaccctgag gatggagctg atgggctgtg acctgaacag ctgcagcatg   4440
cccctgggca tggagagcaa ggccatctct gatgcccaga tcactgccag cagctacttc   4500
accaacatgt ttgccacctg gagccccagc aaggccaggc tgcacctgca gggcaggagc   4560
aatgcctgga ggccccaggt caacaacccc aaggagtggc tgcaggtgga cttccagaag   4620
accatgaagg tgactggggt gaccacccag gggggtgaaga gcctgctgac cagcatgtat   4680
gtgaaggagt tcctgatcag cagcagccag gatggccacc agtggaccct gttcttccag   4740
aatggcaagg tgaaggtgtt ccagggcaac caggacagct tcacccctgt ggtgaacagc   4800
ctggaccccc ccctgctgac cagatacctg aggattcacc cccagagctg ggtgcaccag   4860
attgccctga ggatggaggt gctgggctgt gaggcccagg acctgtactg acctcgagga   4920
ataaaggaaa tttattttca ttgcaatagt gtgttggttt tttgtgtcac gtggcggccg   4980
caggaacccc tagtgatgga gttggccact ccctctctgc gcgctcgctc gctcactgag   5040
gccgggcgac caaaggtcgc ccgacgcccg ggctttgccc gggcggcctc agtgagcgag   5100
cgagcgcgca gagagggagt ggccaa                                        5126
```